(12) United States Patent
Connor

(10) Patent No.: US 11,925,271 B2
(45) Date of Patent: *Mar. 12, 2024

(54) SMOOCH N' SNORE [TM]: DEVICES TO CREATE A PLURALITY OF ADJUSTABLE ACOUSTIC AND/OR THERMAL ZONES IN A BED

(71) Applicant: Sleepme Inc., Mooresville, NC (US)

(72) Inventor: Robert A. Connor, Burnsville, MN (US)

(73) Assignee: Sleepnea LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/571,478

(22) Filed: Jan. 8, 2022

(65) Prior Publication Data

US 2022/0125217 A1 Apr. 28, 2022

Related U.S. Application Data

(63) Continuation-in-part of application No. 16/208,665, filed on Dec. 4, 2018, now abandoned, which is a continuation-in-part of application No. 14/703,916, filed on May 5, 2015, now Pat. No. 10,179,064.

(60) Provisional application No. 61/991,172, filed on May 9, 2014.

(51) Int. Cl.
*A47C 31/00* (2006.01)
*A47C 21/04* (2006.01)

(52) U.S. Cl.
CPC .......... *A47C 31/004* (2013.01); *A47C 21/044* (2013.01); *A47C 21/048* (2013.01); *A47C 31/008* (2013.01)

(58) Field of Classification Search
CPC ... A47C 31/004; A47C 21/044; A47C 21/048; A47C 31/008; A47C 21/006; A47C 27/061; A47C 27/082; A47C 27/083; A47C 21/003; A61B 5/4815; A61B 5/0205; A61B 5/024; A61B 5/0533; A61B 5/1116; A61B 5/14551; A61B 5/369; A61B 5/398; A61B 5/4806; A61B 5/4836
See application file for complete search history.

(56) References Cited

U.S. PATENT DOCUMENTS

| | | | | |
|---|---|---|---|---|
| 1,013,338 A | | 1/1912 | Van Brunt | |
| 1,777,982 A | * | 10/1930 | Popp | A61F 7/02 604/23 |
| 3,209,380 A | * | 10/1965 | Watsky | A47C 27/144 297/452.47 |
| 3,486,177 A | * | 12/1969 | Marshack | A61G 7/057 5/652.2 |
| 3,529,310 A | * | 9/1970 | Olmo | A47C 21/044 297/180.13 |
| 3,653,083 A | * | 4/1972 | Lapidus | A61G 7/05776 5/709 |

(Continued)

*Primary Examiner* — Myles A Throop

(57) ABSTRACT

This invention is a device which creates adjustable acoustic and/or thermal zones in a bed to address sleep issues such as bed partner snoring and hot flashes. Adjustable acoustic bed zones can be created with a flexible movable partition which longitudinally spans a bed from an arch at the head of the bed to an arch at the foot of the bed. Adjustable thermal bed zones can be created with inflow and outflow flexible longitudinal air tubes which are inserted into a space between layers of bedding.

9 Claims, 58 Drawing Sheets

(56) References Cited

U.S. PATENT DOCUMENTS

| | | | | |
|---|---|---|---|---|
| 4,134,166 | A | * | 1/1979 | Schuder ............... A47C 27/081 297/284.3 |
| 4,197,837 | A | * | 4/1980 | Tringali ............. A61G 7/05776 601/149 |
| 5,416,935 | A | * | 5/1995 | Nieh .................... A47C 21/044 297/180.13 |
| 5,555,579 | A | | 9/1996 | Wu |
| 5,640,731 | A | * | 6/1997 | Toedter ................ A47C 21/046 5/713 |
| 5,684,460 | A | | 11/1997 | Scanlon |
| 5,924,767 | A | * | 7/1999 | Pietryga ............... B60N 2/5685 297/180.13 |
| 6,006,524 | A | | 12/1999 | Park |
| 6,425,527 | B1 | * | 7/2002 | Smole ....................... F24F 7/00 5/423 |
| 6,468,234 | B1 | | 10/2002 | Van der Loos et al. |
| 7,461,892 | B2 | * | 12/2008 | Bajic .................. B60N 2/5664 297/452.47 |
| 7,640,764 | B2 | | 1/2010 | Gammons et al. |
| 8,181,290 | B2 | | 5/2012 | Brykalski et al. |
| 8,332,975 | B2 | | 12/2012 | Brykalski et al. |
| 8,353,069 | B1 | * | 1/2013 | Miller .................. A47C 21/044 5/724 |
| 8,402,579 | B2 | * | 3/2013 | Marquette ............... F24H 3/022 5/652.2 |
| 8,418,286 | B2 | | 4/2013 | Brykalski et al. |
| 8,628,462 | B2 | | 1/2014 | Berka et al. |
| 8,755,879 | B2 | | 6/2014 | Hang et al. |
| 8,836,516 | B2 | | 9/2014 | Wolfe et al. |
| 8,887,328 | B2 | | 11/2014 | McKlarney |
| 8,893,329 | B2 | | 11/2014 | Petrovski et al. |
| 8,932,199 | B2 | | 1/2015 | Berka et al. |
| 8,984,687 | B2 | | 3/2015 | Stusynski et al. |
| 9,125,497 | B2 | | 9/2015 | Brykalski et al. |
| 9,186,479 | B1 | | 11/2015 | Franceschetti et al. |
| 9,265,352 | B2 | * | 2/2016 | Oakhill ................ A47C 21/048 |
| 9,326,616 | B2 | * | 5/2016 | DeFranks ............. A47C 21/048 |
| 9,370,457 | B2 | | 6/2016 | Nunn et al. |
| 9,510,688 | B2 | | 12/2016 | Nunn et al. |
| 9,586,021 | B2 | | 3/2017 | Franceschetti et al. |
| 9,603,459 | B2 | | 3/2017 | Brykalski et al. |
| 9,694,156 | B2 | | 7/2017 | Franceschetti et al. |
| 9,877,593 | B2 | | 1/2018 | Van Erlach |
| 9,888,782 | B1 | | 2/2018 | Jannke |
| 9,907,929 | B2 | | 3/2018 | Rink et al. |
| 9,955,791 | B2 | | 5/2018 | Chandler et al. |
| 9,974,394 | B2 | | 5/2018 | Brykalski et al. |
| 9,981,107 | B2 | | 5/2018 | Franceschetti et al. |
| 10,029,591 | B1 | * | 7/2018 | Paez ..................... B60N 2/5628 |
| 10,051,973 | B2 | | 8/2018 | Morgan et al. |
| 10,058,467 | B2 | | 8/2018 | Stusynski et al. |
| 10,105,092 | B2 | | 10/2018 | Franceschetti et al. |
| 10,154,932 | B2 | | 12/2018 | Franceschetti et al. |
| 10,179,064 | B2 | * | 1/2019 | Connor ................ A61F 7/0085 |
| 10,278,511 | B2 | | 5/2019 | Youngblood et al. |
| 10,792,461 | B2 | | 10/2020 | Franceschetti et al. |
| 10,986,933 | B2 | | 4/2021 | Youngblood et al. |
| 10,986,934 | B1 | | 4/2021 | Youngblood et al. |
| 11,013,339 | B2 | | 5/2021 | Youngblood et al. |
| 11,013,883 | B2 | | 5/2021 | Youngblood et al. |
| 11,083,309 | B2 | * | 8/2021 | Hinnant ................ A47C 27/10 |
| 11,103,081 | B2 | | 8/2021 | Sherman et al. |
| 11,147,389 | B1 | | 10/2021 | Youngblood et al. |
| 2002/0129449 | A1 | * | 9/2002 | Harker ............... A61G 7/05784 5/423 |
| 2003/0150060 | A1 | * | 8/2003 | Huang ................ A47C 21/044 5/726 |
| 2005/0173950 | A1 | * | 8/2005 | Bajic ........................ A47C 7/74 297/452.45 |
| 2005/0278863 | A1 | * | 12/2005 | Bahash ................ A47C 21/044 5/652.2 |
| 2006/0162074 | A1 | | 7/2006 | Bader |
| 2007/0033733 | A1 | * | 2/2007 | Jen .......................... A47C 7/74 5/423 |
| 2007/0193278 | A1 | | 8/2007 | Polacek et al. |
| 2008/0028536 | A1 | * | 2/2008 | Hadden-Cook ...... A47C 21/044 5/724 |
| 2008/0060374 | A1 | | 3/2008 | Gammons et al. |
| 2008/0122616 | A1 | | 5/2008 | Warner et al. |
| 2008/0126132 | A1 | | 5/2008 | Warner et al. |
| 2008/0148481 | A1 | * | 6/2008 | Brykalski ............ A47C 21/048 5/423 |
| 2008/0155750 | A1 | | 7/2008 | Mossbeck |
| 2008/0189865 | A1 | | 8/2008 | Bhai |
| 2009/0287063 | A1 | | 11/2009 | Freedman et al. |
| 2010/0011502 | A1 | * | 1/2010 | Brykalski ............... A47C 21/04 5/423 |
| 2010/0099954 | A1 | | 4/2010 | Dickinson et al. |
| 2010/0204764 | A1 | | 8/2010 | Garetz |
| 2010/0240982 | A1 | | 9/2010 | Westbrook et al. |
| 2011/0010014 | A1 | | 1/2011 | Dexman et al. |
| 2011/0035879 | A1 | * | 2/2011 | Grinstead ............ A47C 27/144 62/89 |
| 2011/0115635 | A1 | * | 5/2011 | Petrovski ............. A47C 31/008 340/584 |
| 2011/0289684 | A1 | * | 12/2011 | Parish .................. A47C 21/044 5/421 |
| 2011/0295083 | A1 | | 12/2011 | Doelling et al. |
| 2011/0296621 | A1 | * | 12/2011 | McKenna .......... A61G 7/05776 5/713 |
| 2011/0314837 | A1 | | 12/2011 | Parish et al. |
| 2012/0000207 | A1 | | 1/2012 | Parish et al. |
| 2012/0017371 | A1 | * | 1/2012 | Pollard ................. A47G 9/0215 5/423 |
| 2012/0138067 | A1 | | 6/2012 | Rawls-Meehan |
| 2012/0152260 | A1 | | 6/2012 | Flinsenberg et al. |
| 2012/0227182 | A1 | | 9/2012 | Brykalski et al. |
| 2013/0036549 | A1 | | 2/2013 | McKlarney |
| 2013/0097776 | A1 | | 4/2013 | Brykalski et al. |
| 2013/0131464 | A1 | | 5/2013 | Westbrook et al. |
| 2013/0227783 | A1 | | 9/2013 | Brykalski et al. |
| 2013/0234823 | A1 | | 9/2013 | Kahn et al. |
| 2014/0047644 | A1 | | 2/2014 | Mossbeck |
| 2014/0137330 | A1 | * | 5/2014 | Lisi ...................... A47C 21/044 5/694 |
| 2014/0201910 | A1 | | 7/2014 | Rand |
| 2014/0207292 | A1 | | 7/2014 | Ramagem et al. |
| 2014/0222174 | A1 | | 8/2014 | Teller et al. |
| 2014/0259419 | A1 | | 9/2014 | Stusynski et al. |
| 2014/0276227 | A1 | | 9/2014 | Perez |
| 2014/0323799 | A1 | | 10/2014 | Van Driel et al. |
| 2015/0025327 | A1 | | 1/2015 | Young et al. |
| 2015/0136146 | A1 | | 5/2015 | Hood et al. |
| 2015/0157519 | A1 | | 6/2015 | Stusynski et al. |
| 2015/0352313 | A1 | | 12/2015 | Franceschetti et al. |
| 2015/0355605 | A1 | | 12/2015 | Franceschetti et al. |
| 2016/0007914 | A1 | | 1/2016 | Xu et al. |
| 2016/0015315 | A1 | | 1/2016 | Auphan et al. |
| 2016/0045035 | A1 | | 2/2016 | Van Erlach |
| 2016/0073788 | A1 | | 3/2016 | Franceschetti et al. |
| 2016/0073950 | A1 | | 3/2016 | Franceschetti et al. |
| 2016/0128488 | A1 | | 5/2016 | Franceschetti et al. |
| 2016/0136383 | A1 | | 5/2016 | Franceschetti et al. |
| 2016/0310697 | A1 | | 10/2016 | Franceschetti et al. |
| 2016/0338871 | A1 | | 11/2016 | Nunn et al. |
| 2016/0361515 | A1 | | 12/2016 | Jung et al. |
| 2017/0003666 | A1 | | 1/2017 | Nunn et al. |
| 2017/0027498 | A1 | | 2/2017 | Larson et al. |
| 2017/0028165 | A1 | | 2/2017 | Franceschetti et al. |
| 2017/0135632 | A1 | | 5/2017 | Franceschetti et al. |
| 2017/0135881 | A1 | | 5/2017 | Franceschetti et al. |
| 2017/0135882 | A1 | | 5/2017 | Franceschetti et al. |
| 2017/0135883 | A1 | | 5/2017 | Franceschetti et al. |
| 2017/0164760 | A1 | * | 6/2017 | Hinnant ............... A47C 27/081 |
| 2017/0259028 | A1 | | 9/2017 | Franceschetti et al. |
| 2017/0296773 | A1 | | 10/2017 | Franceschetti et al. |
| 2018/0000255 | A1 | | 1/2018 | Youngblood et al. |
| 2018/0000633 | A1 | | 1/2018 | Coleman et al. |
| 2018/0110960 | A1 | | 4/2018 | Youngblood et al. |
| 2018/0132627 | A1 | | 5/2018 | Van Erlach |
| 2018/0310719 | A1 | | 11/2018 | Wiggermann |
| 2019/0201267 | A1 | | 7/2019 | Demirli et al. |

(56) References Cited

U.S. PATENT DOCUMENTS

| | | |
|---|---|---|
| 2019/0254593 A1 | 8/2019 | Franceschetti et al. |
| 2019/0269878 A1 | 9/2019 | Franceschetti et al. |
| 2019/0269883 A1 | 9/2019 | Jung et al. |
| 2019/0321581 A1 | 10/2019 | Franceschetti et al. |
| 2020/0046134 A1 | 2/2020 | Youngblood et al. |
| 2020/0077942 A1 | 3/2020 | Youngblood et al. |
| 2020/0390998 A1 | 12/2020 | Franceschetti et al. |
| 2020/0397379 A1 | 12/2020 | Franceschetti et al. |
| 2020/0405998 A1 | 12/2020 | Franceschetti et al. |
| 2021/0100378 A1 | 4/2021 | Youngblood et al. |
| 2021/0219736 A1 | 7/2021 | Youngblood et al. |
| 2021/0219737 A1 | 7/2021 | Youngblood et al. |
| 2021/0235880 A1 | 8/2021 | Youngblood et al. |
| 2021/0267379 A1 | 9/2021 | Youngblood et al. |
| 2021/0268226 A1 | 9/2021 | Youngblood et al. |
| 2021/0315389 A1 | 10/2021 | Franceschetti et al. |

\* cited by examiner

SMOOCH N' SNORE [TM]: DEVICES TO CREATE A PLURALITY OF ADJUSTABLE ACOUSTIC AND/OR THERMAL ZONES IN A BED

CROSS-REFERENCE TO RELATED APPLICATIONS

This application is a continuation-in-part of U.S. patent application Ser. No. 16/208,665 filed on 2018 Dec. 4. U.S. patent application Ser. No. 16/208,665 was a continuation-in-part of U.S. patent application Ser. No. 14/703,916 filed on 2015 May 5 which issued as U.S. Pat. No. 10,179,064 on 2019 Jan. 15. U.S. patent application Ser. No. 14/703,916 claimed the priority benefit of U.S. Provisional Patent Application 61/991,172 filed on 2014 May 9. The entire contents of these related applications are incorporated herein by reference.

FEDERALLY SPONSORED RESEARCH

Not Applicable

SEQUENCE LISTING OR PROGRAM

Not Applicable

BACKGROUND-FIELD OF INVENTION

This invention relates to bedding that addresses sleep-related acoustic and thermal issues.

INTRODUCTION

Good sleep is vital for good health. However, many people do not get good sleep due to interruptions from bed partner snoring, different sleep temperature preferences than a bed partner, and/or temporary body temperature variation due to hot flashes. In recent years there have been advances in smart beds and sleep accessories, including temperature-controlled mattresses which are linked to bedding sensors or wearable sensors, which seek to address these issues.

However, these sleep issues have not yet been fully solved by the prior art due to significant design challenges. With respect to snoring, there are challenges in how to design a bed-related structure or device which acoustically insulates a person from a bed partner who snores during sleep, without also limiting interaction with that bed partner before sleep. Sadly, the state-of-the-art solution is sometimes sleeping on the couch. With respect to hot flashes, there are challenges in how to design a bed-related structure or device which provides rapid and temporary cooling for a selected portion of a bed, ideally linked to a wearable device which predicts a hot flash. Sadly, the state-of-the-art solution is sometimes repeatedly tossing covers off and on again. The invention disclosed herein addresses acoustic and thermal sleep issues such as snoring and hot flashes by creating two or more different adjustable acoustic and/or thermal zones in a bed.

REVIEW OF THE RELEVANT ART

U.S. patent applications 20180000255 (Youngblood et al., Jan. 4, 2018, "Article Comprising a Temperature-Conditioned Surface, Thermoelectric Control Unit, and Method for Temperature-Conditioning the Surface of an Article"), 20200046134 (Youngblood et al., Feb. 13, 2020, "Article Comprising a Temperature-Conditioned Surface, Thermoelectric Control Unit, and Method for Temperature-Conditioning the Surface of an Article"), and 20210267379 (Youngblood et al., Sep. 2, 2021, "Article Comprising a Temperature-Conditioned Surface, Thermoelectric Control Unit, and Method for Temperature-Conditioning the Surface of an Article") as well as U.S. Pat. No. 10,986,933 (Youngblood et al., Apr. 27, 2021, "Article Comprising a Temperature-Conditioned Surface, Thermoelectric Control Unit, and Method for Temperature-Conditioning the Surface of an Article") and U.S. Pat. No. 10,133,338 (Youngblood et al., May 25, 2021, "Article Comprising a Temperature-Conditioned Surface, Thermoelectric Control Unit, and Method for Temperature-Conditioning the Surface of an Article") disclose systems, methods, and articles for temperature conditioning a surface.

U.S. patent applications 20180110960 (Youngblood et al., Apr. 26, 2018, "Stress Reduction and Sleep Promotion System"), 20200077942 (Youngblood et al., Mar. 12, 2020, "Stress Reduction and Sleep Promotion System"), 20210219736 (Youngblood et al., Jul. 22, 2021, "System for Heat Exchange with a Circulating Fluid"), 20210219737 (Youngblood et al., Jul. 22, 2021, "Article and System for Heating or Cooling a Surface"), and 20210268226 (Youngblood et al., Sep. 2, 2021, "Stress Reduction and Sleep Promotion System"), as well as U.S. Pat. No. 11,013,883 (Youngblood et al., May 23, 2021, "Stress Reduction and Sleep Promotion System") disclose systems, methods, and articles for stress reduction and sleep promotion, including modification of bed temperature.

U.S. patent application 20210235880 (Youngblood et al., Aug. 5, 2021, "Article Comprising a Temperature-Conditioned Surface, Thermoelectric Control Unit, and Method for Temperature-Conditioning the Surface of an Article") and U.S. Pat. No. 10,278,511 (Youngblood et al., May 7, 2019, "Article Comprising a Temperature-Conditioned Surface, Thermoelectric Control Unit, and Method for Temperature-Conditioning the Surface of an Article") and U.S. Pat. No. 11,013,339 (Youngblood et al., May 25, 2021, "Article Comprising a Temperature-Conditioned Surface, Thermoelectric Control Unit, and Method for Temperature-Conditioning the Surface of an Article") disclose a thermoelectric control unit for regulating liquid temperature in a hydraulic circuit.

U.S. Pat. No. 10,986,934 (Youngblood et al., Apr. 27, 2021, "Multi-Zone Temperature Modulation System for Bed or Blanket") and U.S. Pat. No. 11,147,389 (Youngblood et al., Oct. 19, 2021, "Multi-Zone Temperature Modulation System for Bed or Blanket") disclose a temperature modulation system for a bed, blanket, or other furniture which includes a fluid for moderating temperature change, a number of conduit circuits for directing the fluid through respective zones, a control unit including a thermoelectric device for modulating temperature of the fluid, and a pump. U.S. patent application 20210100378 (Youngblood et al., Apr. 8, 2021, "Weighted Blanket with Thermally Regulated Fluid") discloses a weighted article for assisting sleep, wherein the weighted article includes heating and cooling means.

U.S. patent applications 20150352313 (Franceschetti et al., Dec. 10, 2015, "Methods and Systems for Gathering Human Biological Signals and Controlling a Bed Device"), 20150355605 (Franceschetti et al., Dec. 10, 2015, "Methods and Systems for Gathering and Analyzing Human Biological Signals"), 20170259028 (Franceschetti et al., Sep. 14, 2017, "Methods and Systems for Gathering and Analyzing Human Biological Signals"), 20190269878 (Franceschetti et al., Sep. 5, 2019, "Methods and Systems for Gathering and Analyzing Human Biological Signals"), and 20190321581 (Franceschetti et al., Oct. 24, 2019, "Methods and Systems for Gathering and Analyzing Human Biological Signals"), as well as U.S. Pat. No. 9,186,479 (Franceschetti et al., Nov. 17, 2015, "Methods and Systems for Gathering Human Biological Signals and Controlling a Bed Device"), U.S. Pat. No. 9,981,107 (Franceschetti et al., May 29, 2018, "Methods and Systems for Gathering and Analyzing Human Biological Signals"), and U.S. Pat. No. 10,792,461 (Franceschetti et al., Oct. 6, 2020, "Methods and Systems for Gathering and Analyzing Human Biological Signals") disclose using sensors to measure biometric parameters such as body temperature and heart rate and using this information to adjust the temperature of a bed and/or determine when to wake a person.

U.S. patent applications 20160073950 (Franceschetti et al., Mar. 17, 2016, "Vibrating Alarm System and Operating Methods"), 20160136383 (Franceschetti et al., May 19, 2016, "Vibrating Pillow Strip and Operating Methods"), and 20170296773 (Franceschetti et al., Oct. 19, 2017, "Vibrating Pillow Strip and Operating Methods"), as well as U.S. Pat. No. 9,586,021 (Franceschetti et al., Mar. 7, 2017, "Vibrating Pillow Strip and Operating Methods") disclose methods and systems for: gathering human biological signals, such as heart rate, respiration rate, or temperature; analyzing the gathered human biological signals; and controlling a vibrating pillow strip based on the analysis.

U.S. patent applications 20160128488 (Franceschetti et al., May 12, 2016, "Apparatus and Methods for Heating or Cooling a Bed Based on Human Biological Signals"), 20160310697 (Franceschetti et al., Oct. 27, 2016, "Bed Device System and Methods"), 20170028165 (Franceschetti et al., Feb. 2, 2017, "Bed Device System and Methods"), and 20200390998 (Franceschetti et al., Dec. 17, 2020, "Apparatus and Methods for Heating or Cooling a Bed Based on Human Biological Signals"), as well as U.S. Pat. No. 9,694,156 (Franceschetti et al., Jul. 4, 2017, "Bed Device System and Methods") disclose methods and systems for an adjustable bed device which is heated or cooled based on biological signals from multiple users. U.S. patent applications 20170135632 (Franceschetti et al., May 18, 2017, "Detecting Sleeping Disorders") and 20190254593 (Franceschetti et al., Aug. 22, 2019, "Detecting Sleeping Disorders"), as well as U.S. Pat. No. 10,105,092 (Franceschetti et al., Oct. 23, 2018, "Detecting Sleeping Disorders") disclose automatic adjustment of a bed in response to snoring or sleep apnea.

U.S. patent applications 20170135881 (Franceschetti et al., May 18, 2017, "Adjustable Bedframe and Operating Methods"), 20170135882 (Franceschetti et al., May 18, 2017, "Adjustable Bedframe and Operating Methods for Health Monitoring"), and 20170135883 (Franceschetti et al., May 18, 2017, "Adjustable Bedframe and Operating Methods"), as well as U.S. Pat. No. 10,154,932 (Franceschetti et al., Dec. 18, 2018, "Adjustable Bedframe and Operating Methods for Health Monitoring") disclose adjustment of a bed frame based on biological signals from multiple users. U.S. patent application 20160073788 (Franceschetti et al., Mar. 17, 2016, "Sensor Strip for Gathering Human Biological Signals and Controlling a Bed Device") discloses methods and systems for an adjustable bed device which is heated or cooled based on biological signals from multiple users.

U.S. patent application 20200405998 (Franceschetti et al., Dec. 31, 2020, "Sleep Pod") discloses sleep pods which provide a personalized sleeping experience based on an analysis of biological signals, environmental characteristics, occupant history, and other factors. U.S. patent application 20200397379 (Franceschetti et al., Dec. 24, 2020, "Systems and Methods for Detecting a Biological Signal of a User of an Article of Furniture") discloses a flexible sensor device on furniture which detects one or more biological signals of a user of the furniture. U.S. patent application 20210315389 (Franceschetti et al., Oct. 14, 2021, "Systems and Methods for Regulating a Temperature of an Article of Furniture") discloses a system that adjusts a mattress position in response to a biological signal associated with a user.

U.S. patent applications 20100011502 (Brykalski et al., Jan. 21, 2010, "Climate Controlled Bed Assembly"), 20120227182 (Brykalski et al., Sep. 13, 2012, "Climate Controlled Bed Assembly"), and 20130227783 (Brykalski et al., Sep. 5, 2013, "Environmentally Conditioned Bed Assembly"), as well as U.S. Pat. No. 8,418,286 (Brykalski et al., Apr. 16, 2013, "Climate Controlled Bed Assembly") and U.S. Pat. No. 8,181,290 (Brykalski et al., May 22, 2012, "Climate Controlled Bed Assembly") disclose a climate controlled bed includes an upper portion comprising a core with a top core surface and a bottom core surface. U.S. Pat. No. 9,125,497 (Brykalski et al., Sep. 8, 2015, "Climate Controlled Bed Assembly with Intermediate Layer") and U.S. Pat. No. 9,974,394 (Brykalski et al., May 22, 2018, "Climate Controlled Bed Assembly with Intermediate Layer") disclose a climate controlled bed with an upper portion or mattress having at least one fluid distribution member in fluid communication with an internal passageway.

U.S. Pat. No. 8,332,975 (Brykalski et al., Dec. 18, 2012, "Climate-Controlled Topper Member for Medical Beds") discloses a conditioner mat with an upper layer having openings, a lower layer being fluid impermeable, an interior chamber defined by the upper layer and the lower layer, and a spacer material within the interior chamber. U.S. patent application 20130097776 (Brykalski et al., Apr. 25, 2013, "Thermally Conditioned Bed Assembly") and U.S. Pat. No. 9,603,459 (Brykalski et al., Mar. 28, 2017, "Thermally Conditioned Bed Assembly") disclose a bed with a flow conditioning member in a recessed area of a cushion and a fluid temperature regulation system.

U.S. patent 60/065,24 (Park, Dec. 28, 1999, "Temperature Controller for Bedding") discloses a temperature controller for bedding which can always provide a comfortable sleeping environment by maintaining bedding at a temperature suitable for the human body during sleeping by supplying cold or warm heat transfer medium to the inside of bedding. U.S. patent application 20140276227 (Perez, Sep. 18, 2014, "Sleep Management Implementing a Wearable Data-Capable Device for Snoring-Related Conditions and Other Sleep Disturbances") discloses a wearable device which vibrates to reduce snoring. U.S. patent application 20110115635 (Petrovski et al., May 19, 2011, "Control Schemes and Features for Climate-Controlled Beds") and U.S. Pat. No. 8,893,329 (Petrovski et al., Nov. 24, 2014, "Control Schemes and Features for Climate-Controlled Beds") disclose a climate-conditioned bed with an upper portion having at least a first climate zone and at least one fluid module associated with such a first climate zone.

U.S. patent application 20070193278 (Polacek et al., aug. 23, 2007, "Cooling Device and Method") discloses a device for providing cooling to a body in response to a measured change in temperature of the body's skin surface. U.S. patent application 20140207292 (Ramagem et al., Jul. 24, 2014, "Method and System to Control Thermostat Using Biofeedback") discloses methods and systems for receiving physiological data of occupants of a building and using the information to control or regulate a controllable setpoint of a climate-control system for the building. U.S. patent application 20140201910 (Rand, Jul. 24, 2014, "Tunnel Generating Bed Cooling System") discloses a skin surface cooling system used in bed during sleep which directs forced room air to an area above a flat mattress and under a top bed sheet, creating a tunnel of cool, moving air. U.S. patent application 20120138067 (Rawls-Meehan, Jun. 7, 2012, "System and Method for Mitigating Snoring in an Adjustable Bed") discloses a bed which moves to shift a person to an anti-snoring position when the person snores.

U.S. patent application 20090287063 (Freedman et al., Nov. 19, 2009, "Hygrometric Determination of Hot Flashes") discloses a method of measuring hot flashes based on monitoring skin moisture. U.S. Pat. No. 7,640,764 (Gammons et al., Jan. 5, 2010, "Portable Coolant System") and U.S. patent application 20080060374 (Gammons et al., Mar. 13, 2008, "Portable Coolant System") disclose a portable cooling system with ice. U.S. patent application 20100204764 (Garetz, Aug. 12, 2010, "Method for Treating Hot Flashes Associated with Menopause During Sleep") discloses a method for detecting a hot flash using a skin temperature or humidity sensor and circulating cooling fluid through a vest. U.S. Pat. No. 8,755,879 (Hang et al., Ju. 17, 2014, "Sleep Tracking and Waking Optimization System and Method Therefor") discloses EEG and pressure sensors which need not be attached to a person's head. U.S. Pat. No. 9,888,782 (Jannke, Feb. 13, 2018, "Temperature Controlled Mattress System") discloses a mattress assembly with at least one channel which receives temperature conditioned air flow.

U.S. patent application 20110295083 (Doelling et al., Dec. 1 2011, "Devices, Systems, and Methods for Monitoring, Analyzing, and/or Adjusting Sleep Conditions") discloses therapeutic and diagnostic systems and methods to help an individual with a sleep disordered breathing condition. U.S. patent application 20120152260 (Flinsenberg et al., Jun. 21, 2012, "Snoring Reduction Apparatus") discloses an apparatus for shifting a person to a different sleep position when they snore.

U.S. patent application 20130036549 (McKlarney, Feb. 14, 2013, "System for Cooling a Body Useful for Reducing the Effect of Hot Flashes") and U.S. Pat. No. 8,887,328 (McKlarney, Nov. 18, 2014, "System for Cooling a Body Useful for Reducing the Effect of Hot Flashes") disclose systems, methods, and devices for automatically detecting an imminent a hot flash and addressing related symptoms via cooling. U.S. Pat. No. 10,051,973 (Morgan et al., aug. 21, 2018, "Air Conditioned Mattresses") discloses an air conditioned mattress with at least one encasement configured to receive a conditioned flow of air. U.S. patent application 20080155750 (Mossbeck, Jul. 3, 2008, "Anti-Snore Bedding Having Adjustable Portions") discloses a bed whose configuration changes when a person snores. U.S. patent application 20140047644 (Mossbeck, Feb. 20, 2014, "Anti-Snore Bed Having Inflatable Members") discloses bedding with inflatable members which responds to snoring.

U.S. patent application 20140222174 (Teller et al., Aug. 7, 2014, "Wearable Apparatus to Detect and Monitor Sleep and Other Activities") discloses methods and apparatuses for measuring a state parameter of an individual using signals based on one or more sensors. U.S. patent application 20140323799 (Van Driel et al., Oct. 30, 2014, "System and a Method for Improving a Person's Sleep") discloses a system and a method for improving a person's sleep with a bedding layer comprising a plurality of individually controllable thermally adjustable zones and a plurality of temperature sensors. U.S. Pat. No. 9,877,593 (Van Erlach, Jan. 30, 2018, "Smart Surface for Sleep Optimization"), application 20160045035 (Van Erlach, Feb. 18, 2016, "Smart Surface for Sleep Optimization"), and application 20180132627 (Van Erlach, May 17, 2018, "Smart Surface for Sleep Optimization") disclose the delivery of therapy to a body based on information from two sets of sensors in contact with the body. U.S. patent applications 20130131464 (Westbrook et al., May 23, 2013, "System for the Assessment of Sleep Quality in Adults and Children") and 20100240982 (Westbrook et al., Sep. 23, 2010, "System for the Assessment of Sleep Quality in Adults and Children") disclose systems and methods for assessment of sleep quality which include a sensor strip and a nasal mask to obtain physiological signals.

U.S. patent application 20160015315 (Auphan et al., Jan. 21, 2016, "System and Method to Monitor and Assist Individual's Sleep") discloses a sleep assist system with a loudspeaker, light source, temperature sensor, and control unit. U.S. patent application 20060162074 (Bader, Jul. 27, 2006, "Device and Method for Controlling Physical Properties of a Bed") discloses a bed whose properties are adjusted based on the state of a person on the bed. U.S. Pat. No. 8,932,199 (Berka et al., Jan. 13, 2015, "Systems and Methods for Optimization of Sleep and Post-Sleep Performance") discloses a sleep mask with electromagnetic sensors which awakens a sleeping person at an appropriate sleep stage. U.S. Pat. No. 8,628,462 (Berka et al., Jan. 14, 2014, "Systems and Methods for Optimization of Sleep and Post-Sleep Performance") discloses systems for monitoring a person's sleep and generating sensory stimuli.

U.S. patent application 20160338871 (Nunn et al., Nov. 24, 2016, "Inflatable Air Mattress Snoring Detection and Response") and U.S. Pat. No. 9,370,457 (Nunn et al., Jun. 21, 2016, "Inflatable Air Mattress Snoring Detection and Response") disclose a bed whose firmness is changed in response to snoring. U.S. patent application 20170003666 (Nunn et al., Jan. 5, 2017, "Automation for Improved Sleep Quality") discloses using historical sleep metrics and sensor data to create a corrective plan that specifies a change to an environmental control system. U.S. patent applications 20110289684 (Parish et al., Dec. 1, 2011, "System and Method for Thermoelectric Personal Comfort Controlled Bedding"), 20110314837 (Parish et al., Dec. 29, 2011, "System and Method for Thermoelectric Personal Comfort Controlled Bedding"), and 20120000207 (Parish et al., Jan. 5, 2012, "System and Method for Thermoelectric Personal Comfort Controlled Bedding") disclose a system and method for controlling ventilation in a bed (mattress) including a user-controlled air conditioning control system.

U.S. patent applications 20160361515 (Jung et al., Dec. 15, 2016, "Method and Apparatus for Controlling Temperature Adjustment Device") and 20190269883 (Jung et al., Sep. 5, 2019, "Method and Apparatus for Controlling Temperature Adjustment Device") disclose a method and apparatus for controlling a temperature adjustment device using a sensing device. U.S. patent application 20130234823 (Kahn et al., Sep. 12, 2013, "Method and Apparatus to Provide an Improved Sleep Experience") discloses using sound to guide person to a desired sleep state. U.S. patent application 20170027498 (Larson et al., Feb. 2, 2017, "Devices, Systems, and Methods for Preventing, Detecting, and Treating Pressure-Induced Ischemia, Pressure Ulcers, and Other Conditions") discloses bed sensors for monitoring biometric parameters of a patient in bed and suggesting moving the patient when appropriate. U.S. Pat. No. 8,402,579 (Marquette et al., Mar. 26, 2013, "Climate Controlled Beds and Methods of Operating the Same") discloses a climate controlled seat, bed or other assembly with a blower and two or more thermoelectric devices or other conditioning fluid modules.

U.S. Pat. No. 9,907,929 (Rink et al., Mar. 6, 2018, "Method and Device for Monitoring and Treating Sleep Disorders and Sleep-Related Conditions") discloses methods and devices for monitoring a sleeping person and partially awakening the person during a sleep terror. U.S. Pat. No. 11,103,081 (Sherman et al., aug. 31, 2021, "Climate Controlled Mattress System") discloses a climate control system with a heating mechanism disposed between one or more foam layers of structure and a separate cooling mechanism disposed in the foam layers. U.S. Pat. No. 8,984,687 (Stusynski et al., Mar. 24, 2015, "Partner Snore Feature for Adjustable Bed Foundation") and U.S. Pat. No. 10,058,467 (Stusynski et al., Aug. 28, 2018, "Partner Snore Feature for Adjustable Bed Foundation"), as well as U.S. patent applications 20140259419 (Stusynski et al., Sep. 18, 2014, "Partner Snore Feature for Adjustable Bed Foundation") and 20150157519 (Stusynski et al., Jun. 11, 2015, "Partner Snore Feature for Adjustable Bed Foundation") disclose a bed with two sections, wherein a person on a first section can control the articulation of a second section.

U.S. Pat. No. 9,955,791 (Chandler et al., May 1, 2018, "Climate Controlled Mattress Assembly and Related Method") discloses mattress assemblies that use air bladders to provide climate control. U.S. patent application 20180000633 (Coleman et al., Jan. 4, 2018, "Microclimate Management System with Wireless Sensors") discloses a method for monitoring a patient on a support device including: receiving a temperature reading from a wireless sensor coupled to the patient; comparing the temperature reading to air flowing through an airflow system associated with the patient support device; and modifying the air flowing through the airflow system. U.S. patent application 20100099954 (Dickinson et al., Apr. 22, 2010, "Data-Driven Sleep Coaching System") discloses a system for monitoring a person's EEG to improve their sleep.

U.S. patent application 20180310719 (Wiggermann, Nov. 1, 2018, "Adaptable Mattress") discloses a mattress with a phase changeable component and a thermal management system which controls the temperature of the phase changeable component to change the firmness of the mattress. U.S. Pat. No. 8,836,516 (Wolfe et al., Sep. 16, 2014, "Snoring Treatment") discloses devices for detecting and reducing snoring including microphones and motion sensors. U.S. Pat. No. 5,555,579 (Wu, Sep. 17, 1996, "Mattress Assembly with Semiconductor Thermo-Control") discloses a mattress with a network of grooves covered within a soft covering layer, a control box, and a water pipes within the network of grooves and connected to hot and cold water reservoirs inside the control box. U.S. patent application 20160007914 (Xu et al., Jan. 14, 2016, "Sleep Control Device") discloses systems and methods for stimulating a person when they snore to cause them to shift their sleep position.

SUMMARY OF THIS INVENTION

This invention is a device which creates adjustable acoustic and/or thermal zones in a bed to address acoustic and thermal sleep issues such as snoring and hot flashes. In an example, a flexible movable partition can longitudinally span a bed from an arch at the head of the bed to an arch at the foot of the bed. The partition is moved from a non-deployed first configuration along the side of the bed to a deployed second configuration above the bed which separates the bed into two acoustic zones. This partition can be moved by a person on the bed via a remote control unit or a cell phone application. Alternatively, this partition can move automatically when a sensor detects snoring. This wonderful invention can enable a couple to replace the "sleep on the sofa" solution with the "smooch and snore" solution.

In an example, a device which creates adjustable thermal zones in a bed can include a first set of flexible longitudinal air tubes which are inserted into a space between two layers of bedding to deliver cooled or heated air to that space and a second set of flexible longitudinal air tubes which draw air out from that space. In another example, a device which creates adjustable thermal zones in a bed can include a grid of fluid flow pathways and fluid flow valves on that grid. A data processing unit controls the valves, which directs cooled or heated air to different fluid flow pathways in the grid, thereby enabling the formation of different size and different shape thermal zones on the bed. This invention can enable a person with hot flashes to sleep through them rather than awakening and tossing off covers repeatedly during the night.

BRIEF INTRODUCTION TO THE FIGURES

DETAILED DESCRIPTION OF THE FIGURES

Figure 1:
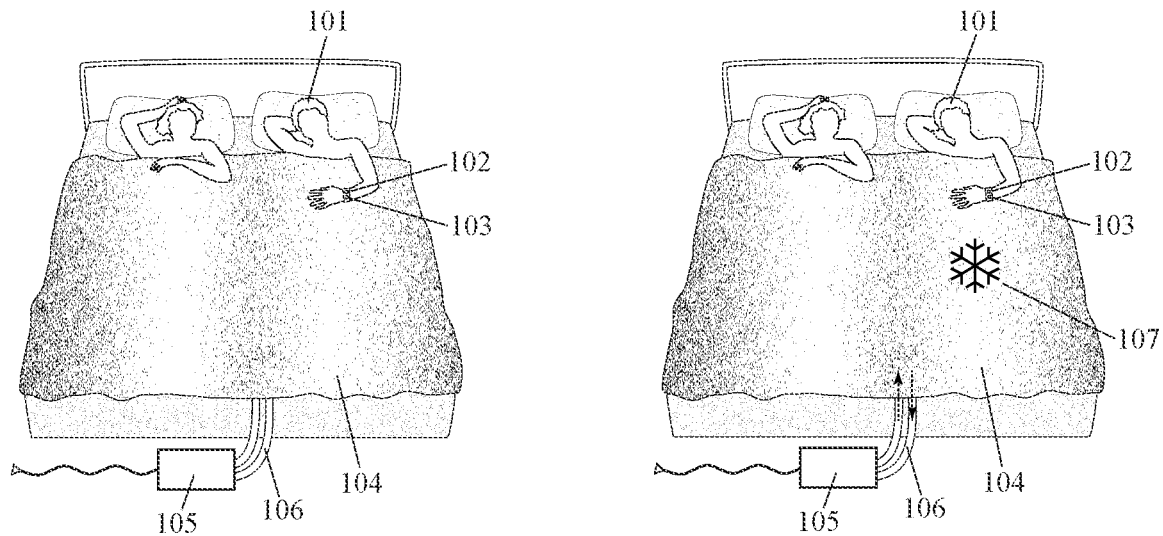
FIG. 1 shows a system for modifying a person's sleep environment which changes bed temperature based on blood pressure.
Figure 126:
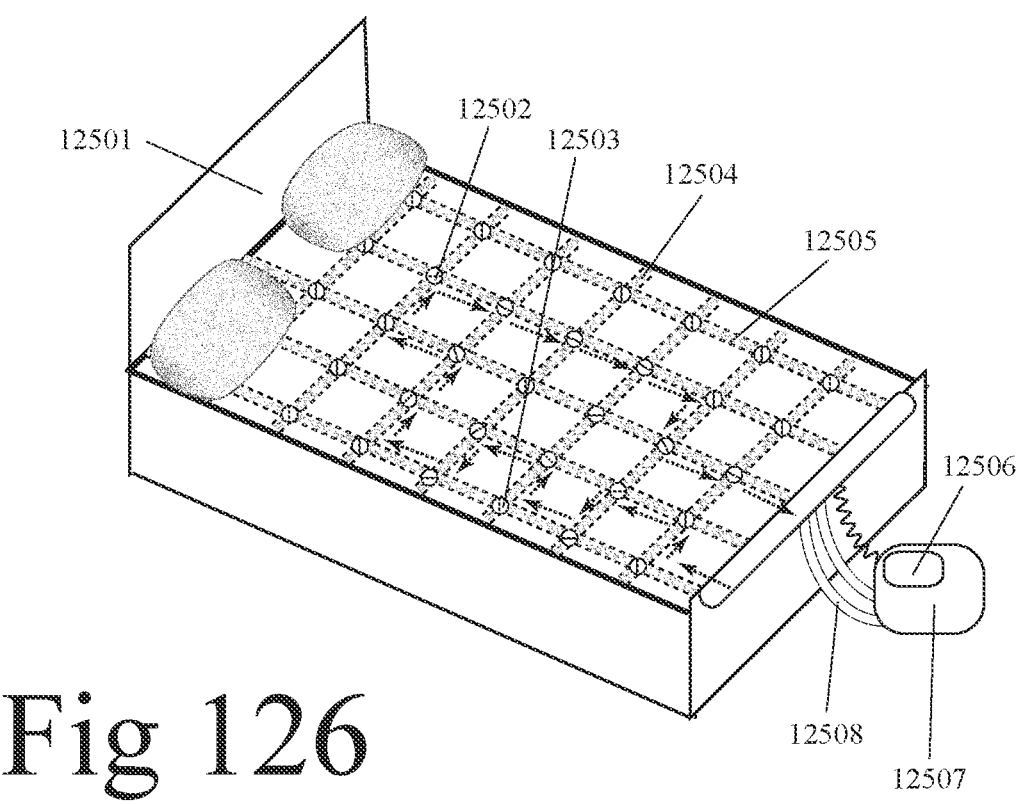
Figure 127:
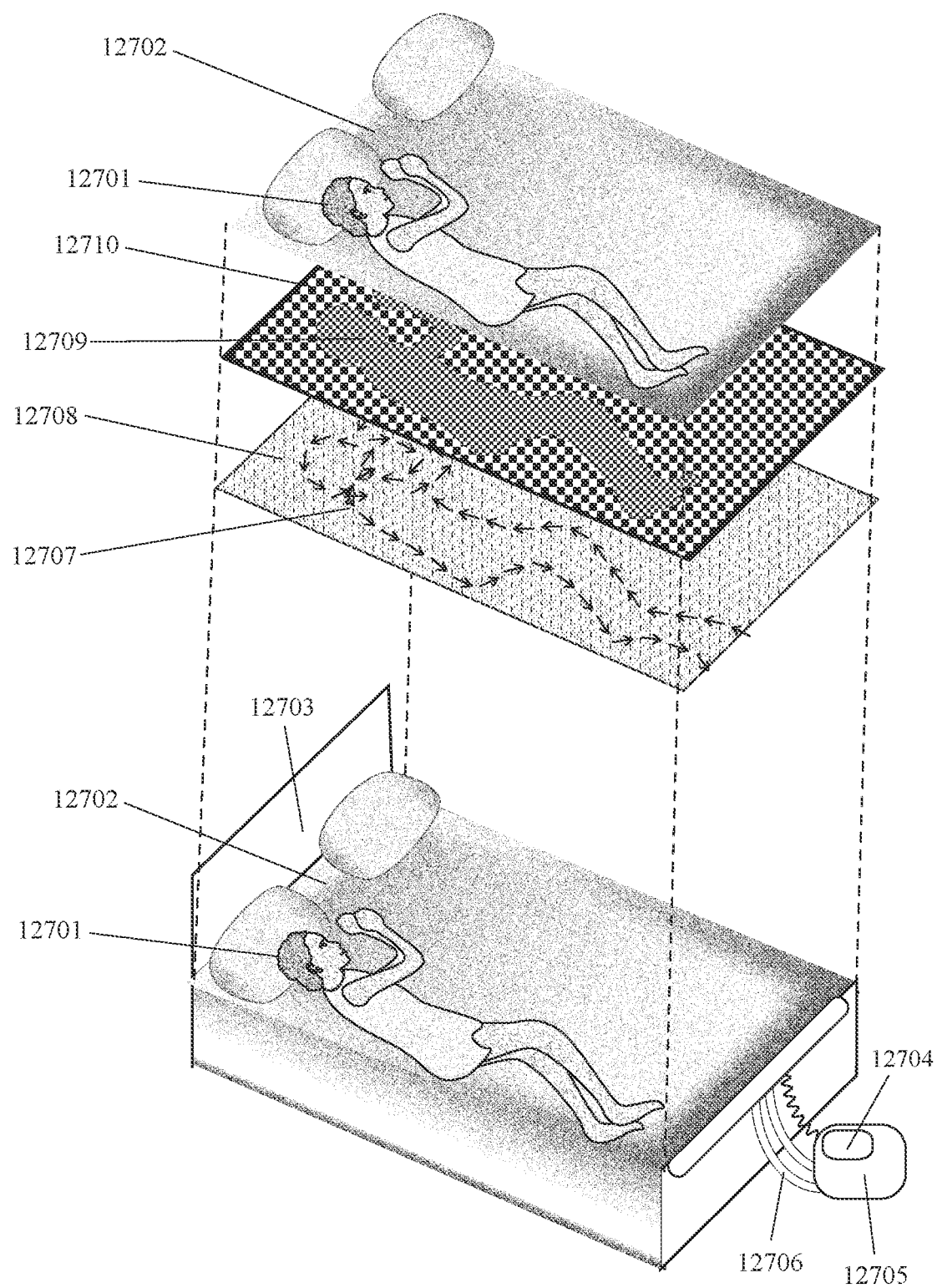
FIG. 127 shows a multi-layer pressure-sensitive device that selectively directs a flow of cooling or heating fluid through an area directly under a sleeping person.

FIGS. 1 through 127 show different examples of how this invention can be embodied, but do not limit the generalizability of the claims. FIGS. 113 and 114, 119 and 120, and 125 and 126 are particularly relevant to the claims in this application. Before discussing specific examples in figures, the following section provides an introduction to concepts and component variations which can be applied to subsequent examples, but are not repeated in the narratives accompanying each figure in order avoid narrative redundancy.

In an example, a device can create adjustable acoustic and/or thermal zones in a bed to address acoustic and thermal sleep issues such as snoring and hot flashes. In an example, a flexible movable partition can longitudinally span a bed from an arch at the head of the bed to an arch at the foot of the bed. The partition can be moved from a non-deployed first configuration along the side of the bed to a deployed second configuration above the bed which separates the bed into two acoustic zones. This partition can be moved by a person on the bed via a remote control unit or a cell phone application. Alternatively, this partition can move automatically when a sensor detects snoring.

In an example, a device can create adjustable thermal zones in a bed using a first set of flexible longitudinal air tubes which are inserted into a space between two layers of bedding to deliver cooled or heated air to that space and a second set of flexible longitudinal air tubes which draw air out from that space. In another example, a device which creates adjustable thermal zones in a bed can include a grid of fluid flow pathways and fluid flow valves on that grid. A data processing unit can control the valves, which direct cooled or heated air to different fluid flow pathways in the grid, thereby enabling the formation of different size and different shape thermal zones on the bed.

In an example, a system for modifying a person's sleep environment can comprise: a wearable motion sensor that is configured to be worn by a sleeping person in order to measure the person's body motion or body configuration; and a mattress on which the person sleeps, wherein the firmness of the mattress is automatically changed based on the person's body motion or body configuration. In an example, the firmness of the mattress is automatically increased when the person is restless based on data from the wearable motion sensor. In an example, the firmness of the mattress is automatically increased by inflation of the mattress when the person is restless based on data from the wearable motion sensor. In an example, the firmness of the mattress is automatically increased by an increase in the compressive resistance of springs in the mattress when the person is restless based on data from the wearable motion sensor.

In an example, the firmness of a mattress is automatically decreased when the person is restless based on data from the wearable motion sensor. In an example, the firmness of a mattress is automatically decreased by deflation of the mattress when the person is restless based on data from the wearable motion sensor. In an example, the firmness of a mattress is automatically decreased by a decrease in the compressive resistance of springs in the mattress when the person is restless based on data from the wearable motion sensor.

In an example, a system for modifying a person's sleep environment can comprise: a wearable motion sensor that is configured to be worn by a sleeping person in order to measure the person's body motion or body configuration; and a mattress on which the person sleeps, wherein the shape, motion, slope, tilt, or configuration of the mattress is automatically changed based on the person's body motion or body configuration. In an example, the longitudinal slope or other longitudinal configuration of the mattress is automatically changed based on the person's body motion or body configuration. In an example, the lateral slope or other lateral configuration of the mattress is automatically changed based on the person's body motion or body configuration.

In an example, a system for modifying a person's sleep environment can comprise: a snoring sensor which is configured to be in proximity to a sleeping person; and a mattress on which the person sleeps, wherein the configuration of the mattress is automatically changed when data from the snoring sensor indicates that the person is snoring. In an example, the firmness of the mattress is automatically increased when data from the snoring sensor indicates that the person is snoring. In an example, the firmness of the mattress is automatically increased by inflation of the mattress when data from the snoring sensor indicates that the person is snoring. In an example, the firmness of the mattress is automatically increased by an increase in the compressive resistance of springs in the mattress when data from the snoring sensor indicates that the person is snoring.

In an example, the firmness of a mattress is automatically decreased when data from the snoring sensor indicates that the person is snoring. In an example, the firmness of a mattress is automatically decreased by deflation of a mattress when data from the snoring sensor indicates that the person is snoring. In an example, the firmness of a mattress is automatically decreased by a decrease in the compressive resistance of springs in a mattress when data from the snoring sensor indicates that the person is snoring. In an example, the longitudinal slope or other longitudinal configuration of a mattress is automatically changed when data from the snoring sensor indicates that the person is snoring. In an example, the lateral slope or other lateral configuration of a mattress is automatically changed when data from the snoring sensor indicates that the person is snoring. In an example, a mattress is automatically vibrated or oscillated when data from the snoring sensor indicates that the person is snoring.

In an example, this invention can be embodied in a system, device, and method that uses wearable technology to collect data for automatic modification of a person's sleep environment comprising: a wearable-sensor component that collects data concerning a selected physiological parameter or anatomic function of a person; a sleep-environment-modifying component which changes at least one selected characteristic of the person's sleep environment; and a data-control component which controls the operation of the sleep-environment-modifying component in order to automatically change the person's sleep environment based on data from the wearable-sensor component.

In various examples, the wearable-sensor component of this invention can be selected from the group consisting of: a blood pressure sensor; an ECG sensor or other sensor measuring electromagnetic energy from (or transmitted through) a person's heart; an EEG sensor or other sensor measuring electromagnetic energy from (or transmitted through) a person's brain; a sensor measuring electromagnetic energy from (or transmitted through) a person's wrist, hand, or arm; a sensor measuring electromagnetic energy from (or transmitted through) a person's torso; a sensor measuring electromagnetic energy from (or transmitted through) another portion of a person's body; an electrical conductivity, impedance, or resistance sensor; a skin moisture sensor or body moisture level sensor; a sensor measuring the quantity or spectrum of light absorbed by a person's body; a sensor measuring the quantity or spectrum of light reflected from a person's body; an accelerometer, gyroscope, or other motion sensor; a oxygen saturation sensor; a pulse and/or heart rate sensor; a respiratory or pulmonary function sensor; a microphone or other sound sensor; a snoring sensor; and a thermistor, other skin temperature sensor, or other body temperature sensor. In an example, the wearable-sensor component of this invention can be in kinetic, electromagnetic, optical, fluid, gaseous, and/or chemical communication with a person's body In various examples, the wearable-sensor component of this invention can be incorporated into one or more of the following wearable devices: a wrist band, smart watch, watch phone, smart bracelet, armband, amulet, smart finger ring, electronically-functional finger ring, artificial finger nail or other device worn on the wrist, hand, or arm; an earring, ear bud, ear plug, hearing aid, pair of headphones, or other ear-worn device; electronically-functional pajamas, smart shirt, smart pants, underpants, briefs, undershirt, bra, socks, ankle strap, ankle bracelet, or other smart clothing or garment; a respiratory mask, nasal pillows, or other face-worn device to direct breathable gas into a person's nose and/or mouth; an electronically-functional cap, hat, head band, hair band, or hair clip; a wearable EEG monitor; an electronically-functional skin patch, adhesive patch, flexible bandage, or tattoo; a smart belt, torso strap, knee tube, or elbow tube; a wearable ECG monitor; a smart button, electronically-functional button, pendant, bead, neck chain, necklace, dog tag, or medallion; a dental appliance, dental insert, dental implant, artificial tooth, tongue insert or attachment, and/or upper-palate attachment; and an electronically-functional contact lens, eye mask, glasses, or other electronically-functional eyewear.

In various examples, the wearable-sensor component of this invention can be attached directly to a person's body or can be incorporated into an article of clothing that is worn by the person using one or more mechanisms selected from the group consisting of: adhesive, armband, bangle, belt, bracelet, buckle, button, chain, channel in a garment, clamp, clasp, clip, elastic band, elastic garment, eyewear, gluing, hook and eye, incorporation into a bandage, incorporation into a tattoo, knitting, magnet, melting, necklace, piercing, pin, pocket, pocket in a garment, pouch, ring, sewing, smart watch, snap, one or more strands, strap, suture, tape, tensile member, textile channel, textile fibers, thermal bonding, tubular garment, waist band, weaving, wrist band, yarn, and zipper. In various examples, the wearable-sensor component of this invention can be configured to be worn on, or attached to, a part of a person's body that is selected from the group consisting of: wrist (one or both), hand (one or both), or finger; neck or throat; eyes (directly such as via contact lens or indirectly such as via eyewear); mouth, jaw, lips, tongue, teeth, or upper palate; arm (one or both); waist, abdomen, or torso; nose; ear; head or hair; and ankle or leg.

In an example, the wearable-sensor component of this invention can be a thermal energy sensor. In an example, the wearable-sensor component of this invention can be selected from the group consisting of: thermistor, thermometer, skin temperature sensor, and thermoluminescence sensor. In an example, the wearable-sensor component of this invention can be a motion sensor and/or force sensor. In an example, the wearable-sensor component of this invention can be selected from the group consisting of: accelerometer (single axis, dual-axial, tri-axial, or other multi-axial), other inertial sensor, gyroscope, inclinometer, tilt sensor, strain gauge, goniometer, stretch sensor, elastomeric sensor, resistive bend sensor, potentiometer, kinematic sensor, torque sensor, pressure sensor, force sensor, flow sensor, vibration sensor, and other motion or force sensor.

In an example, the wearable-sensor component of this invention can be an electromagnetic energy sensor. In an example, the wearable-sensor component of this invention can be selected from the group consisting of: voltmeter, conductivity sensor, skin conductance sensor, resistance sensor, variable resistance sensor, piezoelectric sensor, piezoresistive sensor, impedance sensor, skin impedance sensor, variable impedance sensor, piezocapacitive sensor, RF sensor, galvanic skin response (GSR) sensor, Hall-effect sensor, magnetometer, magnetic field sensor, wearable EM brain activity monitor, electroencephalography (EEG) sensor or monitor, electrogastrographic monitor, EOG sensor, electromyography (EMG) sensor, muscle function monitor, action potential sensor, neural impulse monitor, neural monitor, neurosensor, and other electromagnetic energy sensor. In an example, the wearable-sensor component of this invention can be a cardiovascular monitor. In an example, the wearable-sensor component of this invention can be selected from the group consisting of: blood pressure monitor, heart rate monitor, pulse rate monitor, pulse sensor, blood flow monitor, cardiac monitor, electrocardiogram (ECG) sensor or monitor, or other heart monitor.

In an example, the wearable-sensor component of this invention can be a light energy sensor and/or spectroscopy sensor. In an example, the wearable-sensor component of this invention can be selected from the group consisting of: optical sensor, optoelectronic sensor, photoelectric sensor, light intensity sensor, light-spectrum-analyzing sensor, spectral analysis sensor, spectrometry sensor, spectrophotometer sensor, spectroscopic sensor, spectroscopy sensor, mass spectrometry sensor, Raman spectroscopy sensor, white light spectroscopy sensor, near-infrared spectroscopy sensor, infrared spectroscopy sensor, ultraviolet spectroscopy sensor, backscattering spectrometry sensor, ion mobility spectroscopic sensor, infrared light sensor, laser sensor, ultraviolet light sensor, fluorescence sensor, chemiluminescence sensor, color sensor, chromatography sensor, analytical chromatography sensor, gas chromatography sensor, and variable-translucence sensor. In an example, light energy can be analyzed with respect to one or more parameters selected from the group consisting of: intensity, amplitude, frequency, range, phase, and waveform. In an example, an optical sensor can emit and/or detect white light, infrared light, or ultraviolet light. In an example, the wearable-sensor component of this invention can be an imaging sensor. In an example, the wearable-sensor component of this invention can be selected from the group consisting of: still camera, video camera, and other imaging sensor.

In an example, the wearable-sensor component of this invention can be a moisture sensor or humidity sensor. In an example, the wearable-sensor component of this invention can be a chemical sensor or biological sensor. In an example, the wearable-sensor component of this invention can be selected from the group consisting of: pH level sensor, photochemical sensor, biochemical sensor, electrochemical sensor, chemiresistor, blood oximetry sensor, tissue oximetry sensor, chemoreceptor sensor, electroosmotic sensor, electrophoresis sensor, electroporation sensor, glucose monitor, antibody-based receptor, artificial olfactory sensor, amino acid sensor, cholesterol sensor, fat sensor, gas sensor, microbial sensor, nucleic acid-based sensor, osmolality sensor, sodium sensor, and other biochemical sensor. In an example, the wearable-sensor component of this invention can be selected from the group consisting of: Micro-Electro-Mechanical System (MEMS) sensor, microcantilever sensor, laboratory-on-a-chip, nanoparticle sensor, and nanotube sensor.

In an example, the wearable-sensor component of this invention can be a pulmonary function and/or respiratory function sensor. In an example, the wearable-sensor component of this invention can be selected from the group consisting of: tidal volume sensor, oxygen consumption monitor, spirometry monitor, pulmonary function monitor, respiration monitor, breathing monitor, obstructive sleep apnea monitor, and oxygen saturation monitor. In an example, the wearable-sensor component of this invention can be a sonic energy sensor. In an example, the wearable-sensor component of this invention can be selected from the group consisting of: microphone, acoustic sensor, and ultrasonic sensor. In an example, this invention can further comprise a compass and/or GPS sensor.

In an example, the wearable-sensor component of this invention can be incorporated into an electronically-functional textile, fabric, garment, or wearable accessory which comprises one or more of the following: array of electroconductive members woven using a plain weave, rib weave, basket weave, twill weave, satin weave, leno weave, mock leno weave; array of fiber optic members woven using a plain weave, rib weave, basket weave, twill weave, satin weave, leno weave, mock leno weave; array or mesh of electroconductive fibers; bendable fibers, threads, or yarns; bendable layer, trace, or substrate; elastic fibers, threads, or yarns; elastic layer, trace, or substrate; electroconductive fibers, threads, or yarns; electronically-functional bandage; electronically-functional tattoo; integrated array of electroconductive members; integrated array of fiber optic members; integrated array of sound-conducting members; interlaced electricity-conducting fibers, threads, or yarns; interlaced light-conducting fibers, threads, or yarns; interlaced sound-conducting fibers, threads, or yarns; light-emitting fibers, threads, or yarns; nonconductive fibers, threads, or yarns; nonconductive layer, substrate, or material; plaited fibers, threads, or yarns; sinusoidal fibers, threads, or yarns; stretchable fibers, threads, or yarns; stretchable layer, trace, or substrate; textile-based light display matrix; variable-resistance electroconductive fiber, thread, or yarn; variable-translucence fiber, thread, or yarn; water-resistant fibers, threads, or yarns; a layer or coating of metallic nanoparticles; a graphene layer; and water-resistant layer, trace, or substrate.

In an example, the sleep-environment-modifying component of this invention can be selected from the group consisting of: mattress pad, mattress, box spring, sheet, pillow, other bedding surface on which a person lies while they sleep; blanket, sheet, sleeping bag, and/or other bedding layer over a person while they sleep; portable fan, ceiling fan, portable blower, portable heat pump, or central Heating Ventilation and Air-Conditioning (HVAC) system; laminar air flow system; CPAP, other mask to direct breathable gas into a person's nose and/or mouth, nasal pillows, bedside CPAP device, and/or head-worn CPAP device; acoustic partition or barrier on or over a bed; speaker or other sound-emitting component; cellular phone, smart watch, or other mobile communication device; room light, bed light, or other light-emitting device; pajamas or other garment; and room door or window. In an example, this invention can further comprise one or more actuators selected from the group consisting of: brushless DC motor, brush-type DC motor, electric motor, electromagnetic actuator, hydraulic actuator, induction motor, MEMS actuator, piezoelectric actuator, pneumatic actuator, and stepper motor.

In an example, one or more sleep-environment-modifying components can enable separate control of two or more areas in the same bed. In an example, these two or more areas can comprise separately-controllable sleeping environments. In an example, there can be two separately-controllable sleeping environments for two people sleeping in the same bed. In an example, sleeping environments for two people sleeping on different sides of a bed can be separately adjusted. In an example, two people in the same bed can each have a separate wearable sensor which controls the sleep environment on their side of the bed. In an example, one or more modified characteristics of a sleep environment can be selected from the group consisting of: temperature; humidity; airflow direction, volume, or speed; sound cancellation, sound masking, and/or sound type; light level or type; breathable gas source, composition, and/or pressure level; sleeping surface slope, configuration, and/or movement; and degree or form of electronic communication connectivity and/or filtering.

In an example, the data-control component of this invention can further comprise one or more sub-components selected from the group consisting of: data processing sub-component, data communication sub-component, power source, human-to-computer user interface, computer-to-human interface, digital memory, and one or more other types of sensors. In an example, a data processing sub-component can perform one or more functions selected from the group consisting of: convert analog sensor signals to digital signals, filter sensor signals, amplify sensor signals, analyze sensor data, run software programs, store data in memory, and control the operation of a sleep-environment-modifying component.

In an example, a data processing sub-component can analyze data using one or more statistical methods selected from the group consisting of: multivariate linear regression or least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; and time-series analysis.

In an example, a power source can be a battery. In an example, a power source can harvest, transduce, or generate electrical energy from kinetic energy, thermal energy, biochemical energy, ambient light energy, and/or ambient electromagnetic energy. In an example, a data communication sub-component can perform one or more functions selected from the group consisting of: transmit and receive data via Bluetooth, WiFi, Zigbee, or other wireless communication modality; transmit and receive data to and from an electronically-functional mattress, blanket, mattress pad, or other bedding layer; transmit and receive data to and from a home appliance and/or home control system; transmit and receive data to and from a mobile electronic device such as a cellular phone, mobile phone, smart phone, electronic tablet; transmit and receive data to and from a separate wearable device such as a smart watch or electronically-functional eyewear; transmit and receive data to and from the internet; send and receive phone calls and electronic messages; and transmit and receive data to and from an implantable medical device.

In an example, this invention can communicate with one or more other devices selected from the group consisting of: a communication tower or satellite; a CPAP device; a home appliance or control system; a laptop or desktop computer; a smart phone or other mobile communication device; a wearable cardiac monitor; a wearable electromagnetic brain activity monitor; a wearable pulmonary activity monitor; an implantable medical device; an internet server; and another type of wearable device or an array of wearable sensors.

In an example, a human-to-computer interface can further comprise one or more members selected from the group consisting of: button, knob, dial, or keys; display screen; gesture-recognition interface; microphone; physical keypad or keyboard; pressure-sensitive textile array; speech or voice recognition interface; touch screen; virtual keypad or keyboard; electronically-functional textile interface; EMG-recognition interface; and EEG-recognition interface. In an example, a computer-to-human interface can further comprise one or more members selected from the group consisting of: a coherent-light image projector; a display screen; a laser; a myostimulating member; a neurostimulating member; a non-coherent-light image projector; a speaker or other sound-emitting member; a speech or voice recognition interface; a synthesized voice; a vibrating or other tactile sensation creating member; MEMS actuator; an electromagnetic energy emitter; an electronically-functional textile interface; an infrared light emitter; an infrared light projector; and an LED or LED array.

In an example, the data-control component of this invention can operate the sleep-environment-modifying component in order to automatically change a person's sleep environment based on data from the wearable-sensor component. In an example, this environmental modification can help to keep a person's sleep environment within a desired range for a selected environmental parameter or characteristic. In an example, data from the wearable-sensor component can be analyzed in real time to predict likely changes in the person's sleeping environment and to proactively modify the person's sleeping environment in order to keep the environment within a desired range for a selected environmental parameter or characteristic. In an example, if data from a wearable-sensor component indicates a high probability of an ensuing biologically-caused change in the person's body temperature, then a cooling or heating sleep-environment-modifying component can be activated in a proactive manner to provide appropriate cooling or heating in advance of the actual change in body temperature. This can mitigate (or even avoid) biologically-caused swings in body temperature during sleep. In an example, a sleep-environment-modifying component can only be activated when needed (and can be deactivated when not needed) in order to conserve energy and to more-precisely regulate a person's sleep environment.

In an example, the wearable-sensor component, sleep-environment-modifying component, and data-control component of this invention can all be located together within a single housing or device. In an example, two or more of these components can be located in separate housings or devices, but be in communication with each other so as to comprise a system for automatic modification of a person's sleep environment. In an example, a wearable-sensor component and a data-control component can be located together in a wearable device which is in wireless communication with a separate sleep-environment-modifying component (such as a blanket, mattress, pillow, portable fan, ceiling fan, window air conditioner, central HVAC system, audio speaker, bed light, mobile electronic communication device, room door, or room window). In an example, a wearable-sensor component and a sleep-environment-modifying component can be located together in a wearable device which is in wireless communication with a data-control unit (such as mobile electronic communication device or remote internet-connected computer).

FIGS. 1 through 127 are now discussed in detail.

FIG. 1 shows an example of how this invention can be embodied in a system, device, and method using wearable technology to collect data for automatic modification of a person's sleep environment comprising: a wearable-sensor component that is configured to be worn by a person, wherein this sensor component collects data concerning the person's blood pressure; a sleep-environment-modifying component which changes the temperature of a mattress, blanket, or other bedding material near the person's body; and a data-control component which controls the operation of the sleep-environment-modifying component in order to automatically change the person's sleep environment. The left side of FIG. 1 shows this embodiment at a first point in time and the right side of FIG. 1 shows this embodiment at a second point in time, in sequence, in order to show how blood pressure data can be used to automatically modify the person's sleep environment while the person sleeps.

Specifically, the example shown in FIG. 1 comprises: a wrist band (further comprising blood pressure sensor 102) that is configured to be worn by person 101; a sleep-environment-modifying component (further comprising blanket 104, heat exchanger 105, and flow channel 106) which changes the temperature of blanket 104; and a data-control component 103 which controls the operation of the sleep-environment-modifying component in order to automatically change the temperature of the person's sleep environment. In an example, this system only cools or heats the person's sleep environment when needed, based on data from blood pressure sensor 102. This can help to conserve energy and also to better regulate sleeping environment temperature. In an example, changes in blood pressure can predict biologically-induced swings in body temperature and this prediction can be used to proactively change the blanket's temperature so as to mitigate (or completely avoid) temperature swings. In this example, wearable sensor 102 is a blood pressure sensor that is incorporated into a wrist band. In other examples, a blood pressure sensor can be worn elsewhere on the body.

In this example, heat exchanger 105 pumps cooling or heating fluid (or air or other gas) through flow channel 106 which, in turn, circulates through blanket 104. In this example, a selected blood pressure value or pattern triggers cooling of the person's environment, which is represented by snowflake symbol 107. In another example, a blood pressure value or pattern can trigger heating. Data from blood pressure sensor 102 is collected at a first point in time (as shown on the left side of FIG. 1) and triggers cooling at a second point in time (as shown on the right side of FIG. 1). In this example, heat exchanger 105 further comprises a pump and/or compressor and releases heat into the room air. In another example, a heat exchanger can contain a quantity of a pre-cooled substance, such as ice, to avoid increasing the overall temperature of room air. In another example, a heat exchanger can transfer thermal energy from one side of a bed to the other. This can be particularly useful when one person in a bed tends to be too warm and the other person in a bed tends to be too cool.

In this example, data-control component 103 is part of the wrist band. In other examples, data-control component 103 can be co-located with heat exchanger 105, located in a wirelessly-linked mobile electronic device, or located in a remote computer. In various examples, this invention can directly modify the temperature of air and/or other gas in communication with the surface of the person's body, change the temperature of air under a blanket or other bed covering, change the temperature of a mattress or mattress pad, control the operation of an electric blanket, and/or change the inflation or pressure level of a mattress pad. Relevant example and component variations discussed elsewhere in this disclosure or in priority-linked disclosures can also be applied to this example, but are not repeated here to avoid narrative redundancy.

Figure 2:
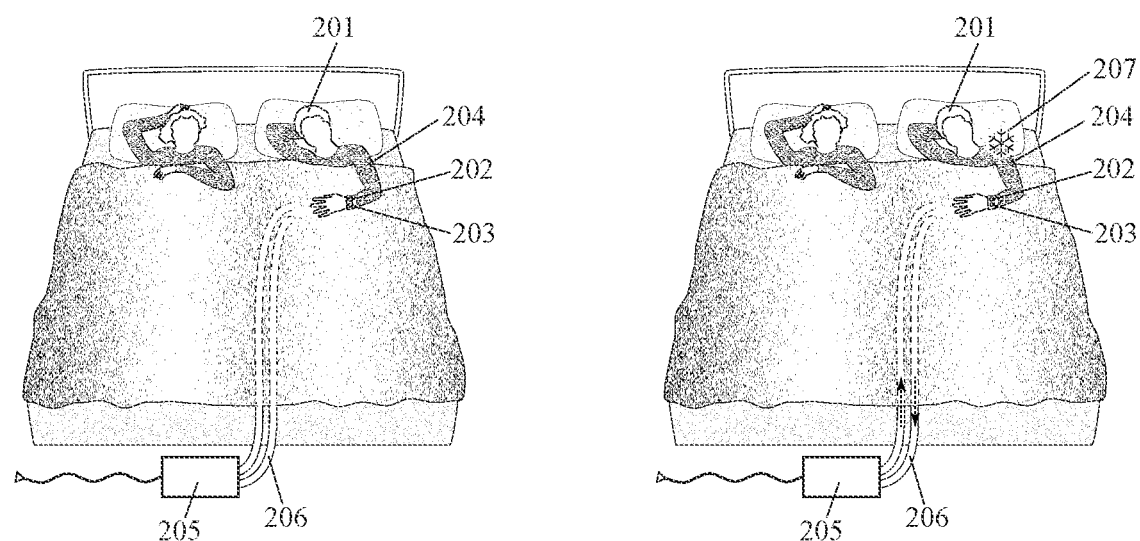
FIG. 2 shows a system for modifying a person's sleep environment which changes garment temperature based on blood pressure.

FIG. 2 shows an example of how this invention can be embodied in a system, device, and method that uses wearable technology to collect data for automatic modification of a person's sleep environment comprising: a wrist-worn component (further comprising blood pressure sensor 202) that is configured to be worn by person 201; a sleep-environment-modifying component (further comprising garment 204 worn by person 201, heat exchanger 205, and flow channel 206) which changes the temperature of garment 204; and a data-control component 203 which controls the operation of the sleep-environment-modifying component in order to automatically change the temperature of garment 204 while the person sleeps. As was the case with FIG. 1, the left side shows this example at a first point in time and the right side shows this example at a second point in time. This shows how data from blood pressure sensor 202 is used to selectively modify garment 204 temperature. In this example, cooling or warming liquid (or air or other gas) is pumped through flow channel 206 and then circulates through garment 204. In this example, garment 204 performs a cooling function, as indicated by snowflake symbol 207. In another example, garment 204 can perform a warming function. Relevant example and component variations discussed elsewhere in this disclosure or in priority-linked disclosures can also be applied to this example, but are not repeated here to avoid narrative redundancy.

Figure 3:
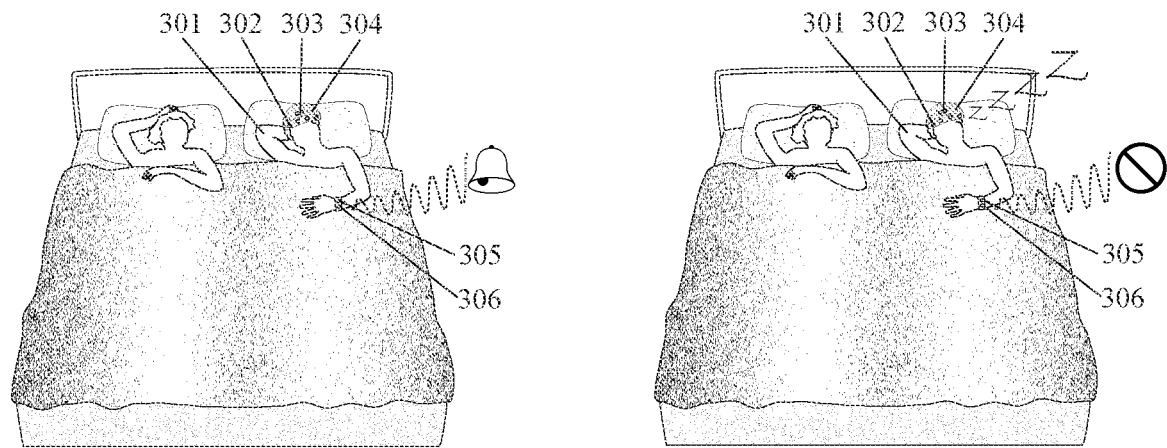
FIG. 3 shows a system for modifying a person's sleep environment which filters electronic communication based on EEG signals.

FIG. 3 shows an example of how this invention can be embodied in a system, device, and method that uses wearable technology to collect data for automatic modification of a person's sleep environment comprising: a wearable-sensor component that collects data concerning EEG signals, electromagnetic energy from the person's brain, and/or electromagnetic energy transmitted through the person's brain; a sleep-environment-modifying component which changes the filtering of electronic communications sent to the person; and a data-control component which controls the operation of the sleep-environment-modifying component in order to automatically change communication filtering based on data from the wearable-sensor component. More specifically, this example comprises: a wearable EEG monitor (further comprising at least one EEG sensor 302 and hat 304) which is worn by person 301; a wrist-worn component (further comprising communication unit 305 and power source 306); and a data-control component 303 which filters electronic communication when data from the EEG monitor indicates that the person is asleep (or falling asleep).

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a system, device, or method can analyze changes in brainwaves in a single frequency band, changes in brainwaves in multiple frequency bands, or changes in brainwaves in a first frequency band relative to those in a second frequency band. In an example, a statistical method can analyze repeating electromagnetic patterns by analyzing their frequency of repetition, their frequency band or range of repetition, their recurring amplitude, their wave phase, and/or their waveform.

In an example, analysis of data from a wearable EEG monitor can indicate when person 301 is probably awake, asleep, or in the process of falling asleep. In the example shown in FIG. 3, when data from the EEG monitor indicates that the person is awake, then the wrist-worn component emits sound-based notifications of incoming communications. This is shown on the left side of FIG. 3. In another example, these notifications can be vibratory. However, when data from the EEG monitor indicates that the person is asleep (or in the process of falling asleep), then the wrist-worn component filters incoming communications and does not emit any sound-based or vibratory notifications. This is shown on the right side of FIG. 3.

In another example, an EEG monitor can be in electronic communication with a smart phone or other non-wearable communication device. In an example, communication notification by a smart phone or other electronic communications device can be filtered, muted, or otherwise modified when data from an EEG monitor indicates that a person is probably sleeping or in the process of falling asleep. Such selective communication filtering and/or modification based on sleep status can be useful for maintaining electronic communication when fully awake without interrupting sleep when asleep or falling asleep. In other examples, this invention can change the filtering, auto-response, notification mode, notification timing, or user interface for communications based on sleep status and/or sleep phase. In an example, this invention can change which communication types or sources result in immediate notification when a person is asleep or falling asleep. More generally, the wearable-sensor component of this invention can collect data concerning electromagnetic energy from (or transmitted through) organs or portions of the person's body other than the brain—such as the heart, eyes, stomach, wrist, hand, or arm.

In the example shown in FIG. 3, changes in data from a wearable EEG monitor are used to trigger a change in the communication notification mode of a wearable communications device. In an example, changes in data from a wearable EEG monitor can be used to trigger a change in the communication notification mode of a non-wearable communications device. In an example, changes in data from a wearable EEG monitor are used to trigger a change in the communication notification mode of a smart phone or other non-wearable mobile communications device. In an example a wearable device with a motion sensor can be in wireless communication with a smart phone or other non-wearable mobile communications device. In an example, when data from a wearable EEG monitor indicates that a person is probably sleeping, then this can trigger a change in the communication notification mode of a smart phone or other non-wearable mobile communications device. In an example, when data from a wearable EEG monitor indicates that a person is probably sleeping, then this can mute sound-based communication notifications from a smart phone or other mobile communications device. Relevant example and component variations discussed elsewhere in this disclosure or in priority-linked disclosures can also be applied to this example, but are not repeated here to avoid narrative redundancy.

Figure 4:
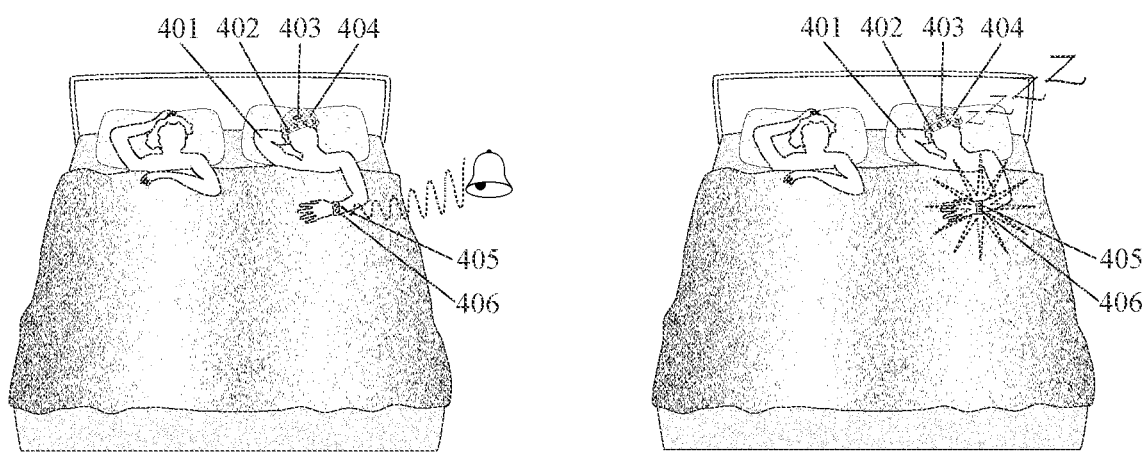
FIG. 4 shows a system for modifying a person's sleep environment which changes the mode of electronic communication based on EEG signals.

FIG. 4 shows an example of how this invention can be embodied in a system, device, and method that uses wearable technology to collect data for automatic modification of a person's sleep environment comprising: a wearable brain activity monitor which collects data concerning a person's EEG signals, electromagnetic energy from the person's brain, and/or electromagnetic energy transmitted through the person's brain; a sleep-environment-modifying component which changes a communication notification mode for communications sent to the person; and a data-control component which controls the operation of the sleep-environment-modifying component in order to automatically change the person's sleep environment based on data from the wearable-sensor component.

More specifically, the example in FIG. 4 comprises: a wearable EEG monitor (further comprising electromagnetic energy sensor 402 and hat 404) that collects data concerning EEG signals from person 401, electromagnetic energy from the person's brain, and/or electromagnetic energy transmitted through the person's brain; a wrist-worn component (further comprising sound-emitting member 405 and light-emitting member 406) which changes a communication notification mode for communications sent to the person; and a data-control component 403 which automatically changes a communication mode when data from the wearable EEG monitor indicates that the person is asleep or falling asleep.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band. In an example, a statistical method can analyze repeating electromagnetic patterns by analyzing their frequency of repetition, their frequency band or range of repetition, their recurring amplitude, their wave phase, and/or their waveform.

Such analysis of electromagnetic activity of a person's brain can indicate whether the person is probably awake, asleep, or falling asleep. As shown on the left side of FIG. 4, a communication notification mode can be based on sound when a person is awake. As shown on the right side of FIG. 4, a communication notification mode can be based on light when a person is asleep or falling asleep. In this example, the person's sleep status is determined based on analysis of data from a wearable EEG monitor which is embodied as a hat. In other examples, a wearable EEG monitor can be embodied in different type of head-worn device, such as an ear insert, electronically-functional eyewear, or an electronically-functional respiratory mask.

In this example, a data-control component is incorporated into an EEG monitor. In another example, a data-control component can be incorporated into a wrist-worn component, smart phone, or other mobile electronic communication device. In this example, communication notification comes from a wrist-worn device, such as a smart watch. In another example, communication notification can come from a smart phone or other mobile electronic device. In various examples, a smart watch, smart eyewear, a smart phone, or other electronic communication device can produce sound-based or tactile-based communication notifications when a person is awake and can produce light-based communication notifications when a person is asleep or falling asleep.

In the example shown in FIG. 4, when data from the EEG monitor indicates that the person is sufficiently awake, then the wrist-worn component emits sound-based notifications for incoming communications as shown on the left side of FIG. 4. However, when data from the EEG monitor indicates that the person is sleeping (or falling asleep), then the wrist-worn component produces emits light-based notifications of incoming communications as shown on the right side of FIG. 4. Light-based notifications can be less likely to awaken the person when the person is sleeping than are sound-based or vibration-based notifications. Such selective modification of communication notification mode based on sleep status can be useful for maintaining electronic communication when a person is awake, without interrupting sleep when the person is asleep. In another example, this invention can modify the notification modality of a non-wearable electronic communication device, such as a smart phone or electronic tablet, based on a person's sleep status and/or sleep phase.

More generally, the wearable-sensor component of this invention can collect data concerning electromagnetic energy from (or transmitted through) other organs or portions of the person's body. In various examples, a sleep-environment-modifying component can: change a communication notification mode for communications sent to a person from sound-based notification to visual-based notification, or vice versa; change a communication notification mode for communications sent to a person from tactile-based notification to visual-based notification, or vice versa; or change a communication notification mode for communications sent to a person from vibration-based notification to visual-based notification, or vice versa. In other examples, a sleep-environment-modifying component can automatically reduce the magnitude of sound, light, or vibration notification when a person is sleeping (or falling asleep) based on data from a wearable-sensor component. This can help to generally maintain a person's electronic connectivity without disturbing the person's sleep. Relevant example and component variations discussed elsewhere in this disclosure or in priority-linked disclosures can also be applied to this example, but are not repeated here to avoid narrative redundancy.

Figure 5:
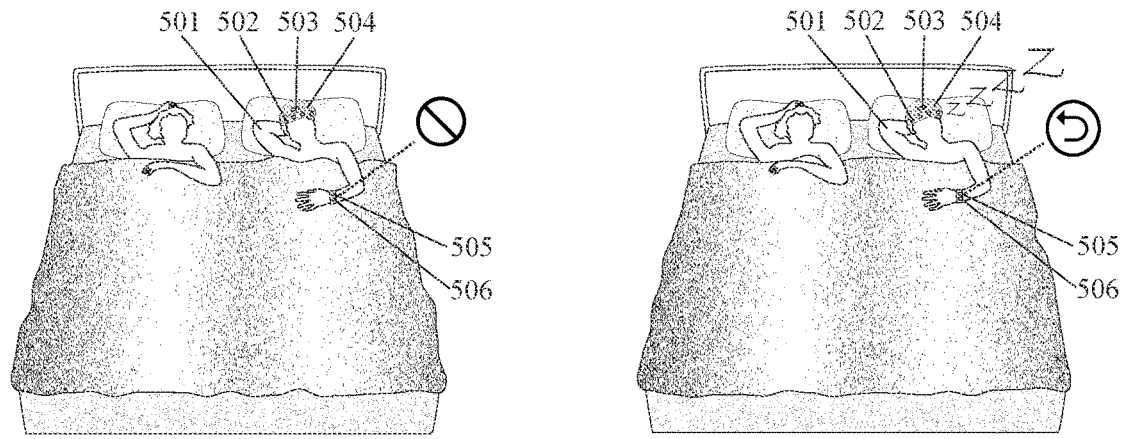
FIG. 5 shows a system for modifying a person's sleep environment which changes an electronic communication auto-response based on EEG signals.

FIG. 5 shows an example of how this invention can be embodied in a system, device, and method that uses wearable technology to collect data for automatic modification of a person's sleep environment comprising: a wearable-sensor component that is configured to be worn by a person, wherein this sensor component collects data concerning EEG signals, electromagnetic energy from the person's brain, and/or electromagnetic energy transmitted through the person's brain; a sleep-environment-modifying component which changes an auto-response to communications sent to the person; and a data-control component which controls the operation of the sleep-environment-modifying component in order to automatically change the person's sleep environment based on data from the wearable-sensor component. More specifically, this comprises: a wearable EEG sensor (further comprising at least one electromagnetic energy sensor 502 and a data processing unit 503 incorporated into hat 504) worn by person 501; a wrist-worn communication device (further comprising data receiver 505) which changes an auto-response to communications sent to the person; and a data-control component 506 which changes the auto-response based on data from the wearable EEG sensor. In this example, at least one electromagnetic energy sensor 502 collects data concerning electromagnetic energy from the person's brain and/or electromagnetic energy transmitted through the person's brain.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band. In an example, a statistical method can analyze repeating electromagnetic patterns by analyzing their frequency of repetition, their frequency band or range of repetition, their recurring amplitude, their wave phase, and/or their waveform.

In an example, analysis of brainwaves or other electromagnetic brain activity can indicate whether the person is probably awake, sleeping, or in the process of falling asleep. In an example, when data from the EEG monitor indicates that the person is awake (as shown in the left side of FIG. 5), then there is no auto-response to communications sent to the person. However, when data from the EEG monitor indicates that the person is sleeping (as shown in the right side of FIG. 5), then the system gives an auto-response message to communications sent to the person. In an example, this auto-response can be an auto-reply message such as "Can't talk right now" or "Sleeping now. Will catch up when I wake up."

In an example, an auto-reply function can occur with a communication device selected from the group consisting of: smart watch; smart phone; smart eyewear; smart earwear; and electronic tablet. In an example, analysis of brainwaves or other electromagnetic brain activity can determine which phase of sleep a person is in and can adjust the filtering, notification, and/or auto-response for incoming communications based on a selected phase of sleep. More generally, a wearable-sensor component can collect data concerning electromagnetic energy from or transmitted through other organs or portions of a person's body. More generally, a wearable-sensor component can collect data concerning at least one selected physiologic parameter or anatomic function of a person and a sleep-environment-modifying component can change an auto-response message given in response to communications sent to the person. Relevant example and component variations discussed elsewhere in this disclosure or in priority-linked disclosures can also be applied to this example, but are not repeated here to avoid narrative redundancy.

Figure 6:
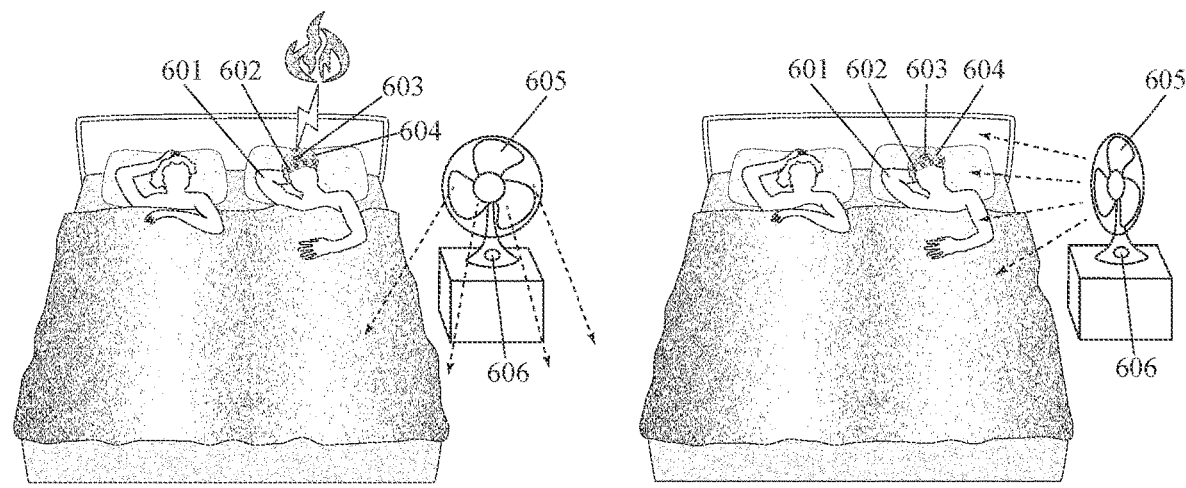
FIG. 6 shows a system for modifying a person's sleep environment which changes airflow from a fan based on EEG signals.

FIG. 6 shows an example of how this invention can be embodied in a system, device, and method using wearable technology to collect data for automatic modification of a person's sleep environment comprising: a wearable-sensor component that is configured to be worn by a person, wherein this sensor component collects data concerning EEG signals, electromagnetic energy from the person's brain, and/or electromagnetic energy transmitted through the person's brain; a sleep-environment-modifying component which changes the direction of a flow of air coming from a portable fan or ceiling fan; and a data-control component which controls the operation of the sleep-environment-modifying component in order to automatically change the person's sleep environment based on data from the wearable-sensor component. In particular, the example in FIG. 6 comprises: a wearable brain activity monitor (further comprising at least one electromagnetic energy sensor 602 and hat 604) that collects data concerning the EEG signals of person 601, electromagnetic energy from the person's brain, and/or electromagnetic energy transmitted through the person's brain; a portable fan 605 with an actuator 606 which can change the direction of a flow of air coming from the fan; and a data-control component 603 which controls the direction of the flow of air from the fan based on data from the wearable brain activity monitor.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band. In an example, a statistical method can analyze repeating electromagnetic patterns by analyzing their frequency of repetition, their frequency band or range of repetition, their recurring amplitude, their wave phase, and/or their waveform.

In an example, analysis of data from the wearable brain activity monitor can predict biologically-induced swings in body temperature. In this example, the stylized "fire" symbol shown above the wearable brain activity monitor on the left side of FIG. 6 symbolizes a pattern of brain activity which predicts a biologically-induced upward swing in the person's body temperature. In this example, the right side of FIG. 6 shows how the system has responded to this prediction by changing the direction of airflow from portable fan 605 so that it better cools person 601. In this manner, an upward swing in the person's body temperature can be mitigated or even avoided. In this example, the sleep-environment-modifying component of this invention is a portable fan that is placed on a surface somewhere in the bedroom. In another example, the sleep-environment-modifying component can be a fan that integrated into a bed (such as the bed headboard). In another example, the fan can be a ceiling fan. In an example, the sleep-environment-modifying component of this invention can: start or stop the operation of a portable fan or ceiling fan; change the speed of airflow from a portable fan or ceiling fan; change the direction of a flow of air and/or other gas which the person breathes; and/or change the flow of air and/or other gas in communication with the surface of the person's body.

In an example, the sleep-environment-modifying component of this invention can selectively direct airflow over person 601 and not over the person's bed partner. In an example, a system, device, and method which increases airflow over a person's body in response to a predicted or actual increase in the person's body temperature can be useful for reducing the effects of hot flashes. In an example of a system, device, and method to address a woman's hot flashes, airflow can be selectively and temporarily directed over the woman's body in response to a hot flash that is predicted by a particular pattern of brainwaves or other electromagnetic brain activity. In other examples, airflow can be selectively and temporarily directed over a woman's body in response to data from a plurality of sensors selected from the group consisting of: EEG monitor, temperature sensor, blood pressure monitor, pulse monitor, moisture sensor, tissue conductivity sensor, tissue impedance sensor, and pulmonary function monitor. Relevant example and component variations discussed elsewhere in this disclosure or in priority-linked disclosures can also be applied to this example, but are not repeated here to avoid narrative redundancy.

Figure 7:
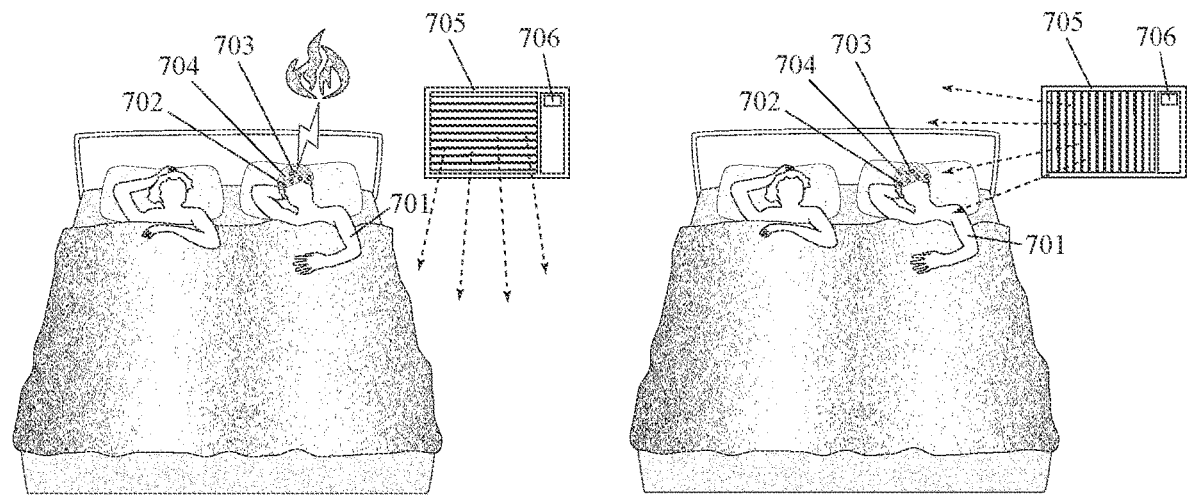
FIG. 7 shows a system for modifying a person's sleep environment which changes airflow from a window air conditioner based on EEG signals.

FIG. 7 shows an example of this invention which is similar to the one shown in FIG. 6, except that it changes the direction of airflow from a window-based air conditioner rather than from a portable fan. FIG. 7 shows how this invention can be embodied in a system, device, and method that uses wearable technology to collect data for automatic modification of a person's sleep environment comprising: a wearable-sensor component that is configured to be worn by a person, wherein this sensor component collects data concerning EEG signals, electromagnetic energy from the person's brain, and/or electromagnetic energy transmitted through the person's brain; a sleep-environment-modifying component which changes the direction of a flow of air from a window-based air conditioner; and a data-control component which controls the operation of the sleep-environment-modifying component in order to automatically change the person's sleep environment based on data from the wearable-sensor component.

In particular, the example in FIG. 7 comprises: a wearable brain activity monitor (further comprising at least one electromagnetic energy sensor 702 and hat 704) that collects data concerning EEG signals, electromagnetic energy from the brain, and/or electromagnetic energy transmitted through the brain; a window-based air conditioner 705 with automatically-adjustable airflow direction (further comprising wireless data receiver 706); and a data-control component 703 which controls the operation of the sleep-environment-modifying component in order to automatically change the sleep environment of person 701 based on data from the wearable brain activity monitor. Example variations similar to those discussed for FIG. 6 are again possible. In addition, the sleep-environment-modifying component can adjust the temperature or speed of airflow from the window-based air conditioner. Relevant example and component variations discussed elsewhere in this disclosure or in priority-linked disclosures can also be applied to this example, but are not repeated here to avoid narrative redundancy.

Figure 8:
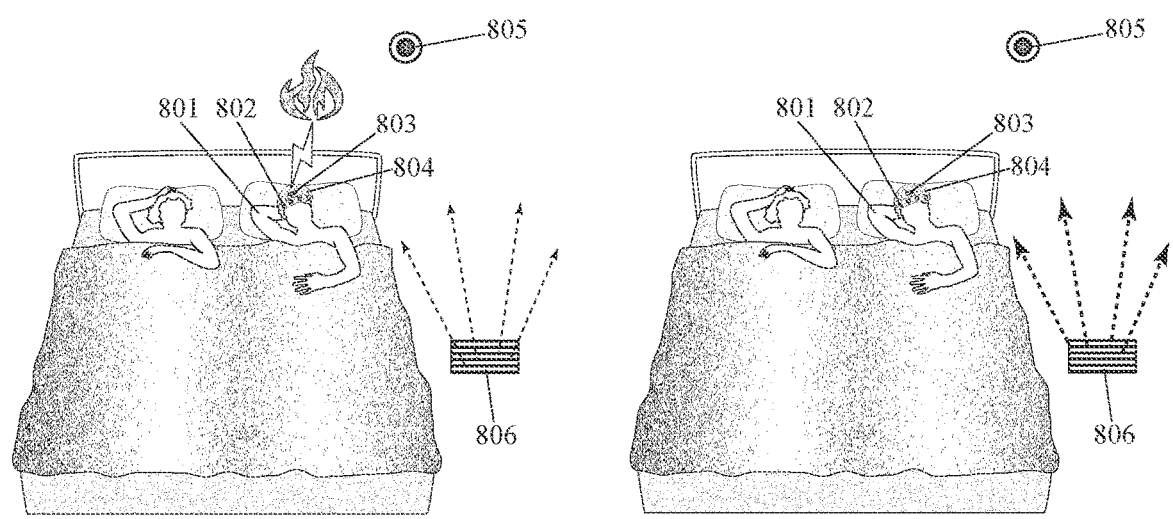
FIG. 8 shows a system for modifying a person's sleep environment which changes airflow from a HVAC system based on EEG signals.

FIG. 8 shows an example of this invention which is similar to those shown in FIGS. 6 and 7, except that it changes the rate of airflow from a central heating, ventilation, and/or air-conditioning (HVAC) system. FIG. 8 shows how this invention can be embodied in a system, device, and method that uses wearable technology to collect data for automatic modification of a person's sleep environment comprising: a wearable-sensor component that is configured to be worn by a person, wherein this sensor component collects data concerning EEG signals, electromagnetic energy from the person's brain, and/or electromagnetic energy transmitted through the person's brain; a sleep-environment-modifying component which changes the inter-room distribution of a flow of air from a central heating, ventilation, and/or air-conditioning (HVAC) system; and a data-control component which controls the operation of the sleep-environment-modifying component in order to automatically change the person's sleep environment based on data from the wearable-sensor component. In another example, the inter-room distribution of airflow from an HVAC system can be automatically changed by selectively opening or closing air valves in duct work. The left portion of this figure shows this example at a first point in time and the right portion of this figure shows this example at a second point in time, in sequence, to show how sensor data is used to modify the person's sleep environment.

More specifically, the embodiment shown in FIG. 8 comprises: a wearable brain activity monitor (further comprising at least one electromagnetic energy sensor 802 and hat 804) that collects data concerning EEG signals, electromagnetic energy from the person's brain, and/or electromagnetic energy transmitted through the person's brain; a sleep-environment-modifying component (wall-mounted HVAC control unit 805) which changes the inter-room distribution of a flow of air from a central heating, ventilation, and/or air-conditioning (HVAC) system; and a data-control component 803 which controls the operation of the sleep-environment-modifying component in order to automatically change the person's sleep environment based on data from the wearable-sensor component. In this example, the data-control component 803 is located in a wearable component (e.g. hat 804) of the system. In another example, a data-control component can be located in the sleep-environment-modifying component (e.g. wall-mounted HVAC control unit 805). In an example, a wearable device with multiple physiologic and/or anatomic function sensors that is worn by a person when the person sleeps can be in wireless communication with a total home environmental control system in order to better control the person's sleep environment.

In this example, analysis of data from the wearable brain activity monitor triggers a change in the inter-room distribution of airflow from a central HVAC system. In another example, the inter-room distribution of airflow from an HVAC system can be automatically changed by selectively opening or closing air valves in duct work. In another example, analysis of data from the wearable brain activity monitor can trigger an overall increase in the rate of airflow through a central HVAC system. In an example, this invention can change the temperature of airflow from a central HVAC system. Example variations similar to those discussed for FIG. 6 are again possible. In an example, a wearable-sensor component can collect data concerning EEG signals, electromagnetic energy from the person's brain, and/or electromagnetic energy transmitted through the person's brain and this data can trigger a change in the direction, temperature, humidity, volume, and/or rate of airflow from a central heating, ventilation, and/or air-conditioning (HVAC) system. More generally, a wearable-sensor component can collect data concerning at least one selected physiologic parameter or anatomic function of the person and the sleep-environment-modifying component changes the direction, temperature, humidity, volume, and/or rate of airflow from a central heating, ventilation, and/or air-conditioning (HVAC) system. Relevant example and component variations discussed elsewhere in this disclosure or in priority-linked disclosures can also be applied to this example, but are not repeated here to avoid narrative redundancy.

Figure 9:
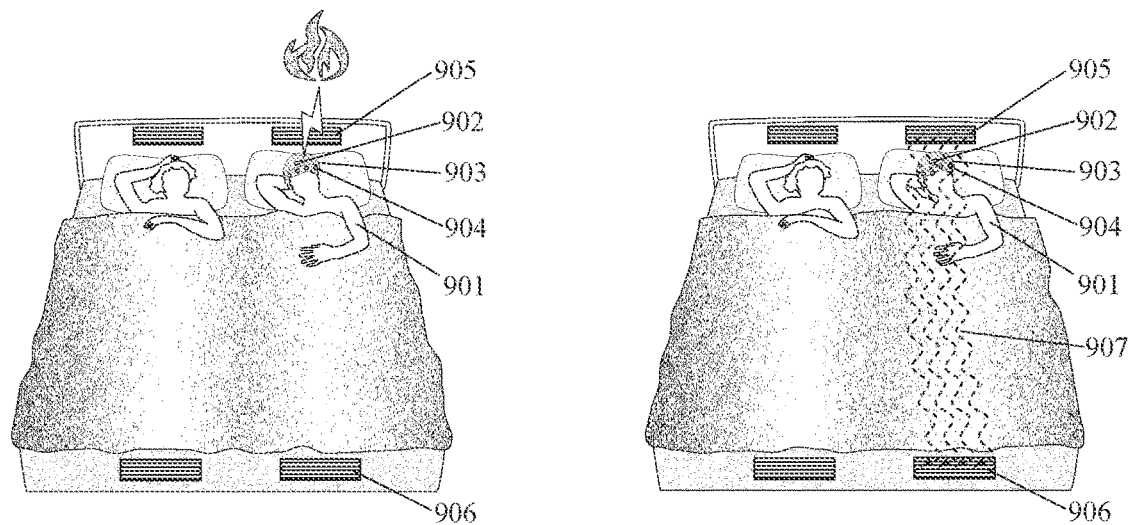
FIG. 9 shows a system for modifying a person's sleep environment which changes airflow from a laminar airflow mechanism based on EEG signals.

FIG. 9 shows an example of how this invention can be embodied in a system, device, and method that uses wearable technology to collect data for automatic modification of a person's sleep environment comprising: a wearable-sensor component that collects data concerning electromagnetic energy from a person's brain; a sleep-environment-modifying component which controls a laminar flow of air and/or other gas in communication with the surface of the person's body; and a data-control component which controls the operation of the sleep-environment-modifying component in order to automatically change the person's sleep environment based on data from the wearable-sensor component. Specifically, the example in FIG. 9 comprises: an EEG monitor (further comprising electromagnetic energy sensor 904 and hat 903) worn by person 901; a laminar airflow mechanism (further comprising outflow vent 905 and inflow vent 906) which creates longitudinal laminar airflow 907 over person 901; and data-control component 902 which controls the operation of the laminar airflow mechanism based on data from the EEG monitor. In an example, laminar airflow can enable selective and individualized control of the sleep environment on one side of a bed vs. the other side. In an example, laminar airflow can selectively control the temperature, humidity, volume, or rate of airflow over just one side of a bed. In an example, such selective control of airflow can cool person 901 without cooling the other person in the same bed. In an example, laminar airflow over one portion of a bed which is controlled by data from a wearable device can create and control a personalized sleeping environment for one bed partner which does not substantially affect the other bed partner.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band. In an example, a statistical method can analyze repeating electromagnetic patterns by analyzing their frequency of repetition, their frequency band or range of repetition, their recurring amplitude, their wave phase, and/or their waveform.

In an example, this invention can trigger laminar airflow 907 when data from the EEG monitor predicts that person 901 will soon have a biologically-induced upward swing in body temperature. In an example, proactive activation of cooling laminar airflow can reduce or avoid the effects of the upward swing in the person's body temperature without cooling the other person in the bed. In this example, laminar airflow flows longitudinally from the head of a bed to the foot of a bed. In an example, laminar airflow can flow diagonally from the head of a bed to a side of a bed. In an example, this laminar airflow can be substantially horizontal. In an example, this laminar airflow can be substantially vertical. In an example, a sleep-environment-modifying component can control the initiation, cessation, temperature, humidity, volume, speed, or spatial configuration of a laminar airflow across a bed. Relevant example and component variations discussed elsewhere in this disclosure or in priority-linked disclosures can also be applied to this example, but are not repeated here to avoid narrative redundancy.

Figure 10:
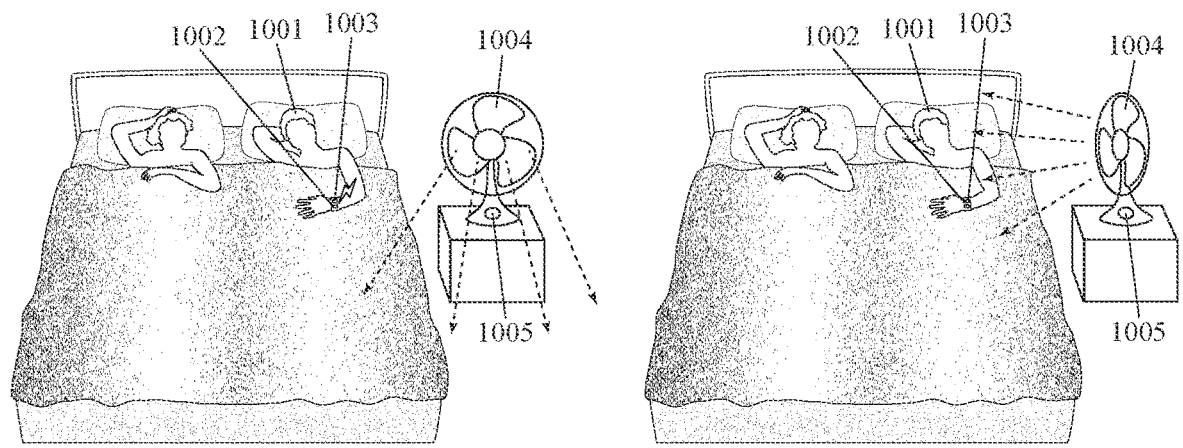
FIG. 10 shows a system for modifying a person's sleep environment which changes airflow from a fan based on a wearable electromagnetic energy sensor.

FIG. 10 shows an example of how this invention can be embodied in a system, device, and method that uses wearable technology to collect data for automatic modification of a person's sleep environment comprising: a wearable-sensor component that is configured to be worn by a person, wherein this sensor component collects data concerning electromagnetic energy from or transmitted through the person's body; a sleep-environment-modifying component which changes the direction of a flow of air coming from a portable fan or ceiling fan; and a data-control component which controls the operation of the sleep-environment-modifying component in order to automatically change the person's sleep environment based on data from the wearable-sensor component. The left portion of this figure shows this example at a first point in time and the right portion of this figure shows this example at a second point in time, in sequence, to show how sensor data is used to modify the person's sleep environment.

More specifically, the embodiment shown in FIG. 10 comprises: a wrist-worn device (further comprising electromagnetic energy sensor 1002) worn by person 1001 which collects data concerning electromagnetic energy from (or transmitted through) a portion of the person's body; a portable fan 1004 with an actuator 1005 which changes the direction of airflow from the fan; and a data-control component 1003 which controls the operation of fan 1004 and/or actuator 1005 based on data from electromagnetic energy sensor 1002. In an example, data from the electromagnetic energy sensor can predict biologically-induced upward swings in the person's body temperature and direct airflow from fan 1004 over the person's body to proactively reduce or avoid such swings in body temperature. In an example, fan 1004 can be turned on or off based on data from electromagnetic energy sensor 1002.

In an example, electromagnetic energy sensor 1002 can measure the conductivity, resistance, and/or impedance of electrical energy flow through tissue in the person's wrist, hand, and/or arm. In an example, a wearable-sensor component can collect data concerning electromagnetic energy from the person's wrist or transmitted through the person's wrist. In an example, the wearable-sensor component can collect data concerning electromagnetic energy from or transmitted through the person's body that is used to: control the operation of a portable fan or ceiling fan which directs airflow toward the person's body; or start and stop a portable fan or ceiling fan. In an example, a controlled fan can be integrated into a bed structure (such as headboard or footboard) rather than be a portable or ceiling fan that is separate from the bed structure. Relevant example and component variations discussed elsewhere in this disclosure or in priority-linked disclosures can also be applied to this example, but are not repeated here to avoid narrative redundancy.

Figure 11:
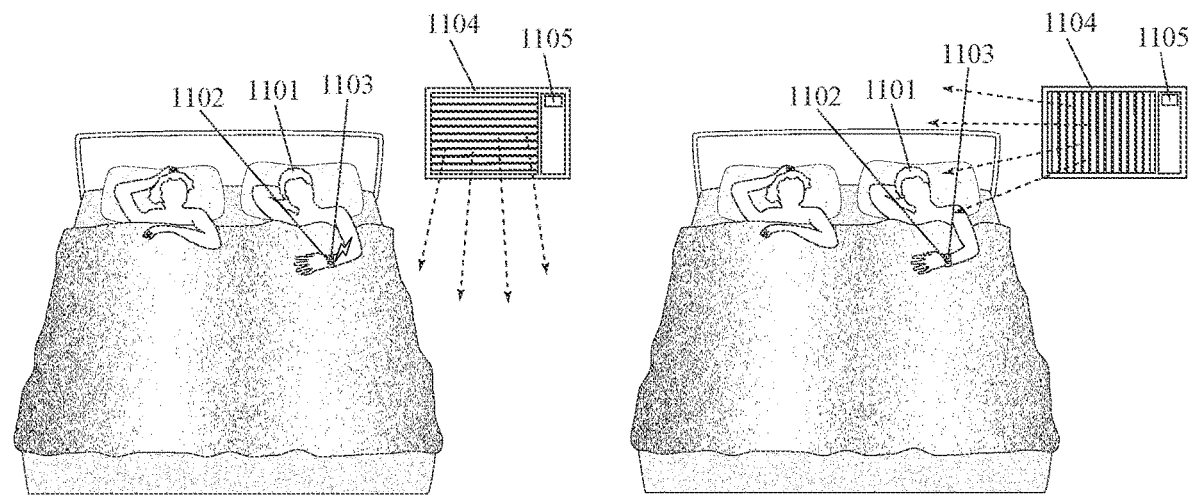
FIG. 11 shows a system for modifying a person's sleep environment which changes airflow from a window air conditioner based on a wearable electromagnetic energy sensor.

FIG. 11 shows an example of how this invention can be embodied in a system, device, and method that uses wearable technology to collect data for automatic modification of a person's sleep environment comprising: a wearable-sensor component that is configured to be worn by a person, wherein this sensor component collects data concerning electromagnetic energy from or transmitted through the person's body; a sleep-environment-modifying component which changes the direction of a flow of air from a window-based air conditioner; and a data-control component which controls the operation of the sleep-environment-modifying component in order to automatically change the person's sleep environment based on data from the wearable-sensor component.

More specifically, the embodiment shown in FIG. 11 comprises: a wrist-worn device (further comprising electromagnetic energy sensor 1102); a sleep-environment-modifying component 1105 which changes the direction of airflow from a window-based air conditioner 1104; and a data-control component 1103 which controls the operation of the sleep-environment-modifying component in order to automatically change the person's sleep environment based on data from the wearable-sensor component. In an example, the direction of airflow from a window-based air conditioner can be changed by one or more actuators which move slats or vents in the air conditioner.

In an example, data from electromagnetic energy sensor 1102 can be used to estimate person 1101's current body temperature or predicted body temperature. In an example, current high body temperature or a predicted upswing in body temperature based on this data can trigger a change in the direction of airflow from window-based air conditioner 1104. In an example, this can reduce or avoid unpleasant spikes or drops in the person's body temperature. In various examples, data from electromagnetic energy sensor 1102 can trigger changes in the activation, cessation, direction, temperature, humidity, volume, and/or speed of airflow from a window-based air conditioner. In an example, airflow from a window-based air conditioner can be directed so as to cool person 1101 without substantively cooling another person in the same bed. Relevant example and component variations discussed elsewhere in this disclosure or in priority-linked disclosures can also be applied to this example, but are not repeated here to avoid narrative redundancy.

Figure 12:
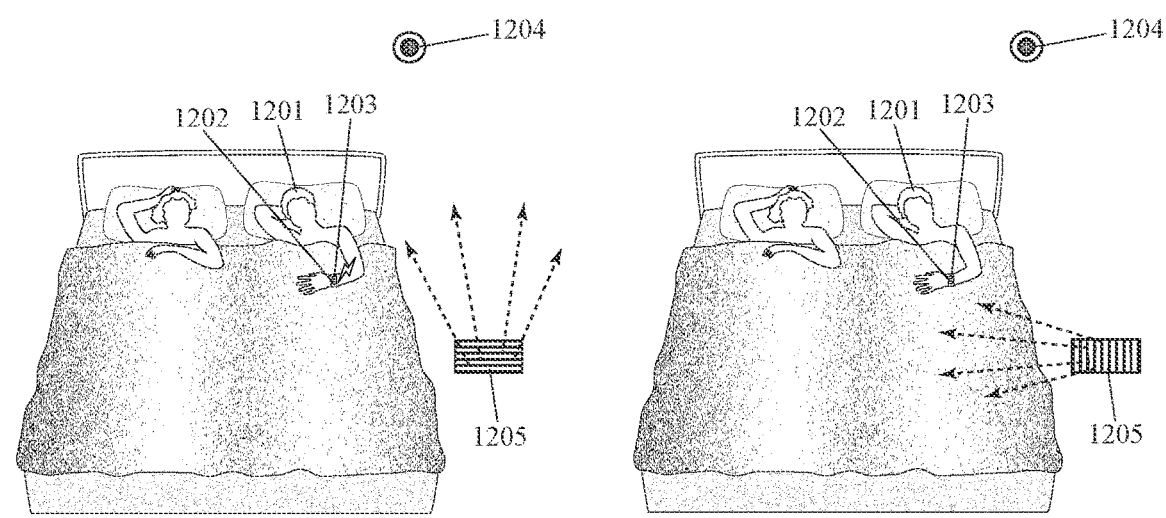
FIG. 12 shows a system for modifying a person's sleep environment which changes airflow from a HVAC system based on a wearable electromagnetic energy sensor.

FIG. 12 shows an embodiment of this invention which is similar to the one shown in FIG. 11, except that this embodiment changes airflow from a central Heating, Ventilation, and/or Air-Conditioning (HVAC) system instead of airflow from a window-based air conditioner. As shown in FIG. 12, this invention can be embodied in a system, device, and method that uses wearable technology to collect data for automatic modification of a person's sleep environment comprising: a wearable-sensor component that is configured to be worn by a person, wherein this sensor component collects data concerning electromagnetic energy from or transmitted through the person's body; a sleep-environment-modifying component which changes the direction of a flow airflow from a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment in FIG. 12 comprises: a wrist-worn device (further comprising electromagnetic energy sensor 1202) worn by person 1201; a sleep-environment-modifying component 1204 which changes the direction of airflow from a central heating, ventilation, and/or air-conditioning (HVAC) system through vent 1205; and a data-control component 1203 which controls the operation of the sleep-environment-modifying component in order to automatically change the person's sleep environment based on data from the wearable-sensor component. In an example, the direction of airflow from a central HVAC system can be changed by actuators which move the slats in vent 1205.

In an example, data from electromagnetic energy sensor 1202 can be used to estimate or predict person 1201's body temperature. In an example, current high body temperature or a predicted upswing in body temperature based on this data can trigger a change in the direction of airflow from the central HVAC system. In an example, this can reduce or avoid unpleasant spikes in the person's body temperature. In various examples, data from electromagnetic energy sensor 1202 can trigger changes in the activation, cessation, direction, temperature, humidity, volume, and/or speed of airflow from an HVAC system. In an example, airflow from an HVAC system can be spatially directed so as to cool person 1201 without substantively cooling another person in the same bed. In an example, analysis of data from wrist-worn electromagnetic energy sensor 1202 can trigger: a change in the inter-room distribution of airflow from an HVAC system; an increase in the rate of airflow through an HVAC system; a change in the temperature of airflow from an HVAC system; a change in the direction, temperature, humidity, volume, and/or rate of airflow from an HVAC system. More generally, a wearable-sensor component can collect data concerning at least one selected physiologic parameter or anatomic function which triggers changes in the direction, temperature, humidity, volume, and/or rate of airflow from an HVAC system. Relevant example and component variations discussed elsewhere in this disclosure or in priority-linked disclosures can also be applied to this example, but are not repeated here to avoid narrative redundancy.

Figure 13:
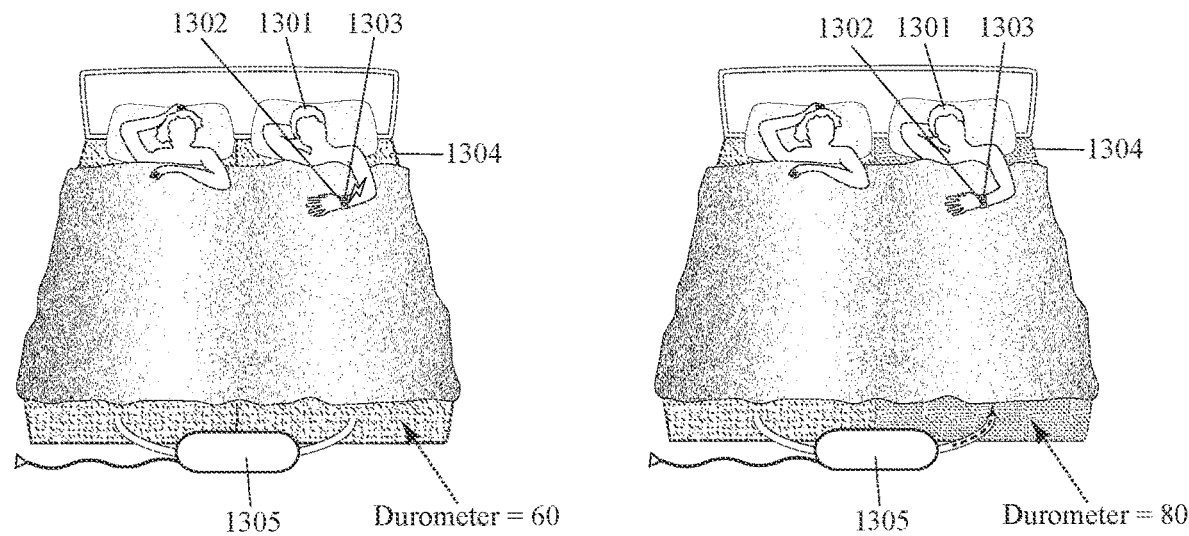
FIG. 13 shows a system for modifying a person's sleep environment which changes the firmness of a bed based on a wearable electromagnetic energy sensor.

FIG. 13 shows an example of how this invention can be embodied in a system, device, and method that uses wearable technology to collect data for automatic modification of a person's sleep environment comprising: a wearable-sensor component that is configured to be worn by a person, wherein this sensor component collects data concerning electromagnetic energy from or transmitted through the person's body; a sleep-environment-modifying component which changes the firmness of a mattress or other bedding material on which the person lies; and a data-control component which controls the operation of the sleep-environment-modifying component in order to automatically change the person's sleep environment based on data from the wearable-sensor component. The left side of FIG. 13 shows this example at a first point in time, wherein the wearable-sensor component is collecting physiological data from person 1301. The right side of FIG. 13 shows this example at a second point in time, wherein this data has triggered a change in the firmness of the side of a mattress on which that person lies.

More specifically, the embodiment shown in FIG. 13 comprises: a wrist-worn device (further comprising an electromagnetic energy sensor 1302) worn by person 1301, wherein this sensor component collects data concerning electromagnetic energy from or transmitted through the person's body; a sleep-environment-modifying component (further comprising mattress 1304 and air pump 1305) which selectively inflates or deflates the side of the mattress on which person 1301 lies; and a data-control component 1303 which controls the operation of the sleep-environment-modifying component in order to automatically change the firmness of the person's mattress based on data from electromagnetic energy sensor 1302.

In this example, the right side of FIG. 13 shows that the inflation of the side of the mattress on which person 1305 lies has been automatically increased in response to data from wrist-worn electromagnetic energy sensor 1302. In an example, a sleep-environment-modifying component can: inflate or deflate a portion of a bed mattress or mattress pad; change the inflation or pressure level of a mattress on which a person lies; change the compressive resistance of springs in a box spring; change the compressive resistance of springs in a mattress; change the durometer or shore value of the bedding surface on which a person lies; and/or change the firmness of a bedding surface on which a person lies. Relevant example and component variations discussed elsewhere in this disclosure or in priority-linked disclosures can also be applied to this example, but are not repeated here to avoid narrative redundancy.

Figure 14:
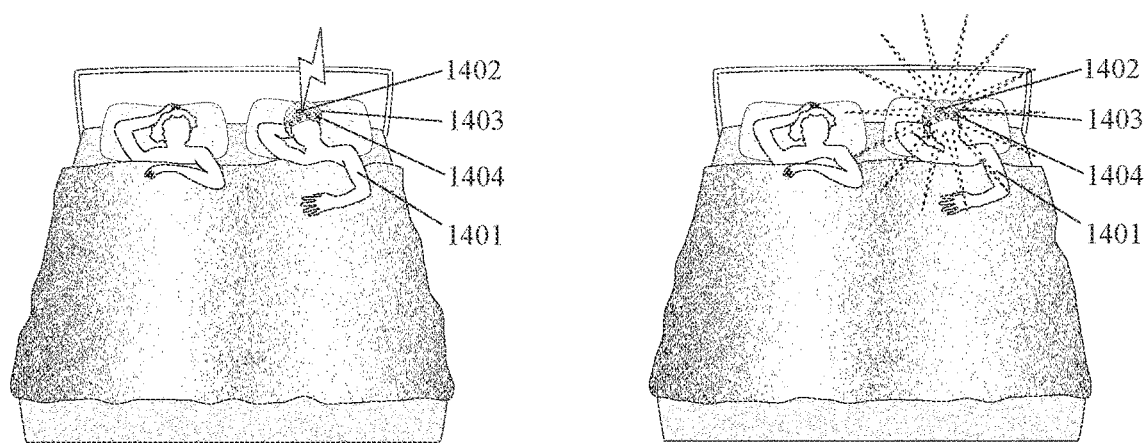
FIG. 14 shows a system for modifying a person's sleep environment which changes ambient light based on EEG signals.

FIG. 14 shows an example of how this invention can be embodied in a system, device, and method that uses wearable technology to collect data for automatic modification of a person's sleep environment comprising: a wearable-sensor component that is configured to be worn by a person, wherein this sensor component collects data concerning EEG signals, electromagnetic energy from the person's brain, and/or electromagnetic energy transmitted through the person's brain while the person is in bed; and a sleep-environment-modifying component which emits light based on data from the wearable-sensor component. Specifically, the example in FIG. 14 comprises: a brain activity monitor (further comprising electromagnetic energy sensor 1404 and hat 1403) worn by person 1401; and a light-emitting member 1402, wherein the light-emitting member emits light based on data from the brain activity monitor.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a system, device, or method can analyze changes in brainwaves in a single frequency band, changes in brainwaves in multiple frequency bands, or changes in brainwaves in a first frequency band relative to those in a second frequency band. In an example, a statistical method can analyze repeating electromagnetic patterns by analyzing their frequency of repetition, their frequency band or range of repetition, their recurring amplitude, their wave phase, and/or their waveform.

In an example, analysis of data from the brain activity monitor can indicate whether person 1401 is sleeping or awake. In an example, analysis of data from the brain activity monitor can indicate what phase of sleep person 1401 is in when person 1401 is sleeping. In an example, activation of light-emitting member 1402 can be based on the person's sleep status and/or sleep phase. In an example, the light can go off when the person falls asleep. In an example, the light can come on when the person wakes up. In an example, the light can come on during one or more selected sleep phases. In an example, a light-emitting member can be incorporated into a wearable device. In an example, a light-emitting member can be part of separate device which is not worn but which is in wireless communication with a brain activity monitor. In an example, light emitted from a light-emitting member can be selected from the group consisting of: visible light; non-coherent light; coherent light; infrared light; and ultraviolet light. In an example, light emitted from a light-emitting member can comprise a pattern or image. In an example, light-emitting member can be an image projector. In an example, light emitted from a light-emitting member can create a projected image or picture on a surface in the environment. Relevant example and component variations discussed elsewhere in this disclosure or in priority-linked disclosures can also be applied to this example, but are not repeated here to avoid narrative redundancy.

Figure 15:
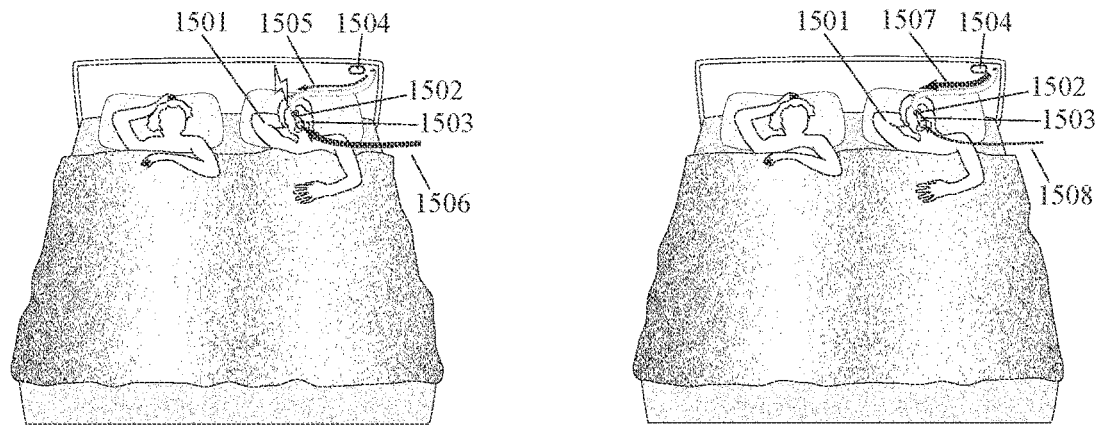
FIG. 15 shows a system for modifying a person's sleep environment which changes a person's air source based on EEG signals.

As shown in FIG. 15, this invention can be embodied in a system, device, and method that uses wearable technology to collect data for automatic modification of a person's sleep environment comprising: a wearable-sensor component that is configured to be worn by a person, wherein this sensor component collects data concerning EEG signals, electromagnetic energy from the person's brain, and/or electromagnetic energy transmitted through the person's brain; a sleep-environment-modifying component which changes the mixture of air and/or other gas from multiple sources which the person breathes; and a data-control component which controls the operation of the sleep-environment-modifying component in order to automatically change the person's sleep environment based on data from the wearable-sensor component.

In more detail, the example in FIG. 15 comprises: an electromagnetic energy sensor 1502 worn by person 1501 which collects data concerning the person's electromagnetic brain activity; a respiratory mask 1503 (and associated air and/or gas pathways) which changes the mixture of air and/or other gas from multiple sources which person 1501 breathes; and a data-control component 1504 which controls the operation of the respiratory mask 1503 (and associated air and/or gas pathways) based on data from the electromagnetic energy sensor 1502. In this example, an electromagnetic energy sensor 1502 which measures the person's brain activity is incorporated into a respiratory mask. In other examples, an electromagnetic energy sensor to measure the person's brain activity can be incorporated into a hat, cap, headband, headphones, earmuff, ear insert, or eyewear.

FIG. 15 shows an example wherein person 1501 breathes a mixture of non-ambient and ambient airflows from a non-ambient source and from ambient air, respectively. At the first point in time shown on the left side of FIG. 15, airflow 1505 from a non-ambient source is less than airflow 1506 from ambient air. At the second point in time shown on the right side of FIG. 15, airflow 1507 from a non-ambient source is greater than airflow 1508 from ambient air. In this example, the change in airflow mixture from the left side to the right side of FIG. 15 is triggered by analysis of data from electromagnetic energy sensor 1502. In an example, analysis of data from electromagnetic energy sensor 1502 can indicate when the person's brain is not receiving sufficient oxygen. In an example, airflow from the non-ambient source can be a flow of oxygen-enriched air or pure oxygen. In an example, data concerning the person's brain activity which is collected by electromagnetic energy sensor 1502 can trigger a greater proportion of non-ambient oxygen in the mixture which the person breathes when the person's brain activity indicates oxygen deprivation.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a system, device, or method can analyze changes in brainwaves in a single frequency band, changes in brainwaves in multiple frequency bands, or changes in brainwaves in a first frequency band relative to those in a second frequency band. In an example, a statistical method can analyze repeating electromagnetic patterns by analyzing their frequency of repetition, their frequency band or range of repetition, their recurring amplitude, their wave phase, and/or their waveform.

In an example, the sleep-environment-modifying component of this invention can change the direction, flow rate, pressure, humidity, temperature, mixture, and/or source of the air or other gas which the person breathes; change the mixture or composition of air and/or other gas which the person breathes; change the proportion of ambient air versus non-ambient air or other gas which the person breathes. In an example, the wearable-sensor component can collect data concerning electromagnetic energy from or transmitted through other organs or portions of the person's body and the sleep-environment-modifying component can change the mixture of air and/or other gas which the person breathes based on this data. Relevant example and component variations discussed elsewhere in this disclosure or in priority-linked disclosures can also be applied to this example, but are not repeated here to avoid narrative redundancy.

Figure 16:
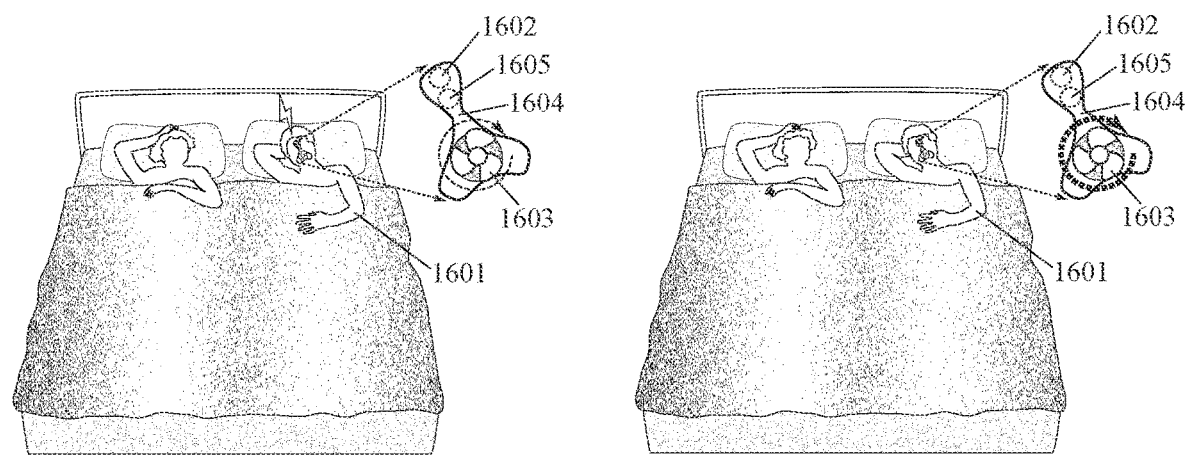
FIG. 16 shows a system for modifying a person's sleep environment which changes a person's air pressure based on EEG signals.

As shown in FIG. 16, this invention can be embodied in a system, device, and method that uses wearable technology to collect data for automatic modification of a person's sleep environment comprising: a wearable-sensor component that is configured to be worn by a person, wherein this sensor component collects data concerning EEG signals, electromagnetic energy from the person's brain, and/or electromagnetic energy transmitted through the person's brain; a sleep-environment-modifying component which changes the pressure of air and/or other gas which the person breathes; and a data-control component which controls the operation of the sleep-environment-modifying component in order to automatically change the person's sleep environment based on data from the wearable-sensor component.

More specifically, the embodiment shown in FIG. 16 comprises: an electromagnetic energy sensor 1602 worn by person 1601 which collects data concerning the person's EEG signals, electromagnetic energy from the person's brain, and/or electromagnetic energy transmitted through the person's brain; a respiratory mask 1604 with impeller 1603 which changes the pressure and/or speed of airflow which person 1601 breathes; and a data-control component 1605 which controls the operation of impellor 1603 based on data from electromagnetic energy sensor 1602. On the left side of FIG. 16, impellor 1603 is spinning at a first rate based on data from electromagnetic energy sensor 1602 at a first point in time. On the right side of FIG. 16, impellor 1603 is spinning at a second rate based on data from electromagnetic energy sensor 1602 at a second point in time, wherein the second rate is faster than the first rate. In an example, when the impellor spins at a faster rate, it increases the pressure and/or speed of airflow which person 1601 breathes.

In an example, analysis of data from electromagnetic energy sensor 1602 can indicate when person 1601 is experiencing respiratory obstruction. In an example, when data from electromagnetic energy sensor 1602 indicates that person 1601 is experiencing respiratory obstruction, then this invention can trigger impellor 1603 to spin faster to provide positive airway pressure to reduce respiratory obstruction. In an example, analysis of data from electromagnetic energy sensor 1602 can predict when person 1601 is likely to experience respiratory obstruction soon. In an example, when data from electromagnetic energy sensor 1602 indicates that person 1601 is likely experience respiratory obstruction soon, then this invention can trigger impellor 1603 to spin faster to provide positive airway pressure to avoid respiratory obstruction. In an example, analysis of data from electromagnetic energy sensor 1602 can indicate when person 1601 is experiencing oxygen deprivation. In an example, when data from electromagnetic energy sensor 1602 indicates that person 1601 is experiencing oxygen deprivation, then this invention can trigger impellor 1603 to spin faster to provide positive airway pressure to provide additional oxygen uptake by the person's body.

In this example, the pressure and/or speed of airflow which the person breathes is modified by a change in the speed of an air impellor which is incorporated into a respiratory mask. In an example, the pressure and/or speed of airflow which the person breathes can be modified by an air impellor which is part of a bedside air pump. In an example, the pressure and/or speed of airflow which the person breathes can be modified by another air-moving mechanism, in respond to analysis of data from an electromagnetic brain activity monitor. In this example, an electromagnetic brain activity monitor is incorporated into a respiratory mask. In an example, an electromagnetic brain activity monitor can be incorporated into a hat, cap, headphones, ear muff, ear insert, or eyewear. In an example, a sleep-environment-modifying component can change the direction, flow rate, pressure, humidity, temperature, mixture, and/or source of the air or other gas which the person breathes. Relevant example and component variations discussed elsewhere in this disclosure or in priority-linked disclosures can also be applied to this example, but are not repeated here to avoid narrative redundancy.

Figure 17:
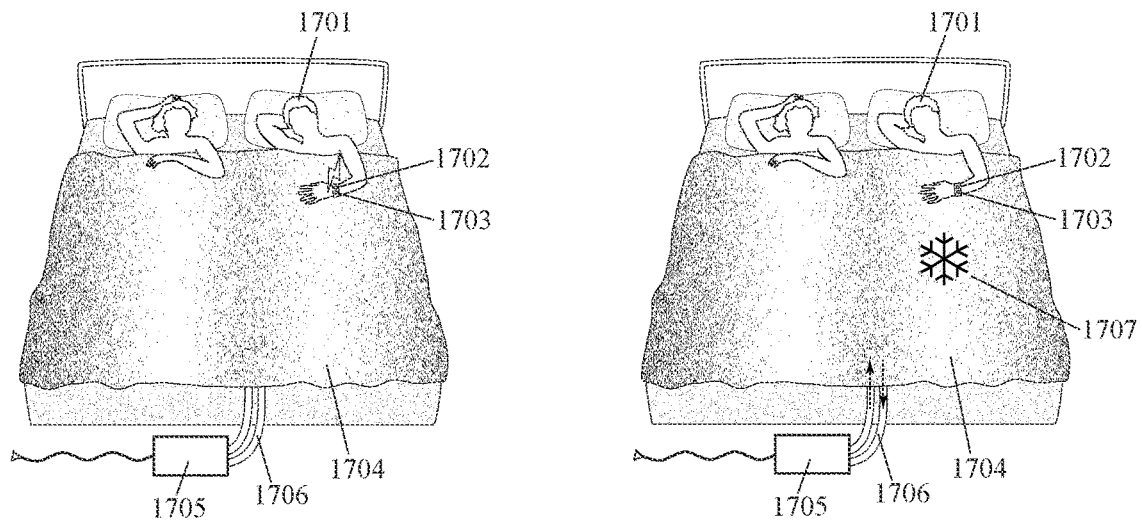
FIG. 17 shows a system for modifying a person's sleep environment which changes bed temperature based on a wearable electromagnetic energy sensor.

As shown in FIG. 17, this invention can be embodied in a system, device, and method that uses wearable technology to collect data for automatic modification of a person's sleep environment comprising: a wearable-sensor component that is configured to be worn by a person, wherein this sensor component collects data concerning electromagnetic energy from (or transmitted through) the person's body; a sleep-environment-modifying component which changes the temperature of the air, mattress, blanket, or other bedding material near the person's body; and a data-control component which controls the operation of the sleep-environment-modifying component in order to automatically change the person's sleep environment based on data from the wearable-sensor component.

More specifically, the embodiment shown in FIG. 17 comprises: a wrist-worn electromagnetic energy sensor 1702 worn by person 1701; a sleep-environment-modifying component (further comprising heat exchanger 1705, flow channel 1706, and blanket 1704) which changes the temperature of the person's sleep environment; and a data-control component 1703 which controls the operation of the sleep-environment-modifying component in order to automatically change the temperature of the person's sleep environment based on data from wrist-worn electromagnetic energy sensor 1702. In this example, the sleep-environment-modifying component pumps a liquid or gas through heat exchanger 1705, flow channel 1706, and blanket 1704 in order to cool the person's sleep environment. This is indicated by "snowflake" symbol 1707. In another example, this component can heat the person's sleep environment. In an example, blanket 1704 can further comprise sinusoidal tubes or channels through which the pumped liquid or gas flows.

In an example, the heat exchanger releases heat into the room air. In an example, the heat exchanger can contain a quantity of a pre-cooled substance, such as ice. In another example, a heat exchanger can transfer thermal energy from one side of a bed to the other. This can be particularly useful when one person in a bed tends to be too warm and the other person in a bed tends to be too cool.

In an example, wrist-worn electromagnetic energy sensor 1702 can measure the electrical conductivity, resistance, or impedance of the person's wrist, hand, or arm. In an example, data from wrist-worn electromagnetic energy sensor 1702 can indicate or predict biologically-caused changes in the person's body temperature. In an example, activation of cooling or heating based on data from wrist-worn electromagnetic energy sensor 1702 can reduce or avoid the effects of biologically-induced swings in body temperature for person 1701. In this example, the electromagnetic energy sensor is incorporated into a band or smart watch which person 1701 wears on their wrist. In other examples, an electromagnetic energy sensor can be incorporated into an armband, chest band, shirt, pants, pajamas, underwear, or other article of clothing which the person wears while sleeping. In this example, the sleep-environment-modifying member includes a cooling or heating blanket. In other examples, the sleep-environment-modifying member can include a cooling or heating mattress, mattress pad, sheet, sleeping bag, or garment. Relevant example and component variations discussed elsewhere in this disclosure or in priority-linked disclosures can also be applied to this example, but are not repeated here to avoid narrative redundancy.

Figure 18:
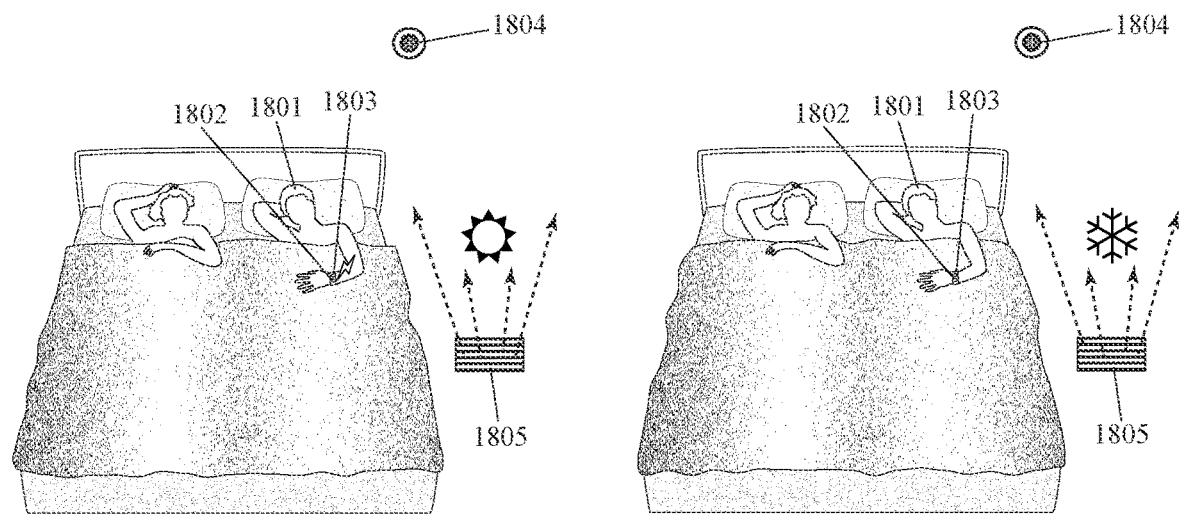
FIG. 18 shows a system for modifying a person's sleep environment which changes the temperature of air from a HVAC system based on a wearable electromagnetic energy sensor.

FIG. 18 shows an example of how this invention can be embodied in a system, device, and method that uses wearable technology to collect data for automatic modification of a person's sleep environment comprising: a wearable-sensor component that is configured to be worn by a person, wherein this sensor component collects data concerning electromagnetic energy from or transmitted through the person's body; a sleep-environment-modifying component which changes the temperature of a flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment shown in FIG. 18 comprises: a wrist-worn electromagnetic energy sensor 1802 that is worn by person 1801 which collects data concerning electromagnetic energy from (or transmitted through) the person's wrist, hand, or arm; a sleep-environment-modifying component 1804 which changes the temperature of airflow from vent 1805 coming from a central heating, ventilation, and/or air-conditioning (HVAC) system; and a data-control component 1803 which is in wireless communication with sleep-environment-modifying component 1804 in order to automatically change the temperature of airflow from vent 1805 based on data from wrist-worn electromagnetic energy sensor 1802. The left side of FIG. 18 shows this embodiment warming the person's sleep environment via warm air coming from vent 1805 based on a first pattern of electromagnetic energy measured by electromagnetic energy sensor 1802. The right side of FIG. 18 shows this embodiment cooling the person's sleep environment via cool air coming from vent 1805 based on a second pattern of electromagnetic energy measured by electromagnetic energy sensor 1802.

In an example, a first pattern of electromagnetic energy measured by electromagnetic energy sensor 1802 can indicate that the person is too warm or will experience an undesirable upswing in body temperature in the near future. In an example, a second pattern of electromagnetic energy measured by electromagnetic energy sensor 1802 can indicate that the person is too cold or will experience an undesirable drop in body temperature in the near future. When undesirable swings in body temperature can be predicted by selected patterns of electromagnetic energy measured from the person's wrist, hand, or arm, then the effects of these undesirable swings can be reduced or avoided by proactive cooling or heating enabled by this invention. In an example, a sleep-environment-modifying component can change the temperature, flow rate, direction, or inter-room distribution of a flow of air from a central heating, ventilation, and/or air-conditioning (HVAC) system. In another example, the inter-room distribution of airflow from an HVAC system can be automatically changed by selectively opening or closing air valves in duct work. Relevant example and component variations discussed elsewhere in this disclosure or in priority-linked disclosures can also be applied to this example, but are not repeated here to avoid narrative redundancy.

Figure 19:
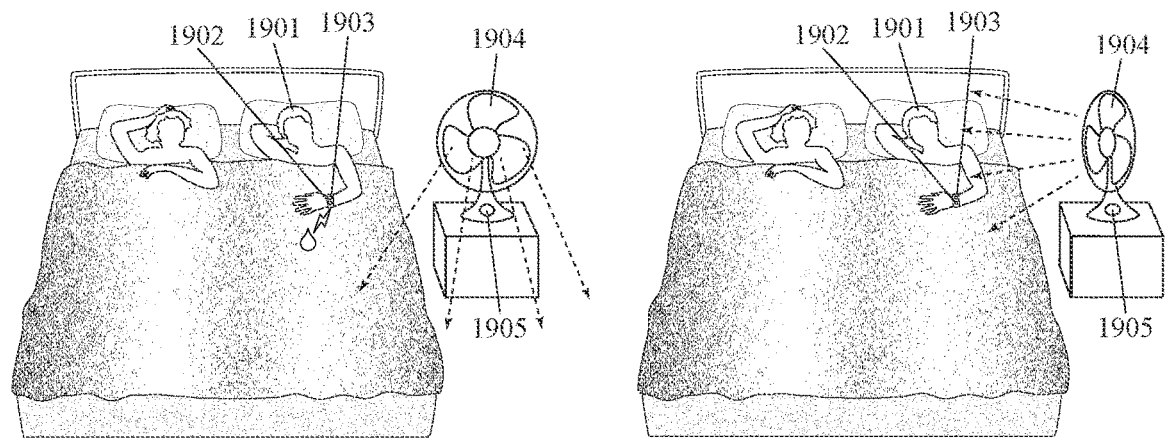
FIG. 19 shows a system for modifying a person's sleep environment which changes airflow from a fan based on a wearable moisture sensor.

FIG. 19 shows an example of how this invention can be embodied in a system, device, and method using wearable technology to collect data for automatic modification of a person's sleep environment comprising: a wearable-sensor component that is configured to be worn by a person in bed, wherein this sensor component collects data concerning the person's skin moisture and/or body moisture level; a sleep-environment-modifying component which changes the direction of airflow from a portable fan or ceiling fan; and a data-control component which controls the operation of the sleep-environment-modifying component in order to automatically change the person's sleep environment based on data from the wearable-sensor component.

More specifically, the embodiment shown in FIG. 19 comprises: moisture sensor 1902 that is worn by person 1901 and collects data concerning the person's skin moisture and/or body moisture level; portable fan 1904 with actuator 1905 which changes the direction of the fan's airflow; and data-control component 1903 which changes the direction of the fan's airflow based on data from moisture sensor 1902.

The left side of FIG. 19 shows this example at a first time when the fan's airflow is directed away from person 1901 and moisture sensor 1902 is collecting data. The right side of FIG. 19 shows this example at a second time when the fan's airflow has been directed toward person 1901 based on data from moisture sensor 1902. In an example, when data from moisture sensor 1902 indicates that the person's skin is very moist, then this invention can trigger actuator 1905 to direct airflow from portable fan 1904 toward person 1901.

In this example, a portable fan which rests on a bedside table. In another example, a fan or other air-moving device can be integrated into the headboard or footboard of a bed. In another example, the fan can be a ceiling fan. In an example, a fan or other air-moving device can be positioned to move air toward, over, or across a person wearing a moisture sensor, but not move air toward, over, or across another person in the same bed. In various examples, a specific pattern of data from a moisture sensor worn by a person can trigger a change in the direction, volume, and/or speed of airflow from a fan or other air-moving device. Relevant example and component variations discussed elsewhere in this disclosure or in priority-linked disclosures can also be applied to this example, but are not repeated here to avoid narrative redundancy.

Figure 20:
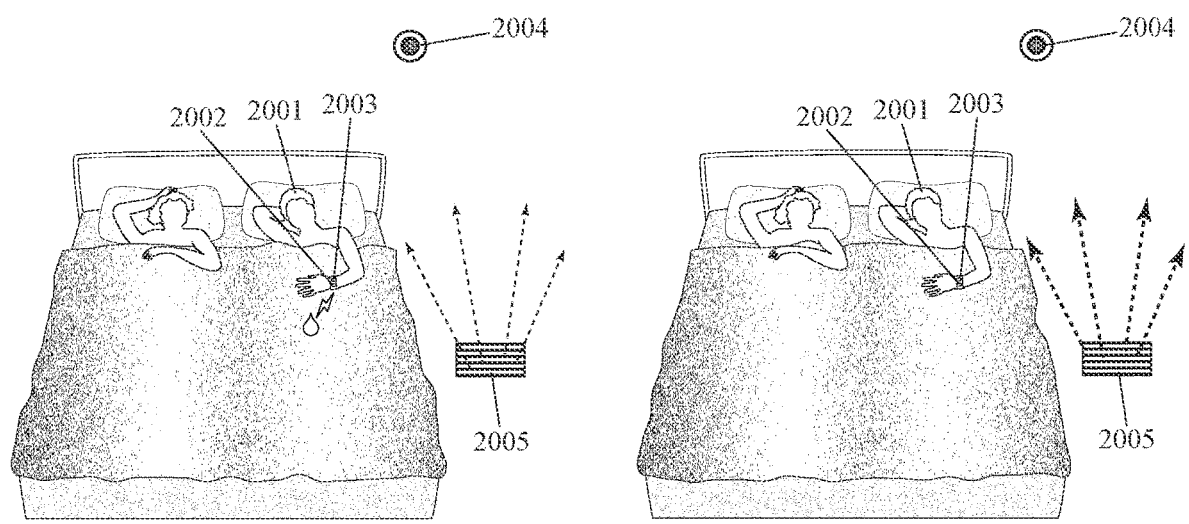
FIG. 20 shows a system for modifying a person's sleep environment which changes airflow from a HVAC system based on a wearable moisture sensor.

As shown in FIG. 20, this invention can be embodied in a system, device, and method using wearable technology to collect data for automatic modification of a person's sleep environment comprising: a wearable-sensor component that is configured to be worn by a person, wherein this sensor component collects data concerning the person's skin moisture and/or body moisture level; a sleep-environment-modifying component which changes the inter-room distribution of a flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment shown in FIG. 20 comprises: wearable moisture sensor 2002 worn by person 2001; sleep-environment-modifying component 2004 which changes the inter-room distribution of airflow from a central heating, ventilation, and/or air-conditioning (HVAC) system and, thus, airflow through vent 2005; and data-control component 2003 which is in wireless communication with sleep-environment-modifying component 2004 in order to automatically change airflow through vent 2005 based on data from wearable moisture sensor 2002. In this example, wearable moisture sensor 2002 is worn on a person's wrist. In other examples, a wearable moisture sensor can be worn on a person's arm, hand, chest, head, leg, or foot. In an example, when data from wearable sensor 2002 indicates that the person's skin and/or body is very moist, then a greater proportion of airflow from a central HVAC system can be directed to the person through vent 2005. Relevant example and component variations discussed elsewhere in this disclosure or in priority-linked disclosures can also be applied to this example, but are not repeated here to avoid narrative redundancy.

Figure 21:
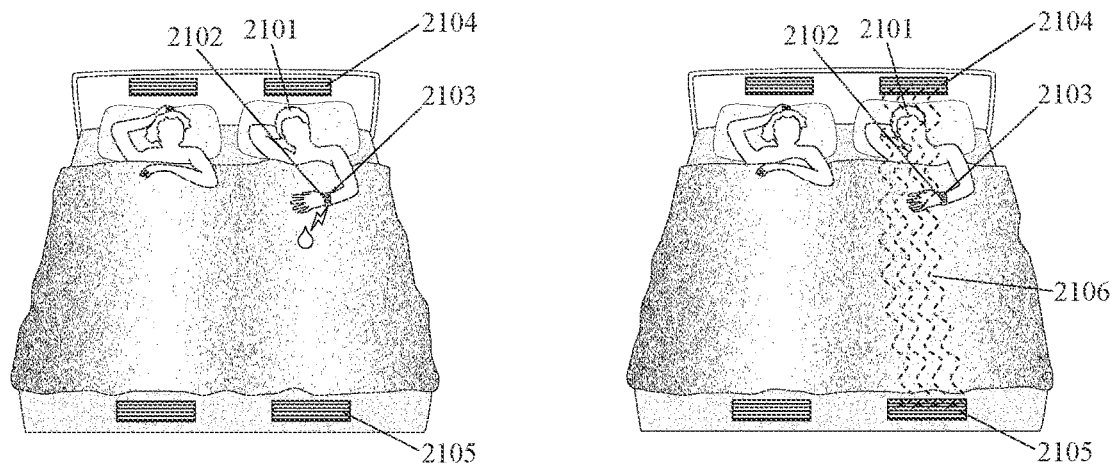
FIG. 21 shows a system for modifying a person's sleep environment which changes airflow from a laminar airflow mechanism based on a wearable moisture sensor.

FIG. 21 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin moisture and/or body moisture level; a sleep-environment-modifying component which changes the laminar flow of air and/or other gas in communication with the surface of the person's body; and a data-control component which controls the operation of the sleep-environment-modifying component in order to automatically change the person's sleep environment based on data from the wearable-sensor component.

More specifically, the embodiment shown in FIG. 21 comprises: a wearable moisture sensor 2102 worn by person 2101, wherein this sensor collects data concerning the person's skin moisture and/or body moisture level; a laminar flow mechanism (further comprising outflow vent 2104 and inflow vent 2105) which directs a laminar airflow 2106 across the person; and a data-control component 2103 which controls the operation of the laminar flow mechanism based on data from the wearable moisture sensor 2102. In an example, when data from wearable moisture sensor 2102 indicates that a person's skin is very moist, then this triggers laminar airflow 2106 over this person. In an example, laminar airflow can draw away excess moisture from a person's body. In an example, laminar airflow can cool a person's body by increasing evaporation of moisture from their skin. In this example, the data-control component 2103 is co-located with the wearable moisture sensor 2102 on a wrist band. In other examples, a data-control component can be co-located with the laminar airflow mechanism, within a mobile communications device, or located elsewhere.

In an example, use of a laminar airflow can help to direct airflow over person 2101 without having substantive airflow over another person in the same bed. In this example, a laminar airflow flows in a longitudinal manner from the head of the bed to the foot of the bed over one half of the bed. In an example, a laminar airflow can flow in the reverse direction, from the foot of the bed to the head of the bed. In another example, a laminar airflow can flow in a diagonal manner, from the head of the bed to a side of the bed. In an example, a laminar airflow can travel across a portion of a bed in a substantially horizontal plane. In an example, a laminar airflow can travel across a portion of a bed in a substantially vertical plane. In an example, a sleep-environment-modifying component can: change the direction, flow rate, pressure, humidity, temperature, mixture, and/or source of the air or other gas which the person breathes; change the spatial configuration of the flow of air and/or other gas which the person breathes; control the operation of a central longitudinal laminar airflow on a bed; and/or control the operation of a laminar airflow between a first person and a second person. Relevant example and component variations discussed elsewhere in this disclosure or in priority-linked disclosures can also be applied to this example, but are not repeated here to avoid narrative redundancy.

Figure 22:
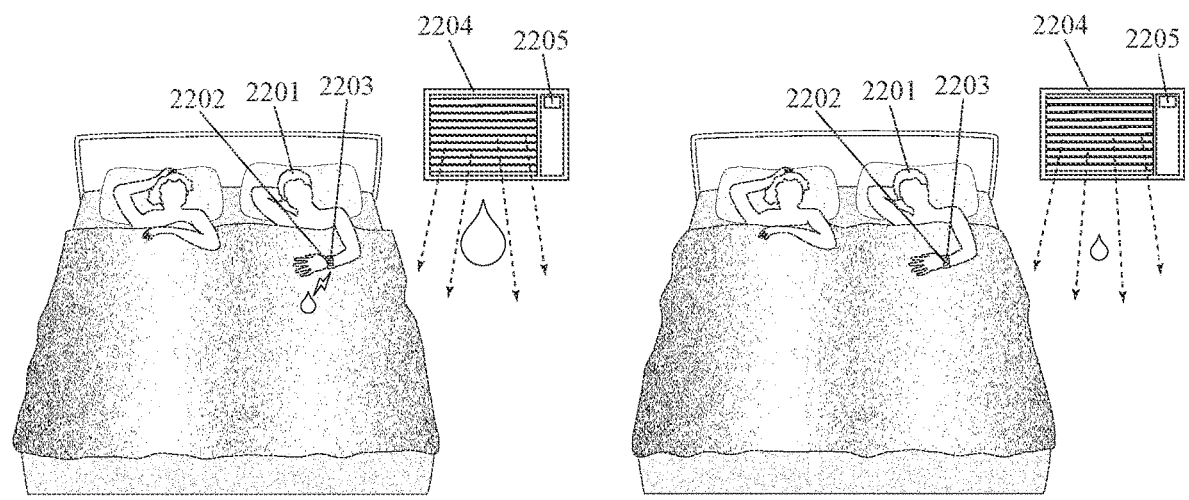
FIG. 22 shows a system for modifying a person's sleep environment which changes the humidity of air from a window air conditioner based on a wearable moisture sensor.

FIG. 22 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin moisture and/or body moisture level; a sleep-environment-modifying component which changes the humidity level of airflow from a window-based air conditioner; and a data-control component which controls the operation of the sleep-environment-modifying component in order to automatically change the person's sleep environment based on data from the wearable-sensor component.

More specifically, the embodiment in FIG. 22 comprises: a wrist-worn moisture sensor 2202 worn by person 2201; a sleep-environment-modifying component 2205 which changes the humidity level of airflow from a window-based air conditioner 2204; and a data-control component 2203 which controls the operation of the sleep-environment-modifying component in order to automatically change the person's sleep environment based on data from the wearable-sensor component. In this example, a moisture sensor is worn by a person on their wrist. In other examples, a moisture sensor can be worn on a person's arm, hand, leg, chest, neck, head, or ear. In other examples, one or more moisture sensors can be incorporated into pajamas, underwear, or other garments.

The left side of FIG. 22 shows the invention at a first time wherein airflow from window-based air conditioner 2204 has a first humidity level or moisture content based on a first pattern of data from wrist-worn moisture sensor 2202. The right side of FIG. 22 shows the invention at a second time wherein airflow from window-based air conditioner 2204 has a second humidity level or moisture content based on a second pattern of data from wrist-worn moisture sensor 2202. In this example, the second humidity level or moisture content is less than the first humidity level or moisture content. In an example, this invention can reduce the humidity level or moisture content of airflow from a window-based air conditioner when data from a wearable moisture sensor indicates that a person's skin is very moist. In an example, a wearable-sensor component can collect data concerning the person's skin moisture and/or body moisture level. In an example, a sleep-environment-modifying component can: change the humidity level of air and/or other gas surrounding a person; change the humidity level of air and/or other gas in communication with the surface of the person's body; and/or change the humidity or moisture level of airflow from a window-based air conditioner. Relevant example and component variations discussed elsewhere in this disclosure or in priority-linked disclosures can also be applied to this example, but are not repeated here to avoid narrative redundancy.

Figure 23:
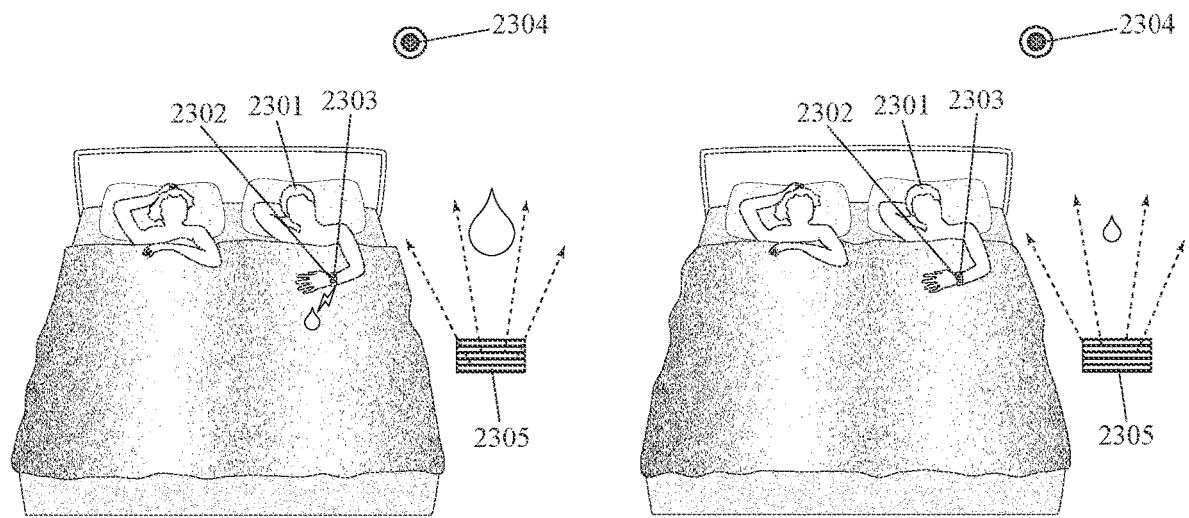
FIG. 23 shows a system for modifying a person's sleep environment which changes the humidity of air from a HVAC system based on a wearable moisture sensor.

The example of this invention shown in FIG. 23 is similar to the example shown in FIG. 22 except that it modifies airflow from a central heating, ventilation, and/or air conditioning (HVAC) system rather than airflow from a window-based air conditioner. FIG. 23 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin moisture and/or body moisture level; a sleep-environment-modifying component which changes the humidity level of a flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment shown in FIG. 23 comprises: moisture sensor 2302 worn by person 2301 that collects data concerning the person's skin moisture and/or body moisture level; a sleep-environment-modifying component 2304 which changes the humidity level of airflow from vent 2305 from a central heating, ventilation, and/or air-conditioning (HVAC) system; and a data-control component 2303 which controls the operation of sleep-environment-modifying component 2304 in order to automatically change the humidity level of airflow from vent 2305 based on data from moisture sensor 2302. In the left side of FIG. 23, airflow from vent 2305 has a first humidity level based on a first pattern of data from moisture sensor 2302. In the right side of FIG. 23, airflow from vent 2305 has been changed to have a second humidity level based on a second pattern of data from moisture sensor 2302. In this example, the second humidity level is less than the first humidity level.

In an example, this embodiment can help to selectively and differentially cool person 2301 when they get hot and sweaty. In an example, this embodiment can trigger a dryer flow of air from a central HVAC system when data from moisture sensor 2302 indicates that person 2301 is hot and sweaty. In an example, a dry flow of air can cool person 2301 by increasing evaporation of moisture from the person's skin. In an example, this embodiment can help to dry person 2301 when they get hot and sweaty. In an example, this embodiment can trigger a dryer flow of air from a central HVAC system when data from moisture sensor 2302 indicates that person 2301 is hot and sweaty. In an example, a dry flow of air can dry person 2301 by increasing evaporation of moisture from the person's skin. In an alternative example, this embodiment can increase the humidity level of airflow from a central HVAC system when data from moisture sensor 2302 indicates that a person's skin is too dry.

In an example, a wearable-sensor component can collect data concerning the person's skin moisture and/or body moisture level and a sleep-environment-modifying component can control the operation of a central heating, ventilation, and/or air-conditioning (HVAC) system. In an example, a wearable-sensor component can collect data concerning the person's skin moisture and/or body moisture level and a sleep-environment-modifying component can start or stop a central heating, ventilation, and/or air-conditioning (HVAC) system. Relevant example and component variations discussed elsewhere in this disclosure or in priority-linked disclosures can also be applied to this example, but are not repeated here to avoid narrative redundancy.

Figure 24:
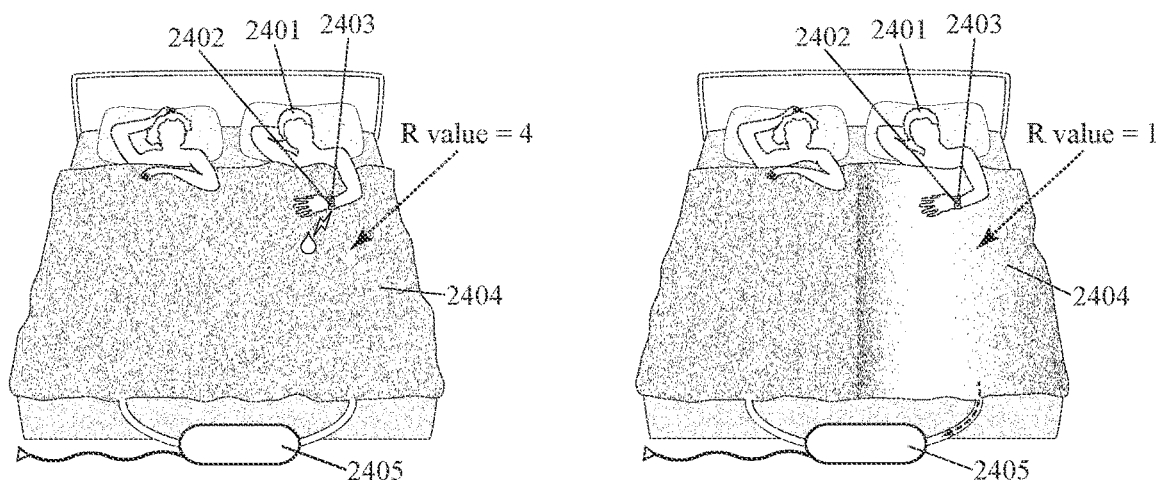
FIG. 24 shows a system for modifying a person's sleep environment which changes the insulation value of a blanket based on a wearable moisture sensor.

FIG. 24 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin moisture and/or body moisture; a sleep-environment-modifying component which changes the insulation value (e.g. R-value) of a blanket or other bedding layer over the person; and a data-control component which controls the operation of the sleep-environment-modifying component in order to automatically change the person's sleep environment based on data from the wearable-sensor component.

More specifically, the embodiment shown in FIG. 24 comprises: a wearable moisture sensor 2402 worn by person 2401; a sleep-environment-modifying component (further comprising air pump 2405 and inflatable blanket 2404) which changes the R-value of blanket 2404 over the person; and a data-control component 2403 which controls the operation of the sleep-environment-modifying component in order to automatically change the blanket's R-value based on data from wearable moisture sensor 2402. In this example, the data-control component 2303 is co-located with moisture sensor 2402 in a wrist band. In other examples, data-control component can be co-located with air pump 2405, part of a mobile communications device, or located elsewhere.

The left side of FIG. 24 shows this embodiment at a first point in time wherein the inflatable blanket has an (insulation) R-value of 4 based on a first pattern of data from moisture sensor 2402. The right side of FIG. 24 shows this embodiment at a second point in time wherein the blanket has been deflated to an (insulation) R-value of 1 based on a second pattern of data from moisture sensor 2402. In an example, when data from moisture sensor 2402 indicates that a person's skin is moist and/or sweaty, then this triggers deflation of the inflatable blanket to reduce the blanket's R-value which, in turn, reduces the temperature of air under the blanket over the person.

In an example, an inflatable blanket can have two sides with separately-adjustable inflation values in order to enable separate adjustment of the (insulation) R-values of two sides of the bed. In an example, these two sides can be separated by a central longitudinal axis from the head of the blanket to the foot of the blanket. In an example, when combined with wearable sensors which are worn by people who sleep on different sides of the bed, this comprises a system for differential adjustment of the temperature of the sleeping environments for two people in the same bed.

In another example, the R-value of a blanket can be adjusted by means other than differential inflation. In another example, the R-value of a blanket can be adjusted by changing the thickness of the blanket by activating an array of microscale actuators or a piezoelectric textile. In an example, a sleep-environment-modifying component can: change the thickness of a blanket or other bedding layer over the person; control MEMS actuators in a blanket or other bedding layer to change the R-value of the blanket or other bedding layer; and/or change the thickness of a sleeping bag. Relevant example and component variations discussed elsewhere in this disclosure or in priority-linked disclosures can also be applied to this example, but are not repeated here to avoid narrative redundancy.

Figure 25:
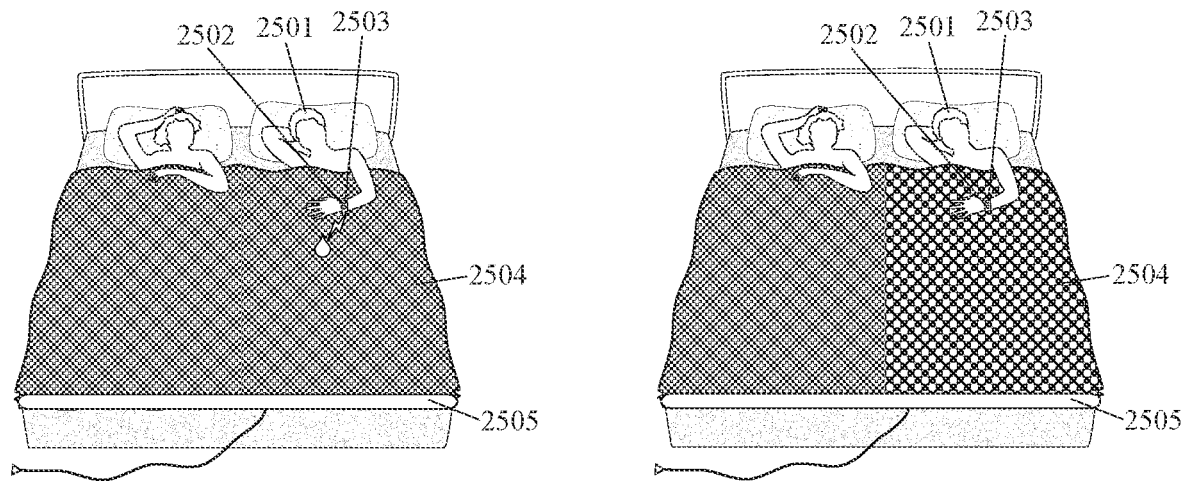
FIG. 25 shows a system for modifying a person's sleep environment which changes the porosity of a blanket based on a wearable moisture sensor.

FIG. 25 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin moisture and/or body moisture level; a sleep-environment-modifying component which changes the porosity of a blanket or other bedding layer covering the person; and a data-control component which controls the operation of the sleep-environment-modifying component in order to automatically change the person's sleep environment based on data from the wearable-sensor component.

More specifically, the embodiment shown in FIG. 25 comprises: a wearable moisture sensor 2502 worn by person 2501 which collects data concerning the person's skin moisture and/or body moisture level; a sleep-environment-modifying component (further comprising blanket control member 2505 and variable-porosity blanket 2504) which changes the porosity of the portion of blanket 2504 covering the person; and a data-control component 2503 which controls the operation of the sleep-environment-modifying component in order to automatically change the porosity of the portion of blanket 2504 covering the person based on data from the wearable moisture sensor 2502. In an example, blanket control member 2505 can change the porosity of variable-porosity blanket 2504 by sending a selected electric current through piezoelectric fibers, strands, or textiles in blanket 2504. In an example, blanket control member 2505 can change the porosity of variable-porosity blanket 2504 by activating microscale actuators in blanket 2504. In an example, activation of piezoelectric and/or microscale actuators in the blanket creates or enlarges pores in a blanket that makes the blanket more porous to airflow.

The left side of FIG. 25 shows this embodiment at a first time wherein variable-porosity blanket 2504 has a first porosity level which is based on a first pattern of data from wearable moisture sensor 2502. The right side of FIG. 25 shows this embodiment at a second time wherein the porosity of variable-porosity blanket 2504 has be changed to a second porosity level based on a second pattern of data from wearable moisture sensor 2502. In this example, the second porosity level is greater than the first porosity level. In an example, when data from wearable moisture sensor 2502 indicates that person 2501 is sweaty (and/or has a high skin moisture level), then this invention can trigger an increase in the porosity of blanket 2504. This enables greater circulation of fresh air over the person's body surface which can reduce their skin moisture level. In an example, the porosity levels of two sides of a blanket can be differentially adjusted to enable greater body surface airflow for a first person on a first side of the bed without substantively changing body surface airflow for a second person on second side of the bed. In an example, a sleep-environment-modifying component of this invention can: change the porosity of a blanket or other bedding layer covering a person; control MEMS actuators in a blanket or other bedding layer to change the porosity of the blanket or other bedding layer; or change the porosity of a sheet over a person. Relevant example and component variations discussed elsewhere in this disclosure or in priority-linked disclosures can also be applied to this example, but are not repeated here to avoid narrative redundancy.

Figure 26:
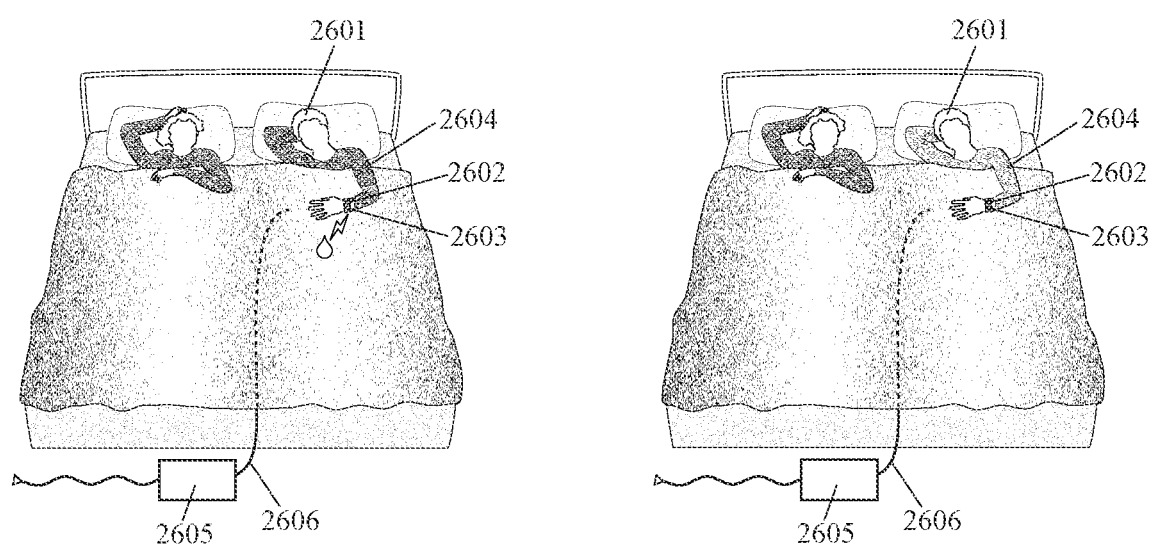
FIG. 26 shows a system for modifying a person's sleep environment which changes the porosity of a garment on a wearable moisture sensor.

FIG. 26 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin moisture and/or body moisture level; a sleep-environment-modifying component which changes the porosity of a garment worn by the person; and a data-control component which controls the operation of the sleep-environment-modifying component in order to automatically change the person's sleep environment based on data from the wearable-sensor component.

The left side of FIG. 26 shows this example at a first point of time during which a moisture sensor 2602 collects data concerning the skin moisture of person 2601. The right side of FIG. 26 shows this example at a second point in time during which the person's garment 2604 has been made more porous in response to data from moisture sensor 2602. The example shown in FIG. 26 comprises: moisture sensor 2602 which collects data concerning the skin moisture level of person 2601; adjustable-porosity garment 2604 whose porosity is adjusted based on data from moisture sensor 2602; and data-control component 2603 which controls changes in garment porosity based on data from moisture sensor 2602.

In an example, garment 2604 can be an upper body garment, a lower body garment, or a combined upper and lower body garment. In an example, garment 2604 can be connected to an electromagnetic control unit by wires. In an example, garment 2604 can be in wireless electromagnetic communication with an electromagnetic control unit. In this example, garment 2604 further comprises piezoelectric fabric whose porosity is changed by electromagnetic energy coming through wire 2606 from electromagnetic control unit 2605. In an example, application of electromagnetic energy to piezoelectric fabric decreases the width of fibers in a weave and thereby increases fabric porosity. In an example, garment 2604 can comprise a textile with an array of inflatable fibers. In an example, the porosity of garment 2604 can be adjustable by inflation or deflation of this array of inflatable fibers.

In an example, adjustable-porosity garment 2604 has a first porosity level when the skin moisture of person 2601 is at a first moisture level and the porosity of adjustable-porosity garment 2604 is changed to a second porosity level when the skin moisture of person 2601 changes to a second moisture level. In an example, the second moisture level is greater than the first moisture level and the second porosity level is greater than the first porosity level. In an example, an automatic increase in a garment's porosity based on an increase in skin moisture can help to evaporate and remove excess skin moisture, such as during a hot flash while a person sleeps. Relevant example and component variations discussed elsewhere in this disclosure or in priority-linked disclosures can also be applied to this example, but are not repeated here to avoid narrative redundancy.

Figure 27:
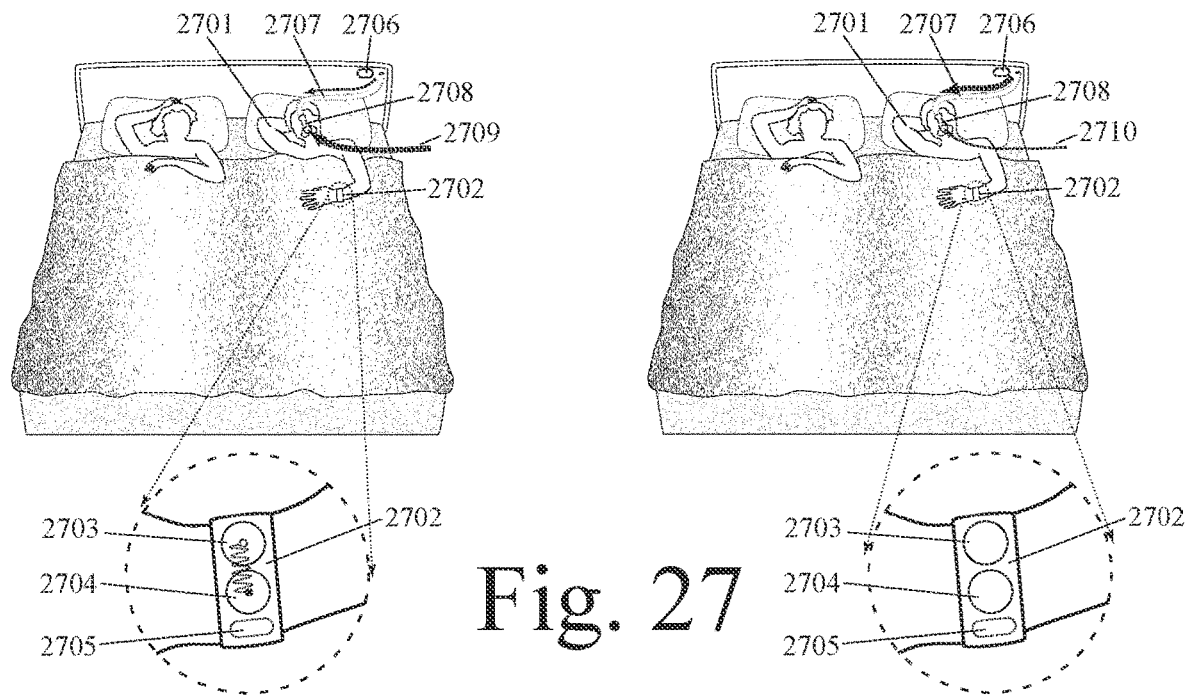
FIG. 27 shows a system for modifying a person's sleep environment which changes a person's air source based on a wearable light energy sensor.

FIG. 27 shows an example of how this invention can be embodied in a system, device, and method that uses wearable technology to collect data for automatic modification of a person's sleep environment comprising: a wearable-sensor component that is configured to be worn by a person, wherein this sensor component collects data concerning light absorbed by the person's body or reflected from the person's body; a sleep-environment-modifying component which changes the mixture or composition of air and/or other gas which the person breathes; and a data-control component which controls the operation of the sleep-environment-modifying component in order to automatically change the person's sleep environment based on data from the wearable-sensor component.

The example shown in FIG. 27 comprises: light-emitting member 2703; light sensor 2704; power source or transducer 2705; breathable gas tube 2707; respiratory mask 2708; and data-control component 2706. In this example, data-control component 2706 changes the composition of air and/or gas which person 2701 breathes based on changes in data from light sensor 2704. In an example, when data from light sensor 2704 indicates a drop in the person's oxygen saturation level, then data-control component 2706 increases oxygen-rich gas flow through gas tube 2707.

In an example, light-emitting member 2703 and light sensor 2704 are co-located on wrist band 2702. In other examples, a light-emitting member and a light sensor can be co-located on another type of wearable device or incorporated into a garment that is worn by a person while they sleep. In an example, light-emitting member 2703 emits light energy toward the person's body. In an example, a light-emitting member directs light energy toward a portion of the person's body and a light sensor measures light reflected off the surface of the person's body or light passing through a portion of the person's body.

In an example, light energy emitted from light-emitting member 2703 can be coherent light. In an example, this light energy can be non-coherent light. In an example, light-emitting member 2703 can emit light in the visible portion of the light spectrum, in the infrared or near infrared portion of the light spectrum, and/or in the ultraviolet portion of the light spectrum. In an example, light sensor 2704 collects data concerning light energy which is reflected from, transmitted through, or absorbed by tissue of the person's body. In an example, light energy which is reflected from, transmitted through, or absorbed by body tissue is analyzed using spectroscopy. In an example, light sensor 2704 can be a spectroscopic sensor.

In an example, analysis of data from light sensor 2704 can provide information concerning the person's oxygen saturation level. In an example, spectral analysis of light reflected from, transmitted through, or absorbed by the person's body tissue can indicate whether the person's body is receiving sufficient oxygen. In an example, when data from light sensor 2704 indicates that person 2701 has low oxygenation, then this invention can increase a flow of oxygen-rich gas through breathable gas tube 2707 into mask 2708. This increases the proportion and/or mixture of oxygen in gas breathed by the person through mask 2708. In an example, this can help to increase the person's oxygen level during episodes of obstructive sleep apnea or other temporary adverse respiratory events during sleep. In another example, when data from light sensor 2704 indicates low oxygen saturation, then this invention can increase the pressure of gas flow through gas tube 2707. This can provide a temporary increase in airway pressure which can address an episode of obstructive sleep apnea.

The left side of FIG. 27 shows a first level of oxygen-rich air coming through breathable gas tube 2707 in response to a first level of oxygen saturation based on data from light sensor 2704. The right side of FIG. 27 shows a second level of oxygen-rich air coming through breathable gas tube 2707 in response to a second level of oxygen saturation based on data from light sensor 2704. In this example, the second level of oxygen-rich air is greater than the first level of oxygen-rich air. This is indicated by a thicker dotted-line "flow arrow" following breathable gas tube 2707 on the right side of FIG. 27 than on the left side of FIG. 27. In this example, the second level of oxygen saturation is lower than the first level of oxygen saturation. In this example, a lower level of oxygen saturation at the second point in time shown on the right side of FIG. 27 triggers a greater level of oxygen-rich air. In an example, an automatic increase in the oxygen level based on a person's low oxygen saturation can help to prevent the person having prolonged oxygen deprivation.

In an example, a wearable light sensor can collect data concerning light energy which is reflected from, transmitted through, and/or absorbed by a person's body. This data can then be analyzed and one or more selected data patterns can trigger one or more selected changes in the mixture of air and/or other gas from multiple sources which the person breathes. In an example, a first gas source can be a non-ambient gas source (such as pure oxygen) and a second gas source can be ambient air. In an example, this invention can adjust the mixture, relative volume, rate, concentration, pressure and/or temperature of gas flow from a non-ambient source vs. ambient air based on data from a wearable light sensor. Relevant example and component variations discussed elsewhere in this disclosure or in priority-linked disclosures can also be applied to this example, but are not repeated here to avoid narrative redundancy.

Figure 28:
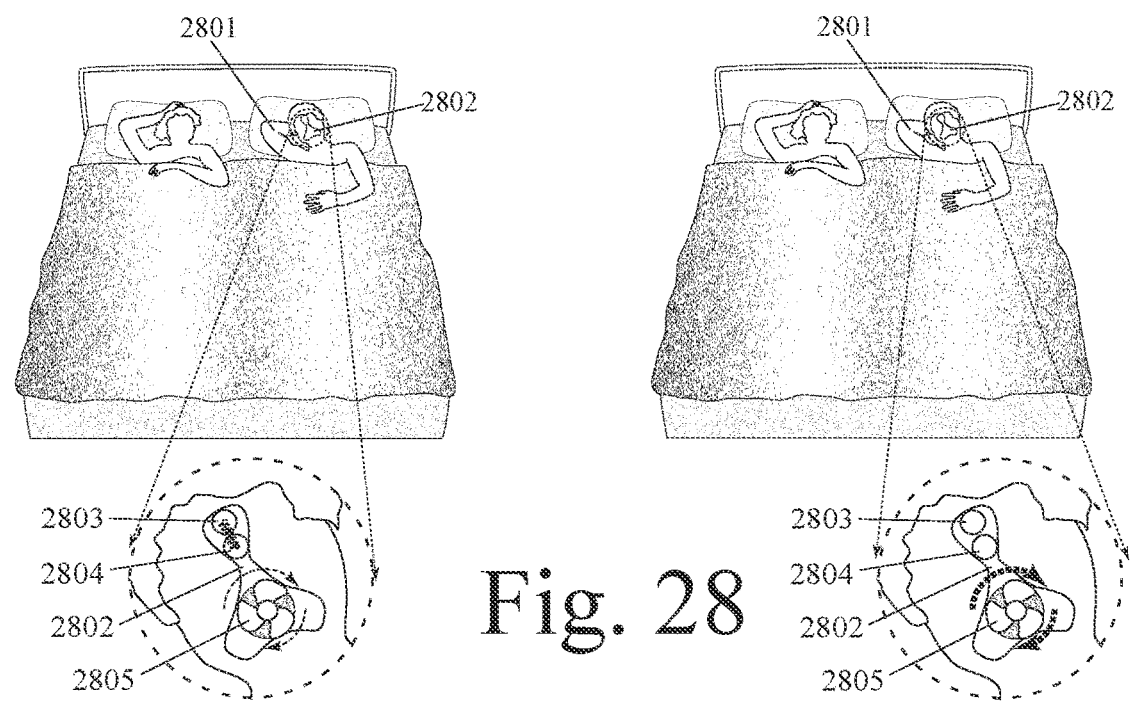
FIG. 28 shows a system for modifying a person's sleep environment which changes a person's air pressure based on a wearable light energy sensor.

FIG. 28 shows an example of how this invention can be embodied in a system, device, and method that uses wearable technology to collect data for automatic modification of a person's sleep environment comprising: a wearable-sensor component that is configured to be worn by a person, wherein this sensor component collects data concerning light absorbed by the person's body or reflected from the person's body; a sleep-environment-modifying component which changes the pressure of air and/or other gas which the person breathes; and a data-control component which controls the operation of the sleep-environment-modifying component in order to automatically change the person's sleep environment based on data from the wearable-sensor component.

Specifically, the example shown in FIG. 28 comprises: light-emitting member 2803; light sensor 2804; and air-moving member 2805. In this example, these three components are co-located as parts of respiratory air mask 2802 which is worn by person 2801. In this example, the operation of air-moving member 2803 is controlled by analysis of data from light sensor 2804. In an example, air-moving member 2803 can be turned on or off based on data from light sensor 2804. In an example, the flow speed of air moved by air-moving member 2803 can be increased or decreased based on data from light sensor 2804. In an example, air-moving member 2803 can be an impellor or fan. In an example, the rotational speed of air-moving member 2803 can be increased or decreased based on data collected by light sensor 2804.

In an example, light-emitting member 2803 directs a beam of light toward a portion of the body of person 2801. In an example, this beam of light is reflected off of the surface of the person's body. In an example, this beam of light passes through the tissue of the person's body. In an example, this beam of light can be selected from the group consisting of: visible light; infrared light; near infrared light; and ultraviolet light. In an example, this beam of light can be coherent light. In an example, this beam of light can be non-coherent light.

In an example, light sensor 2804 collects data concerning light that is reflected from, passes through, and/or is absorbed by a portion of the person's body. In an example, data from light sensor 2804 can be analyzed using spectroscopic analysis. In an example, the spectrum of light which is reflected from, transmitted through, and/or absorbed by body tissue can be analyzed. In an example, spectral analysis of light which is reflected from, transmitted through, and/or absorbed by body tissue can provide information concerning physiological processes or medical conditions in the person's body. In an example, spectral analysis of light reflected from, transmitted through, and/or absorbed by body tissue can provide information concerning oxygen saturation level, respiratory function, glucose level, body temperature, and/or cardiac function. In an example, light sensor 2804 measures the amount, intensity, or spectrum of light which is reflected from tissue in a portion of the body of person 2801. In an example, light sensor 2804 measures the amount, intensity, or spectrum of light which passes through tissue in a portion of the body of person 2801.

The left side of FIG. 28 shows air-moving member 2803 spinning at a first speed based on a first pattern of data from light sensor 2804. The right side of FIG. 28 shows air-moving member 2803 spinning at a second speed based on a second pattern of data from light sensor 2804. In an example, the second speed is faster than the first speed. In an example, the faster speed can increase the pressure of airflow which person 2801 breathes in order to provide positive airway pressure to address an episode of temporary airway obstruction. In an example, when data from light sensor 2804 indicates a low level of oxygen saturation, then this invention increases the speed of air-moving member 2803 in order to provide increased air pressure to open up the person's airway. In this example, this invention can function as a bio-interactive mask to address obstructive sleep apnea. In an example, respiratory air mask 2802 can address obstructive sleep apnea by increasing the rotation rate of air-moving member 2803 (and thus the pressure of air breathed by person 2801) in response to lower oxygen saturation as measured by data from light sensor 2804. Relevant example and component variations discussed elsewhere in this disclosure or in priority-linked disclosures can also be applied to this example, but are not repeated here to avoid narrative redundancy.

Figure 29:
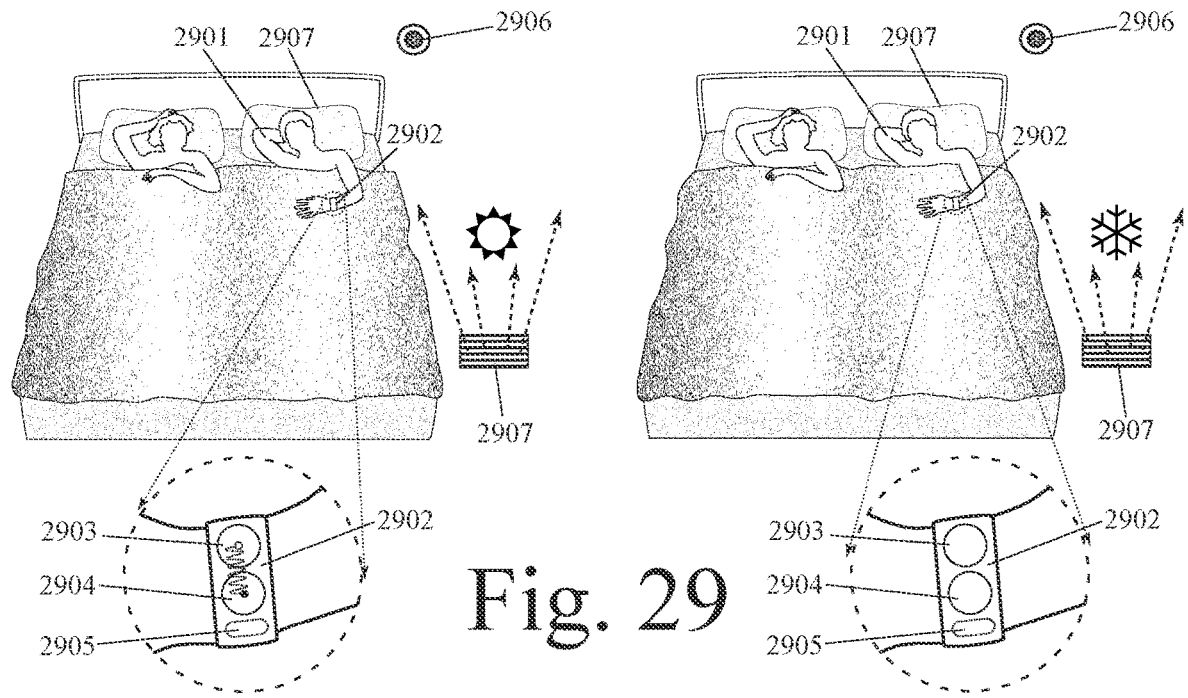
FIG. 29 shows a system for modifying a person's sleep environment which changes the temperature of air from a HVAC system based on a wearable light energy sensor.

FIG. 29 shows an example of how this invention can be embodied in a system, device, and method that uses wearable technology to collect data for automatic modification of a person's sleep environment comprising: a wearable-sensor component that is configured to be worn by a person, wherein this sensor component collects data concerning light absorbed by the person's body or reflected from the person's body; a sleep-environment-modifying component which changes the temperature, flow rate, direction, or inter-room distribution of a flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the example shown in FIG. 29 comprises: light-emitting member 2903; light sensor 2904; heating, ventilation, and/or air-conditioning (HVAC) system control unit 2906; and data-control component 2905. In this example, data-control component 2905 controls the temperature, flow rate, direction, and/or inter-room distribution of an HVAC system based on data from light sensor 2904. In this example, air from the HVAC system enters the bedroom of person 2901 through vent 2907. In another example, the inter-room distribution of airflow from an HVAC system can be automatically changed by selectively opening or closing air valves in duct work.

In this example, light-emitting member 2903, light sensor 2904, and data-control component 2905 are co-located as parts of a wrist-worn band 2902. In another example, these components can be co-located in another wearable device or integrated into a garment. In another example, a data-control component can be part of a mobile communication device such as a smart phone. In another example, a data-control component can be co-located with a HVAC system control unit. In an example, this device can be part of an overall home environmental control system.

In an example, light-emitting member emits a beam of light which is directed toward the body of person 2901. In an example, this beam of light is selected from the group consisting of: visible light, infrared light, near-infrared light, and ultraviolet light. In an example, this beam of light is coherent. In an example, this beam of light is non-coherent. In an example, this beam of light is reflected off the surface of the person's body and sensed by light sensor 2904. In an example, the beam of light is partially transmitted through the tissue of the person's body and sensed by light sensor 2904. In an example, light sensor 2904 collects data concerning light that is reflected from, transmitted through, and/or absorbed by the person's body.

In an example, light sensor 2904 collects data concerning the amount, intensity, and/or spectrum of light that is reflected from, transmitted through, and/or absorbed by the person's body. In an example, data from light sensor 2904 is analyzed using spectroscopic analysis. In an example, spectroscopic analysis of data from light sensor 2904 provides information concerning oxygen saturation, respiratory function, glucose level, cardiac function, body temperature, sleep status, and/or sleep phase. In an example, light sensor 2904 measures the intensity and/or spectrum of light reflected from the tissue and/or surface of a portion of the body of person 2901. In an example, light sensor 2904 measures the intensity and/or spectrum of light passing through the tissue of a portion of the body of person 2901. In an example, light sensor 2904 measures the intensity and/or spectrum of light absorbed by the tissue of a portion of the body of person 2901. In an example, light sensor 2904 is a spectroscopic sensor. In an example, the spectrum of light reflected, transmitted, or absorbed by tissue is used to collect information on the level of oxygen in the blood or tissue of person 2901.

The left side of FIG. 29 shows this example at a first point in time wherein: there is a first pattern of data collected from light sensor 2904; and air from vent 2907 is set to be at a first temperature. The right side of FIG. 29 shows this example at a second point in time wherein: there is a second pattern of data collected from light sensor 2904; and air from vent 2907 is set to be at a second temperature. In an example, the second temperature is lower than the first temperature, as indicated by the "sun" symbol above vent 2907 on the left side of FIG. 29 and the "snowflake" symbol above vent 2907 on the right side of FIG. 29. In an example, the first pattern of data (on the left side of this figure) triggers the lower airflow temperature (on the right side of this figure) after a lag time. In an example, the second pattern of data (on the right side of this figure) triggers the lower airflow temperature (on the right side of this figure) in real time (virtually immediately).

In an example, analysis of data from light sensor 2904 can predict when person 2901 is likely to experience a temporary biologically-induced upswing in temperature such as a hot flash. In an example, such prediction can be used to trigger a prophylactic decrease in airflow temperature from vent 2907, before the upswing in body temperature occurs, so as to mitigate (or even avoid) the effects of the upswing. Since biologically-induced changes in body temperature can occur so rapidly, it can be advantageous to use predictive data from a wearable sensor which can detect changes in body chemistry, function, and/or temperature sooner than a non-wearable sensor. Also, in an example, analysis of data from light sensor 2904 can predict the duration of a temporary biologically-induced upswing in body temperature. The predicted duration of biologically-induced upswing in body temperature can be used to control the duration of a temporary decrease in air temperature from vent 2907.

In an example, HVAC system control unit 2906 can temporarily decrease the temperature of all air coming from the HVAC system throughout the entire house in response to data from light sensor 2904. In an example, HVAC system control unit 2906 can adjust the inter-room distribution of thermal energy via an HVAC system. In an example, HVAC system control unit 2906 can transfer thermal energy from one room to another within a home in order to temporarily adjust temperature of the room in which person 2901 is sleeping based on data from light sensor 2904. Relevant example and component variations discussed elsewhere in this disclosure or in priority-linked disclosures can also be applied to this example, but are not repeated here to avoid narrative redundancy.

Figure 30:
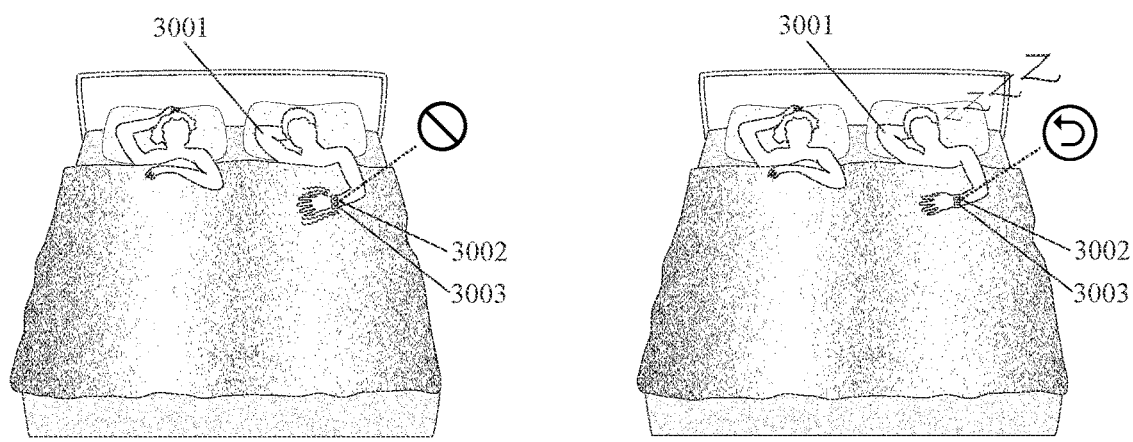
FIG. 30 shows a system for modifying a person's sleep environment which changes an electronic communication auto-response based on a motion sensor.

FIG. 30 shows an example of how this invention can be embodied in a system, device, and method that uses wearable technology to collect data for automatic modification of a person's sleep environment comprising: a wearable-sensor component that is configured to be worn by person 3001, wherein this sensor component collects data concerning the person's body motion or configuration; a sleep-environment-modifying component which changes the filtering, auto-response, notification mode, notification timing, or user interface for communications sent to the person; and a data-control component which controls the operation of the sleep-environment-modifying component in order to automatically change the person's sleep environment based on data from the wearable-sensor component.

The example shown in FIG. 30 comprises: motion sensor 3002; and wireless communications component 3003. In this example, motion sensor 3002 is an accelerometer. In other examples, motion sensor 3002 can be a gyroscope or inclinometer. In this example, wireless communications component 3003 can receive phone calls, text messages, and/or emails. In this example, a selected pattern of data from motion sensor 3002 triggers a change in the filtering, auto-response, notification mode, notification timing, or user interface for communications sent to wireless communications component 3003. In an example, when data from motion sensor 3002 indicates that person 3001 is probably sleeping, then this triggers a change in the filtering, auto-response, notification mode, notification timing, or user interface for communications sent to wireless communications component 3003.

In this example, when data from motion sensor 3002 indicates that person 3001 is probably sleeping, then this triggers an auto-response message to communications sent to wireless communications component 3003. In an example, this auto-response message can be—"I am unavailable at this time", "I cannot answer now but please leave a message," "I am asleep," or simply "Z-Z-Z-Z." In this example, lack of an auto-response message is indicated by the "circle and diagonal slash" symbol shown on the left side of FIG. 30. In this example, activation of an auto-response message is indicated by the "U-turn arrow" symbol shown on the right side of FIG. 30.

The left side of FIG. 30 shows this example at a first point in time, wherein a first pattern of data from motion sensor 3002 indicates a first level of movement by person 3001. The right side of FIG. 30 shows this example at a second point in time, wherein a second pattern of data from motion sensor 3002 indicates a second level of movement by person 3001. In this example, the first level of movement is greater than the second level of movement, as is symbolically-indicated by wiggly dotted lines around f the person's hand on the left side of FIG. 30, but not on the right side of FIG. 30. In this example, the first level of movement (on the left side of FIG. 30) indicates that the person is probably awake and the second level of movement (on the right side of FIG. 30) indicates that the person is probably sleeping.

In this example, wireless communications component 3003 operates without an auto-response function when the person is probably awake (as shown on the left side of FIG. 30) based on data from motion sensor 3002 and operates with an auto-response function when the person is probably asleep (as shown on the right side of FIG. 30) based on data from motion sensor 3002. In an example, when the person is awake, then this invention can provide the person with normal notifications of incoming communications. However, when the person is asleep, then this invention can mute notifications of incoming communications and provide communication senders with an auto-response message so that they know that the person is not just ignoring their communication. In an example, this auto-response message can generally say that the person is not available to receive communications at this time or can explicitly say that the person is sleeping. In an example, this invention can enable a person to maintain as much electronic connectivity as possible without having their sleep disturbed.

In other examples, data from a wearable motion sensor can be used to automatically change a user interface mode for communications sent to the person from a touch-based user interface to a sound-based interface or from a visual-based user interface to a sound-based interface; change an auto-response message given in response to communications sent to the person; change the filtering of communications sent to the person; and/or change which communication types or sources result in immediate notification of the person. Relevant example and component variations discussed elsewhere in this disclosure or in priority-linked disclosures can also be applied to this example, but are not repeated here to avoid narrative redundancy.

Figure 31:
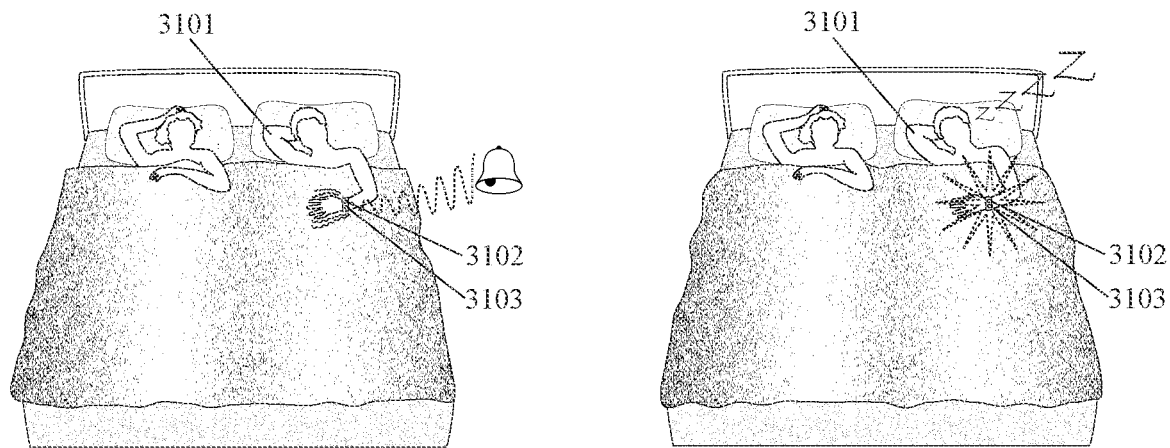
FIG. 31 shows a first system for modifying a person's sleep environment which changes the mode of electronic communication based on a motion sensor.

FIG. 31 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which changes a communication notification mode for communications sent to the person from sound-based notification to visual-based notification, or vice versa; and a data-control component which controls the operation of the sleep-environment-modifying component in order to automatically change the person's sleep environment based on data from the wearable-sensor component.

More specifically, the example in FIG. 31 comprises: motion sensor 3102; and wireless communication component 3103. In this example, the communication notification mode of wireless communication component 3103 is changed based on data from motion sensor 3102. In this example, the communication mode is changed from a sound-based notification mode to a light-based notification mode when data from motion sensor 3102 indicates that person 3101 is probably sleeping. In an example, a light-based notification mode is less likely to disturb the person's sleep than a sound-based notification mode. This can enable person 3101 to maintain electronic connectivity while awake without being disturbed by incoming communications when asleep. In this example, the person's sleep status is inferred by a lack of motion detected by motion sensor 3102. In an example, specific patterns of motion detected by motion sensor 3102 can indicate that a person is probably awake and lack of those specific patterns of motion can indicate that the person is probably sleeping.

The left side of FIG. 31 shows this example at a first point in time wherein person 3101 is evaluated as being awake based on patterns of data from motion sensor 3102 which indicate a high level of movement and/or a specific pattern of movement. Accordingly, at this first point in time, incoming communications to person 3101 trigger a sound-based notification indicated by the "bell" symbol on the left side of FIG. 31. The right side of FIG. 31 shows this example at a second point in time wherein person 3101 is evaluated as being asleep based on patterns of data from motion sensor 3102 which indicate a low level of movement and/or lack of a specific pattern of movement. Accordingly, at this second point in time, incoming communications to person 3101 trigger a light-based notification, as symbolically indicated by the dotted lines extending from the wrist band on the right side of FIG. 31. In an example, light-based notification is less likely to disturb the person's sleep than is sound-based notification. In an example, this change in notification mode based on sleep status can help person 3101 to maintain electronic connectivity while they are awake, without having incoming communications disturb them when they are asleep. Relevant example and component variations discussed elsewhere in this disclosure or in priority-linked disclosures can also be applied to this example, but are not repeated here to avoid narrative redundancy.

Figure 32:
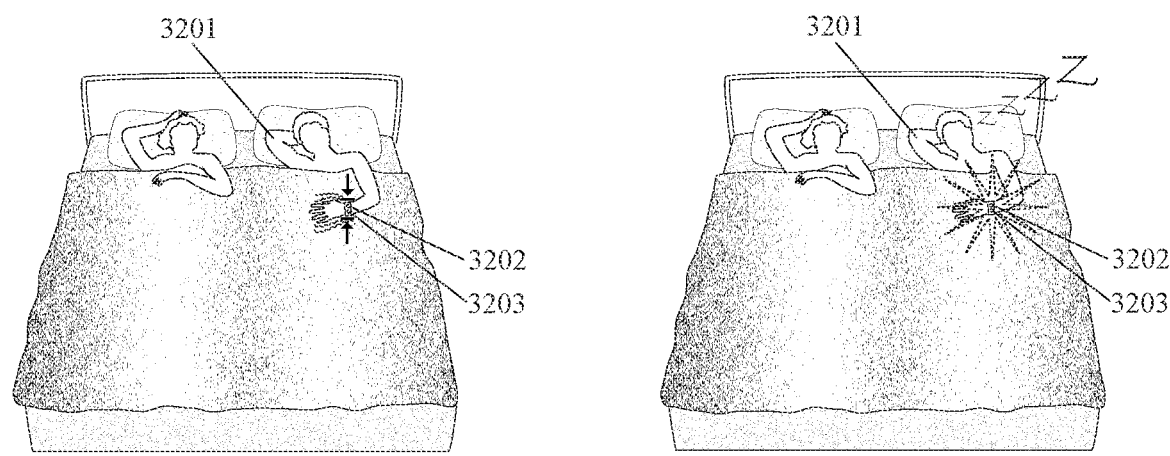
FIG. 32 shows a second system for modifying a person's sleep environment which changes the mode of electronic communication based on a motion sensor.

FIG. 32 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which changes a communication notification mode for communications sent to the person from tactile-based notification to visual-based notification, or vice versa; and a data-control component which controls the operation of the sleep-environment-modifying component in order to automatically change the person's sleep environment based on data from the wearable-sensor component.

More specifically, the example shown in FIG. 32 comprises: motion sensor 3202; and wireless communication component 3203. In this example, the communication notification mode of wireless communication component 3203 is changed based on data from motion sensor 3202. In this example, the communication mode is changed from a tactile-based notification to a light-based notification when data from motion sensor 3202 indicates that person 3201 is probably sleeping. The left side of FIG. 32 shows this example at a first point in time wherein person 3201 is awake, based on analysis of data from motion sensor 3202 which indicates a high level of movement and/or a specific pattern of movement. Accordingly, at this first point in time, incoming communications to person 3201 trigger a tactile-based notification. In this example, tactile-based notification comprises a mild contraction of the wrist band which houses motion sensor 3202 and wireless communication component 3203. In another example, tactile-based notification can comprise one or more moving members of a wearable device which move over the surface of the person's skin when there is an incoming communication.

The right side of FIG. 32 shows this example at a second point in time wherein person 3201 is asleep, based on analysis of data from motion sensor 3202 which indicates a low level of movement and/or lack of a specific pattern of movement. On the right side of FIG. 32, the communication mode has been changed to light-based notification. In an example, light-based notification is less likely to disturb the person's sleep than is tactile-based notification. In an example, this example can help a person to maintain electronic connectivity while they are awake without having incoming communications disturb them when they are asleep.

In this example, changes in data from a wearable motion sensor can be used to trigger a change in the communication notification mode of a wearable communications device. In an example, changes in data from a wearable motion sensor can be used to trigger a change in the communication notification mode of a non-wearable communications device. In an example, changes in data from a wearable motion sensor can be used to trigger a change in the communication notification mode of a smart phone or other non-wearable mobile communications device. In an example a wearable device with a motion sensor can be in wireless communication with a smart phone or other non-wearable mobile communications device. In an example, when data from a wearable motion sensor indicates that a person is probably sleeping, then this can trigger a change in the communication notification mode of a smart phone or other non-wearable mobile communications device or mute sound-based communication notifications from a smart phone or other mobile communications device. Relevant example and component variations discussed elsewhere in this disclosure or in priority-linked disclosures can also be applied to this example, but are not repeated here to avoid narrative redundancy.

Figure 33:
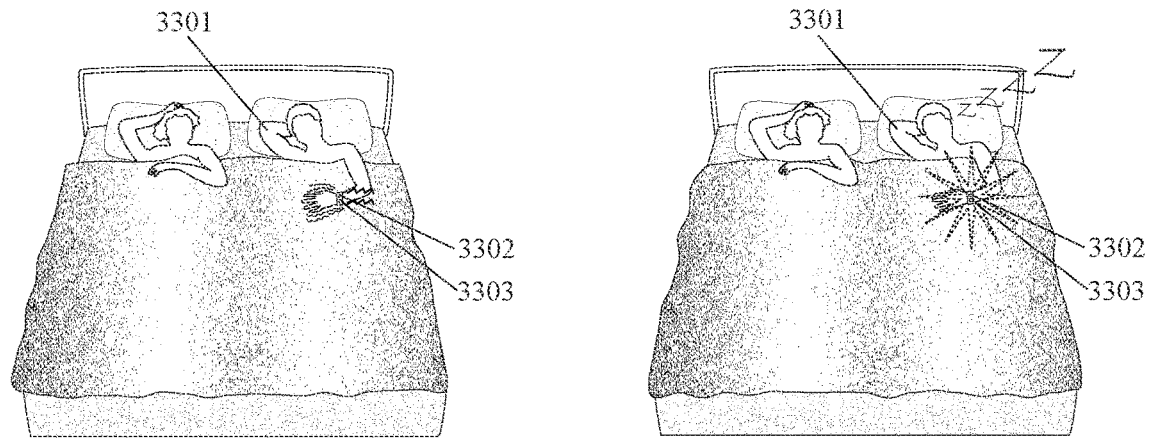
FIG. 33 shows a third system for modifying a person's sleep environment which changes the mode of electronic communication based on a motion sensor.

As shown in FIG. 33, this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which changes a communication notification mode for communications sent to the person from vibration-based notification to visual-based notification, or vice versa; and a data-control component which controls the operation of the sleep-environment-modifying component in order to automatically change the person's sleep environment based on data from the wearable-sensor component. Specifically, the example shown in FIG. 33 comprises: wearable motion sensor 3302; and wireless communication component 3303, wherein a communication notification mode of this component is changed based on data from motion sensor 3302. In this example, the communication mode is changed from a vibration-based notification mode to a light-based notification mode when data from motion sensor 3302 indicates that person 3301 is probably sleeping. In an example, sleep status can be inferred from analysis of patterns of data from motion sensor 3302. In an example, movements of a particular magnitude, frequency, or configuration can indicate that person 3301 is probably awake. In an example, lack of such movements for a selected period of time can indicate that person 3301 is probably asleep. In an alternative example, the person's sleep status can be determined by a camera attached to the headboard which detects a sequence of little "Z" symbols ascending from the person's head.

The left side of FIG. 33 shows this example at a first point in time wherein person 3301 is probably awake based on analysis of data from motion sensor 3302 which indicates a selected pattern, amount, frequency, or configuration of body motion. Accordingly, at this first point in time, incoming communications to person 3301 trigger a vibration-based notification. The right side of FIG. 33 shows this example at a second point in time wherein person 3301 is probably asleep based on analysis of data from motion sensor 3302 which indicates the lack of a selected pattern, amount, frequency, or configuration of body motion. Accordingly, at this second point in time, incoming communications to person 3301 trigger a light-based notification. In an example, light-based notification is less likely to disturb the person's sleep than vibration-based notification. In an example, this example embodiment of the invention can help person 3301 to maintain electronic connectivity when awake, without having incoming communications disturb them when asleep. Relevant example and component variations discussed elsewhere in this disclosure or in priority-linked disclosures can also be applied to this example, but are not repeated here to avoid narrative redundancy.

Figure 34:
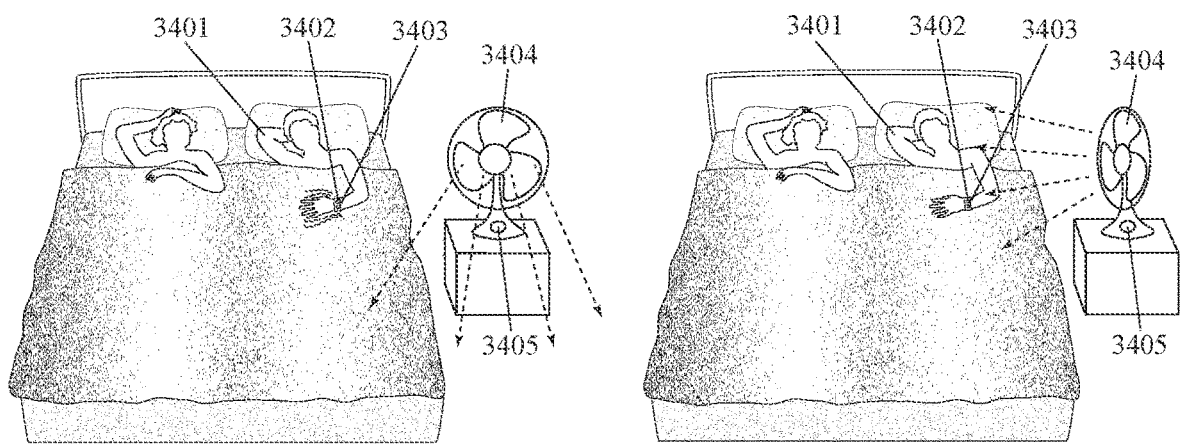
FIG. 34 shows a system for modifying a person's sleep environment which changes airflow from a fan based on a motion sensor.

FIG. 34 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which changes the direction of a flow of air coming from a portable fan or ceiling fan; and a data-control component which controls the operation of the sleep-environment-modifying component in order to automatically change the person's sleep environment based on data from the wearable-sensor component. The left portion of this figure shows this example at a first point in time and the right portion of this figure shows this example at a second point in time, in sequence, to show how sensor data is used to modify the person's sleep environment.

More specifically, the example shown in FIG. 34 comprises: wearable motion sensor 3402; power source or transducer 3403; portable fan 3404; and data-control component 3405 which changes the direction of airflow from portable fan 3404 based on data from wearable motion sensor 3402. In an example, when data collected by wearable motion sensor 3402 indicates a selected amount, frequency, and/or configuration of body motion, then data-control component 3405 moves portable fan 3404 so as to direct airflow toward person 3401. In an example, when data collected by wearable motion sensor 3402 indicates a selected amount, frequency, and/or configuration of body motion, then the data-control component turns on portable fan 3404.

The left side of FIG. 34 shows active movement of the person's hand which is detected by data collected from motion sensor 3402. The right side of FIG. 34 shows portable fan 3404 having been turned toward the person by data-control component 3405 in response to active movement of the person's hand. In this example, a high level of motion by person 3401 has triggered airflow from a portable fan to be directed toward the person. For example, airflow can be directed toward the person when they are awake, but not when they are asleep. In another example, a low level of motion by person 3401 can trigger airflow from a portable fan to be directed toward the person. For example, airflow can be directed toward the person when they are asleep, but not when they are awake. In an example, if a person becomes restless in their sleep when they are too warm, then this device can direct airflow toward the person when they transition from a period of less movement to a period of greater movement. In an example, if a person becomes restless in their sleep when they are too cold, then this device can direct airflow away from the person when they transition from a period of less movement to a period of greater movement.

In this example, the data-control component is co-located with the portable fan. In an example, a data-control component can be co-located with motion sensor 3402 on a wrist band or other wearable device. In an example, a data-control component can be part of a non-wearable electronic device such as a smart phone. In this example, the fan is a portable fan which rests on a surface in the person's bedroom. In another example, a fan can be a ceiling fan or a fan which is attached to the bed headboard. In an example, a wearable motion sensor can collect data concerning a person's body motion or configuration and cause changes in: the direction of a flow of air and/or other gas which the person breathes; the flow of air and/or other gas in communication with the surface of the person's body; or the operation of a portable fan or blower which directs airflow toward the person's body. Relevant example and component variations discussed elsewhere in this disclosure or in priority-linked disclosures can also be applied to this example, but are not repeated here to avoid narrative redundancy.

Figure 35:
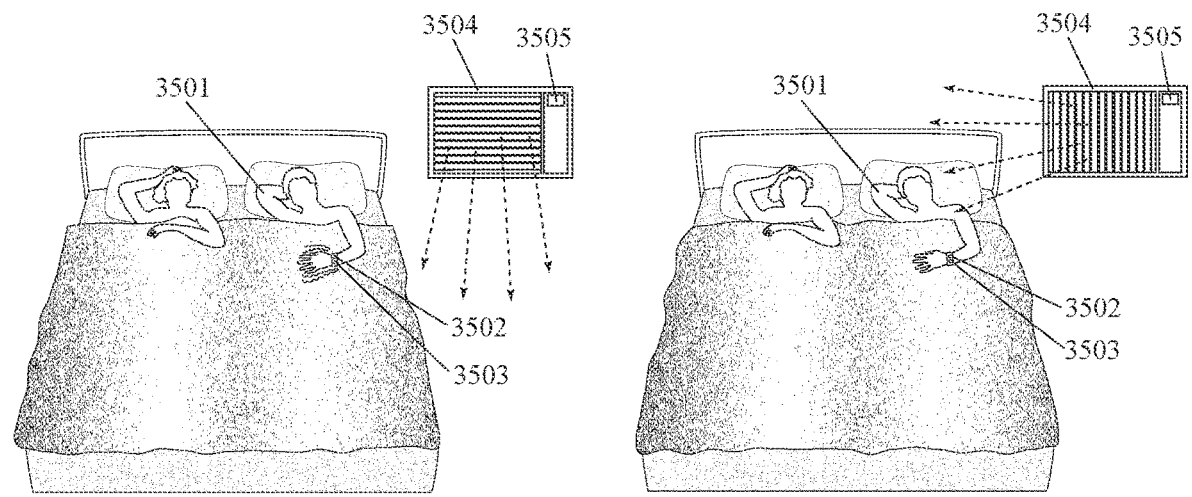
FIG. 35 shows a system for modifying a person's sleep environment which changes airflow from a window air conditioner based on a motion sensor.

The example of this invention which is shown in FIG. 35 is similar to the one shown in FIG. 34, except that airflow comes from a window-based air conditioner rather than a fan. A significant difference is that a window-based air conditioner can change the temperature of airflow as well as the direction and volume of airflow. FIG. 35 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which changes the direction of a flow of air from a window-based air conditioner; and a data-control component which controls the operation of the sleep-environment-modifying component in order to automatically change the person's sleep environment based on data from the wearable-sensor component.

More specifically, the example shown in FIG. 35 comprises: wearable motion sensor 3502; power source or transducer 3503; window-based air conditioner 3504; and data-control component 3505 which controls the operation of window-based air conditioner 3504 based on data from wearable motion sensor 3502. In an example, wearable motion sensor 3502 collects data concerning the person's body motion or configuration and data-control component 3505 changes the direction, volume, or temperature of airflow from window-based air conditioner 3504. In this example, a decrease in body motion from the left side of FIG. 35 to the right side of FIG. 35, as detected by wearable motion sensor 3502, triggers a shift in the direction of airflow from window-based air conditioner 3504 toward person 3501. In an alternative example, an increase in body motion could trigger a shift in the direction of airflow from window-based air conditioner 3504 toward person 3501. In an example, a shift in the direction of airflow from a window-based air conditioner can be implemented by changing the orientation of slats or vents in the outflow pathway of the air conditioner.

In the example shown in FIG. 35, a change in body motion detected by a motion sensor triggers a change in the direction of airflow from a window-based air conditioner. In another example, a change in body motion detected by a motion sensor can trigger a chance in the volume or speed of airflow from a window-based air conditioner. In another example, a change in body motion detected by a motion sensor can trigger a change in the temperature of airflow from a window-based air conditioner. In an example, if a particular level, frequency, or pattern of body motion is associated with a hot flash, then this invention can trigger increased airflow or cooler airflow toward a person when the person's pattern of body motion indicates that a hot flash is occurring or is likely to occur soon. Relevant example and component variations discussed elsewhere in this disclosure or in priority-linked disclosures can also be applied to this example, but are not repeated here to avoid narrative redundancy.

Figure 36:
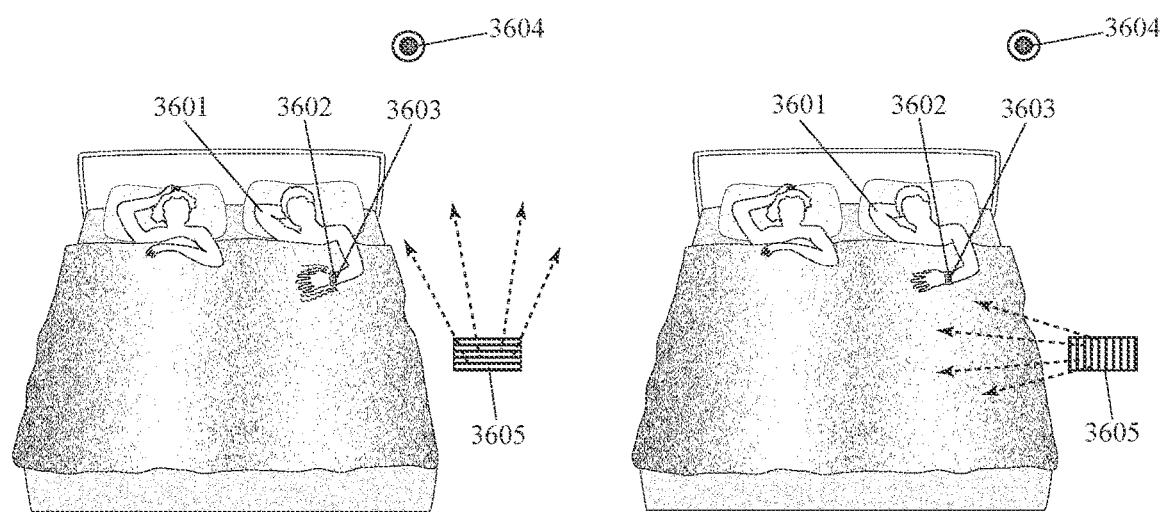
FIG. 36 shows a system for modifying a person's sleep environment which changes airflow from a HVAC system based on a motion sensor.

FIG. 36 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which changes the direction of a flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the example shown in FIG. 36 comprises: a wearable motion sensor 3602; a power source or transducer 3603; a central heating, ventilation, and/or air conditioning (HVAC) system control unit 3604; and a vent 3605 for airflow from the HVAC system. In this example, the direction, volume, speed, or temperature of airflow from vent 3605 is controlled by HVAC control unit 3604 based on data from wearable motion sensor 3602. In this example, when person 3601 is relatively active, as detected by data collected from wearable motion sensor 3602 (shown on the left side of FIG. 36), then airflow from vent 3605 is not directed toward person 3601. However, when person 3601 becomes relatively inactive, as detected by data collected from wearable motion sensor 3601 (shown on the right side of FIG. 36), then airflow from vent 3605 is directed toward person 3601. In an example, HVAC system control unit 3604 can change the direction of airflow from vent 3605 by changing the orientation of slats on vent 3605.

In an example, a wearable motion sensor can collect data concerning a person's body motion or configuration and a sleep-environment-modifying component can change the inter-room distribution of a flow of air from a central heating, ventilation, and/or air-conditioning (HVAC) system. In another example, the inter-room distribution of airflow from an HVAC system can be automatically changed by selectively opening or closing air valves in duct work. In an example, a wearable motion sensor can collect data concerning a person's body motion or configuration and a sleep-environment-modifying component can change the rate of the flow of air from a central heating, ventilation, and/or air-conditioning (HVAC) system.

In this example, one or more aspects of the operation of a central HVAC system are changed based on data from a wearable motion sensor. In this example, one or more aspects of the operation of a central HVAC system can be changed based on data from a wearable temperature sensor. In this example, one or more aspects of the operation of a central HVAC system can be changed based on data from a wearable electromagnetic energy sensor. In various examples, these operational aspects can include: a change in the volume or airflow through the central HVAC system; a change in the inter-room distribution of airflow from a central HVAC system; a change in the temperature of airflow from a central HVAC system; and a change in the direction of airflow from a central HVAC system coming from a specific room vent. Relevant example and component variations discussed elsewhere in this disclosure or in priority-linked disclosures can also be applied to this example, but are not repeated here to avoid narrative redundancy.

Figure 37:
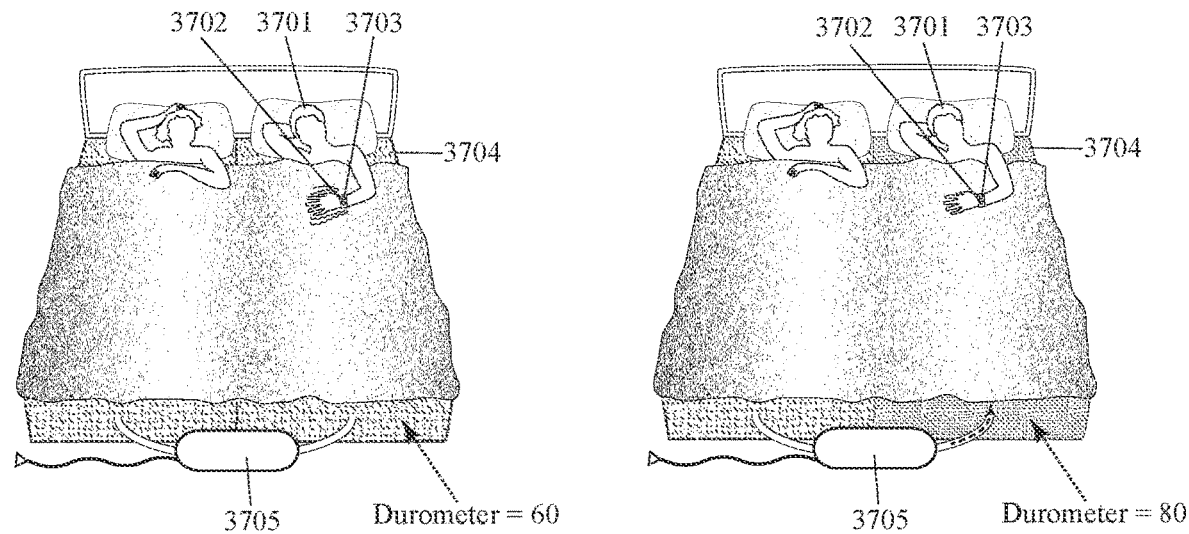
FIG. 37 shows a system for modifying a person's sleep environment which changes the firmness of a bed based on a motion sensor.

FIG. 37 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which changes the firmness of a bedding surface on which the person lies; and a data-control component which controls the operation of the sleep-environment-modifying component in order to automatically change the person's sleep environment based on data from the wearable-sensor component.

Specifically, the example shown in FIG. 37 comprises: motion sensor 3702 worn by person 3701; adjustable-firmness mattress 3704; and data-control component 3703. In this example, the firmness of mattress 3704 can be increased by inflation using air pump 3705 or can be decreased by deflation using air pump 3705. In this example, the operation of air pump 3705 is controlled by data-control component 3703 based on data collected by motion sensor 3702. In the left side of FIG. 37, mattress 3704 is inflated to a durometer of 60 based on a first pattern of motion as measured by motion sensor 3702. In the right side of FIG. 37, mattress 3704 is further inflated to a durometer of 80 based on a second pattern of motion as measured by motion sensor 3702. In an example, the second pattern of motion involves less motion than the first pattern of motion. In an example, a (portion of a) mattress on which a person sleeps can be adjusted to a higher durometer (or other measure of firmness) when the person is restless, as measured by motion sensor 3702. In another example, a (portion of a) mattress on which a person sleeps can be adjusted to a lower durometer (or other level of firmness) when the person is restless, as measured by motion sensor 3702.

In an example, a wearable motion sensor can collect data concerning a person's body motion or configuration. In an example, this data can be use to change: the firmness of a mattress or other bedding material on which a person lies; the compressive resistance of springs in a box spring; the compressive resistance of springs in a mattress; the durometer or shore value of a bedding surface on which a person lies; the durometer or shore value of a mattress on which a person lies; the inflation or pressure level of a mattress on which a person lies; and the inflation or pressure level of a mattress pad on which a person lies. Relevant example and component variations discussed elsewhere in this disclosure or in priority-linked disclosures can also be applied to this example, but are not repeated here to avoid narrative redundancy.

Figure 38:
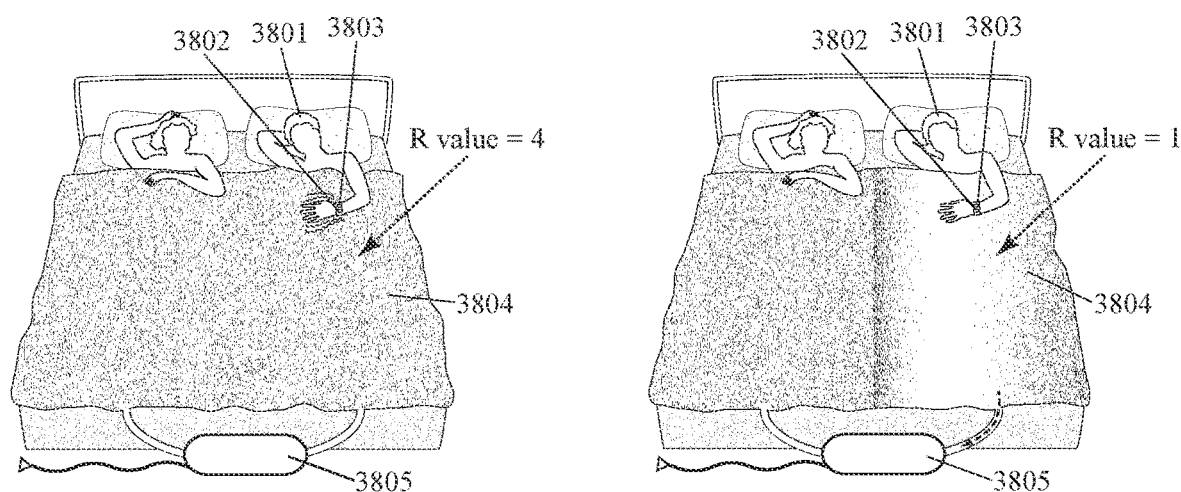
FIG. 38 shows a system for modifying a person's sleep environment which changes the insulation value of a blanket based on a motion sensor.

FIG. 38 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which changes the R-value a blanket or other bedding layer over the person; and a data-control component which controls the operation of the sleep-environment-modifying component in order to automatically change the person's sleep environment based on data from the wearable-sensor component.

More specifically, the embodiment shown in FIG. 38 comprises: motion sensor 3802 worn by person 3801; adjustable R-value blanket 3804; and data-control component 3803 which adjusts the R-value of blanket 3804 based on data from motion sensor 3802. In this example, the R-value of blanket 3804 is adjusted by its inflation or deflation by air pump 3805. In this example, the operation of air pump 3805 is controlled by data-control component 3803 based on data from motion sensor 3802. The left side of FIG. 38 shows blanket 3804 with a higher R-value (4) based on a higher level of body motion, as detected by motion sensor 3802. The right side of FIG. 38 shows blanket 3804 with a lower R-value (1) based on a lower level of body motion, as detected by motion sensor 3802. In this example, the R value of adjustable R-value blanket 3804 is decreased by partial deflation using air pump 3805.

In an example, a selected level or frequency of body motion can automatically trigger a change in the R-value of a blanket. In an example, an intentional pattern of hand or arm motion can be used to control the R-value of a blanket. In an example, when a person slides their hand or arm upwards toward the head of the bed, this increases the R-value of a blanket and when the person slides their hand or arm downwards toward the foot of the bed, this decreases the R-value of a blanket. In an example, when a person shakes their hand, this decreases the R-value of a blanket. In an example, when a person pulls a blanket up closer to their head, this increases the R-value of the blanket. In an example, when a person pulls a blanket down away from their head, this decreases the R-value of the blanket. In an example, the temperature of an electric blanket can be controlled in a like manner based on motions of a person's body. In an example, a wearable-sensor component can collect data concerning the person's body motion or configuration. In an example, this data can be used to change the thickness of a blanket or other bedding layer over the person and/or control MEMS actuators in a blanket or other bedding layer to change the R-value of a blanket or other bedding layer. Relevant example and component variations discussed elsewhere in this disclosure or in priority-linked disclosures can also be applied to this example, but are not repeated here to avoid narrative redundancy.

Figure 39:
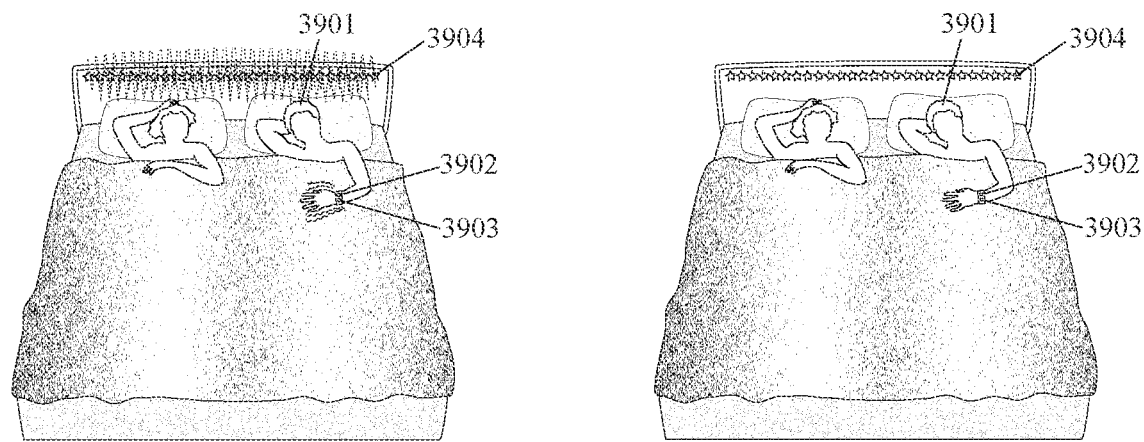
FIG. 39 shows a system for modifying a person's sleep environment which changes ambient lighting based on a motion sensor.

As shown in FIG. 39, this invention can also be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which emits light; and a data-control component which controls the operation of the sleep-environment-modifying component in order to automatically change the person's sleep environment based on data from the wearable-sensor component.

In detail, the example that is shown in FIG. 39 comprises: wearable motion sensor 3902 configured to be worn by person 3901; bed-illuminating lights 3904; and data-control component 3903. In this example, data-control component 3903 controls the operation of bed-illuminating lights 3904 based on data from wearable motion sensor 3902. In this example, when the person is more active, then the lights are on, as shown on the left side of FIG. 39. However, when the person becomes inactive, then the lights turn off, as shown on the right side of FIG. 39. In an example, this can cause lights to be on when a person is awake and lights to go off when a person falls asleep. In other examples, the level of brightness or intensity of lights 3904 can be changed by the level of activity of person 3901. In other examples, the color of lights 3904 can be changed by selected levels or patterns of body motion as measured by wearable motion sensor 3902. In this example, lights which are controlled by data from motion sensor 3902 are integrated into a bed structure. In other examples, data from motion sensor 3902 can control the operation of lights elsewhere in the room. Relevant example and component variations discussed elsewhere in this disclosure or in priority-linked disclosures can also be applied to this example, but are not repeated here to avoid narrative redundancy.

Figure 40:
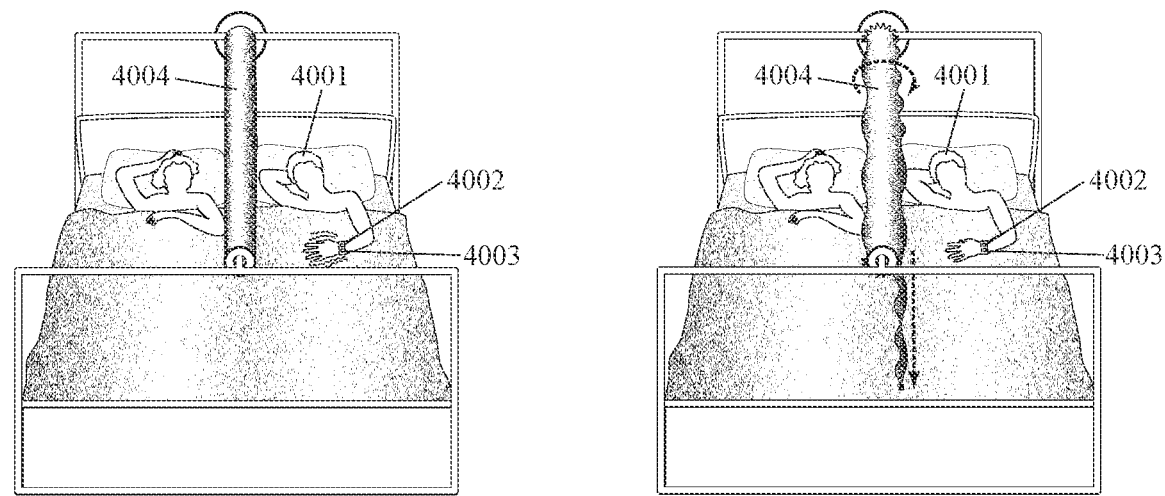
FIG. 40 shows a system for modifying a person's sleep environment which deploys an acoustic partition based on a motion sensor.

FIG. 40 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's body motion or configuration; a sleep-environment-modifying component which controls the operation of an acoustic partition or barrier between a second person and the person; and a data-control component which controls the operation of the sleep-environment-modifying component in order to automatically change the person's sleep environment based on data from the wearable-sensor component.

More specifically, the example in FIG. 40 comprises: a wearable motion sensor 4002 which is worn by person 4001; an acoustic partition 4004 which moves downward to separate two sides of a bed; and a data-control component 4003 which controls the operation of acoustic partition 4004 based on data from wearable motion sensor 4002. In an example, when data from wearable motion sensor 4002 shows a pattern of activity which suggests that person 4001 is awake, then data-control component 4003 keeps acoustic partition 4004 in a retracted position. This is shown on the left side of FIG. 40. However, when data from wearable motion sensor 4002 shows a pattern of inactivity which suggests that person 4001 is asleep, then data-control component 4003 lowers acoustic partition 4004 between person 4001 and another person on the other side of the bed. In an example, an automatically-deployed acoustic partition such as this one can enable a couple to fall asleep together in the same bed, but then create an acoustic partition when they are asleep so that one person's snoring does not bother the other person.

In this example, an acoustic partition comprises a single plane. In this example, an acoustic partition can comprise multiple planes or a concave enclosure. In this example, an acoustic partition is dropped down in a vertical manner from a roller suspended above the central longitudinal axis of a bed. In another example, an acoustic partition can be moved into place in a horizontal manner, spanning between the head of a bed and the foot of the bed. In this example, an acoustic partition is deployed by unrolling it. In another example, an acoustic partition can be deployed by inflating it. In another example, an acoustic partition can be deployed by unfolding it. In another example, an acoustic partition can be deployed by expanding it. In an example, an acoustic partition can be deployed by lowering it over a person. In an example, a motion sensor can be an accelerometer. In an example, a motion can be a gyroscope or inclinometer. In an example, data from a motion sensor can be used to: control the operation of an acoustic partition or barrier between a first person and a second person in the same bed; or control the operation of a central longitudinal acoustic partition or barrier on a bed. Relevant example and component variations discussed elsewhere in this disclosure or in priority-linked disclosures can also be applied to this example, but are not repeated here to avoid narrative redundancy.

Figure 41:
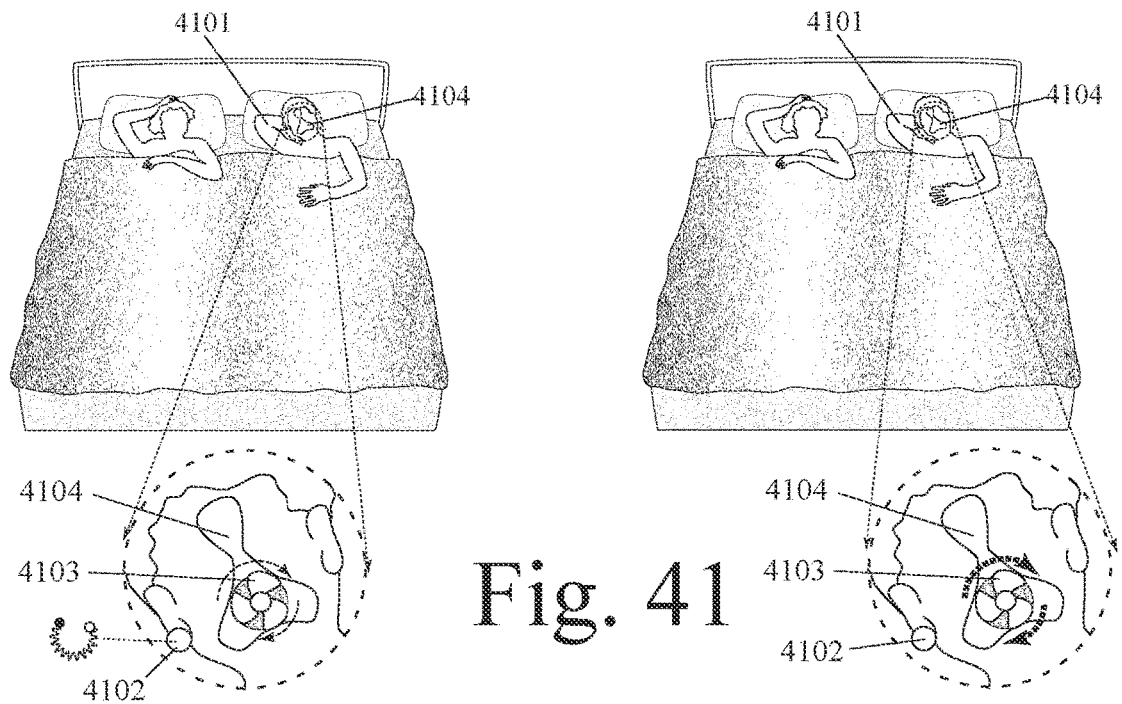
FIG. 41 shows a system for modifying a person's sleep environment which changes a person's air pressure based on an oxygen saturation sensor.

As shown in FIG. 41, this invention can be embodied in a system, device, and method that uses wearable technology to collect data for automatic modification of a person's sleep environment comprising: a wearable-sensor component that is configured to be worn by a person, wherein this sensor component collects data concerning the person's oxygen saturation; a sleep-environment-modifying component which changes the rate of the flow of air and/or other gas which the person breathes; and a data-control component which controls the operation of the sleep-environment-modifying component in order to automatically change the person's sleep environment based on data from the wearable-sensor component.

More specifically, the example shown in FIG. 41 comprises: oxygen saturation sensor 4102; and air-moving member 4103. In this example, the operation of air-moving member 4103 is changed based on data from oxygen saturation sensor 4102. In an example, when data from oxygen saturation sensor 4102 indicates a low level of oxygen saturation, then this triggers an increase the volume, speed, and/or pressure of airflow from air-moving member 4103. In an example, when low oxygen saturation is due to obstruction of a person's airway by soft tissue, then increased airway pressure from air-moving member 4103 can help to reopen the person's airway.

In this example, oxygen saturation sensor 4102 is worn on a person's ear and air-moving member 4103 is part of respiratory mask 4104. In an example, oxygen saturation sensor 4102 and air-moving member 4103 can be co-located as parts of a respiratory mask. In an example, an oxygen saturation sensor can be incorporated into a different type of wearable device or an article of clothing. In this example, air-moving member 4103 is an impellor or fan that draws ambient air into respiratory mask 4104. In this example, an increase in the rotational speed of air-moving member 4103 increases the pressure of air in the respiratory mask, which can help to provide positive airway pressure to address an episode of obstructive sleep apnea.

The left side of FIG. 41 shows air-moving member rotating at a first speed in response to a first level of oxygen saturation measured by oxygen saturation sensor 4102. The right side of FIG. 41 shows air-moving member rotating at a second speed in response to a second level of oxygen saturation measured by oxygen saturation sensor 4102. In this example, the second speed is faster than the first speed. In this example, the faster speed is triggered by a lower level of oxygen saturation. In an example, when this device detects an undesirably-low level of oxygen saturation, then this device triggers an increase in the rotational speed of air-moving member 4105 to increase airflow through the person's lungs and restore oxygen saturation to a healthy level. In an example, this device can comprise a positive airway pressure mask that provides additional airflow and/or airway pressure when needed to maintain a proper blood oxygen level.

In an example, a wearable oxygen saturation sensor and/or monitor can collect data concerning a person's oxygen saturation and/or blood oxygen level. In example, this data can be used to: change the direction, flow rate, pressure, humidity, temperature, mixture, and/or source of the air or other gas which a person breathes; change the rate of the flow of air and/or other gas in communication with the surface of the person's body; change the rate of the flow of air and/or other gas which the person breathes; change a laminar flow of air and/or other gas in communication with the surface of the person's body; change the laminar flow of air and/or other gas which the person breathes; change the rate of the flow of air from a central heating, ventilation, and/or air-conditioning (HVAC) system; or change the rate of the flow of air from a window-based air conditioner. Relevant example and component variations discussed elsewhere in this disclosure or in priority-linked disclosures can also be applied to this example, but are not repeated here to avoid narrative redundancy.

Figure 42:
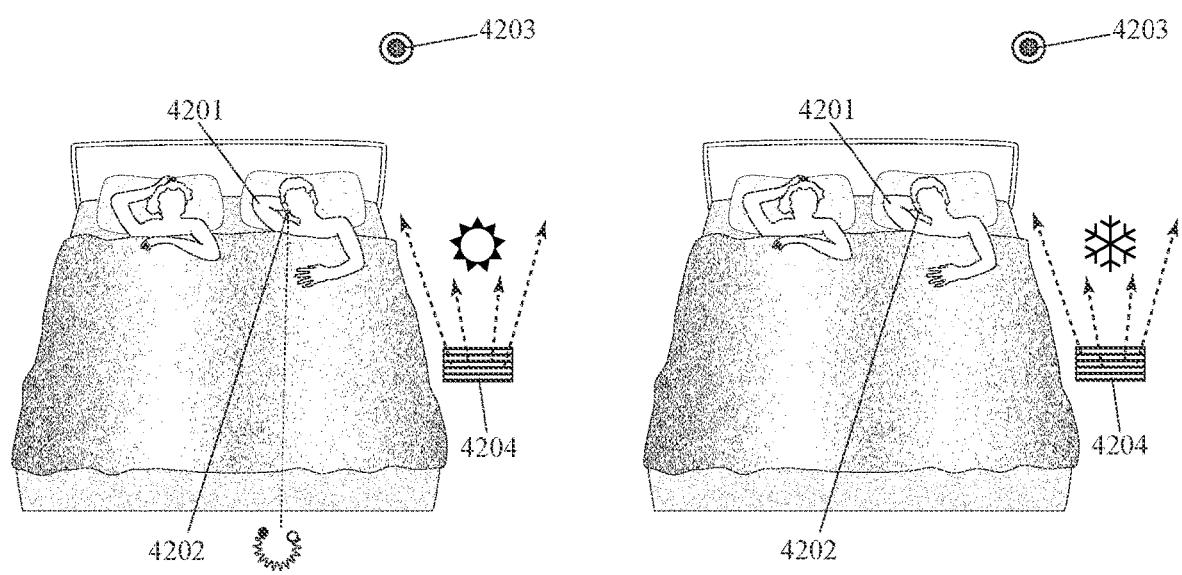
FIG. 42 shows a system for modifying a person's sleep environment which changes the temperature of air from an HVAC system based on an oxygen saturation sensor.

FIG. 42 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's oxygen saturation; a sleep-environment-modifying component which controls the operation of a central heating, ventilation, and/or air-conditioning (HVAC) system; and a data-control component which controls the operation of the sleep-environment-modifying component in order to automatically change the person's sleep environment based on data from the wearable-sensor component.

More specifically, the example shown in FIG. 42 comprises: wearable oxygen saturation sensor 4202; central heating, ventilation, and/or air-conditioning (HVAC) system control unit 4203; and outflow vent 4204 from the HVAC system. In this example, data from wearable oxygen saturation sensor 4202 is used by HVAC system control unit to change the operation of the HVAC system and/or outflow vent 4204. In this example, data from oxygen saturation sensor 4202 is used by HVAC system control unit 4203 to change the temperature of airflow from the HVAC system coming out from vent 4204.

The left side of FIG. 42 shows a first situation in which HVAC system control unit 4203 responds to data from wearable oxygen saturation sensor 4202 by setting a high temperature for airflow from the HVAC system coming out from vent 4204. This is represented by the "sun" symbol above vent 4204 on the left side of FIG. 42. The right side of FIG. 42 shows a second situation in which HVAC system control unit 4203 responds to data from wearable oxygen saturation sensor 4202 by setting a low temperature for airflow from the HVAC system coming out from vent 4204. In another example, data from oxygen saturation can be used to change the direction, rate, or volume of airflow from the HVAC system coming out from vent 4204. In another example, a data-control component which controls the operation of a central HVAC system can be incorporated into a wearable device or smart phone rather than a wall-mounted control unit. Relevant example and component variations discussed elsewhere in this disclosure or in priority-linked disclosures can also be applied to this example, but are not repeated here to avoid narrative redundancy.

Figure 43:
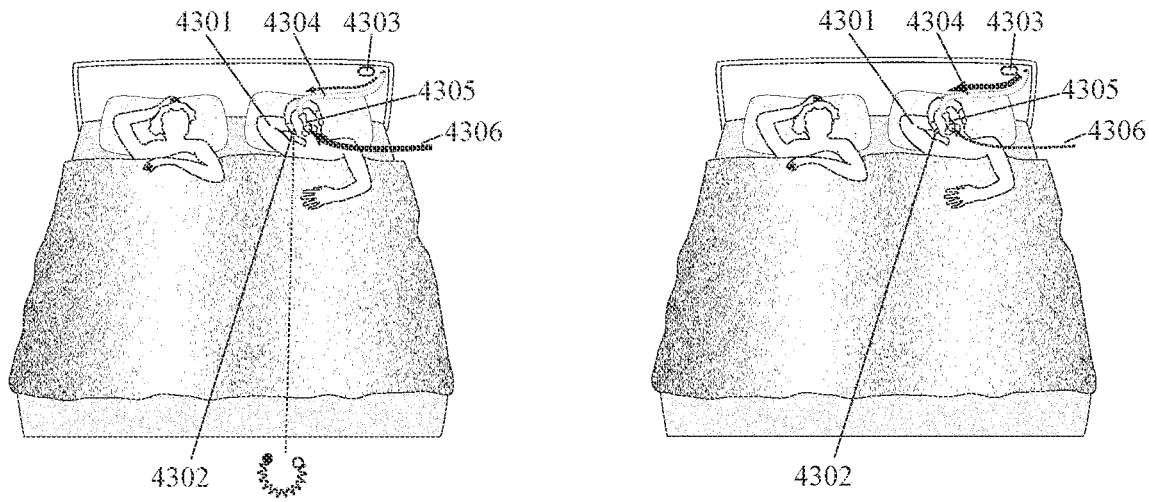
FIG. 43 shows a system for modifying a person's sleep environment which changes a person's air source based on an oxygen saturation sensor.

As shown in FIG. 43, this invention can be embodied in a system, device, and method that uses wearable technology to collect data for automatic modification of a person's sleep environment comprising: a wearable-sensor component that is configured to be worn by a person, wherein this sensor component collects data concerning the person's oxygen saturation; a sleep-environment-modifying component which changes the mixture of air and/or other gas from multiple sources which the person breathes; and a data-control component which controls the operation of the sleep-environment-modifying component in order to automatically change the person's sleep environment based on data from the wearable-sensor component.

More specifically, the embodiment shown in FIG. 43 comprises: wearable oxygen saturation sensor 4302; gas flow tube 4304; respiratory mask 4305; and data-control component 4303. In this example, the flow of breathable gas through gas flow tube 4304 is changed by data-control component 4303 based on data from wearable oxygen saturation sensor 4302. In an example, gas flow tube 4304 is connected to a source of oxygen-rich gas. In an example, the flow of an oxygen-rich gas through gas flow tube 4304 can be automatically increased by data-control component 4303 when data from wearable saturation oxygen saturation sensor indicates that person 4301 has a low oxygen saturation level.

In an example, the mixture or proportions of a flow of oxygen-rich gas through gas flow tube 4304 vs. ambient airflow 4306 which is breathed by person 4301 through respiratory mask 4305 can be automatically adjusted based on data from wearable oxygen saturation sensor 4302. The left side of FIG. 43 shows a first flow of breathable gas through gas tube 4304 based on a first pattern of data from wearable oxygen saturation sensor 4302 and the right side of FIG. 43 shows a second flow of breathable gas through gas flow tube 4304 based on a second pattern of data from wearable oxygen saturation sensor 4302. In this example, the second flow is greater than the first flow, as symbolically represented by a larger dotted-line arrow along gas flow tube 4304.

In various examples, data from wearable oxygen saturation sensor 4302 can be used to change and/or control the rate, volume, mixture, temperature, or moisture level of breathable gas flowing through gas flow tube 4304, airflow 4306 drawn from ambient air; or both. In this example, oxygen saturation sensor 4302 is an optical sensor that measures parameters concerning light reflected from, transmitted through, or absorbed by a person's body tissue. In other examples, oxygen saturation sensor can measure electromagnetic energy or sonic energy. In this example, oxygen saturation sensor 4302 is worn on a person's earlobe. In other examples, oxygen saturation sensor can be worn on a person's finger or elsewhere on a person's body. In an example, data from a wearable oxygen saturation sensor can be used to: change the mixture of air and/or other gas from multiple sources which a person breathes; change the mixture or composition of air and/or other gas which a person breathes; change the proportion of ambient air versus non-ambient air or other gas which a person breathes; and/or change the source of air and/or other gas which a person breathes. Relevant example and component variations discussed elsewhere in this disclosure or in priority-linked disclosures can also be applied to this example, but are not repeated here to avoid narrative redundancy.

Figure 44:
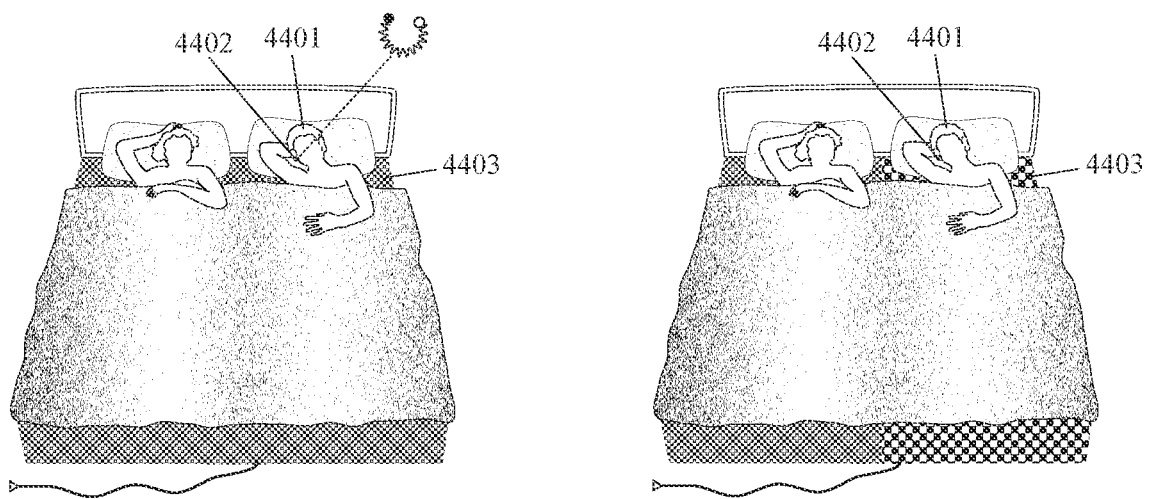
FIG. 44 shows a system for modifying a person's sleep environment which changes the porosity of a mattress based on an oxygen saturation sensor.

FIG. 44 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's oxygen saturation; a sleep-environment-modifying component which changes the porosity of a bedding surface or layer on which the person lies; and a data-control component which controls the operation of the sleep-environment-modifying component in order to automatically change the person's sleep environment based on data from the wearable-sensor component.

More specifically, the embodiment shown in FIG. 44 comprises an oxygen saturation sensor 4402 and an adjustable-porosity mattress 4403. In this example, the porosity of mattress 4403 is adjusted based on data from oxygen saturation sensor 4402. In an example, when data from oxygen saturation sensor 4402 indicates a low level of oxygen saturation, then this device increases the porosity of mattress 4403. In an example, this embodiment of the device may help to prevent a person, such as an infant, from suffocating while sleeping in the event that they turn face down toward the mattress or become completely covered with a blanket. In an example, this device may help to avoid Sudden Infant Death (SID).

In an example, mattress 4403 can further comprise piezoelectric members and the porosity of mattress 4403 can be adjusted by application of electromagnetic energy to these piezoelectric members based on data from oxygen saturation sensor 4402. In an example, mattress 4403 can further comprise an array of actuators and the porosity of mattress 4403 can be adjusted by operating this array of actuators based on data from oxygen saturation sensor 4402. In an example, mattress 4403 can further comprise an array of inflatable members and the porosity of mattress 4403 can be adjusted by inflation or deflation of these inflatable members based on data from oxygen saturation sensor 4402. In an example, mattress 4403 can further comprise an array of micro-impellors which increase airflow through the mattress based on data from oxygen saturation sensor 4402. In an example, data from a wearable oxygen saturation sensor can change the porosity of a sheet, blanket, or other bedding layer over a person. Relevant example and component variations discussed elsewhere in this disclosure or in priority-linked disclosures can also be applied to this example, but are not repeated here to avoid narrative redundancy.

Figure 45:
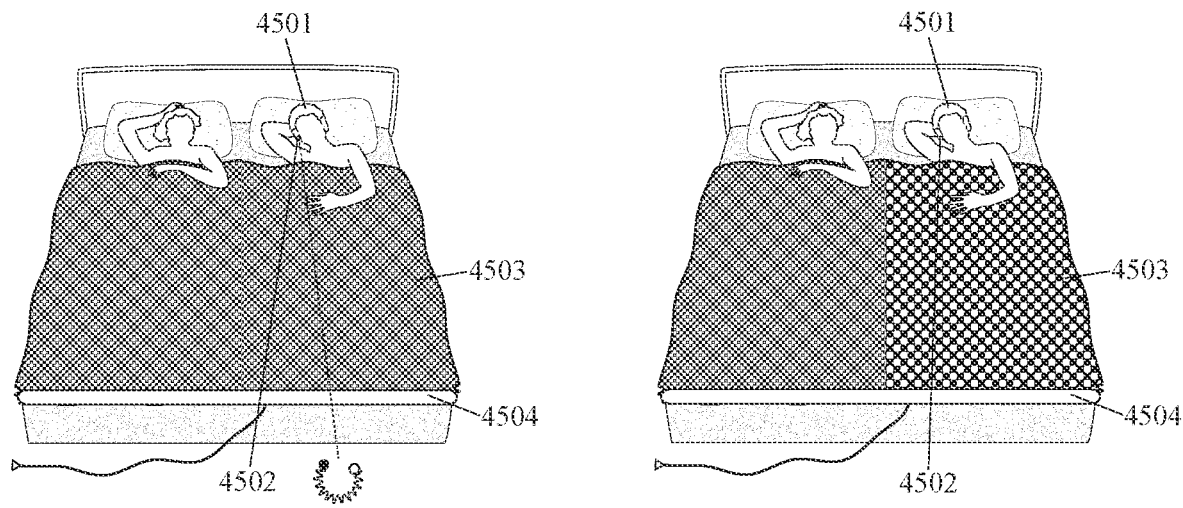
FIG. 45 shows a system for modifying a person's sleep environment which changes the porosity of a blanket based on an oxygen saturation sensor.

FIG. 45 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's oxygen saturation; a sleep-environment-modifying component which changes the porosity of a blanket or other bedding layer covering the person; and a data-control component which controls the operation of the sleep-environment-modifying component in order to automatically change the person's sleep environment based on data from the wearable-sensor component.

Specifically, the embodiment shown in FIG. 45 comprises oxygen saturation sensor 4502 and adjustable-porosity blanket 4503. In this example, the porosity of blanket 4503 is adjusted based on data from oxygen saturation sensor 4502. In an example, when oxygen sensor 4502 indicates that person 4501 has a low oxygen saturation level, then porosity control mechanism 4504 increases the porosity of blanket 4503. In an example, increasing the porosity of a bed covering can help to reduce the chances of suffocation, especially if person 4501 is an infant or immobile person. In an example, blanket 4503 can further comprise piezoelectric fabric whose porosity can be changed by application of electromagnetic energy. In an example, blanket 4503 can further comprise an array of micro-actuators whose activation changes the porosity of blanket 4503. In an example, blanket 4503 can further comprise an array of inflatable members whose selective inflation or deflation changes the porosity of blanket 4503.

The left side of FIG. 45 shows adjustable-porosity blanket 4503 with a first porosity level based on a first pattern of data from oxygen saturation sensor 4502. The right side of FIG. 45 shows adjustable-porosity blanket 4503 with a second porosity level based on a second pattern of data from oxygen saturation sensor 4502. In this example, the second porosity level is greater than the first porosity level, as symbolically represented by a larger checkerboard pattern on the right side of FIG. 45. In this example, the porosities of the two sides of blanket 4503 are individually adjustable. In another example, the porosity of a blanket with uniform porosity can be adjusted based on data from an oxygen saturation sensor.

In this example, an oxygen saturation sensor is worn on a person's earlobe. In other examples, an oxygen saturation sensor can be worn on other portions of a person's body. In this example, oxygen saturation sensor analyzes the spectrum of light passing through body tissue. In other examples, an oxygen saturation sensor can analyze the spectrum of light reflected from body tissue. In various examples, an oxygen saturation sensor can measure light energy, electromagnetic energy, or sonic energy. In an example, data from an oxygen saturation sensor can be used to automatically change the gaseous porosity of a blanket, sheet, quilt, or other bedding layer covering a person. Relevant example and component variations discussed elsewhere in this disclosure or in priority-linked disclosures can also be applied to this example, but are not repeated here to avoid narrative redundancy.

Figure 46:
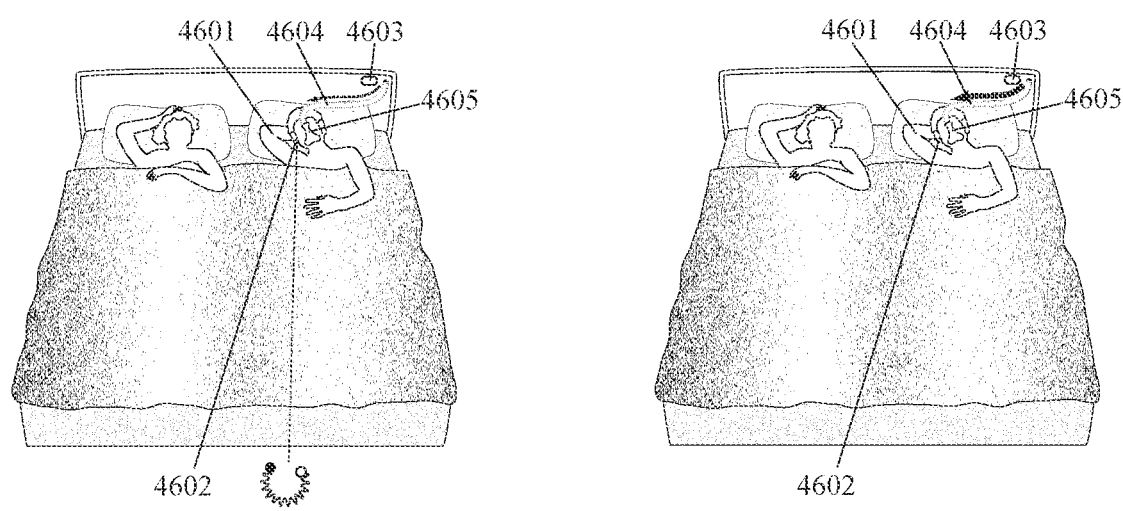
FIG. 46 shows a system for modifying a person's sleep environment which changes a person's air pressure based on an oxygen saturation sensor.

As shown in FIG. 46, this invention can be embodied in a system, device, and method that uses wearable technology to collect data for automatic modification of a person's sleep environment comprising: a wearable-sensor component that is configured to be worn by a person, wherein this sensor component collects data concerning the person's oxygen saturation; a sleep-environment-modifying component which changes the pressure of air and/or other gas which the person breathes; and a data-control component which controls the operation of the sleep-environment-modifying component in order to automatically change the person's sleep environment based on data from the wearable-sensor component.

More specifically, the embodiment shown in FIG. 46 comprises oxygen saturation sensor 4602; gas flow tube 4604; respiratory mask 4605; and data-control component 4603. In this example, the pressure of airflow through gas flow tube 4604 is controlled by data-control component 4603 based on data from oxygen sensor 4602. In an example, when data from oxygen saturation sensor 4602 indicates that person 4601 has a low oxygen saturation level, then this triggers an increase in the pressure of airflow through gas flow tube 4604. In an example, when low oxygen saturation is caused by obstruction of the person's airway by soft tissue, then increased airflow pressure through gas flow tube 4604 can open the airway and increase oxygen saturation.

In this example, oxygen saturation sensor 4602 measures light energy passing through tissue of a person's body. In an example, oxygen saturation sensor 4602 can be an optical sensor. In an example, oxygen saturation sensor 4602 can collect data concerning the intensity and/or spectrum of light energy passing through, or reflected from, body tissue. In an example, oxygen saturation sensor 4602 can be a spectroscopic sensor. In an example, data concerning light energy that is collected by oxygen saturation sensor 4602 can be analyzed using spectroscopy. In other examples, an oxygen saturation sensor can be a biochemical sensor, electromagnetic energy sensor, or sonic energy sensor. In this example, oxygen saturation sensor 4602 is worn on a person's earlobe. In other examples, an oxygen saturation sensor can be worn on a person's nose or finger, incorporated into a respiratory mask, incorporated into a garment, or incorporated into another type of wearable device.

The left side of FIG. 46 shows a flow of breathable gas at a first pressure level moving through gas flow tube 4604 into respiratory mask 4605 based on a first level of oxygen saturation. The right side of FIG. 46 shows a flow of breathable gas at a second pressure level moving through gas flow tube 4604 into respiratory mask 4605 based on a second level of oxygen saturation. In this example, the second pressure level is greater than the first pressure level. In an example, the second pressure level can provide elevated airway pressure in order to push soft tissue and open up a person's airway in the event of an episode of obstructive sleep apnea. In an example, the flow of breathable gas through gas tube 4605 can be drawn from ambient air. In an example, the flow of breathable gas through gas tube 4605 can come from a mixture of a non-ambient gas source and ambient air. In an example, data from a wearable oxygen saturation sensor can be used to change the direction, flow rate, pressure, humidity, temperature, mixture, and/or source of the air or other gas which a person breathes. Relevant example and component variations discussed elsewhere in this disclosure or in priority-linked disclosures can also be applied to this example, but are not repeated here to avoid narrative redundancy.

Figure 47:
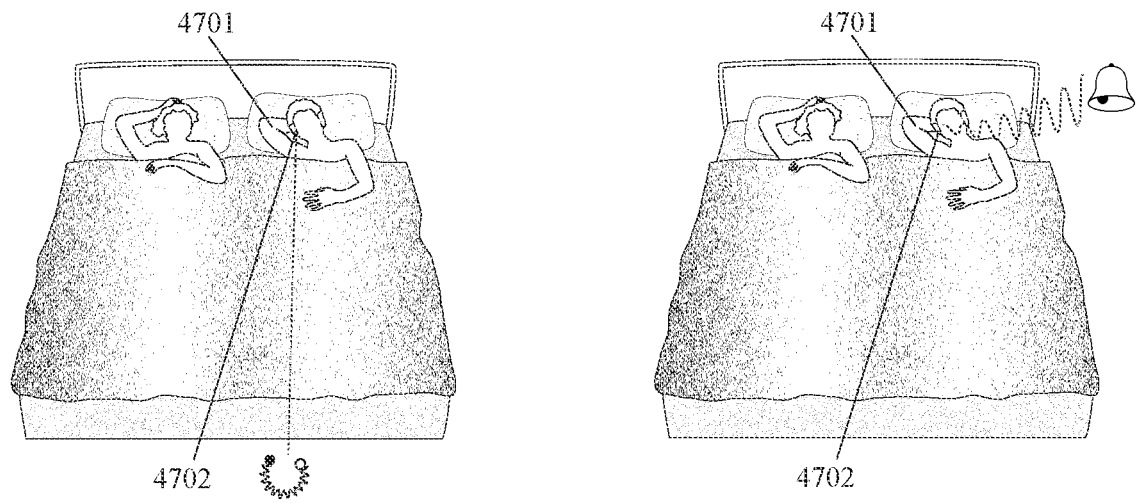
FIG. 47 shows a system for modifying a person's sleep environment which sends an alarm based on an oxygen saturation sensor.

FIG. 47 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's oxygen saturation; a sleep-environment-modifying component which emits sound; and a data-control component which controls the operation of the sleep-environment-modifying component in order to automatically change the person's sleep environment based on data from the wearable-sensor component.

More specifically, the embodiment shown in FIG. 47 comprises a wearable oxygen saturation monitor 4702 that emits sound when it detects a low level of oxygen saturation. In this example, this oxygen saturation sensor is worn on person's 4701 earlobe. In other examples, an oxygen saturation sensor can be worn on a location selected from the group consisting of: nose, finger, wrist, neck, ankle, and tongue. In another example, an oxygen saturation monitor can be incorporated into an article of clothing that a person wears to bed. In an example, data from a wearable oxygen saturation monitor can be wirelessly transmitted to a separate electronic device which, in turn, emits an alarm if the oxygen saturation level becomes too low. In an example, data from a wearable oxygen saturation monitor can be wirelessly transmitted to a separate electronic communications device which sends a phone call, text, email, or other electronic communication if the oxygen saturation level becomes too low.

In an example, a wearable oxygen saturation monitor can measure light energy. In an example, a wearable oxygen saturation monitor can measure the intensity or spectrum of light that passes through body tissue. In an example, a wearable oxygen saturation monitor can measure the intensity or spectrum of light that is reflected off the surface of body tissue. In an example, a wearable oxygen saturation monitor can measure electromagnetic energy. In an example, a wearable oxygen saturation monitor can measure sonic energy. In an example, a wearable oxygen monitor can be a biochemical monitor. Relevant example and component variations discussed elsewhere in this disclosure or in priority-linked disclosures can also be applied to this example, but are not repeated here to avoid narrative redundancy.

Figure 48:
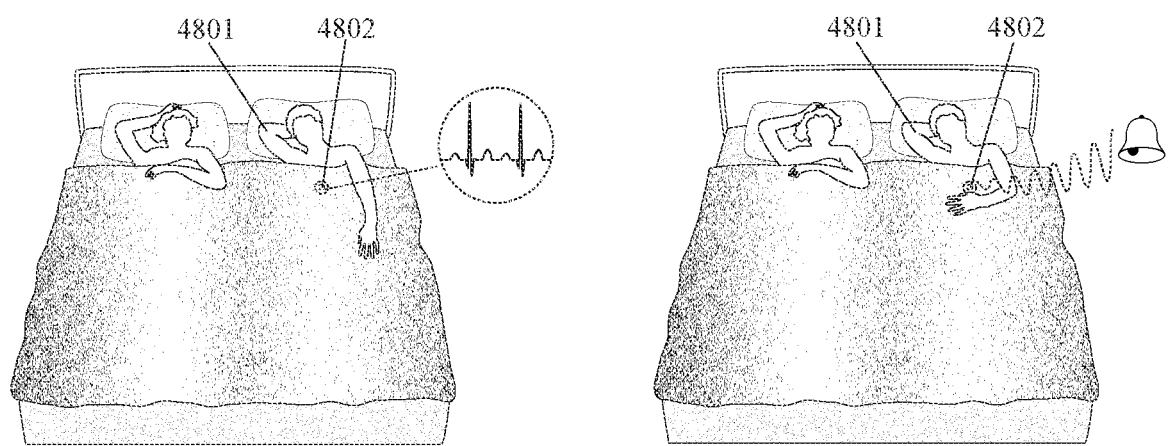
FIG. 48 shows a system for modifying a person's sleep environment which sends an alarm based on a cardiac function monitor.

FIG. 48 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's pulse, heart rate, and/or other cardiac function; a sleep-environment-modifying component which emits sound; and a data-control component which controls the operation of the sleep-environment-modifying component in order to automatically change the person's sleep environment based on data from the wearable-sensor component.

More specifically, the embodiment shown in FIG. 48 comprises a wearable cardiac function monitor 4802 which emits sound when a selected pattern of cardiac activity is detected. In an example, a wearable cardiac function monitor can measure person's 4801 pulse, heart rate, electrocardiographic signals, or other parameters concerning a person's cardiac function. In an example, a wearable cardiac function monitor can be a wearable ECG monitor. In an example, a cardiac function monitor can sound an alarm if data concerning cardiac function indicates an adverse event or condition. In an example, a cardiac function monitor can wirelessly transmit data to a separate electronic device, such as a smart phone, which can sound an alarm if data concerning cardiac function indicates an adverse event or condition. In an example, a wearable cardiac function monitor can send a communication if it detects an adverse event or condition. In an example, a wearable cardiac function monitor can be in wireless communication with a separate electronic device which can sound an alarm or send a communication if an adverse event or condition is detected.

In an example, a wearable cardiac function monitor can measure electromagnetic energy transmitted through a person's body tissue. In an example, data from a wearable cardiac function monitor can be analyzed using Fourier Transformation methods to identify significant repeating patterns of electromagnetic activity. In an example, a wearable cardiac function monitor can measure light energy transmitted through (or reflected from) a person's body tissue. In an example, data from a wearable cardiac function monitor can be analyzed using spectroscopy. In an example, a wearable cardiac function monitor can measure levels and/or changes of pressure and/or force at points of contact with one or more body surfaces or tissues. In an example, a wearable cardiac function monitor can measure sonic energy transmitted through (or reflected from) a person's body tissue. In an example this sonic energy can be ultrasonic. In an example, a wearable cardiac function monitor can be worn on a person's chest or torso. In an example, a wearable cardiac function monitor can be worn on a person's finger, wrist, hand, or arm. In an example, a wearable cardiac function monitor can be worn on a person's ear or nose. In an example, a wearable cardiac function monitor can be incorporated into an article of clothing that a person wears to bed. Relevant example and component variations discussed elsewhere in this disclosure or in priority-linked disclosures can also be applied to this example, but are not repeated here to avoid narrative redundancy.

Figure 49:
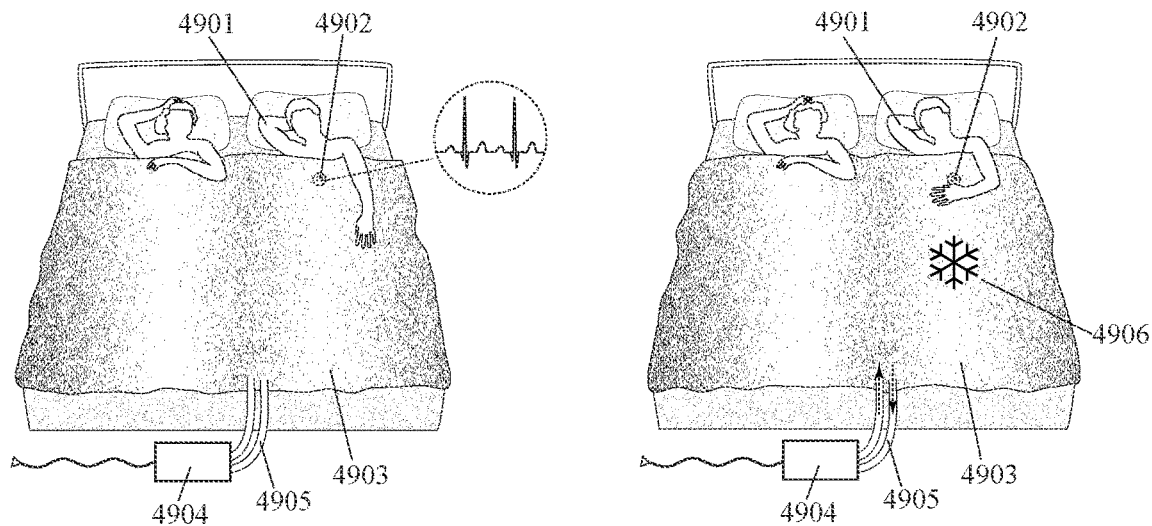
FIG. 49 shows a system for modifying a person's sleep environment which changes bed temperature based on a cardiac function monitor.

FIG. 49 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's pulse, heart rate, and/or other cardiac function; a sleep-environment-modifying component which changes the temperature of the air, mattress, blanket, or other bedding material near the person's body; and a data-control component which controls the operation of the sleep-environment-modifying component in order to automatically change the person's sleep environment based on data from the wearable-sensor component.

More specifically, the embodiment shown in FIG. 49 comprises: wearable cardiac function monitor 4902 worn by person 4901; and adjustable-temperature blanket 4903. In an example, this device adjusts the temperature of blanket 4903 when a selected pattern is detected in cardiac function data collected from wearable cardiac function monitor 4902. In an example, data from wearable cardiac function monitor 4902 can predict the pending occurrence of a hot flash and this can trigger a decrease in the temperature of blanket 4903. In an example, the effects of a hot flash can be mitigated or even avoided by prophylactic reduction in the temperature of a person's sleeping environment. In an example, data from wearable cardiac function monitor 4902 can indicate an adverse event or condition. In an example, the temperature of adjustable-temperature blanket 4903 can be changed based on detection of such an adverse event or condition. In an example, outcomes from an adverse cardiac event can be improved by a responsive decrease in a person's body temperature. In an alternative example, outcomes from an adverse cardiac event can be improved by a responsive increase in a person's body temperature.

In this example, the temperature of blanket 4903 is adjusted by having thermal exchange pump 4904 pump a warm or cool gas or fluid through flow conduits 4905 into circulation through blanket 4903. In an example, there can be sinusoidal tubes or channels within blanket 4903 through which a warming or cooling gas or liquid circulates. In the example shown in FIG. 49, the temperature of blanket 4903 is decreased in response to a selected pattern of data from wearable cardiac monitor 4902. This cooling is symbolically represented by the "snowflake" symbol 4906 on the right side of FIG. 49. The left side of FIG. 49 shows this example at a first point in time wherein a specific pattern of cardiac activity is detected based on data collected by wearable cardiac monitor 4902. The right side of FIG. 49 shows this example at a second point in time wherein blanket 4903 has been cooled in response to detection of this specific pattern of cardiac activity.

In an example, a wearable cardiac function monitor can measure pulse and/or heart rate. In an example, a wearable cardiac function monitor can measure blood pressure. In an example, a wearable cardiac function monitor can measure patterns of electromagnetic activity which originate in the heart. In an example, a wearable cardiac function monitor can be an ECG monitor. In an example, data from a wearable cardiac function monitor can be used to: change the temperature of a blanket over a person; change the temperature of a mattress under a person; or change the temperature of a mattress pad. In an example, a wearable cardiac function monitor can control the operation of an electric blanket to increase the temperature of a person's sleeping environment in response to a selected pattern of data from the wearable cardiac function monitor. In an example, a wearable cardiac function monitor can control the operation of a cooling blanket to decrease the temperature of a person's sleeping environment in response to a selected pattern of data from the wearable cardiac function monitor. Relevant example and component variations discussed elsewhere in this disclosure or in priority-linked disclosures can also be applied to this example, but are not repeated here to avoid narrative redundancy.

Figure 50:
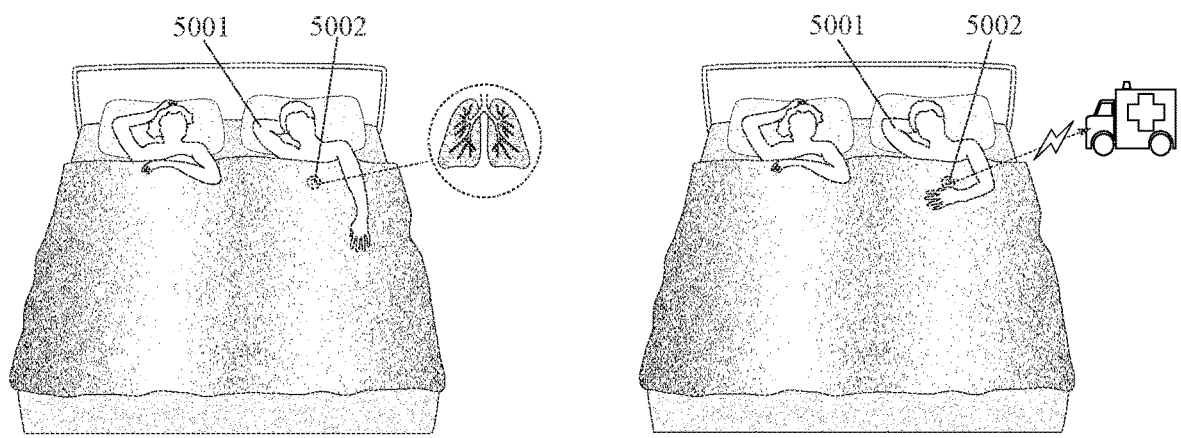
FIG. 50 shows a system for modifying a person's sleep environment which sends a communication based on a pulmonary function monitor.

FIG. 50 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's respiratory functioning; a sleep-environment-modifying component which sends a communication/alert if sensed parameter is abnormal; and a data-control component which controls the operation of the sleep-environment-modifying component in order to automatically change the person's sleep environment based on data from the wearable-sensor component.

More specifically, the embodiment shown in FIG. 50 comprises a wearable pulmonary function monitor 5002, with electronic communication capability, which sends a communication when it detects an adverse pulmonary event or condition. In an example, this communication can be sent to a healthcare provider, non-professional caregiver or relative, or a health tracking service. In an example, this communication can include information on specific parameters of the adverse pulmonary event or condition. In an example, this communication can be interactive, allowing the recipient to initiate advanced data collection from the device from a remote location.

In an example, a wearable pulmonary function monitor can collect motion, force, and/or pressure data caused by motion of a person's body, such as motion of a person's chest or torso associated with respiration. In an example, a wearable pulmonary function monitor can comprise an accelerometer or other inertial-based motion sensor. In an example, a wearable pulmonary function monitor can comprise piezoelectric fibers which generate electrical current when stretched or bent by body motion, such as motion of a person's chest or torso associated with respiration. In an example, a wearable pulmonary function monitor can comprise electro-conductive fibers whose resistance and/or impedance to electrical current changes when these fibers are stretched or bent by body motion, such as motion of a person's chest or torso associated with respiration.

In an example, a wearable pulmonary monitor can comprise pressure sensors, force sensors, or motion sensors which are in direct contact with the surface of a person's chest or torso. In an example, a wearable pulmonary monitor can comprise pressure sensors, force sensors, or motion sensors which are in gaseous or fluid communication with one or more pressurized channels, tubes, pockets, pouches, or compartments which span a portion of a person's chest or torso.

In an example, a wearable pulmonary function monitor can collect data concerning electromagnetic energy originating from a person's lungs or the muscles associated with a person's lungs. In an example, a wearable pulmonary function monitor can be an EMG monitor. In an example, a wearable pulmonary function monitor can measure the volume or speed of airflow into or out of a person's airway during respiratory cycles. In an example, a wearable pulmonary function monitor can collect sonic data concerning a person's respiratory function. In an example, a wearable pulmonary function monitor can comprise a wearable microphone. In an example, a wearable pulmonary function monitor can record sounds from a person's chest and/or torso. In an example, a wearable pulmonary function monitor can record sounds from a person's mouth and/or nose.

The left side of FIG. 50 shows this embodiment at a first point in time wherein pulmonary function monitor 5002 is collecting data concerning the pulmonary functioning of person 5001. The right side of FIG. 50 shows this embodiment at a second point in time wherein the pulmonary function monitor has initiated a communication to a health care provider based on a selected pattern of data measured by pulmonary function monitor 5002. In an example, a wearable pulmonary function monitor can trigger a communication/alert if it detects an abnormal respiratory event or condition. Relevant example and component variations discussed elsewhere in this disclosure or in priority-linked disclosures can also be applied to this example, but are not repeated here to avoid narrative redundancy.

Figure 51:
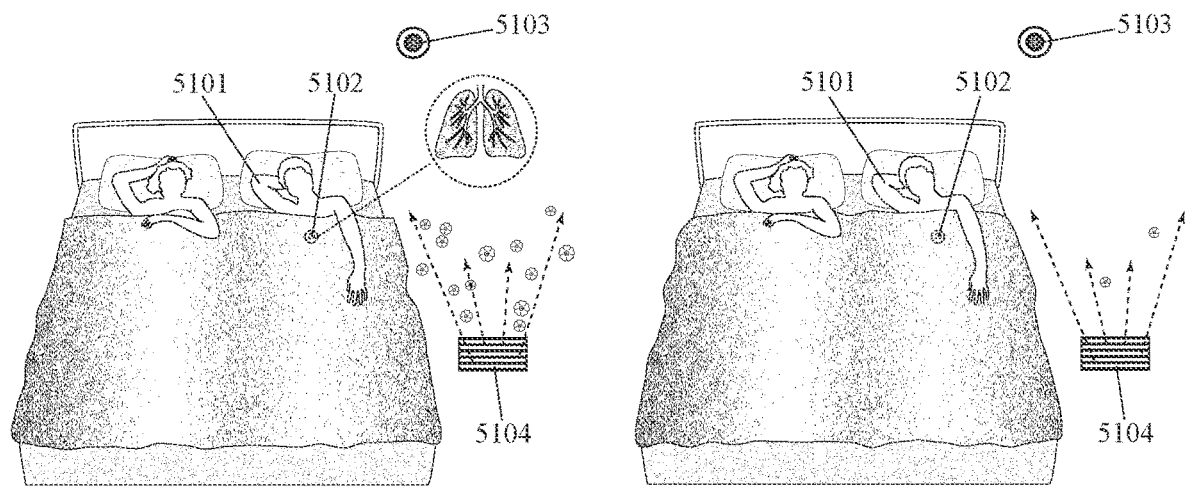
FIG. 51 shows a system for modifying a person's sleep environment which changes air filtration based on a pulmonary function monitor.

FIG. 51 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's respiratory functioning; a sleep-environment-modifying component which changes the filtration of air through a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment shown in FIG. 51 comprises a wearable pulmonary function sensor 5102 and a central heating, ventilation, and/or air-conditioning (HVAC) system control unit 5103. In this example, HVAC system control unit 5103 changes the operation of an HVAC system based on data from wearable pulmonary function sensor 5102 worn by person 5101. In various examples, the one or more aspects of the operation of a central HVAC system which are changed based on data from a wearable pulmonary function sensor can be selected from the group consisting of: degree of airflow filtration; airflow temperature; airflow moisture; airflow volume; inter-room airflow distribution; airflow direction; and mixture of fresh vs. re-circulated airflow.

In this example, data from pulmonary function sensor 5102 triggers a change in the degree of air filtration performed by the HVAC system. The left side of FIG. 51 shows this embodiment at a first point in time wherein data collected by pulmonary function sensor 5102 matches a selected data pattern. The right side of FIG. 51 shows this embodiment at a second point in time wherein air filtration by the central HVAC system has been increased by HVAC system control unit 5103 in response to detection of the selected data pattern. In an example, when wearable pulmonary function sensor 5102 detects sounds of respiratory congestion, then this can trigger a higher level of airflow filtration by a central HVAC system. In FIG. 51, a higher level of airflow filtration (from the left side to the right side of the figure) is symbolically-represented by a reduction in the "pollen symbols" floating above vent 5104. In an example, it may be cumbersome, expensive, unhealthy, or infeasible to constantly run an HVAC system at maximum air filtration. In an example, constant use of a special filter can quickly clog the filter, but selected use of a special filter can help it to be effective for a longer period of time. In an example, this system, device, and method can increase air filtration when it is most needed to reduce respiratory congestion. Relevant example and component variations discussed elsewhere in this disclosure or in priority-linked disclosures can also be applied to this example, but are not repeated here to avoid narrative redundancy.

Figure 52:
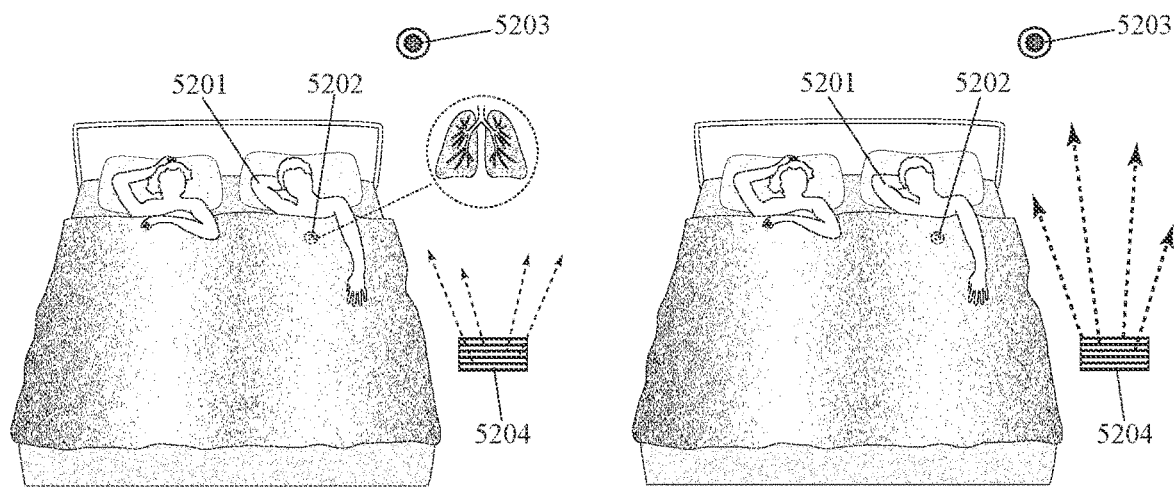
FIG. 52 shows a system for modifying a person's sleep environment which changes airflow from a HVAC system based on a pulmonary function monitor.

FIG. 52 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's respiratory functioning; a sleep-environment-modifying component which changes the rate of the flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment shown in FIG. 52 comprises: wearable pulmonary function sensor 5202 worn by person 5201; and central heating, ventilation, and/or air-conditioning (HVAC) system control unit 5203. In this example, one or more aspects of the operation of the HVAC system are changed by HVAC system control unit 5203 based on data from wearable pulmonary function sensor 5202. In various examples, these one or more aspects of HVAC system operation can be selected from the group consisting of: airflow volume; airflow temperature; airflow moisture level; airflow filtration; airflow temperature; inter-room airflow distribution; mixture of outside vs. inside air sources; and airflow speed. In the example shown in FIG. 52, the volume of airflow from the HVAC system is changed based on data from wearable pulmonary function sensor 5202.

The left side of FIG. 52 shows a first volume of airflow from vent 5204 coming from an HVAC system based on a first pattern of data collected from wearable pulmonary function sensor 5202. The right side of FIG. 52 shows a second volume of airflow from vent 5204 coming from an HVAC system based on a second pattern of data collected from wearable pulmonary function sensor 5202. In this example, the second volume is greater than the first volume, as symbolically represented by longer and thicker dotted-line arrows arising from vent 5204 on the right side of FIG. 52 vs. the left side.

In an example, a wearable pulmonary function sensor can be selected from the group consisting of: wearable accelerometer, gyroscope, or other inertial-based motion sensor; a garment, strap, band, or other wearable accessory comprising piezoelectric members which generate electrical current when stretched or bent; a garment, strap, band, or other wearable accessory comprising electroconductive members whose resistance or impedance to electrical current changes when they are stretched or bent; a microphone or other sonic energy sensor; an EMG sensor or other electromagnetic energy sensor; and a spectroscopic sensor or other optical sensor. In an example, the operation of an HVAC system can be controlled directly by a component in a wearable device. In an example, data from a wearable pulmonary function sensor can be used to change the volume, rate, direction or inter-room distribution of a flow of air from an HVAC system. Relevant example and component variations discussed elsewhere in this disclosure or in priority-linked disclosures can also be applied to this example, but are not repeated here to avoid narrative redundancy.

Figure 53:
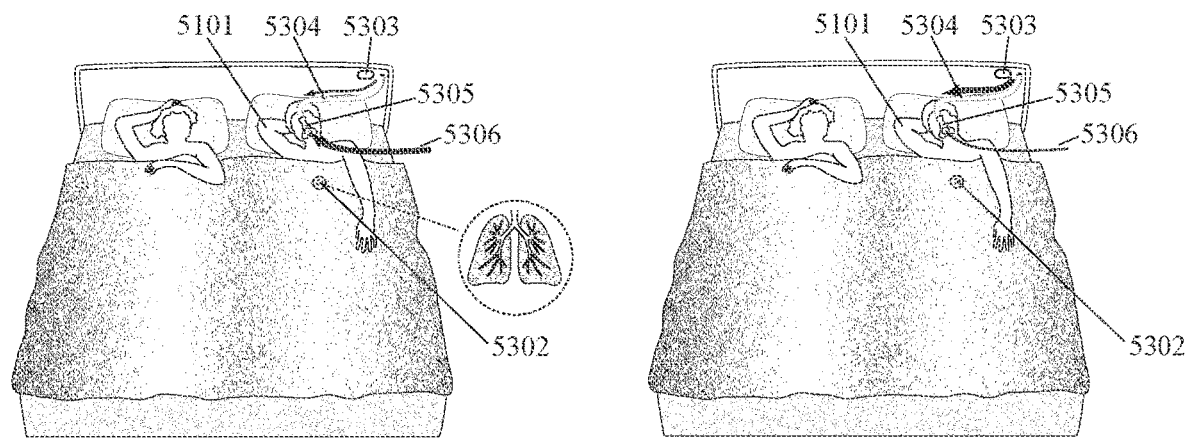
FIG. 53 shows a system for modifying a person's sleep environment which changes a person's breathable airflow based on a pulmonary function monitor.

FIG. 53 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's respiratory functioning; a sleep-environment-modifying component which changes the proportion of ambient air versus non-ambient air or other gas which the person breathes; and a data-control component which controls the operation of the sleep-environment-modifying component in order to automatically change the person's sleep environment based on data from the wearable-sensor component.

More specifically, the embodiment shown in FIG. 53 comprises: pulmonary function sensor 5302; gas flow tube 5304; respiratory mask 5305; and data-control component 5303. In this example, the flow of breathable gas through gas flow tube 5304 into respiratory mask 5305 is controlled by data-control component 5303 based on data from pulmonary function sensor 5302. In an example, this embodiment can increase the flow of breathable gas through gas flow tube 5304 when data from pulmonary function sensor 5302 indicates that person 5301 is experiencing an adverse respiratory event. In an example, the breathable gas that flows through gas flow tube 5304 can be oxygen rich. In an example, this embodiment can change the relative mixture or proportions of oxygen rich gas vs. ambient airflow 5306 which is breathed by person 5301 through respiratory mask 5305 based on data from pulmonary function sensor 5302.

The left side of FIG. 53 shows this embodiment at a first point in time wherein there is a first volume of gas flow through gas flow tube 5304 based on a first pattern of data from pulmonary function sensor 5302. The right side of FIG. 53 shows this embodiment at a second point in time wherein there is a second volume of gas flow through gas flow tube 5304 based on a second pattern of data from pulmonary function sensor 5302. In an example, the second volume of gas flow is greater than the first volume of gas flow. In an example, the first pattern of data indicates normal pulmonary function and the second pattern of data indicates inadequate or impaired pulmonary function. In an example, a higher volume of oxygen-rich gas flow can help to maintain proper blood oxygenation during an episode of inadequate or impaired respiratory function.

In an example, a wearable pulmonary function sensor can be selected from the group consisting of: wearable accelerometer, gyroscope, or other inertial-based motion sensor; a garment, strap, band, or other wearable accessory comprising piezoelectric members which generate electrical current when stretched or bent; a garment, strap, band, or other wearable accessory comprising electroconductive members whose resistance or impedance to electrical current changes when they are stretched or bent; a microphone or other sonic energy sensor; an EMG sensor or other electromagnetic energy sensor; and a spectroscopic sensor or other optical sensor. In an example, the operation of an HVAC system can be controlled directly by a component in a wearable device. In an example data from a wearable pulmonary function sensor can be used to change the proportion of ambient air versus non-ambient air, mixture or composition of air and/or other gas, or sources of air and/or other gas which the person breathes. Relevant example and component variations discussed elsewhere in this disclosure or in priority-linked disclosures can also be applied to this example, but are not repeated here to avoid narrative redundancy.

Figure 54:
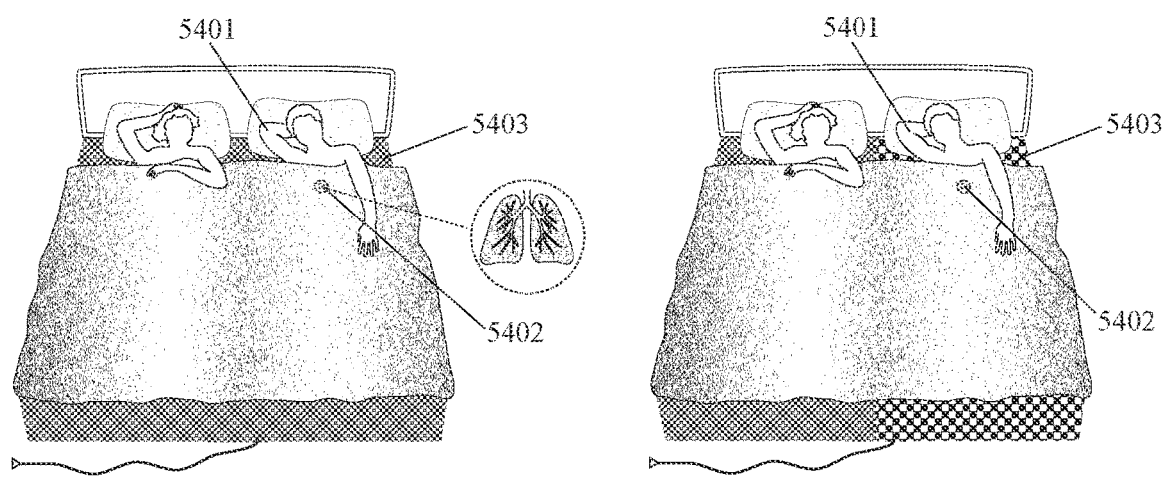
FIG. 54 shows a system for modifying a person's sleep environment which changes the porosity of a mattress based on a pulmonary function monitor.

FIG. 54 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's respiratory functioning; a sleep-environment-modifying component which changes the porosity of a bedding surface or layer on which the person lies; and a data-control component which controls the operation of the sleep-environment-modifying component in order to automatically change the person's sleep environment based on data from the wearable-sensor component.

More specifically, the embodiment shown in FIG. 54 comprises: wearable pulmonary function monitor 5402 worn by person 5401; and adjustable-porosity mattress 5403. In this example, the porosity of mattress 5403 is changed automatically based on data from wearable pulmonary monitor 5402. In an example, a pulmonary function monitor can be selected from the group consisting of: a microphone which measures sounds related to a person's respiration; an accelerometer or other inertial-based motion sensor which measures body motion related to a person's respiration; a piezoelectric member which generates electrical current based on body motion related to a person's respiration; electroconductive fabric or textile whose resistance or impedance to electrical current is changes by body motion related to a person's respiration; and an optical sensor which measures light energy transmitted through or reflected from a body surface wherein the intensity or spectrum of this light energy is affected by a person's pulmonary function.

In an example, the porosity of mattress 5403 can be changed by application of electrical current to piezoelectric fibers, strands, or structures which are incorporated into the mattress. In an example, mattress 5403 can further comprise an array of actuators whose activation changes the porosity of mattress 5403. In an example, mattress 5403 can further comprise an array of inflatable members whose inflation or deflation changes the porosity of mattress 5403. Relevant example and component variations discussed elsewhere in this disclosure or in priority-linked disclosures can also be applied to this example, but are not repeated here to avoid narrative redundancy.

Figure 55:
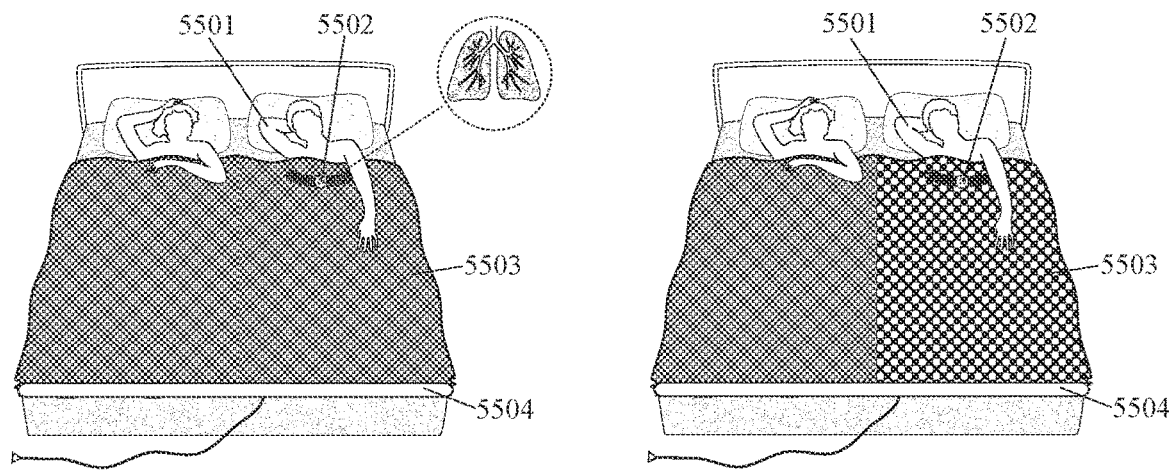
FIG. 55 shows a system for modifying a person's sleep environment which changes the porosity of a blanket based on a pulmonary function monitor.

The example of this invention which is shown in FIG. 55 is similar to the one shown in FIG. 54, except the porosity of a blanket is changed in response to data from a pulmonary function monitor instead of the porosity of a mattress. FIG. 55 shows how this invention can be embodied in a system, device, and method using wearable technology to collect data for automatic modification of a person's sleep environment comprising: a wearable-sensor component worn by a person, wherein this sensor component collects data concerning the person's respiratory functioning; a sleep-environment-modifying component which changes the porosity of a blanket or other bedding layer covering the person; and a data-control component which controls the operation of the sleep-environment-modifying component in order to automatically change the person's sleep environment based on data from the wearable-sensor component.

More specifically, the embodiment shown in FIG. 55 comprises: wearable pulmonary function monitor 5502 worn by person 5501; and adjustable-porosity blanket 5503. This embodiment further comprises blanket control unit 5504. In this example, the gaseous porosity of blanket 5503 is changed in response to changes in data collected by wearable pulmonary function monitor 5502. In an example, if pulmonary function monitor 5502 indicates respiratory distress, then this device can increase the porosity of blanket 5503. In an example, the porosity of blanket 5503 can be changed by a means selected from the group consisting of: application or adjustment of electrical current to piezoelectric fibers or strands incorporated into the blanket; activation of an array of microscale actuators incorporated into the blanket; inflation or deflation of an array of inflatable members incorporated into the blanket. In an example, pulmonary function monitor 5502 can monitor pulmonary function by a means selected from the group consisting of: measuring sounds related to respiration; measuring body motion related to respiration; measuring patterns of electromagnetic energy related to respiration; and measuring light transmitted through or reflected from body tissue related to respiration.

In an example, data collected by a wearable pulmonary function or respiratory function monitor can be used to change the porosity of a blanket, sheet, or other bedding layer covering a person while they sleep. In an example, data collected by a wearable pulmonary function or respiratory function monitor can be used to control an array of MEMS actuators which, in turn, change the porosity of a blanket, sheet, or other bedding layer covering a person while they sleep. Relevant example and component variations discussed elsewhere in this disclosure or in priority-linked disclosures can also be applied to this example, but are not repeated here to avoid narrative redundancy.

Figure 56:
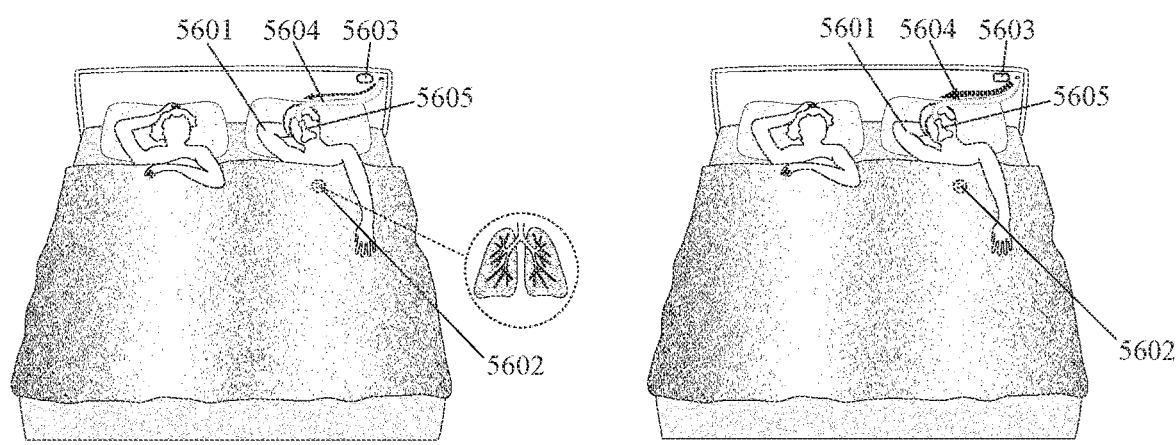
FIG. 56 shows a system for modifying a person's sleep environment which changes a person's air source based on a pulmonary function monitor.

FIG. 56 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's respiratory functioning; a sleep-environment-modifying component which changes the pressure of air and/or other gas which the person breathes; and a data-control component which controls the operation of the sleep-environment-modifying component in order to automatically change the person's sleep environment based on data from the wearable-sensor component.

More specifically, the embodiment shown in FIG. 56 comprises: wearable pulmonary function monitor 5602; gas inflow tube 5604; respiratory mask 5605; and data-control component 5603. In this example, the flow of breathable gas through gas inflow tube 5604 is automatically changed based on changes in data from wearable pulmonary function monitor 5602. In an example, the gas which flows through gas inflow tube 5604 into mask 5605 is richer in oxygen than ambient air. In an example, when data from wearable pulmonary function monitor 5602 indicates that person 5601 is probably experiencing respiratory distress and/or insufficient oxygenation, then this embodiment increases the flow of oxygen-rich breathable gas through gas inflow tube 5604.

The left side of FIG. 56 shows this embodiment at a first point in time wherein there is a first volume of gas flowing through gas inflow tube 5604 based on a first pattern of data collected by wearable pulmonary function monitor 5602. The right side of FIG. 56 shows this embodiment at a second point in time wherein there is a second volume of gas flowing through gas inflow tube 5604 based on a second pattern of data collected by wearable pulmonary function monitor 5602. In this example, the second volume is greater than the first volume, as symbolically represented by a thicker dotted-line arrow near gas inflow tube 5604 on the right side of FIG. 56 than on the left side of FIG. 56. In an example, the second pattern of data collected by wearable pulmonary function monitor 5602 can indicate an adverse respiratory event, episode, or condition.

In an example, a pulmonary function monitor can collect data concerning a person's pulmonary function by recording sounds related to the person's respiration. In an example, a pulmonary function monitor can collect data concerning a person's pulmonary function by measuring electromagnetic energy emitted from muscles or nerves related to the person's respiration. In an example, a pulmonary function monitor can collect data concerning a person's pulmonary function by measuring motion of one or more portions of the person's body related to the person's respiration. In an example, body motion related to respiration can be measured by an accelerometer, gyroscope, or inclinometer. In an example, body motion related to respiration can be measure by piezoelectric and/or electro-conductive fibers, threads, yarns, or strands incorporated into an article of clothing or accessory which a person wears while sleeping. In an example, movement of a person's lungs changes the shape of piezoelectric and/or electro-conductive fibers, threads, yarns, or strands which changes the flow of electrical current from or through these fibers, threads, yarns, or strands.

In an example, the volume, rate, composition, temperature, moisture level, pressure level, filtration level, and/or source of breathable gas entering respiratory mask 5605 can be automatically changed based on data collected by a wearable pulmonary function monitor. In an example, data collected by a wearable pulmonary function sensor or respiratory function monitor can be analyzed to identify the occurrence of an adverse respiratory event, episode, or condition. In an example, an adverse respiratory event, episode, or condition by person 5601 can automatically trigger a change in the volume, rate, composition, temperature, moisture level, pressure level, filtration level, and/or source of gas breathed by person 5601 in order to help correct the adverse respiratory event, episode, or condition. In an example, this analysis can occur in data-control component 5603. In another example, this analysis can occur in a remote location or within a data processor which is part of the wearable pulmonary function monitor. Relevant example and component variations discussed elsewhere in this disclosure or in priority-linked disclosures can also be applied to this example, but are not repeated here to avoid narrative redundancy.

Figure 57:
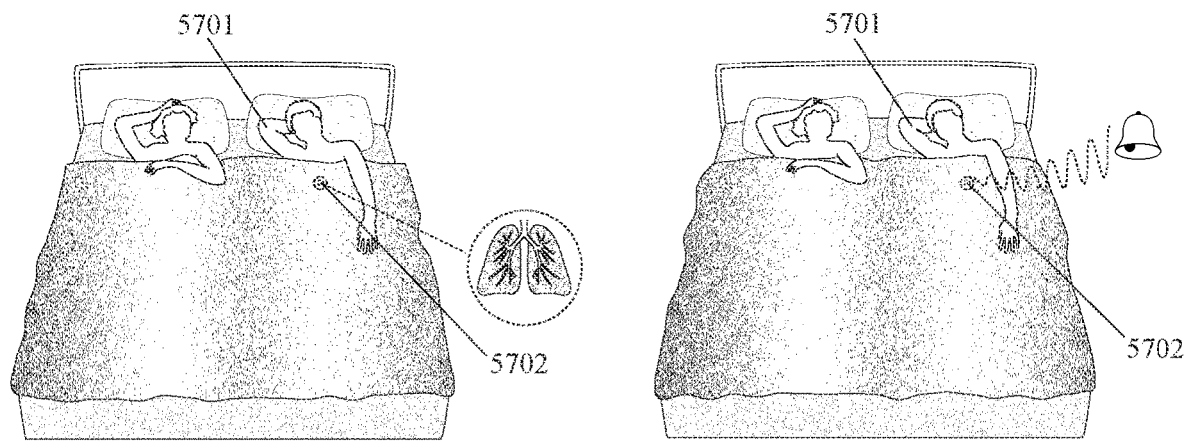
FIG. 57 shows a system for modifying a person's sleep environment which sounds an alarm based on a pulmonary function monitor.

FIG. 57 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's respiratory functioning; a sleep-environment-modifying component which emits sound; and a data-control component which controls the operation of the sleep-environment-modifying component in order to automatically change the person's sleep environment based on data from the wearable-sensor component.

More specifically, the embodiment shown in FIG. 57 comprises a wearable pulmonary function monitor 5702 which emits sounds when it detects an adverse respiratory event. In an example, pulmonary function monitor 5702 can collect data concerning a person's pulmonary function by recording sounds related to the person's respiration. In an example, pulmonary function monitor 5702 can collect data concerning a person's pulmonary function by measuring electromagnetic energy emitted from muscles or nerves related to the person's respiration. In an example, pulmonary function monitor 5702 can collect data concerning a person's pulmonary function by measuring motion of one or more portions of the person's body related to the person's respiration. In an example, body motion related to respiration can be measured by an accelerometer, gyroscope, or inclinometer. In an example, body motion related to respiration can be measure by piezoelectric and/or electro-conductive fibers, threads, yarns, or strands incorporated into an article of clothing or accessory which a person wears while sleeping. In an example, movement of a person's lungs changes the shape of piezoelectric and/or electro-conductive fibers, threads, yarns, or strands which changes the flow of electrical current from or through these fibers, threads, yarns, or strands. Relevant example and component variations discussed elsewhere in this disclosure or in priority-linked disclosures can also be applied to this example, but are not repeated here to avoid narrative redundancy.

Figure 58:
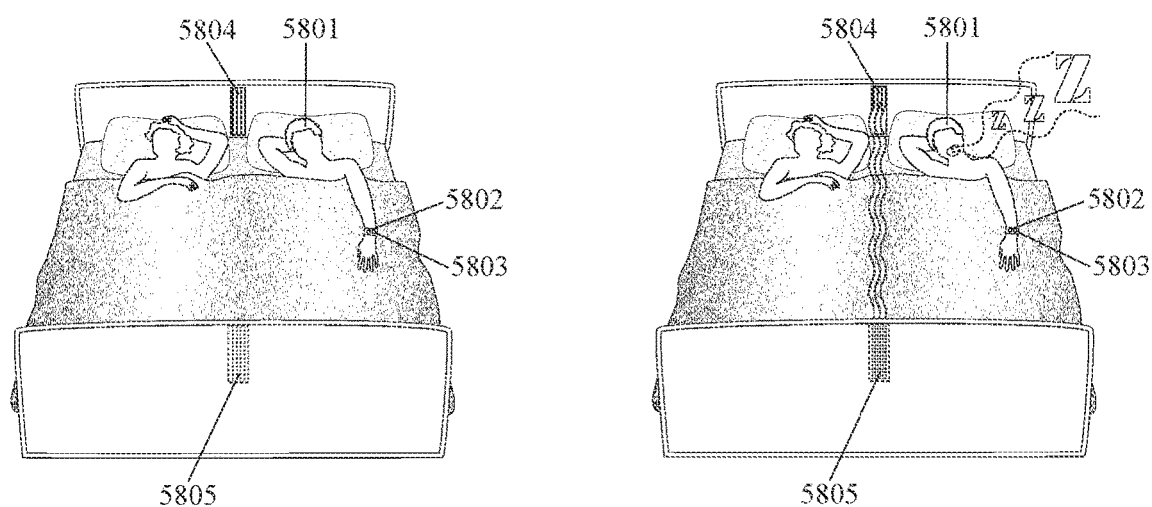
FIG. 58 shows a first system for modifying a person's sleep environment which changes airflow from a laminar airflow mechanism system based on a snoring sensor.

FIG. 58 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which controls the operation of a laminar airflow between a second person and the person; and a data-control component which controls the operation of the sleep-environment-modifying component in order to automatically change the person's sleep environment based on data from the wearable-sensor component.

More specifically, the embodiment shown in FIG. 58 comprises: a snoring sensor 5802; a data-control component 5803; and a laminar airflow mechanism comprising outflow vent 5804 and inflow vent 5805. In this example, when data from snoring sensor 5802 indicates that person 5801 is snoring, then data this triggers activation of a laminar airflow from outflow vent 5804 to inflow vent 5805. In an example, this laminar airflow can reduce the transmission of snoring sounds from person 5801 to a bed partner. In an example, this laminar airflow can longitudinally span the mid-section of a bed from an outflow vent near the head of the bed to an inflow vent near the foot of the bed. In an example, this laminar airflow can longitudinally span the top of a bed in a substantially vertical plane.

In an example, a laminar airflow can be directed to span a snoring person so as to actually disrupt the airflow patterns which cause snoring. In an example, a laminar airflow passing over a snoring person's head can interfere with airflow oscillation within the person's airway which causes snoring sounds. In an example, a pulsating laminar airflow can disrupt oscillation of soft tissue within a person's air which causes snoring sounds. In an example, the frequency of airflow pulsation can be matched to the frequency of snoring sound to optimally disrupt the creation of snoring sounds within a person's airway. In an example, the direction, pulsation, volume, and/or speed of an airflow proximal to a sleeping person can be automatically adjusted based on data from a snoring sensor in order disrupt or cancel the creation of snoring sounds in the sleeping person's airway. In an example, the direction, pulsation, volume, and/or speed of a laminar airflow spanning a sleeping person can be automatically adjusted based on data from a snoring sensor in order disrupt or cancel the creation of snoring sounds in the sleeping person's airway.

In an example, snoring sensor 5802 can comprise a microphone or other sound-based sensor. In an example, the frequency, amplitude, and/or waveform of sound recorded by a microphone or other sound-based sensor can be analyzed by data-control component 5803 in order to identify snoring by person 5801. In an example, data from a snoring sensor can be analyzed in a separate electronic device such as a smart phone or electronic tablet with which the snoring sensor is in wireless communication. In this example, sound sensor 5802 is worn by person 5801 as part of a wrist band. In other examples, a sound sensor can be worn on a person's neck, ear, nose, head, torso, finger, hand, arm, or neck. In an example, a snoring sensor can be incorporated into an article of clothing. In an example, a snoring sensor can be incorporated into the headboard of a bed, a pillow, a blanket, or another part of a bed structure or bedding.

In an example, the volume or speed of airflow through a laminar airflow mechanism can be controlled by the volume or duration of snoring. In an example, the volume or speed of laminar airflow can be increased when the volume or duration of snoring increases. The left side of FIG. 58 shows this embodiment at a first point in time wherein a central longitudinal laminar airflow mechanism is not activated because data from snoring sensor 5802 indicates that person 5801 is not snoring. The right side of FIG. 58 shows this embodiment at a second point in time wherein a central longitudinal laminar airflow mechanism is activated in response to data from snoring sensor 5802 which indicates that person 5801 is snoring. In this figure, laminar airflow is symbolically represented by an array of parallel sinusoidal dotted-lines from outflow vent 5804 to inflow vent 5805. In this figure, the person's snoring is symbolically represented by a series of ascending "Z's" over the person's head.

In an example, data from a wearable snoring sensor can be used to: change the operation of a central longitudinal laminar airflow on a bed; change the laminar flow of air and/or other gas in communication with the surface of the person's body; change the laminar flow of air and/or other gas which the person breathes; or change the spatial configuration of the flow of air and/or other gas which the person breathes. In an example, laminar airflow proximal to a snoring person can disrupt the transmission of snoring sound to a bed partner and/or disrupt the oscillation of soft tissue in the person's airway which creates snoring sound. Relevant example and component variations discussed elsewhere in this disclosure or in priority-linked disclosures can also be applied to this example, but are not repeated here to avoid narrative redundancy.

Figure 59:
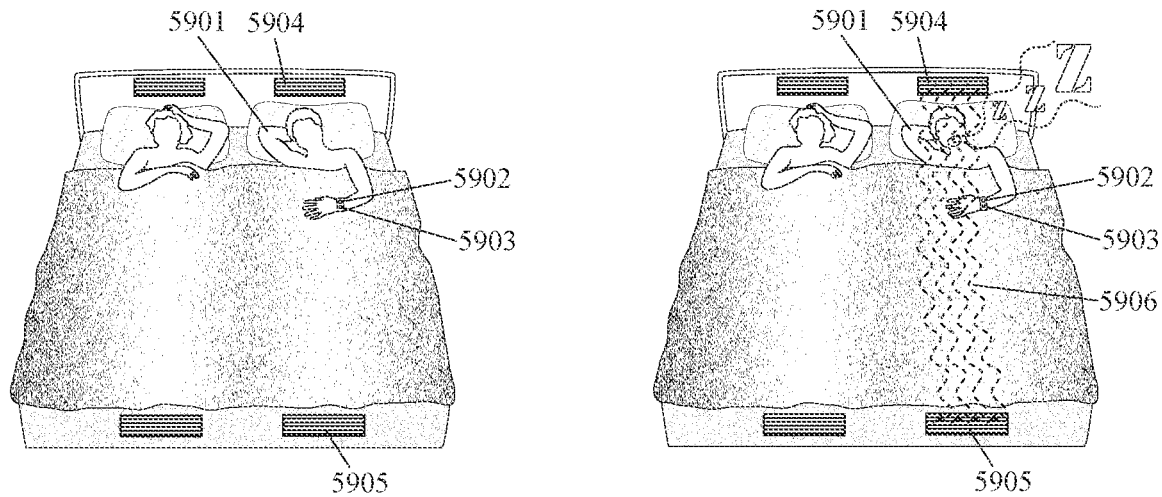
FIG. 59 shows a second system for modifying a person's sleep environment which changes airflow from a laminar airflow mechanism system based on a snoring sensor.

The embodiment of this invention which is shown in FIG. 59 is similar to the one shown in FIG. 58, except that a laminar airflow spans a person in a plane which is substantially horizontal. More generally, FIG. 59 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which changes the direction, flow rate, pressure, humidity, temperature, mixture, and/or source of the air or other gas which the person breathes; and a data-control component which controls the operation of the sleep-environment-modifying component in order to automatically change the person's sleep environment based on data from the wearable-sensor component.

The embodiment of this invention that is shown in FIG. 59 comprises: a snoring sensor 5902; a data-control component 5903; and a laminar airflow mechanism which further comprises outflow vent 5904 and inflow vent 5905. In this example, a bed is equipped with two laminar flow mechanisms, one for each side of the bed, and these two laminar flow mechanisms can be separately controlled. In this example, data from a snoring sensor is used to change the direction, flow rate, pulsation frequency, or spatial configuration of one or more laminar airflows spanning a bed. In an example, when data from a snoring sensor indicates that a person is snoring, then the device activates a laminar airflow proximal to the person which disrupts the creation of snoring within the person's airway and/or disrupts the transmission of sonic energy from the snoring person to a bed partner.

In this example, a laminar airflow spans a bed in a substantially horizontal plane from the head of the bed to the foot of the bed. In another example, a laminar airflow can span a bed in a diagonal manner from the head of a bed to a side of the bed. In an example, a laminar airflow can span a bed from one side of the bed to the other side of the bed. In an example, a laminar airflow triggered by a snoring person can span a bed from the side with a bed partner to the side with the snoring person, so as to reduce transmission of sonic energy from the snoring person to the bed partner.

In an example, a snoring sensor can comprise a microphone or other sound sensor. In an example, a snoring sensor can be worn on a person's wrist, ear, neck, head, or torso. In an example, a snoring sensor can be incorporated into a bed headboard. In an example, a snoring sensor can be incorporated into a pillow or blanket. In an example, a snoring sensor can be incorporated into a respiratory mask. In an example, data from a snoring sensor can be used to: change the rate of the flow of air and/or other gas in communication with the surface of a person's body; change the flow of air and/or other gas in communication with the surface of a person's body; or change the rate of the flow of air and/or other gas which a person breathes. Relevant example and component variations discussed elsewhere in this disclosure or in priority-linked disclosures can also be applied to this example, but are not repeated here to avoid narrative redundancy.

Figure 60:
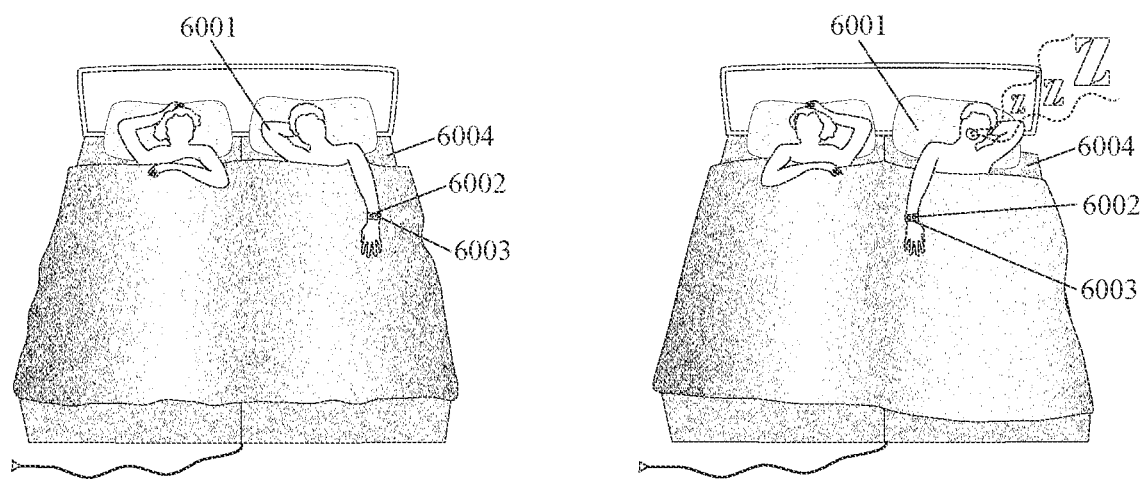
FIG. 60 shows a system for modifying a person's sleep environment which changes the lateral slope of a bed based on a snoring sensor.

FIG. 60 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which changes the latitudinal slope or other latitudinal configuration of a bedding surface on which the person lies; and a data-control component which controls the operation of the sleep-environment-modifying component in order to automatically change the person's sleep environment based on data from the wearable-sensor component.

More specifically, the embodiment shown in FIG. 60 comprises: snoring sensor 6002; data-control component 6003; and mattress 6004 with an adjustable lateral configuration. In this example, the lateral slope of mattress 6004 is automatically changed based on data from snoring sensor 6002. In an example, when data from snoring sensor 6002 indicates that person 6001 is snoring, then this device automatically adjusts the lateral configuration of the portion of mattress 6004 on which person 6001 sleeps so as to change the orientation and/or configuration of the person's body. In an example, this change in body orientation and/or configuration can help to reduce the person's snoring. In an example, this change in body orientation and/or configuration can orient the person's head away from a bed partner so as to reduce the magnitude of snoring sound heard by the bed partner.

In an example, the lateral configuration of mattress 6004 can be changed by differential deflation or inflation of inflatable components comprising mattress 6004. In an example, the lateral configuration of mattress 6004 can be changed by differential activation of one or more actuators comprising mattress 6004. In an example, data from snoring sensor 6002 can trigger a change in the lateral slope of a portion of mattress 6004 which causes a snoring person to roll over on their side and thereby reduce snoring. In an example, data from snoring sensor 6002 can trigger a change in the lateral slope of a portion of mattress 6004 which causes a snoring person to roll over on their side, facing away from their bed partner, and thereby reduce the impact of snoring on their bed partner. In an example, the lateral configuration of mattress 6004 can be changed in a non-linear manner, such as creating a convex or concave sleeping surface to reduce snoring and/or the impact of snoring on a bed partner.

In an example, a snoring sensor can be a microphone or other sound-based sensor. In an example, a snoring sensor can be worn on a person's wrist, hand, arm, neck, ear, nose, head, or torso. In an example, a snoring sensor can be incorporated into a bed headboard, pillow, blanket, mattress, or other bed structure or layer. In an example, a snoring sensor can be incorporated into a portable electronic device such as a smart phone or electronic tablet. In an example, data from a snoring sensor or snoring monitor can be used to change the shape, orientation, motion, slope, tilt, or configuration of a mattress or other bedding surface on which a person lies. In an example, data from a snoring sensor or snoring monitor can be used to: control one or more actuators which move a mattress on which a person lies; change the direction of movement of a mattress on which a person lies; change the shape of a mattress on which a person lies; or change the magnitude of movement of a mattress on which the person lies.

The left side of FIG. 60 shows this embodiment at a first point in time in which mattress 6004 has a first configuration based on a first pattern of data from snoring sensor 6002. The right side of FIG. 60 shows this embodiment at a second point in time in which mattress 6004 has a second configuration based on a second pattern of data from snoring sensor 6002. In this example, the first configuration is substantially flat and the second configuration comprises a downward lateral slope toward the side of the bed. In this example, the first pattern of data indicates that person 6001 is not snoring and the second pattern of data indicates that person 6001 is snoring. In an example, the change in person 6001's orientation or configuration caused by the downward slope of mattress 6004 will subsequently reduce snoring. In an example, the change in person 6001's orientation or configuration caused by the downward slope of mattress 6004 reduces the magnitude of snoring sound heard by the person's bed partner. Relevant example and component variations discussed elsewhere in this disclosure or in priority-linked disclosures can also be applied to this example, but are not repeated here to avoid narrative redundancy.

Figure 61:
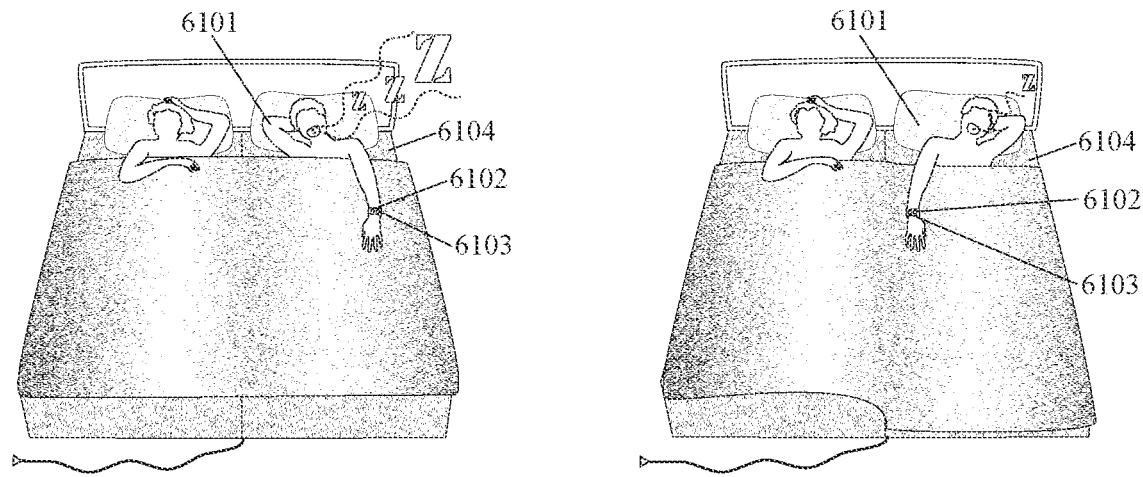
FIG. 61 shows a system for modifying a person's sleep environment which changes the longitudinal slope of a bed based on a snoring sensor.

As shown in FIG. 61, this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which changes the longitudinal slope or other longitudinal configuration of a bedding surface on which the person lies; and a data-control component which controls the operation of the sleep-environment-modifying component in order to automatically change the person's sleep environment based on data from the wearable-sensor component.

More specifically, the embodiment shown in FIG. 61 comprises: snoring sensor 6102; data-control component 6103; and mattress 6104 with an adjustable longitudinal configuration. In this example, the longitudinal slope of mattress 6104 is automatically changed based on data from snoring sensor 6102. In an example, when data from snoring sensor 6102 indicates that person 6101 is snoring, then this device automatically adjusts the longitudinal configuration of the portion of mattress 6104 on which person 6101 sleeps so as to change the orientation and/or configuration of the person's body. In an example, this change in body orientation and/or configuration can help to reduce the person's snoring. In an example, the longitudinal configuration of mattress 6104 can be changed by differential deflation or inflation of inflatable components comprising mattress 6104. In an example, the longitudinal configuration of mattress 6104 can be changed by differential activation of one or more actuators comprising mattress 6104. In an example, the longitudinal configuration of mattress 6104 can be changed in a non-linear manner, such as creating a convex or concave sleeping surface.

In an example, a snoring sensor can be a microphone or other sound-based sensor. In an example, a snoring sensor can be worn on a person's wrist, hand, arm, neck, ear, nose, head, or torso. In an example, a snoring sensor can be incorporated into a bed headboard, pillow, blanket, mattress, or other bed structure or layer. In an example, a snoring sensor can be incorporated into a portable electronic device such as a smart phone or electronic tablet. In an example, data from a snoring sensor or snoring monitor can be used to change the shape, orientation, motion, slope, tilt, or configuration of a mattress or other bedding surface on which a person lies. In an example, data from a snoring sensor or snoring monitor can be used to: control one or more actuators which move a mattress on which a person lies; change the direction of movement of a mattress on which a person lies; change the shape of a mattress on which a person lies; or change the magnitude of movement of a mattress on which the person lies.

The left side of FIG. 61 shows this embodiment at a first point in time wherein which mattress 6104 is substantially flat and wherein data from snoring sensor 6102 indicates that person 6101 is snoring. The right side of FIG. 61 shows this embodiment at a second point in time wherein the longitudinal slope of mattress has been changed in response to the person's snoring and wherein this change in slope has decreased the person's snoring. In this example, the changed configuration of mattress 6104 is a downward slope from the head of the bed to the foot of the bed. In this example, only the half of the mattress on which person 6101 lies has its longitudinal configuration changed based on data from snoring sensor 6202. In an example, data from a wearable snoring sensor can be used to change the longitudinal slope or other longitudinal configuration of a mattress, box spring, or other bedding surface on which a person lies in order to reduce snoring or the perception of snoring by a bed partner. Relevant example and component variations discussed elsewhere in this disclosure or in priority-linked disclosures can also be applied to this example, but are not repeated here to avoid narrative redundancy.

Figure 62:
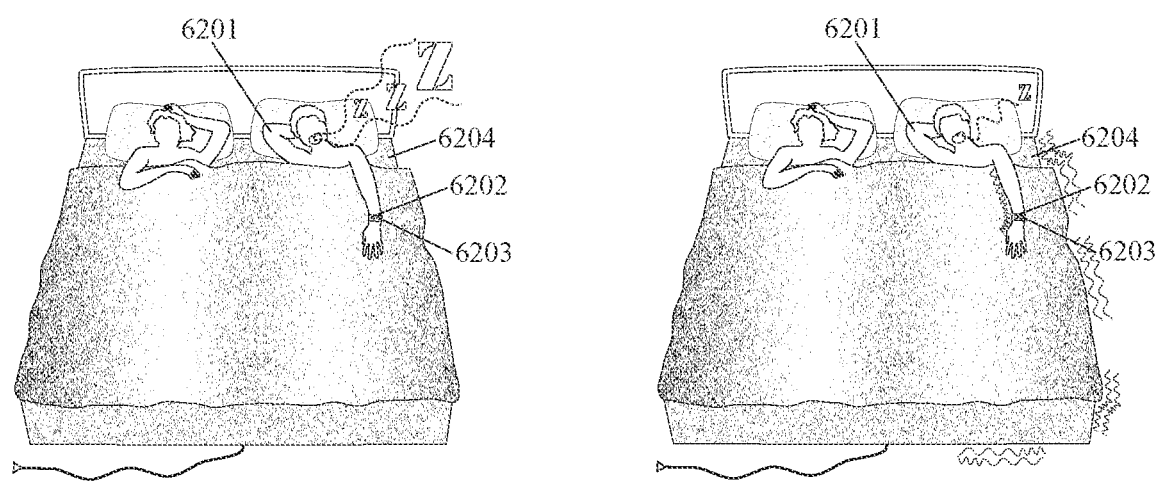
FIG. 62 shows a system for modifying a person's sleep environment which vibrates a bed based on a snoring sensor.

FIG. 62 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which starts or stops the vibration or oscillation of a bedding surface on which the person lies; and a data-control component which controls the operation of the sleep-environment-modifying component in order to automatically change the person's sleep environment based on data from the wearable-sensor component.

More specifically, the embodiment shown in FIG. 62 comprises: wearable snoring sensor 6202; data-control component 6203; and moving mattress 6204. In an example, when data from snoring sensor 6202 indicates that person 6201 is snoring, then this triggers vibration or other movement of the side of mattress 6205 on which person 6201 lies in order to disrupt the person's snoring. The left side of FIG. 62 shows this embodiment at a first point in time wherein data from wearable snoring sensor 6202 indicates that person 6201 is snoring. The right side of FIG. 62 shows this embodiment at a second point in time wherein the side of mattress 6204 on which person 6201 lies is vibrating, wherein this vibration has reduced the magnitude of the person's snoring.

In an example, a snoring sensor can comprise a microphone. In an example, a snoring sensor can be configured to be worn on a body part selected from the group consisting of: wrist, hand, arm, neck, ear, nose, head, and torso. In an example, a snoring sensor can be incorporated into a pillow, blanket, mattress, or bed headboard. In an example, a snoring sensor can be part of a smart phone or other mobile electronic device. In an example, a moving mattress can vibrate, shake, or move in a larger-scale repeating pattern. In an example, a moving mattress can slowly oscillate from right to left when snoring is detected. In an example, data from a snoring sensor can be used to change: the frequency of repeated movements of a mattress or other bedding surface on which a person lies; or the operation of one or more actuators which change the frequency of repeated movements of a mattress or other bedding surface on which a person lies. Relevant example and component variations discussed elsewhere in this disclosure or in priority-linked disclosures can also be applied to this example, but are not repeated here to avoid narrative redundancy.

Figure 63:
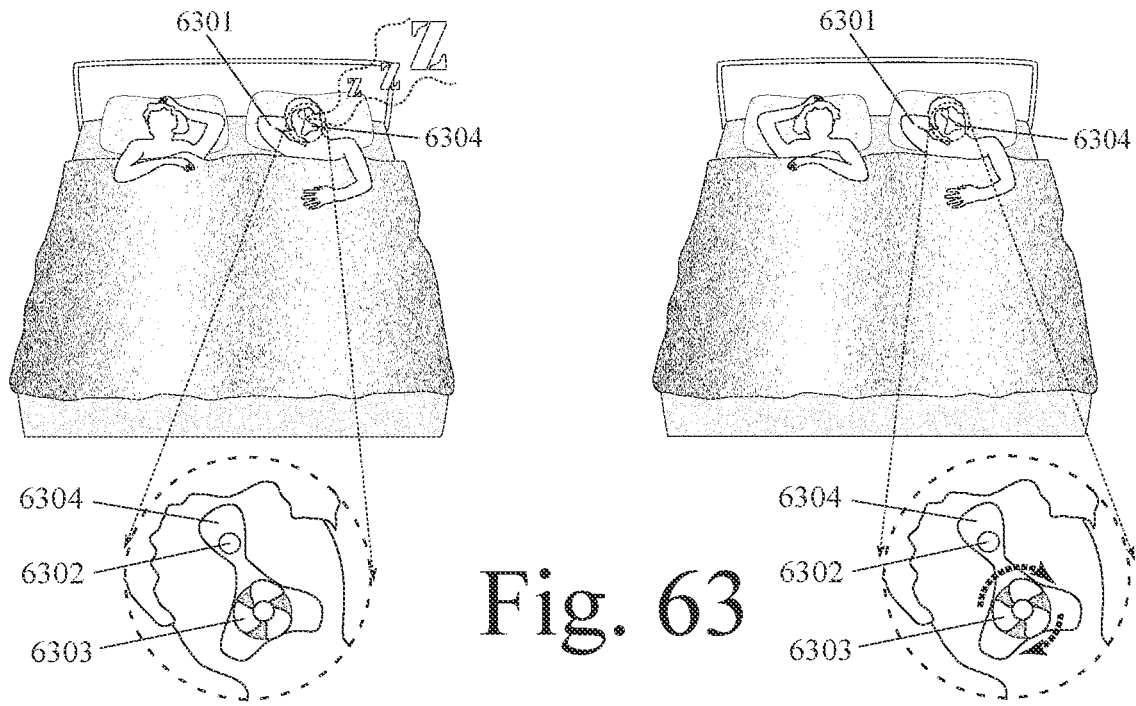
FIG. 63 shows a system for modifying a person's sleep environment which changes a person's air pressure based on a snoring sensor.

FIG. 63 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which changes the pressure of air and/or other gas which the person breathes; and a data-control component which controls the operation of the sleep-environment-modifying component in order to automatically change the person's sleep environment based on data from the wearable-sensor component.

More specifically, the embodiment shown in FIG. 63 comprises: snoring sensor 6302; respiratory mask 6304; and air-moving member 6303. In this example, when data from snoring sensor 6302 indicates that person 6301 is snoring, then this triggers an increase in the rotation of air-moving member 6303 which increases the air pressure within mask 6304. In an example, when data from snoring sensor 6302 indicates that person 6301 is snoring, then this can activate air-moving member 6303 to start moving air which increases air pressure within the mask about the pressure level of ambient air. In an example, elevated air pressure can help to open the person's airway and disrupt the person's snoring. In this example, air-moving member 6303 is an air impellor or fan. In other examples, air-moving member 6303 can be a different type of air pump or air-moving mechanism. In this example, snoring sensor 6302 and air-moving member 6303 are co-located as parts of respiratory mask 6304. In another example, snoring sensor may be located elsewhere and in wireless communication with air-moving member 6303. In an example, snoring sensor 6302 can comprise a microphone.

In an example, data from a wearable snoring sensor can be used to change the pressure of air and/or other gas which a person breathes. In an example, this change in pressure can reduce or stop snoring. In an example, data from a wearable snoring sensor can be used to create pulses in airflow which a person breathes. In an example, these pulses can reduce or stop snoring. In an example, respiratory mask 6304 can cover a person's nose and mouth. In an example, a respiratory mask can cover only a person's nose. In an alternative example, this invention can comprise a snoring sensor, nasal pillows, and an air-moving member. Relevant example and component variations discussed elsewhere in this disclosure or in priority-linked disclosures can also be applied to this example, but are not repeated here to avoid narrative redundancy.

Figure 64:
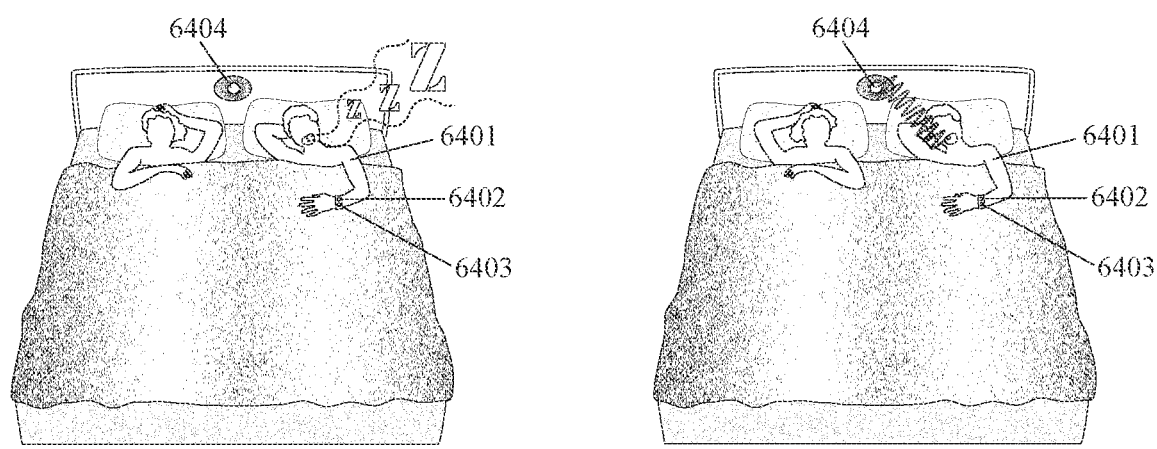
FIG. 64 shows a system for modifying a person's sleep environment with sound cancelling based on a snoring sensor.

FIG. 64 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which emits sound that is opposite in phase to ambient sound; and a data-control component which controls the operation of the sleep-environment-modifying component in order to automatically change the person's sleep environment based on data from the wearable-sensor component.

More specifically, the embodiment shown in FIG. 64 comprises: snoring sensor 6402; data-control component 6403; and sound-cancelling mechanism 6404. In this example, when data from snoring sensor 6402 indicates that person 6401 is snoring, then this triggers the emission of sound patterns from sound-cancelling mechanism 6404 which cancel out the sound patterns of snoring. In an example, snoring sensor collects data on the frequency, magnitude, and waveform of snoring sounds from person 6401. In an example, the sound patterns which are emitted from sound-cancelling mechanism 6404 are created to be inverse patterns of snoring sounds, such these two sounds cancel each other out when they collide in the air. In an example, the sound-cancelling mechanism can further comprise a loud speaker which is incorporated into a bed headboard. In an example, a sound cancelling mechanism can further comprise a loud speaker which is placed on a surface elsewhere in the room.

The left side of FIG. 64 shows this embodiment in a first configuration wherein data from snoring sensor 6402 indicates that person 6401 is snoring and this snoring sound can be heard by the person's bed partner. The right side of FIG. 64 shows this embodiment in a second configuration wherein sounds emitted from sound-cancelling mechanism 6404 collide with, and cancel out, snoring sounds from person 6401 before those snoring sounds reach the person's bed partner. In an example, sonic energy emitted from sound-cancelling mechanism 6404 can be focused in a specific direction (such as toward person 6401) by means of a parabolic shaped sound reflector. In an example, data from a wearable snoring sensor can be used to trigger an emission of sound that is opposite in phase to snoring sound. Relevant example and component variations discussed elsewhere in this disclosure or in priority-linked disclosures can also be applied to this example, but are not repeated here to avoid narrative redundancy.

Figure 65:
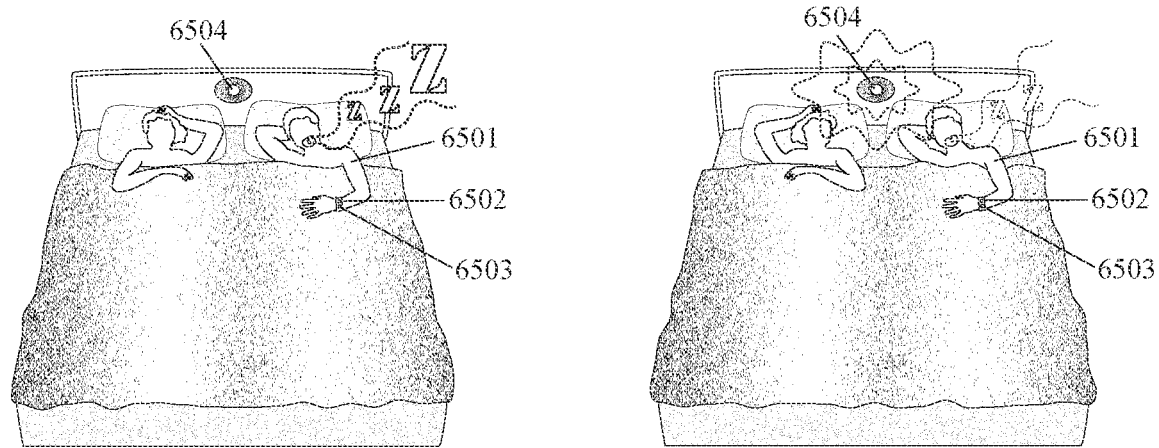
FIG. 65 shows a system for modifying a person's sleep environment with sound masking based on a snoring sensor.

FIG. 65 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which emits sound with the same central frequency or frequency range as ambient sound; and a data-control component which controls the operation of the sleep-environment-modifying component in order to automatically change the person's sleep environment based on data from the wearable-sensor component.

More specifically, the embodiment shown in FIG. 65 comprises: a snoring sensor 6502; a data-control component 6503; and a sound-masking member 6504. In an example, when data from snoring sensor 6502 indicates that person 6501 is snoring, then this triggers a sound-masking sonic emission from member 6504. In an example, the frequency range of a sound-masking sonic emission can be based on the frequency range of snoring sound detected by snoring sensor 6502. In an example, the amplitude of a sound-masking sonic emission can be based on the amplitude of snoring sound detected by snoring sensor 6502. In an example, a sound-masking sonic emission can be white noise or pink noise. In an example a sound-masking sonic emission can reduce the perception of snoring noise by a person's bed partner.

The left side of FIG. 65 shows this embodiment at a first point in time wherein data from snoring sensor 6502 indicates that person 6501 is snoring and this snoring sound is clearly heard by the person's bed partner. The right side of FIG. 65 shows this embodiment at a second point in time wherein sound-masking member 6504 has been activated in response to detected snoring and wherein a sound-masking sonic emission has reduced the perception of snoring sound by the person's bed partner. In an example, a snoring sensor can further comprise a microphone. In an example, a snoring sensor can be worn on a portion of a person's body selected from the group consisting of: wrist; hand; finger; arm; neck; ear; nose; and torso. In an example, a sound-masking member can be located on a bed headboard. In an example, a sound-masking member can be incorporated into a mobile electronic device such as a smart phone or electronic tablet. In an example, a sound-masking member can be placed on a surface elsewhere in a bedroom. In an example, a data-control unit can be co-located with the sound-masking member instead of co-located with the snoring sensor. In an example, data from a snoring sensor can be used to control a sleep-environment-modifying component which emits sound with the same central frequency or frequency range as ambient sound. Relevant example and component variations discussed elsewhere in this disclosure or in priority-linked disclosures can also be applied to this example, but are not repeated here to avoid narrative redundancy.

Figure 66:
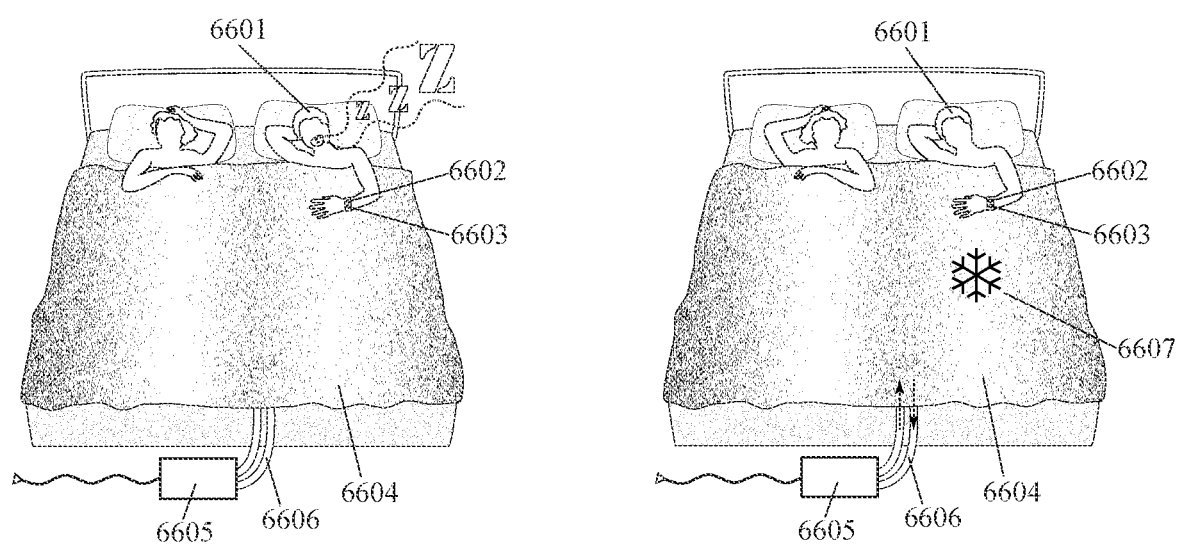
FIG. 66 shows a system for modifying a person's sleep environment which changes bed temperature based on a snoring sensor.

FIG. 66 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which changes the temperature of the air, mattress, blanket, or other bedding material near the person's body; and a data-control component which controls the operation of the sleep-environment-modifying component in order to automatically change the person's sleep environment based on data from the wearable-sensor component.

More specifically, the embodiment shown in FIG. 66 comprises: snoring sensor 6602; data-control component 6603; and temperature-changing blanket 6604. In this example, data-control component 6603 changes the temperature of blanket 6604 based on data from snoring sensor 6602. In an example, changing the sleep environment temperature of person 6601 can reduce snoring behavior. The left side of FIG. 66 shows this embodiment at a first point in time wherein data from snoring sensor 6602 indicates that person 6601 is snoring. The right side of FIG. 66 shows this embodiment at a second point in time wherein temperature-changing blanket 6604 is cooling person 6601, as symbolically represented by "snowflake" symbol 6607.

In an example, a snoring sensor can comprise a microphone. In an example, a snoring sensor can be worn on a person's wrist, hand, finger, neck, ear, nose, head, or torso. In an example, a snoring sensor can be incorporated into a smart phone or other mobile electronic device. In an example, a snoring sensor can be incorporated into a garment. In an example, a snoring sensor can be incorporated into a bed headboard, mattress, blanket, or box spring.

In this example, the temperature of temperature-changing blanket is reduced by circulation of a cooling liquid or gas from heat exchanger 6605 via flow tubes 6606. In this example, heat exchanger transfers heat from the blanket to air in the room. In another example, a heat exchanger can further comprise a compartment to contain ice or another pre-cooled substance. In an example, a cooling liquid or gas can circulate through sinusoidal tubes or channels in blanket 6604. In this example, blanket 6604 provides a cooling function. In another example, blanket 6604 can provide a warming function. In an example, a warming function can be provided by a traditional electric blanket rather than by a blanket with circulating fluid or gas.

In an example, a reduction in the temperature of a person's sleep environment can reduce that person's snoring. In an example, an increase in the temperature of a person's sleep environment can reduce that person's snoring. In an example, a person's snoring can be reduced by a change in temperature which changes the tone or flexibility of soft tissue along the person's airway. In an example, a person's snoring can be reduced by a change in temperature which changes the resonant frequency of vibrating tissue or airway space along a person's airway. In an example, a person's snoring can be reduced by a change in temperature which changes the opening size of a person's airway. In an example, data from a snoring sensor is used to change the temperature of a blanket, a mattress pad, a mattress, a pillow, or airflow in gaseous communication with a sleeping person. Relevant example and component variations discussed elsewhere in this disclosure or in priority-linked disclosures can also be applied to this example, but are not repeated here to avoid narrative redundancy.

Figure 67:
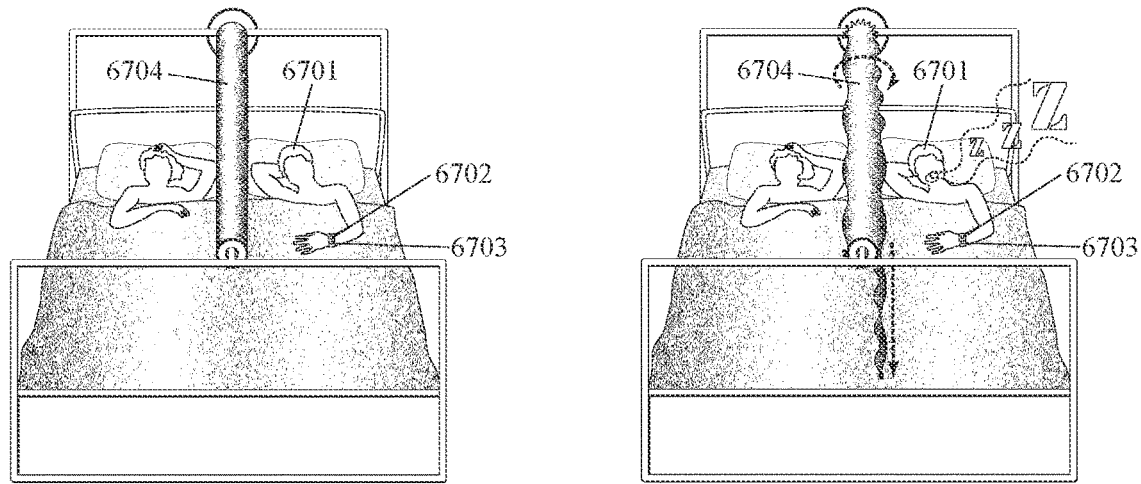
FIG. 67 shows a "smooch and snore-couch no more" system for modifying a person's sleep environment which deploys an acoustic partition based on a snoring sensor.

FIG. 67 shows an example of how this invention can be embodied in a system, device, and method that uses wearable technology to collect data for automatic modification of a person's sleep environment comprising: a wearable-sensor component that is configured to be worn by a person, wherein this sensor component collects data concerning snoring; a sleep-environment-modifying component which controls the operation of an acoustic partition or barrier between a second person and the person; and a data-control component which controls the operation of the sleep-environment-modifying component in order to automatically change the person's sleep environment based on data from the wearable-sensor component.

More specifically, the embodiment shown in FIG. 67 comprises: snoring sensor 6702, data-control component 6703; and movable acoustic partition 6704. In this example, when data from snoring sensor 6702 indicates that person 6701 is snoring, then this triggers the deployment of moving acoustic partition 6704. In this example, acoustic partition is wrapped around a cylindrical member above the central longitudinal axis of a bed for two people when it is not deployed and unrolls downward to form an acoustic partition between the two people when it is deployed. In this example, a movable acoustic partition is unrolled downward to form a partition in a vertical plane which that is substantially along the central longitudinal axis of a bed.

The left side of FIG. 67 shows this embodiment at a first point in time when data from snoring sensor 6702 indicates that person 6701 is not snoring and moving acoustic partition 6704 is not deployed. The right side of FIG. 67 shows this embodiment at a second point in time when data from snoring sensor 6702 indicates that person 6701 is snoring and this indication triggers the deployment of moving acoustic partition 6704. In this example, the deployment of moving acoustic partition 6704 between the two people helps to reduce the transmission of snoring sound from person 6701 to the person's bed partner. In an example, a snoring sensor can comprise a microphone. In an example, a snoring sensor can be worn on a person's wrist, hand, arm, neck, ear, nose, head, or torso. In an example, a snoring sensor can be incorporated into a bed headboard, mattress, box spring, blanket, or pillow. In an example, a snoring sensor can be part of a mobile electronic device such as a smart phone.

In an example, a movable acoustic partition can be deployed by inflation instead of unrolling. In an example, a movable acoustic partition can be deployed by sliding or unfolding. In an example, a movable acoustic partition can be an acoustic curtain which slides across the central longitudinal axis of a bed along a rod located above the bed. In an example, a movable acoustic partition can be deployed by being lowered onto a portion of a bed. In an example, analysis of data from a snoring sensor or snoring monitor can be used to: control the operation of an acoustic partition or barrier between a second person and the person; and/or control the operation of a central longitudinal acoustic partition or barrier on a bed. In an example, this analysis can occur in a data-control component which is co-located with the snoring sensor or monitor. In an example, this analysis can occur in a data processing in a remote device with which a snoring sensor or monitor is in wireless communication. Relevant example and component variations discussed elsewhere in this disclosure or in priority-linked disclosures can also be applied to this example, but are not repeated here to avoid narrative redundancy.

Figure 68:
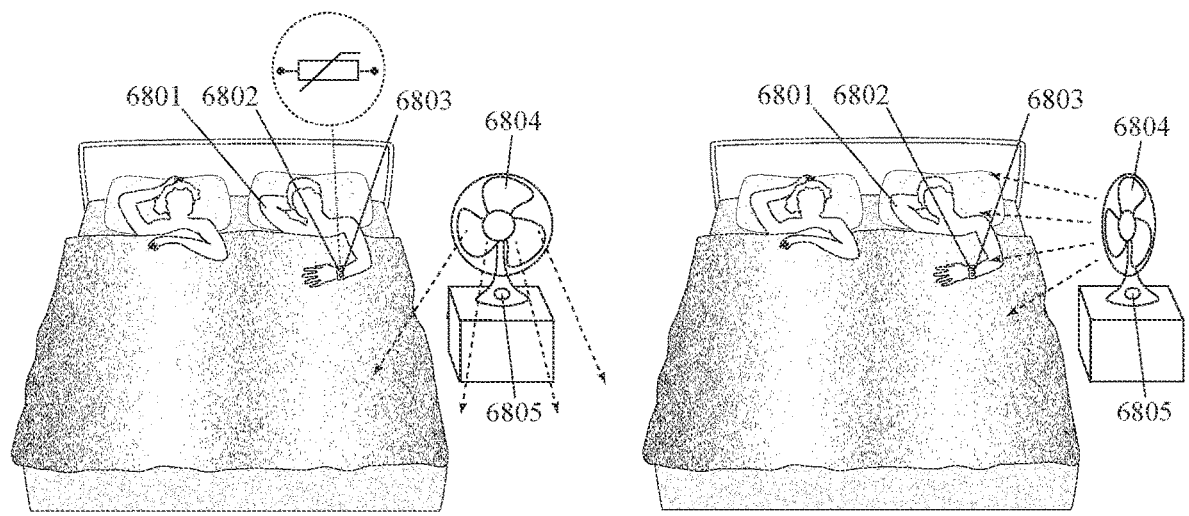
FIG. 68 shows a first system for modifying a person's sleep environment which changes airflow from a fan based on a wearable thermal energy sensor.

FIG. 68 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the direction of a flow of air coming from a portable fan or blower; and a data-control component which controls the operation of the sleep-environment-modifying component in order to automatically change the person's sleep environment based on data from the wearable-sensor component.

More specifically, the embodiment shown in FIG. 68 comprises: wearable thermal energy sensor 6802; power source or transducer 6803; portable fan 6804; and data-control component 6805. In this example, the operation of portable fan 6804 is controlled by data from wearable thermal energy sensor 6802. In this example, when data from wearable thermal energy sensor 6802 indicates an increase in the temperature of person 6801, then this triggers portable fan 6804 to direct airflow toward person 6801. In this example, when data from wearable thermal energy sensor 6802 indicates that person 6801 is too warm, then data-control component 6805 changes the direction of airflow from portable fan 6804 toward person 6801.

In an example, when data from wearable thermal energy sensor 6802 indicates that a person is experiencing a temporary biologically-caused upswing in body temperature (such as a hot flash), then this can trigger airflow from an air-moving device to be directed toward the person for a period of time. In an example, when data from wearable thermal energy sensor 6802 predicts that a person will probably experience a temporary biologically-caused increase in body temperature (such as a hot flash) soon, then this can trigger airflow from an air-moving device to be directed toward the person for prophylactic reduction in the person's body temperature to mitigate or avoid the effects of the upswing in body temperature. In an example, airflow can be triggered for a predefined period of time. In an example, airflow can be activated until the upswing in body temperature is over, based on data from the wearable thermal energy sensor. In an example, data from a wearable thermal energy sensor can be combined with data from another type of body sensor (such as a heart rate sensor, skin moisture sensor, or skin impedance sensor) to predict a temporary upswing in a person's body temperature and trigger airflow toward the person.

In this example, wearable thermal energy sensor 6802 is a thermistor, as symbolically represented by the thermistor electrical component symbol shown within a dotted-line circle in FIG. 68. In an example, wearable thermal energy sensor can be a thermometer or other type of temperature-measuring sensor. In this example, a wearable thermal energy sensor is worn on a person's wrist. In an example, a wearable thermal energy sensor can be worn on a person's finger, hand, arm, neck, ear, head, torso, leg, or foot. In an example, a wearable thermal energy sensor can be incorporated into an article of clothing that a person wears to bed. In an example, a wearable thermal energy sensor can be incorporated into an electronically-functional bandage, sticker, or tattoo.

In an example, data from a wearable thermal energy sensor can be used to change the activation, direction, volume, speed, or temperature of airflow from an air-moving device. In an example, an air-moving device can be a portable fan which is placed on a surface in a person's bedroom to selectively direct air towards the person when the person is too warm. In an example, an air-moving device can be a fan which is incorporated into a bed headboard or other part of a bed structure. In an example, an air-moving device can be a fan which is incorporated into a box spring, mattress, or other bedding structure or layer. In an example, an air-moving device can be mounted in a room window. In an example, the temperature of airflow which is triggered by data from a wearable thermal energy sensor can also be adjusted by an air-moving device with heat transfer capability, such as an air conditioner.

In this example, a data-control component is co-located with an air-moving device. In another example, a data-control component can be co-located with a wearable thermal energy sensor. In another example, a data-control component can be located in a separate device, such as a smart phone or electronic tablet, with which both the wearable thermal energy sensor and the air-moving device are in wireless communication. In an example, data from a wearable thermal energy sensor can be used to: change the direction of a flow of air coming from a portable fan or blower; control the operation of a portable fan or blower which directs airflow toward a person's body; change the rate of the flow of air from a window-based air conditioner; start or stop a portable fan or blower; change the direction of a flow of air and/or other gas which the person breathes; or change the rate of the flow of air and/or other gas in communication with the surface of the person's body.

The left side of FIG. 68 shows this embodiment at a first point in time in which airflow from portable fan 6804 is directed in a first direction (away from person 6801) based on a first pattern of data from wearable thermal energy sensor 6802. The right side of FIG. 68 shows this embodiment at a second point in time in which airflow from portable fan 6804 is directed in a second direction (toward person 6801) based on a second pattern of data from wearable thermal energy sensor 6802. In this example, the first pattern of data indicates a normal body temperature and the second pattern of data indicates a higher body temperature. In an example, the first pattern of data indicates a normal body temperature and the second pattern of data predicts a coming upswing in body temperature. In an example, the direction of airflow toward person 6801 can help to mitigate or avoid the effects of a hot flash. Relevant example and component variations discussed elsewhere in this disclosure or in priority-linked disclosures can also be applied to this example, but are not repeated here to avoid narrative redundancy.

Figure 69:
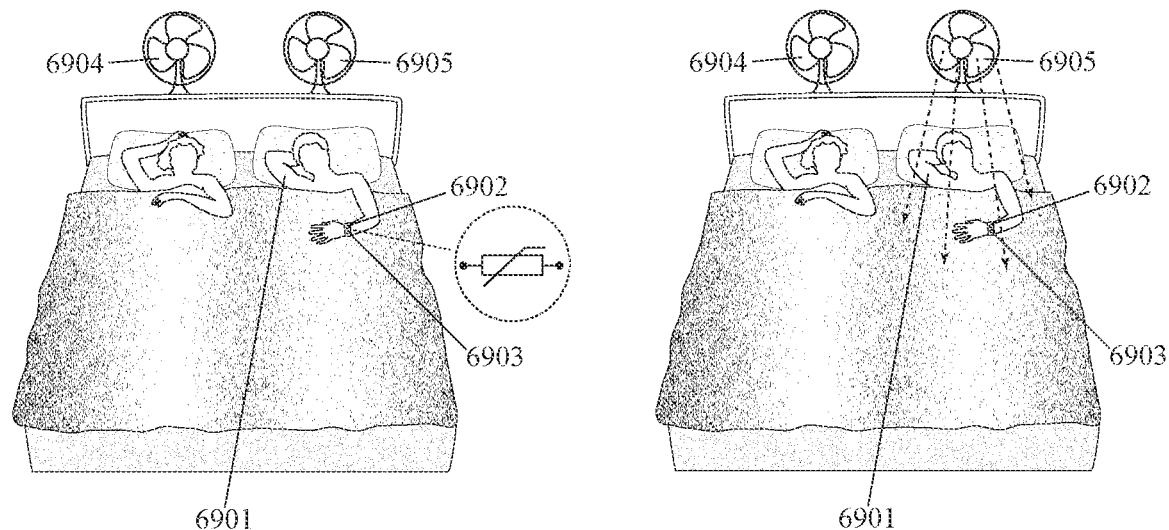
FIG. 69 shows a second system for modifying a person's sleep environment which changes airflow from a fan based on a wearable thermal energy sensor.

FIG. 69 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the flow of air and/or other gas in communication with the surface of the person's body; and a data-control component which controls the operation of the sleep-environment-modifying component in order to automatically change the person's sleep environment based on data from the wearable-sensor component. More specifically, the embodiment shown in FIG. 69 comprises: wearable thermal energy sensor 6902; air-moving member 6905; and data-control component 6903. In this example, when data from wearable thermal energy sensor 6902 indicates that person 6901 is too warm or predicts an upswing in the body temperature of person 6901, then this triggers activation of air-moving member 6905 which directs airflow over person 6901.

In this example, wearable thermal energy sensor 6902 is a thermistor. In other examples, wearable thermal energy sensor can be a thermometer or other type of temperature sensor. In this example, wearable thermal energy sensor 6902 is worn on a person's wrist. In other examples, a wearable thermal energy sensor can be worn on a person's finger, hand, arm, neck, ear, head, torso, leg, or foot. In an example, a wearable thermal energy sensor can be incorporated into an article of clothing that a person wears to bed. In this example, air-moving member 6905 is a fan which is incorporated into the headboard of a bed. In other examples, an air-moving member can be incorporated into another part of a bed structure or bedding layer, such as a mattress, box spring, or blanket. In an example, an air-moving member can be a portable fan which is located on a separate surface in a person's bedroom. In an example, an air-moving member can be a window-mounted air conditioner. In this example, data-control component 6903 is co-located with wearable thermal energy sensor 6902 as part of a wrist member. In another example, a data-control component can be co-located with an air-moving member. In another example, a data-control component can be incorporated into a mobile electronic device such as a cell phone or electronic tablet.

In this example, there are two air-moving members, 6904 and 6905, which are incorporated into a bed structure. In this example, each of the two air-moving members directs air over half of the bed so that airflow over two bed partners on different sides of the bed can be separately and differentially adjusted. In this example, only one of the people in the bed has a wearable thermal energy sensor. In another example, each person in the bed can have their own wearable thermal energy sensor and data from these two sensors can be used to separately and differentially adjust the sleeping environments of the two sides of the bed.

In an example, data from a wearable thermal energy sensor can be used to determine when the skin and/or body temperature of person 6901 is too high and this can trigger activation of an air-moving member. In an example, data from a wearable thermal energy sensor can be used to predict a biologically-induced temporary upswing in body temperature (such as a hot flash) and this can trigger activation of an air-moving member. In an example, data from a wearable thermal energy sensor can be combined with data from other wearable sensors (such as a blood pressure sensor, a skin impedance or conductivity sensor, a skin moisture sensor, an ECG sensor, an EMG sensor, and/or an EEG sensor) in order to predict a biologically-induced temporary change in body temperature (such as a hot flash). In an example, airflow from an air-moving member can be triggered for a predetermined amount of time and then it automatically shuts off. In an example, airflow from an air-moving member can continue until data from a wearable thermal energy sensor indicates that a person's temperature has decreased to a normal level.

The left side of FIG. 69 shows this embodiment at a first point in time wherein air-moving member 6905 is not activated based on a first pattern of data from wearable thermal energy sensor 6902. The right side of FIG. 69 shows this embodiment at a second point in time wherein air-moving member 6905 is activated based on a second pattern of data from wearable thermal energy sensor 6902. In an example, data from a wearable thermal energy sensor can be used to automatically: turn a fan on; change the flow of air and/or other gas in communication with the surface of a person's body; change the direction, flow rate, pressure, humidity, temperature, mixture, and/or source of the air or other gas which the person breathes; or change the rate of the flow of air and/or other gas which the person breathes. Relevant example and component variations discussed elsewhere in this disclosure or in priority-linked disclosures can also be applied to this example, but are not repeated here to avoid narrative redundancy.

Figure 70:
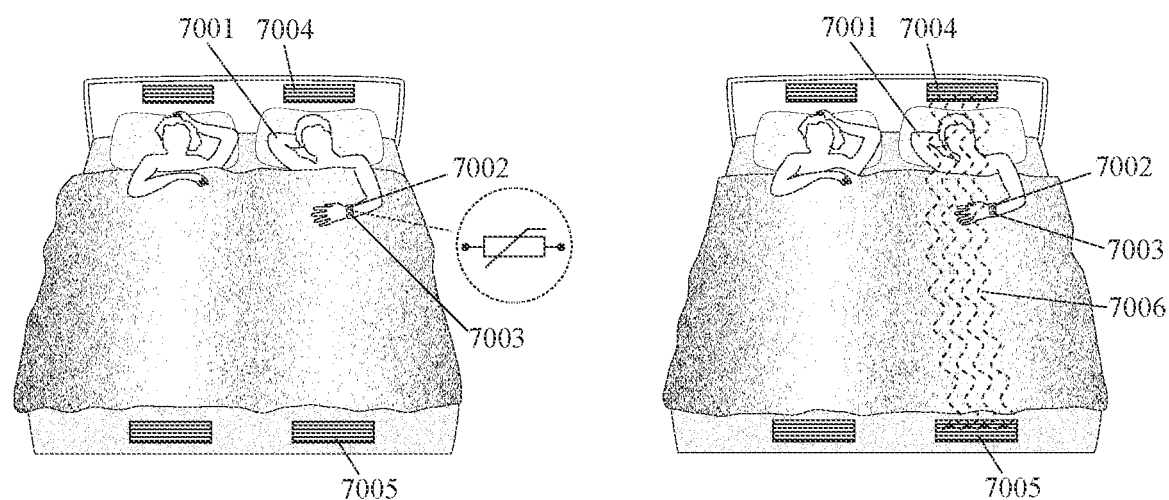
FIG. 70 shows a system for modifying a person's sleep environment which changes airflow from a laminar airflow mechanism based on a wearable thermal energy sensor.

FIG. 70 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the laminar flow of air and/or other gas in communication with the surface of the person's body; and a data-control component which controls the operation of the sleep-environment-modifying component in order to automatically change the person's sleep environment based on data from the wearable-sensor component.

More specifically, the embodiment shown in FIG. 70 comprises: a wearable thermal energy sensor 7002; a data-control component 7003; and a laminar airflow mechanism comprising outflow vent 7004 and inflow vent 7005. In an example, when data from wearable thermal energy sensor 7002 indicates that the body temperature of person 7001 is too high, then this triggers activation of a laminar airflow over person 7001 from outflow vent 7004 to inflow vent 7005. In an example, when data from wearable thermal energy sensor 7002 predicts a temporary upswing in the body temperature of person 7001, then this triggers a prophylactic laminar airflow over person 7001 to mitigate or avoid the effects of this upswing.

In an example, wearable thermal energy sensor 7002 can be a thermistor, as symbolically represented by the thermistor electronic component symbol on the left side of FIG. 70. In an example, wearable thermal energy sensor 7002 can be a thermometer or other type of temperature sensor. In this example, a wearable thermal energy sensor is incorporated into a smart watch or wrist band. In other examples, a wearable thermal energy sensor can be incorporated into garment which a person wears in bed. In other examples, a wearable thermal energy sensor can be worn on a person's finger, hand, arm, neck, ear, head, torso, leg, or foot.

In an example, a data-control component can control the manner in which a laminar airflow is changed based on data from a wearable thermal energy sensor. In this example, a data-control component is co-located with a wearable thermal energy sensor in a smart watch or wrist band. In an example, data-control component can be located in a separate device and in wireless communication with a wearable thermal energy sensor. In an example, a data-control component can be integrated into a smart phone, electronic tablet, or other mobile electronic device.

In this example, a laminar airflow mechanism comprises an outflow vent which is part of a bed headboard and an inflow vent which is part of a bed footboard, mattress, or box spring. In this example, a laminar airflow spans a person in a plane which is substantially horizontal. In this example, a laminar airflow spans a person in a longitudinal manner from the head of a bed to the foot of a bed. In an example, a laminar airflow can span a person in a diagonal manner from the head of a bed to the side of a bed. In this example, a bed has two laminar airflow mechanisms, one on each side of the bed, which can be separately and differentially activated to provide individual sleeping environment modification for two people in the same bed.

In an example, a laminar airflow can help to cool a person who is experiencing an upswing in body temperature as detected by a wearable thermal energy sensor. In an example, the volume, speed, temperature, or spatial configuration of a laminar airflow can be adjusted based on selected patterns of data from a wearable thermal energy sensor. In an example, data from a wearable thermal energy sensor can be used to: change the laminar flow of air and/or other gas in communication with the surface of a person's body; control the operation of a central longitudinal laminar airflow on a bed; change the spatial configuration of the flow of air and/or other gas which the person breathes; or change the laminar flow of air and/or other gas which the person breathes. In an example, a laminar airflow mechanism can enable relatively-precise control of airflow across one side of a bed and not the other.

The left side of FIG. 70 shows this embodiment at a first point in time wherein a laminar airflow mechanism is not activated, due to a first pattern of data from a wearable thermal energy sensor. In an example, this first pattern of data can indicate a normal body temperature. The right side of FIG. 70 shows this embodiment at a second point in time wherein a laminar airflow mechanism has been activated, based on a second pattern of data from a wearable thermal energy sensor. In this example, this second pattern of data indicates an undesirably high body temperature. Relevant example and component variations discussed elsewhere in this disclosure or in priority-linked disclosures can also be applied to this example, but are not repeated here to avoid narrative redundancy.

Figure 71:
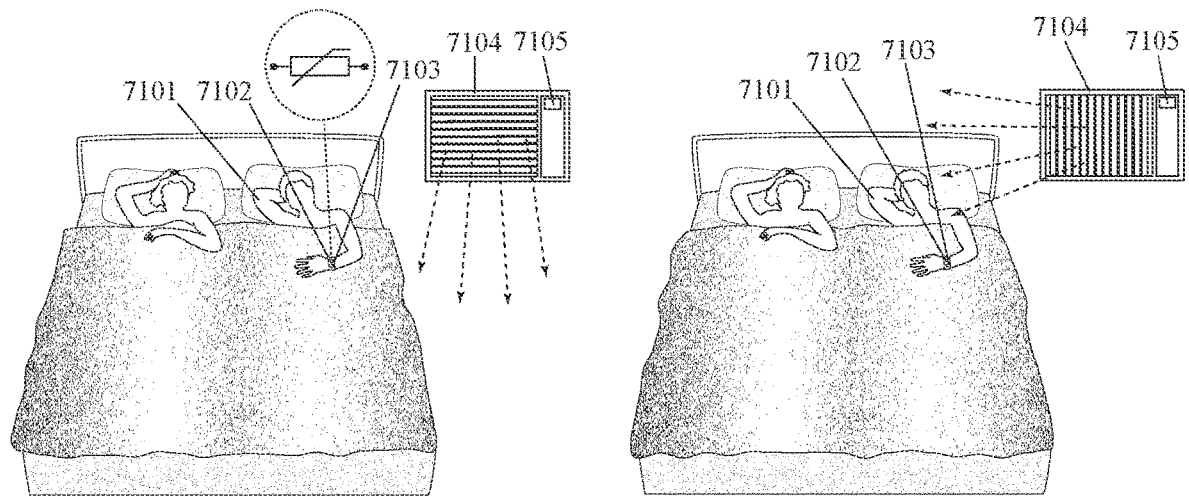
FIG. 71 shows a system for modifying a person's sleep environment which changes airflow from a window air conditioner based on a wearable thermal energy sensor.

FIG. 71 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the direction of a flow of air from a window-based air conditioner; and a data-control component which controls the operation of the sleep-environment-modifying component in order to automatically change the person's sleep environment based on data from the wearable-sensor component.

More specifically, the embodiment shown in FIG. 71 comprises: wearable thermal energy sensor 7102, power source or transducer 7103, window-based air conditioner 7104, and data-control component 7105. In this example, the direction, volume, speed, or temperature of airflow from window-based air conditioner 7104 is changed based on data from wearable thermal energy sensor 7102. In this example, data-control component 7105 changes the direction, volume, speed, or temperature of airflow from window-based air conditioner 7104 based on data from wearable thermal energy sensor 7102.

The left side of FIG. 71 shows this embodiment at a first point in time wherein airflow from window-based air conditioner 7104 is not directed toward person 7101, based on a first level of thermal energy detected by wearable thermal energy sensor 7102. The right side of FIG. 71 shows this embodiment at a second point in time wherein airflow from window-based air conditioner 7104 has been directed toward person 7101 based on a second level of thermal energy detected by wearable thermal energy sensor 7102. In this example, the second level of thermal energy is greater than the first level of thermal energy. In an example, directing airflow toward person 7101 when data from wearable thermal energy sensor 7102 indicates that person 7101 is too warm can help to cool off person 7101 when needed.

In this example, wearable thermal energy sensor 7102 is a thermistor, as represented symbolically by the symbol for a thermistor electronic component shown in a dotted-line circle on the left side of FIG. 71. In another example, a wearable thermal energy sensor can be a thermometer or other type of temperature-measuring sensor. In this example, wearable thermal energy sensor 7102 is part of a smart watch, wrist band, or other wrist-worn device. In other examples, a wearable thermal energy sensor can be incorporated into a different type of wearable device or an article of clothing which person 7101 wears to bed.

In an example, the direction of airflow from window-based air conditioner 7104 can be controlled by changing the direction or orientation of airflow vents on the air conditioner. In an example, data-control component 7105 can change the direction or orientation of airflow vents on window-based air conditioner 7104 based on data from wearable thermal energy sensor 7102. In an example, a data-control component can be co-located with a wearable thermal energy sensor on a wearable device. In an example, a data-control component can be part of a smart phone, electronic tablet, or other mobile electronic device. In an example, a data-control component can be part of a home environmental control system. In an example, data from a wearable thermal energy sensor can be used to control the operation of a window-based air conditioner or central HVAC system.

In an example, a system, device, and method for adjusting the temperature or a person's sleeping environment based on a person's body temperature, as measured by a wearable thermal energy sensor, can help to mitigate or avoid the adverse effects of temporary, biologically-induced upswings in body temperature such as hot flashes. In an example, a ventilation or cooling system or device can have a first configuration when a person's skin and/or body temperature is within a normal range, based on data from a wearable thermal energy sensor. In an example, a ventilation or cooling system or device can have a second configuration when a person's skin and/or body temperature is above a normal range, based on data from a wearable thermal energy sensor. In an example the second configuration can comprise one or more of the following: a change in the direction of airflow toward the person; a cooling airflow directed toward the person; and an increase in airflow volume directed toward the person. Relevant example and component variations discussed elsewhere in this disclosure or in priority-linked disclosures can also be applied to this example, but are not repeated here to avoid narrative redundancy.

Figure 72:
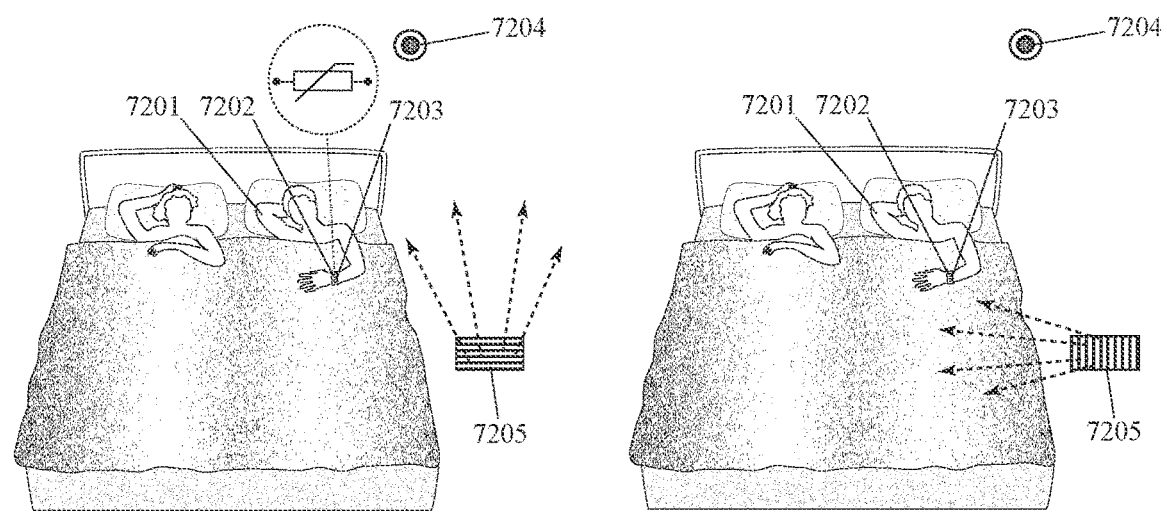
FIG. 72 shows a first system for modifying a person's sleep environment which changes airflow from a HVAC system based on a wearable thermal energy sensor.

FIG. 72 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the direction of a flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment shown in FIG. 72 comprises: a wearable thermal energy sensor 7202; a power source or transducer 7203; a central heating, ventilation, and/or air-conditioning (HVAC) system control unit 7204; and an outflow vent 7205. In an example, the direction of airflow from outflow vent 7205 is automatically changed by HVAC system control unit 7204 based on data from wearable thermal energy sensor 7202. In an example, when wearable thermal energy sensor 7202 indicates that the skin and/or body temperature of person 7201 is too high, then this triggers airflow from vent 7205 to be directed toward person 7201. In other examples, when wearable thermal energy sensor 7202 indicates that the skin and/or body temperature of person 7201 is too high, then this triggers a decrease in the temperature of airflow through a HVAC system and/or from vent 7205.

The left side of FIG. 72 shows this embodiment at a first point in time wherein airflow from vent 7205 is not directed toward person 7201 because data from wearable thermal energy sensor 7202 indicates that the person's skin and/or body temperature is within a normal range. The right side of FIG. 72 shows this embodiment at a second point in time wherein airflow from vent 7205 is directed toward person 7201 because data from wearable thermal energy sensor 7202 indicates that the person's skin and/or body temperature is above a normal range. In an example, the direction of airflow from vent 7205 can be changed by moving slats or other air-directing members on airflow vent 7205. In an example, actuators which move slats on vent 7205 can be controlled by HVAC control unit 7204.

In an example, wearable thermal energy sensor 7202 can be a thermistor, as indicated by the electrical component symbol for a thermistor which is shown in a dotted-line circle on the left side of FIG. 72. In an example, a wearable thermal energy sensor can be a thermometer or other type of temperature-measuring sensor. In this example, wearable thermal energy sensor 7202 is worn on a person's wrist. In other examples, a wearable thermal energy sensor can be worn on a person's finger, hand, arm, neck, head, torso, leg, or ankle. In an example, a wearable thermal energy sensor can be integrated into an article of clothing that a person wears to bed.

In an example, an HVAC control unit can be co-located with a wearable thermal energy sensor in a wearable device. In an example, an HVAC control unit can be incorporated into a smart phone, electronic tablet, or other portable electronic device. In an example, an HVAC control unit can change one or more of the following operational aspects of an HVAC system based on data from a wearable thermal energy sensor: the direction of airflow from an HVAC system; the inter-room distribution of airflow from an HVAC system; the overall temperature of airflow from an HVAC system; the inter-room transfer of thermal energy by an HVAC system; the mix of internal (re-circulated) vs. external (environmental) air in airflow through an HVAC system; the level of air filtering by an HVAC system; and the volume of airflow through an HVAC system. Relevant example and component variations discussed elsewhere in this disclosure or in priority-linked disclosures can also be applied to this example, but are not repeated here to avoid narrative redundancy.

Figure 73:
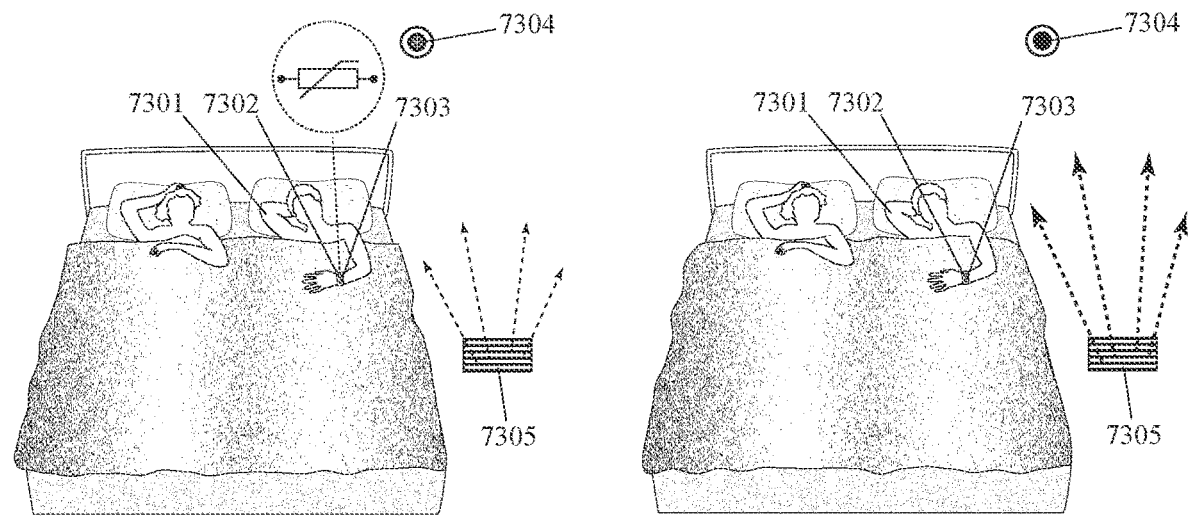
FIG. 73 shows a second system for modifying a person's sleep environment which changes airflow from a HVAC system based on a wearable thermal energy sensor.

FIG. 73 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the inter-room distribution of a flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment shown in FIG. 73 comprises: wearable thermal energy sensor 7302; power source or transducer 7303; central heating, ventilation, and/or air-conditioning (HVAC) system control unit 7304; and outflow vent 7305. In this example, the inter-room distribution of airflow from an HVAC system is changed by HVAC system control unit 7304 based on data from wearable thermal energy sensor 7302. In an example, when data from wearable thermal energy sensor 7302 indicates that person 7301 is too warm, then this triggers greater airflow into the person's room through outflow vent 7305.

In this example, the overall volume of airflow through an HVAC system remains substantially constant, but a greater proportion of this airflow is directed into the room of person 7301 when person 7301 is too warm. This can be done by opening or otherwise moving the slats on vent 7305. In another example, the inter-room distribution of airflow from an HVAC system can be automatically changed by selectively opening or closing air valves in duct work. In another example, the overall volume of airflow through the HVAC system can be increased for all rooms served by the system. In other examples, the temperature or direction of airflow from vent 7305 can be changed based on data from wearable thermal energy sensor 7302.

In an example, wearable thermal energy sensor 7302 can be a thermistor, as indicated by the thermistor electronic component symbol shown in a dotted-line circle on the left side of FIG. 73. In other examples, a wearable thermal energy sensor can be a thermometer or other type of temperature sensor. In this example, wearable thermal energy sensor 7302 is worn on a person's wrist. In other examples, a wearable thermal energy sensor can be worn on a person's finger, hand, arm, neck, ear, nose, head, torso, leg, or foot. In an example, a wearable energy can be incorporated into a shirt, shorts, pants, or other garment that a person wears to bed.

The left side of FIG. 73 shows this embodiment at a first point in time wherein the person's skin and/or body temperature based on data from wearable thermal energy sensor 7302 is within a selected range and, as a result, there is a first volume of airflow from vent 7305. The right side of FIG. 73 shows this embodiment at a second point in time wherein the person's skin and/or body temperature based on data from wearable thermal energy sensor 7302 is above this selected range and, as a result, there is a second volume or airflow from vent 7305. In an example, the second volume or airflow is greater than the first volume of airflow, as symbolically represented by thicker and longer dotted-lines arrows coming out of vent 7305 on the right side of FIG. 73 vs. the left side of FIG. 73.

In an example, data from wearable thermal energy sensor can be used to change one or more of the following aspects of the operation of a central heating, ventilation, and/or air-conditioning (HVAC) system: the overall volume of airflow through an HVAC system; the overall rate of airflow through an HVAC system; the overall temperature of airflow through an HVAC system; the inter-room distribution of airflow from an HVAC system; and the transfer of thermal energy between different rooms served by a central HVAC system. Relevant example and component variations discussed elsewhere in this disclosure or in priority-linked disclosures can also be applied to this example, but are not repeated here to avoid narrative redundancy.

Figure 74:
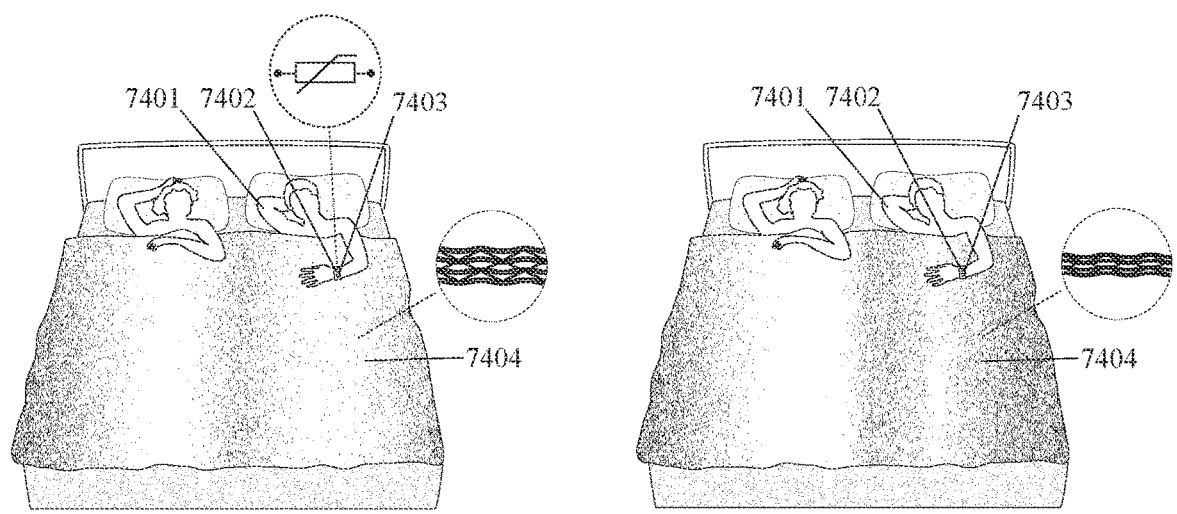
FIG. 74 shows a system for modifying a person's sleep environment which changes the thickness of a blanket based on a wearable thermal energy sensor.

FIG. 74 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which controls MEMS actuators in a blanket or other bedding layer to change the thickness of the blanket or other bedding layer; and a data-control component which controls the operation of the sleep-environment-modifying component in order to automatically change the person's sleep environment based on data from the wearable-sensor component.

More specifically, the embodiment shown in FIG. 74 comprises: wearable thermal energy sensor 7402; data-control component 7403; and variable-thickness blanket 7404. In this example, the thickness of blanket 7404 is controlled by data-control component 7403 based on data from wearable thermal energy sensor 7402. In an example, when data from wearable thermal energy sensor 7402 indicates that person 7401 has an undesirably high skin and/or body temperature, then this triggers a decrease in the thickness of variable-thickness blanket 7404.

In an example, variable-thickness blanket 7404 can further comprise an array of actuators and the thickness of blanket 7404 can be changed by activation of this array of actuators. In an example, variable-thickness blanket 7404 can comprise an array of piezoelectric members and the thickness of blanket 7404 can be changed by application of an electrical current to these piezoelectric members. In an example, variable-thickness blanket 7404 can further comprise an array of inflatable members and the thickness of blanket 7404 can be changed by inflation or deflation of these inflatable members.

The left side of FIG. 74 shows this embodiment at a first point in time wherein blanket 7404 has a first thickness based on a first pattern of data from wearable thermal energy sensor 7402. The right side of FIG. 74 shows this embodiment at a second point in time wherein blanket 7404 has a second thickness based on a second pattern of data from wearable thermal energy sensor 7402. In an example, the second thickness is less than the first thickness. In an example, the first pattern of data indicates a skin and/or body temperature that is within a selected (normal) range and the second pattern of data indicates a skin and/or body temperature that is above this selected (normal) range. In an example, when data from wearable thermal energy sensor 7402 indicates that person 7401 is too warm, then this automatically triggers a reduction in the thickness of variable-thickness blanket 7404.

In this example, wearable thermal energy sensor 7402 is a thermistor. In other examples, wearable thermal energy sensor can be a thermometer or other type of temperature sensor. In an example, the location of wearable thermal energy sensor can be selected from the group consisting of: wrist, hand, finger, arm, torso, abdomen, leg, foot, head, ear, and nose. In an example, a wearable thermal energy sensor can be incorporated into a smart watch or wrist band. In an example, a wearable thermal energy sensor can be incorporated into an article of clothing which a person wears to bed. In an example, this article of clothing can be selected from the group consisting of: shirt; shorts; pants; hat; or sock.

In an example, data from a wearable thermal energy sensor concerning a person's skin and/or body temperature can be used to automatically change: the thickness of a blanket, sheet, quilt, or other bedding layer worn over the person; the R-value and/or insulation value of a blanket, sheet, quilt, or other bedding layer worn over the person; or the thickness or insulation value of a sleeping bag. In an example, when data from a wearable thermal energy sensor indicates that a person is too warm, then this system or device can automatically decrease the thickness and/or insulation value of a blanket, sheet, quilt, or other bedding layer worn by the person. In an example, this decrease can be for a predefined period of time. In an example, this decrease can continue until the person's temperature decreases, based on data from the wearable thermal energy sensor. Relevant example and component variations discussed elsewhere in this disclosure or in priority-linked disclosures can also be applied to this example, but are not repeated here to avoid narrative redundancy.

Figure 75:
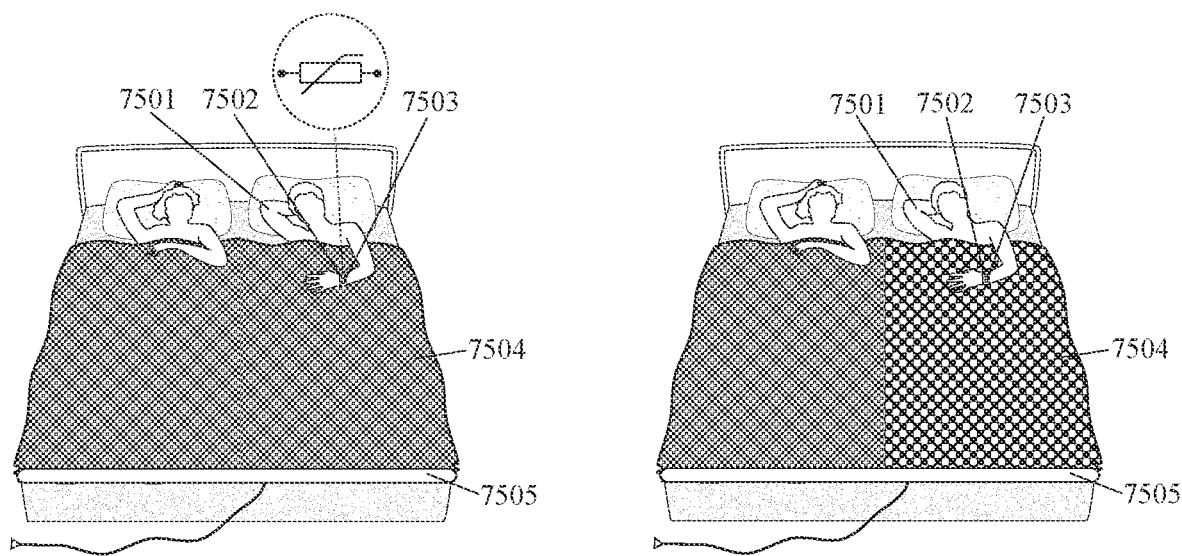
FIG. 75 shows a system for modifying a person's sleep environment which changes the porosity of a blanket based on a wearable thermal energy sensor.

FIG. 75 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the porosity of a sheet, blanket, or other bedding layer over the person; and a data-control component which controls the operation of the sleep-environment-modifying component in order to automatically change the person's sleep environment based on data from the wearable-sensor component.

More specifically, the embodiment shown in FIG. 75 comprises: wearable thermal energy sensor 7502; data-control component 7503; and variable-porosity blanket 7504. In this example, the porosity of variable-porosity blanket is controlled by blanket control mechanism 7505. In this example, the porosity of variable-porosity blanket 7504 is changed based on data from wearable thermal energy sensor 7502. In an example, when data from wearable thermal energy sensor 7502 indicates that person 7501 has a high skin and/or body temperature, then this triggers an increase in the gaseous porosity of blanket 7504 in order to help the person lose body heat and/or moisture.

In an example, variable-porosity blanket 7504 can further comprise microscale actuators and the porosity of blanket 7504 can be changed by selective activation of these microscale actuators. In an example, variable-porosity blanket 7504 can further comprise piezoelectric members (such as piezoelectric strands, fibers, or threads) and the porosity of blanket 7504 can be changed by application of electrical current to these piezoelectric members. In an example, variable porosity blanket 7504 can further comprise inflatable members and the porosity of blanket 7504 can be changed by the inflation of these inflatable members.

In an example, wearable thermal energy sensor 7502 can be a thermistor, as indicated symbolically by the thermistor electrical component symbol within a dotted-line circle on the left side of FIG. 75. In an example, a wearable thermal energy sensor can be a thermometer or other temperature-measuring sensor. In an example, a wearable thermal energy sensor can measure a person's skin temperature. In an example, a wearable thermal energy sensor can measure a person's internal body temperature. In an example, a wearable thermal energy sensor can be incorporated into a smart watch, wrist band, wait band, arm band, headband, or other wearable accessory. In an example, a wearable thermal energy sensor can be incorporated into an article of clothing which a person wears to bed.

In an example, data from a wearable thermal energy sensor can be combined with data from other wearable sensors (such as a moisture sensor, a heart rate sensor, and an electromagnetic energy sensor) to predict when a person will soon have a temporary biologically-induced upswing in temperature, such as a hot flash. In an example, when such combined data indicates that a person will probably have a temperature upswing in the near future, then this embodiment can reduce the porosity of a blanket in a prophylactic manner to mitigate or avoid the effects of the temperature upswing. In an example, this reduction in porosity can be for a predefined period of time or can be until a temperature upswing is over. In an example, data from a wearable thermal energy sensor can be used to: change the porosity of a blanket or other bedding layer covering a person; change the porosity of a sheet over a person; and/or control MEMS actuators in a blanket or other bedding layer in order to change the porosity of the blanket or other bedding layer. Relevant example and component variations discussed elsewhere in this disclosure or in priority-linked disclosures can also be applied to this example, but are not repeated here to avoid narrative redundancy.

Figure 76:
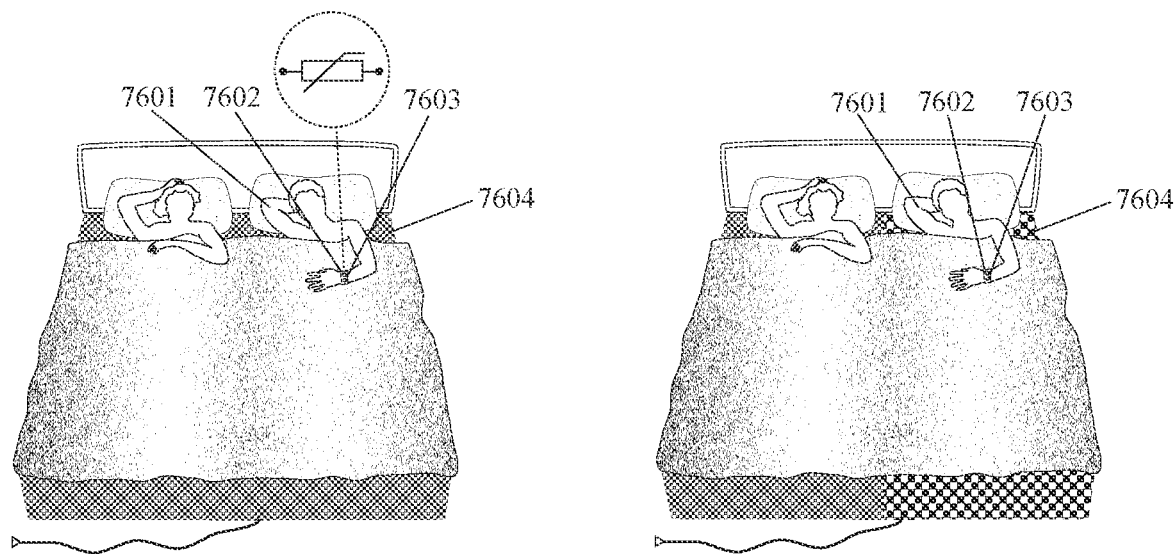
FIG. 76 shows a system for modifying a person's sleep environment which changes the porosity of a mattress based on a wearable thermal energy sensor.

The embodiment of this invention which is shown in FIG. 76 is similar to the embodiment shown in FIG. 75, except that it comprises a variable-porosity mattress instead of a variable porosity blanket. FIG. 76 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the porosity of a bedding surface or layer on which the person lies; and a data-control component which controls the operation of the sleep-environmentmodifying component in order to automatically change the person's sleep environment based on data from the wearable-sensor component.

More specifically, the embodiment shown in FIG. 76 comprises: wearable thermal energy sensor 7602; data-control component 7603; and variable-porosity mattress 7604. In an example, data-control component 7603 triggers an increase in the porosity of variable-porosity mattress 7604 when data from wearable thermal energy sensor 7602 indicates a high skin and/or body temperature for person 7601. In an example, data from a wearable thermal energy sensor can be used to change the porosity of a mattress, mattress pad, or box spring. Relevant example and component variations discussed elsewhere in this disclosure or in priority-linked disclosures can also be applied to this example, but are not repeated here to avoid narrative redundancy.

Figure 77:
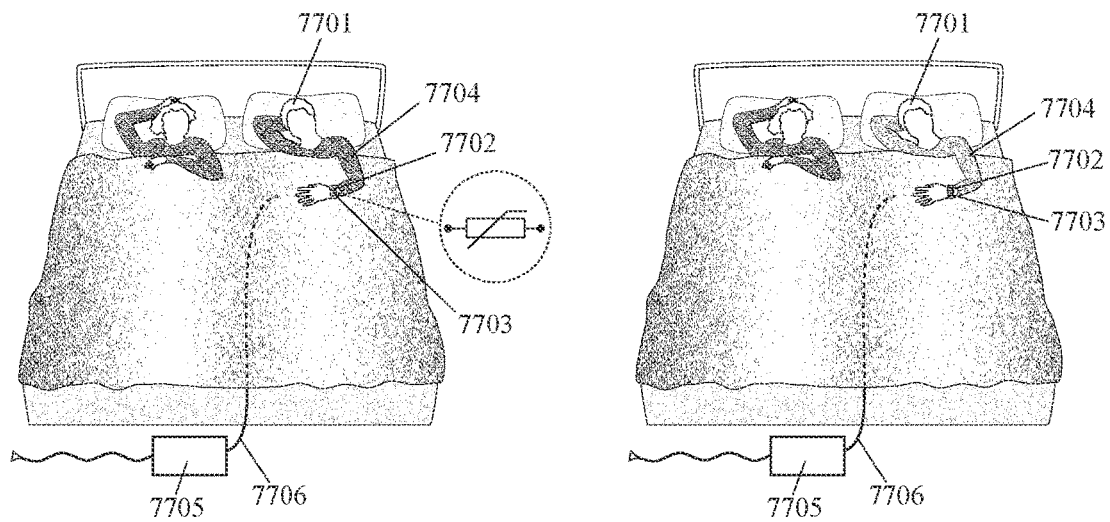
FIG. 77 shows a system for modifying a person's sleep environment which changes the porosity of a garment based on a wearable thermal energy sensor.

FIG. 77 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the porosity of a garment worn by the person; and a data-control component which controls the operation of the sleep-environment-modifying component in order to automatically change the person's sleep environment based on data from the wearable-sensor component.

More specifically, the embodiment shown in FIG. 77 comprises: wearable thermal energy sensor 7702; data-control component 7703; and variable-porosity garment 7704. In an example, data-control component 7703 changes the porosity of variable-porosity garment 7704 based on data from wearable thermal energy sensor 7702. In an example, when data from wearable thermal energy sensor 7702 indicates a high skin temperature and/or body temperature for person 7701, then data-control component 7703 increases the porosity of garment 7704 to help person 7701 lose excess body heat. In an example, when data from wearable thermal energy sensor 7702 indicates a low skin temperature and/or body temperature for person 7701, then data-control component 7703 decreases the porosity of garment 7704 to help person 7701 conserve body heat.

In an example, variable-porosity garment 7704 can further comprise piezoelectric fabric whose porosity can be changed by application of electrical current via wire 7706 from garment control unit 7705. In an example, a variable-porosity garment can further comprise an array of microscale actuators and the porosity of this garment can be changed by selective activation of these actuators. In an example, a variable-porosity garment can further comprise an array of inflatable members and the porosity of this garment can be changed by selective inflation or deflation of these members. In an example, a variable-porosity garment can be selected from the group consisting of: shirt; shorts; pants; pajamas; hat; socks; and union suit. In an example, variable porosity garment 7704 can further comprise: Cotton, Nylon, Rayon, Danconn or Polyester.

The left side of FIG. 77 shows this embodiment at a first point in time wherein garment 7704 has a first porosity level based on a first pattern of data from wearable thermal energy sensor 7702. The right side of FIG. 77 shows this embodiment at a second point in time wherein garment 7704 has a second porosity level based on a second pattern of data from wearable thermal energy sensor 7702. In an example, the second porosity level is greater than the first porosity level. In an example, the first pattern of data indicates that the person's skin and/or body temperature is within a normal range and the second pattern of data indicates that the person's skin and/or body temperature is above the normal range.

In an example, wearable thermal energy sensor 7702 can be a thermistor, as symbolically indicated by the thermistor electrical component symbol shown in a dotted-line circle on the left side of FIG. 77. In an example, wearable thermal energy sensor 7702 can be a thermometer or other type of thermal energy sensor. In an example, wearable thermal energy sensor can be part of a smart watch or wrist band. In an example, wearable thermal energy sensor 7702 can be incorporated into variable-porosity garment 7704. In an example, wearable thermal energy sensor can be worn elsewhere on a person's body selected from the group consisting of: finger, hand, arm, torso, waist, neck, head, ear, nose, leg, back, and foot. Relevant example and component variations discussed elsewhere in this disclosure or in priority-linked disclosures can also be applied to this example, but are not repeated here to avoid narrative redundancy.

Figure 78:
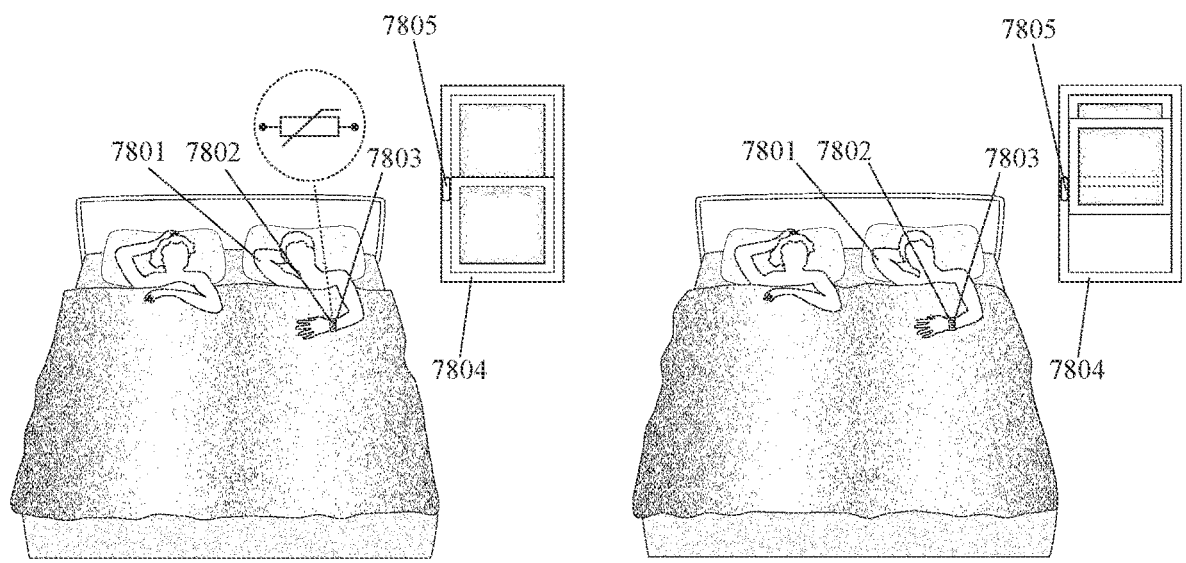
FIG. 78 shows a system for modifying a person's sleep environment which automatically opens a window based on a wearable thermal energy sensor.

FIG. 78 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which opens or closes a room window; and a data-control component which controls the operation of the sleep-environment-modifying component in order to automatically change the person's sleep environment based on data from the wearable-sensor component.

More specifically, the embodiment shown in FIG. 78 comprises: wearable thermal energy sensor 7802; data-control component 7803; and auto-adjustable window 7804. In an example, data-control component 7803 automatically opens auto-adjustable window 7804 when data from wearable thermal energy sensor 7802 indicates that person 7801 has a high skin and/or body temperature. The left side of FIG. 78 shows this embodiment at a first point in time wherein window 7804 is closed because data from wearable thermal energy sensor 7802 indicates that person 7801 has a normal skin and/or body temperature. The right side of FIG. 78 shows this embodiment at a second point in time wherein window 7804 has been automatically opened because wearable thermal energy sensor 7802 has indicated that person 7801 has a high skin and/or body temperature.

In an example, auto-adjustable window 7804 can be opened by data-control component 7803 through wireless communication between data-control component 7803 and window actuator 7805. In an example, auto-adjustable window 7804 can be opened for a predefined duration of time when a person's skin and/or body temperature reaches a high level. In an example, auto-adjustable window 7804 can be automatically opened in response to data indicating a high skin and/or body temperature and can be automatically closed in response to data indicating a return to a normal skin and/or body temperature. In an example, automatic opening and closing of a window in response to swings in a person's skin and/or body temperature while sleeping can help to mitigate the effects of temporary swings in body temperature such as hot flashes.

In an example, a wearable thermal energy sensor can be a thermistor. In an example, a wearable thermal energy sensor can be a thermometer or other type of temperature sensor. In an example, a wearable thermal energy sensor can be configured to be worn on a portion of a person's body selected from the group consisting of: finger, hand, wrist, arm, torso, waist, back, leg, ankle, foot, ear, nose, and head. In an example, a wearable thermal energy sensor can be integrated into a garment. In an example, data from a wearable thermal energy sensor can be used to open or close a room window or door. Relevant example and component variations discussed elsewhere in this disclosure or in priority-linked disclosures can also be applied to this example, but are not repeated here to avoid narrative redundancy.

Figure 79:
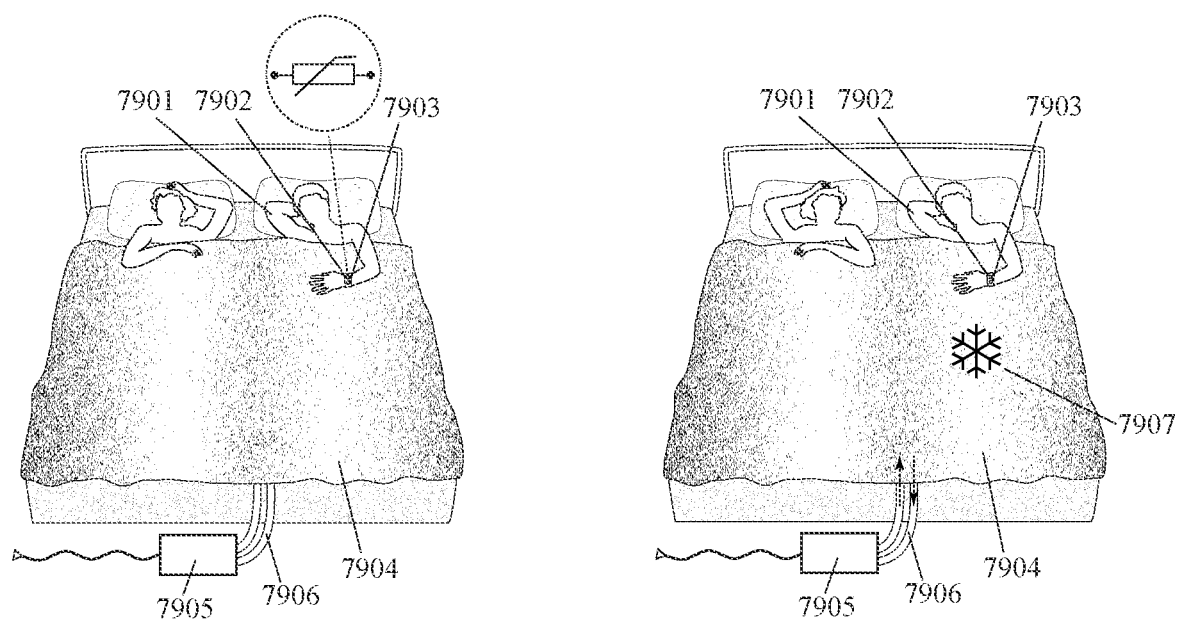
FIG. 79 shows a first system for modifying a person's sleep environment which changes bed temperature based on a wearable thermal energy sensor.

FIG. 79 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the temperature of a blanket over the person; and a data-control component which controls the operation of the sleep-environment-modifying component in order to automatically change the person's sleep environment based on data from the wearable-sensor component.

More specifically, the embodiment shown in FIG. 79 comprises: wearable thermal energy sensor 7902; data-control component 7903; and adjustable-temperature blanket 7904. In an example, data-control component 7903 changes the temperature of adjustable-temperature blanket 7904 based on data from wearable thermal energy sensor 7902. In an example, when data from wearable thermal energy sensor 7902 indicates that person 7901 has a high skin and/or body temperature, then it triggers circulation of a cooling fluid or gas through blanket 7904. In this example, the cooling fluid or gas which is circulated through adjustable-temperature blanket 7904 is cooled by heat pump 7905 and conducted to blanket 7904 via flow tubes 7906.

In an example, when data from wearable thermal energy sensor 7902 indicates that person 7901 has a skin and/or body temperature that is within a normal range, then fluid or gas is not circulated through adjustable-temperature blanket 7904. In an example, when data from wearable thermal energy sensor 7902 indicates that person 7901 has a skin and/or body temperature that is above a normal range, then data-control component 7903 triggers a flow of cooling fluid or gas through adjustable-temperature blanket 7904. In an example, adjustable-temperature blanket 7904 can further comprise sinusoidal fluid or gas pathways through which a cooling fluid or gas can circulate.

The left side of FIG. 79 shows this embodiment at a first point in time wherein data from wearable thermal energy sensor 7902 indicates that the temperature of person 7901 is within a normal range and, accordingly, there is no circulation of cooling fluid or gas through adjustable-temperature blanket 7904. The right side of FIG. 79 shows this embodiment at a second point in time wherein data from wearable thermal energy sensor 7902 indicates that the temperature of person 7901 is above a normal range and, accordingly, this has triggered a flow of cooling fluid or gas through adjustable-temperature blanket 7904.

In this manner, this embodiment can help to automatically cool person 7901, while they sleep, when they experience an upswing in body temperature such as a hot flash. In an example, cooling fluid or gas can circulate through an adjustable-temperature blanket for a predefined duration of time when this circulation is triggered by a high body temperature detected by wearable thermal energy sensor 7902. In an example, cooling fluid or gas can be triggered to circulate through an adjustable-temperature blanket based on a high body temperature and can continue until a person's body temperature drops to a normal level.

In an example, a wearable thermal energy sensor can be a thermistor, as represented by the thermistor electrical component symbol shown in a dotted-line circle on the right side of FIG. 79. In an example, a wearable thermal energy sensor can be a thermometer or other type of temperature-measuring sensor. In an example, a wearable thermal energy sensor can be part of a smart watch or wrist band. In an example, a wearable thermal energy sensor can be configured to be worn on a portion of a person's body selected from the group consisting of: finger, hand, wrist, arm, torso, waist, back, leg, ankle, foot, neck, ear, nose, and head. In an example, a wearable thermal energy sensor can be incorporated into a garment (such as a shirt, pair of shorts, pair of pants, one-piece pajamas, sock, or hat).

In an example a data-control component can be co-located with a wearable thermal energy sensor as part of a smart watch or wrist band. In an example, a data-control component can be worn elsewhere on a person's body, as part of an accessory or electronically-functional clothing. In an example, a data-control component can be part of a smart phone or other portable electronic device. In an example, data from a wearable thermal energy sensor can be used to: change the temperature of a blanket over a person; change the temperature of the air, mattress, blanket, or other bedding material near a person's body; change the temperature of air and/or other gas in communication with the surface of the person's body; or change the temperature of air under a blanket or other bed covering. Relevant example and component variations discussed elsewhere in this disclosure or in priority-linked disclosures can also be applied to this example, but are not repeated here to avoid narrative redundancy.

Figure 80:
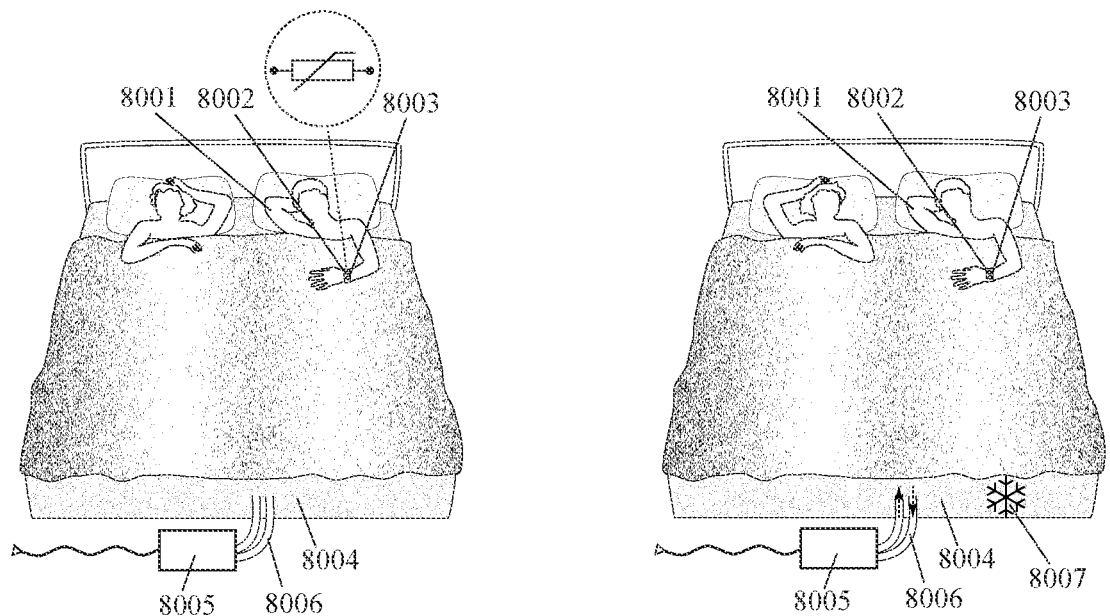
FIG. 80 shows a second system for modifying a person's sleep environment which changes bed temperature based on a wearable thermal energy sensor.

The embodiment of this invention which is shown in FIG. 80 is similar to the one shown in FIG. 79 except that it comprises an adjustable-temperature mattress instead of an adjustable-temperature blanket. The embodiment shown in FIG. 80 is a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the temperature of a mattress; and a data-control component which controls the operation of the sleep-environment-modifying component in order to automatically change the person's sleep environment based on data from the wearable-sensor component.

More specifically, the embodiment shown in FIG. 80 comprises: wearable thermal energy sensor 8002; data-control component 8003; and adjustable-temperature mattress 8004. In this example, this embodiment further comprises heat pump 8005 which pumps cooling fluid or gas through flow tubes 8006 into adjustable-temperature mattress 8004. This cooling function is symbolically represented by "snowflake" symbol 8007. In this example, data-control component 8003 activates heat pump 8005 to circulate cooling fluid or gas through channels or pathways in mattress 8004 when data from wearable thermal energy sensor 8002 indicates that the temperature of person 8001 is too high.

In an example, when data from wearable thermal energy sensor 8002 indicates that person 8001 has a skin and/or body temperature that is within a normal range, then fluid or gas is not circulated through adjustable-temperature mattress 8004. In an example, when data from wearable thermal energy sensor 8002 indicates that person 8001 has a skin and/or body temperature that is above a normal range, then data-control component 8003 triggers a flow of cooling fluid or gas through adjustable-temperature mattress 8004. In an example, adjustable-temperature mattress 8004 can further comprise sinusoidal fluid or gas pathways through which a cooling fluid or gas can circulate.

The left side of FIG. 80 shows this embodiment at a first point in time wherein data from wearable thermal energy sensor 8002 indicates that the temperature of person 8001 is within a normal range and, accordingly, there is no circulation of cooling fluid or gas through adjustable-temperature mattress 8004. The right side of FIG. 80 shows this embodiment at a second point in time wherein data from wearable thermal energy sensor 8002 indicates that the temperature of person 8001 is above a normal range and, accordingly, this has triggered a flow of cooling fluid or gas through adjustable-temperature mattress 8004.

In this manner, this embodiment can help to automatically cool person 8001, while they sleep, when they experience an upswing in body temperature such as a hot flash. In an example, cooling fluid or gas can circulate through an adjustable-temperature mattress for a predefined duration of time when this circulation is triggered by a high body temperature detected by wearable thermal energy sensor 8002. In an example, cooling fluid or gas can be triggered to circulate through an adjustable-temperature mattress based on a high body temperature and can continue until a person's body temperature drops to a normal level.

In an example, a wearable thermal energy sensor can be a thermistor, as represented by the thermistor electrical component symbol shown in a dotted-line circle on the right side of FIG. 80. In an example, a wearable thermal energy sensor can be a thermometer or other type of temperature-measuring sensor. In an example, a wearable thermal energy sensor can be part of a smart watch or wrist band. In an example, a wearable thermal energy sensor can be configured to be worn on a portion of a person's body selected from the group consisting of: finger, hand, wrist, arm, torso, waist, back, leg, ankle, foot, neck, ear, nose, and head. In an example, a wearable thermal energy sensor can be incorporated into a garment (such as a shirt, pair of shorts, pair of pants, one-piece pajamas, sock, or hat).

In an example a data-control component can be co-located with a wearable thermal energy sensor as part of a smart watch or wrist band. In an example, a data-control component can be worn elsewhere on a person's body, as part of an accessory or electronically-functional clothing. In an example, a data-control component can be part of a smart phone or other portable electronic device. In an example, data from a wearable thermal energy sensor can be used to: change the temperature of a mattress over a person; change the temperature of the air, mattress, mattress, or other bedding material near a person's body; change the temperature of air and/or other gas in communication with the surface of the person's body; or change the temperature of air under a mattress or other bed covering. Relevant example and component variations discussed elsewhere in this disclosure or in priority-linked disclosures can also be applied to this example, but are not repeated here to avoid narrative redundancy.

Figure 81:
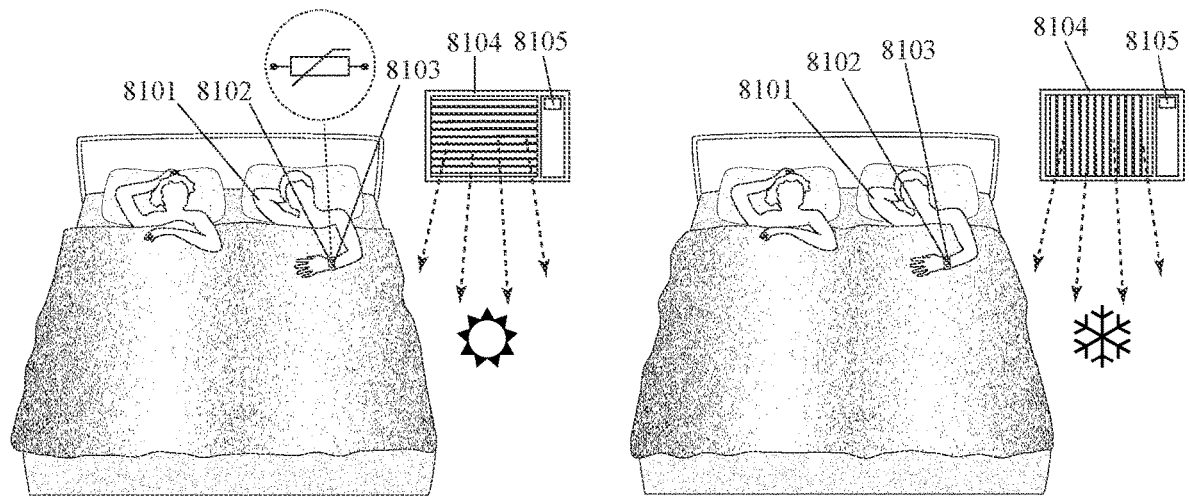
FIG. 81 shows a system for modifying a person's sleep environment which changes the temperature of air from a window air conditioner based on a wearable thermal energy sensor.

As shown in FIG. 81, this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the temperature of a flow of air from a window-based air conditioner; and a data-control component which controls the operation of the sleep-environment-modifying component in order to automatically change the person's sleep environment based on data from the wearable-sensor component.

More specifically, the embodiment shown in FIG. 81 comprises: wearable thermal energy sensor 8102; power source or transducer 8103; window-based air conditioner 8104; and data-control component 8105. In an example, data-control component 8105 controls the temperature of airflow from window-based air conditioner 8104 based on data from wearable thermal energy sensor 8102. In an example, when data from wearable thermal energy sensor 8102 indicates that the skin and/or body temperature of person 8101 is above a normal range, then this triggers a lower temperature of airflow from window-based air conditioner 8104.

In an example, data from a wearable thermal energy sensor can be analyzed to predict a future upswing in skin and/or body temperature such as a hot flash. In an example, data from a wearable thermal energy sensor can be analyzed along with data from other types of body sensors (such as a heart rate sensor, EMG sensor, EEG sensor, and body moisture sensor) in order to predict a temporary upswing in skin and/or body temperature such as a hot flash. In an example, when data from one or more sensors indicate that an upswing in body temperature will probably occur soon, then this embodiment can activate a prophylactic decrease in airflow temperature in order to mitigate or avoid the effects of the upswing. In an example, when data from one or more sensors indicate that an upswing in body temperature will probably occur soon, then this embodiment can turn on a window-based air conditioner in order to mitigate or avoid the effects of a temperature upswing.

In an example, when a decrease in airflow temperature and/or activation of a window-based air conditioner is triggered, then this decrease or activation can continue for a predefined period of time. In an example, when a decrease in airflow temperature and/or activation of a window-based air conditioner is triggered, then this decrease or activation can continue until data from a wearable thermal energy sensor indicates that a person's temperature has returned to a normal level. In an example, a data-control component can be located as part of a window-based air conditioner. In an example, a data-control component can be co-located with a wearable thermal energy sensor as part of a wearable device. In an example, a data-control component can be integrated into a cell phone or other mobile electronic device.

The left side of FIG. 81 shows this embodiment at a first point in time wherein airflow from window-based air conditioner 8104 has a first temperature based on a first pattern of data from wearable energy sensor 8102. The right side of FIG. 81 shows this embodiment at a second point in time wherein airflow from window-based air conditioner 8104 has a second temperature based on a second pattern of data from wearable energy sensor 8102. In this example, the second temperature is lower than the first temperature, as symbolically indicated by the transition from a "sun" symbol on the left side vs. a "snowflake" symbol on the right side of FIG. 81. In this example, the first pattern of data indicates that the skin and/or body temperature of person 8101 is not too high. In this example, the second pattern of data indicates that the skin and/or body temperature of person 8101 is too high.

In an example, wearable thermal energy sensor 8102 can be a thermistor. In an example, wearable thermal energy sensor 8102 can be a thermometer or other type of temperature sensor. In an example, a wearable thermal energy sensor can be configured to be worn on a portion of a person's body selected from the group consisting of: finger, hand, wrist, arm, torso, waist, back, leg, ankle, foot, ear, nose, and head. In an example, a wearable thermal energy sensor can be placed within a person's mouth. In an example, a wearable thermal energy sensor can be incorporated into a shirt, briefs, bra, shorts, pants, sock, hat, pajamas or other garment that a person wears to bed. In an example, a wearable thermal energy sensor can be incorporated into a wrist band, smart watch, or electronically-functional eyewear. In an example, data from a wearable thermal energy sensor can be used to automatically change the temperature of a flow of air from a window-based air conditioner. Relevant example and component variations discussed elsewhere in this disclosure or in priority-linked disclosures can also be applied to this example, but are not repeated here to avoid narrative redundancy.

Figure 82:
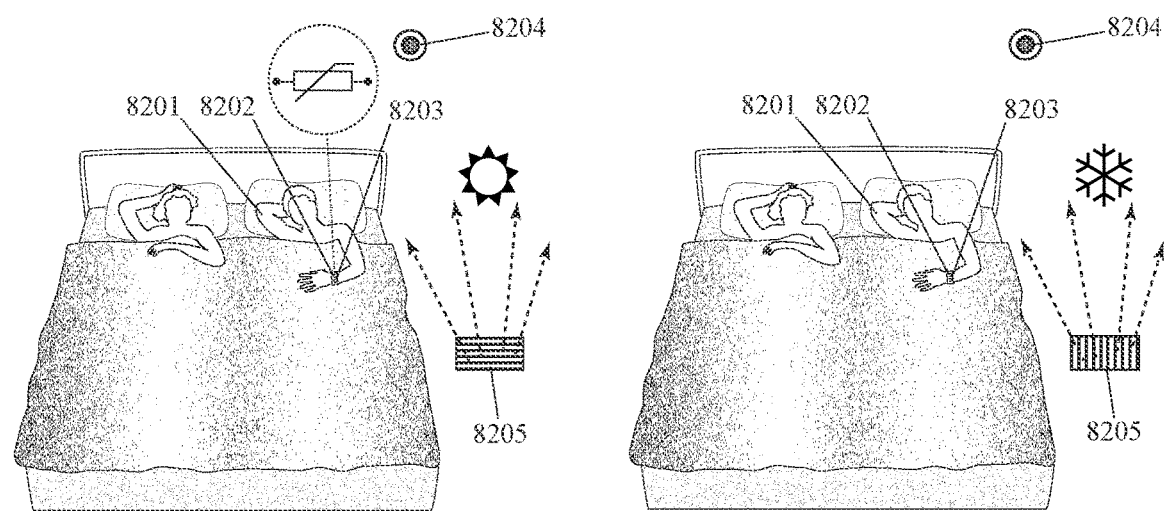
FIG. 82 shows a system for modifying a person's sleep environment which changes the temperature of air from a HVAC system based on a wearable thermal energy sensor.

FIG. 82 shows an example of how this invention can be embodied in a system, device, and method that uses wearable technology to collect data for automatic modification of a person's sleep environment comprising: a wearable-sensor component that is configured to be worn by a person, wherein this sensor component collects data concerning the person's skin temperature and/or body temperature; a sleep-environment-modifying component which changes the temperature of a flow of air from a central heating, ventilation, and/or air-conditioning (HVAC) system; and a data-control component which controls the operation of the sleep-environment-modifying component in order to automatically change the person's sleep environment based on data from the wearable-sensor component.

More specifically, the embodiment shown in FIG. 82 comprises: wearable thermal energy sensor 8202; power source or transducer 8203; HVAC control unit 8204; and HVAC vent 8205. In an example, HVAC control unit 8204 controls the temperature of airflow from HVAC vent 8205 based on data from wearable thermal energy sensor 8202. In an example, when data from wearable thermal energy sensor 8202 indicates that the skin and/or body temperature of person 8201 is above a normal range, then this triggers a lower temperature of airflow from HVAC vent 8205.

In an example, data from a wearable thermal energy sensor can be analyzed to predict a future upswing in skin and/or body temperature, such as a hot flash. In an example, data from a wearable thermal energy sensor can be analyzed along with data from other types of body sensors (such as a heart rate sensor, EMG sensor, EEG sensor, and body moisture sensor) in order to predict a temporary upswing in skin and/or body temperature, such as a hot flash. In an example, when data from one or more sensors indicate that an upswing in body temperature will probably occur soon, then this embodiment can activate a prophylactic decrease in airflow temperature in order to mitigate or avoid the effects of the upswing. In an example, when data from one or more sensors indicate that an upswing in body temperature will probably occur soon, then this embodiment can activate airflow from an HVAC system in order to mitigate or avoid the effects of the upswing.

In an example, when airflow or a change in temperature of airflow from an HVAC system is triggered, then this change can continue for a predefined period of time. In an example, when airflow or a change in airflow temperature from an HVAC system is triggered, then this change can continue until data from a wearable thermal energy sensor indicates that a person's temperature has returned to a normal level. In an example, an HVAC control unit can be located on a wall. In an example, an HVAC control function can be incorporated into a wearable device. In an example, an HVAC control function can be incorporated into a cell phone or other mobile electronic device.

The left side of FIG. 82 shows this embodiment at a first point in time wherein airflow from HVAC vent 8205 has a first temperature based on a first pattern of data from wearable energy sensor 8202. The right side of FIG. 82 shows this embodiment at a second point in time wherein airflow from HVAC vent 8205 has a second temperature based on a second pattern of data from wearable energy sensor 8202. In this example, the second temperature is lower than the first temperature, as symbolically indicated by the transition from a "sun" symbol on the left side vs. a "snowflake" symbol on the right side of FIG. 82. In this example, the first pattern of data indicates that the skin and/or body temperature of person 8201 is not too high. In this example, the second pattern of data indicates that the skin and/or body temperature of person 8201 is too high.

In an example, wearable thermal energy sensor 8202 can be a thermistor. In an example, wearable thermal energy sensor 8202 can be a thermometer or other type of temperature sensor. In an example, a wearable thermal energy sensor can be located on or within a portion of a person's body selected from the group consisting of: finger, hand, wrist, arm, torso, waist, back, leg, ankle, foot, ear, nose, mouth, and head. In an example, a wearable thermal energy sensor can be incorporated into a shirt, briefs, bra, shorts, pants, sock, hat, pajamas or other garment that a person wears to bed. In an example, a wearable thermal energy sensor can be incorporated into a wrist band, smart watch, or electronically-functional eyewear. Relevant example and component variations discussed elsewhere in this disclosure or in priority-linked disclosures can also be applied to this example, but are not repeated here to avoid narrative redundancy.

Figure 83:
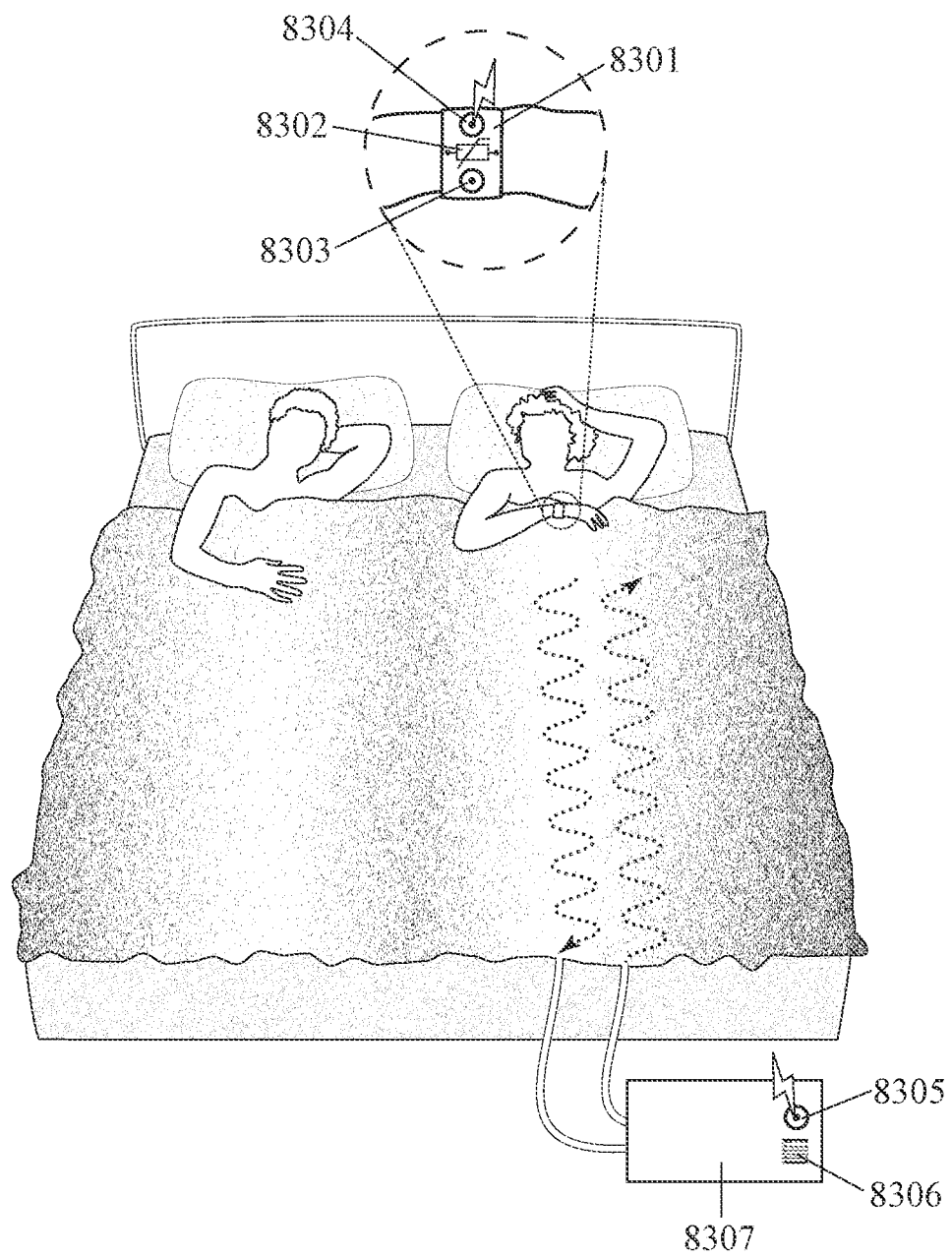
FIG. 83 shows a system which changes the temperature of air in proximity to a sleeping person based on data from a wearable thermal energy sensor, using an intra-room cooling and/or heating member.

FIG. 83 shows an example of how this invention can be embodied in a system for changing the temperature of air in close proximity to the body of a sleeping person comprising: (a) a wearable attachment member 8301 that is configured to be worn by a person while they sleep; (b) a wearable sensor 8302 which is part of, or attached to, the wearable attachment member, wherein this wearable sensor collects data concerning the person's current body temperature and/or data used to predict the person's future body temperature; (c) a power source 8303 which is part of, or attached to, the wearable attachment member; (d) a wireless data transmitter 8304 which is part of, or attached to, the attachment member; (e) a wireless data receiver 8305, wherein data from the wearable sensor is transmitted from the wireless data transmitter to the wireless data receiver; (f) a data processing unit 8306 which processes data from the wearable sensor; and (g) a cooling and/or heating member 8307 whose operation changes the temperature of air in close proximity to the sleeping person in response to data concerning the person's current body temperature and/or data used to predict the person's future body temperature. In an example, close proximity can be defined as being within six inches of the surface of a person's body. In an example, close proximity can be defined as being within 1 inch of a person's body A dashed-line circle in the upper central portion of FIG. 83 shows an enlarged view of the wearable attachment member 8301 which is worn on the right wrist of the person who is sleeping on the right side of the bed. In this example, the person on the right side of the bed is the person about whom data concerning body temperature is being monitored and used to decrease or increase the temperature of air in proximity to their body. In an example, this system can comprise different devices which are physically separate, but are in electromagnetic communication with each other. In an example, some components of this system can be physically part of, or attached to, a wearable attachment member and other components of this system can be physically part of a separate cooling and/or heating member. In an example, components of a wearable attachment member can be in electromagnetic communication with components of a cooling and/or heating member. In an example, a wearable attachment member and a cooling and/or heating member can together comprise a system for iterative modification of a person's sleeping environment.

In the example shown in FIG. 83, a wearable attachment member 8301 is worn on a person's wrist and/or forearm. In various examples, a wearable attachment member can be worn: on a wrist, forearm, hand, finger, and/or upper arm; on or around a neck; over eyes, in or around an ear, in a mouth, in a nose, around a head, and/or on top of a head; on a torso, waist, and/or hip; and on a leg, ankle, and/or foot. In this example, a wearable attachment member can be selected from the group consisting of: wrist band, smart watch, fitness band, sleep band, bracelet, forearm band, and wearable sleeve.

In various examples, a wearable attachment member can be selected from the group consisting of: adhesive patch, amulet, ankle band, ankle bracelet, ankle strap, arm band, artificial finger nail, bandage, belt, bra, bracelet, cap, cardiac monitor, CPAP or other respiratory mask, ear bud, ear muffs, ear plug, ear ring, ECG monitor, EEG monitor, EMG monitor, electronically-functional tattoo, EOG monitor, eye mask, eye patch, eyewear, finger ring, finger sleeve, fitness band, forearm band, forearm sleeve, glove, hair band, hat, headband, headphones, heart monitor, lower body garment, necklace, pajamas, pants, shirt, sleep band, smart belt, smart watch, smart watch, sock, sternal conductance monitor, sternal patch, torso band, underpants, undershirt, wrist band, and wrist sleeve.

In the example shown in FIG. 83, a wearable sensor 8302 is a temperature sensor. In an example, a wearable sensor can measure core body temperature. In an example, a wearable sensor can measure skin temperature. In an example, a wearable sensor can be a thermistor and/or thermometer. In an example, a change in core body temperature can be associated with a hot flash and/or help to predict a hot flash. In an example, a change in skin temperature can be associated with a hot flash and/or help to predict a hot flash. In an example, a specifically-identified pattern of body temperature change can be associated with a hot flash and/or help to predict a hot flash.

In an example, a wearable sensor can be a skin conductance sensor. In an example, a wearable sensor can be a sternal skin conductance sensor. In an example, a wearable sensor can be a sternal skin conductance (SSC) sensor which measures the conduction of electricity through a person's skin. In an example, an increase in skin conductance can be associated with a hot flash and/or help to predict a hot flash. In an example, an increase in skin conductance which is greater than a selected amount (e.g. increase >2 micro mho) and which occurs in less than a selected period of time (e.g. time period <30 seconds) can be associated with a hot flash and/or help to predict a hot flash. In an example, a specifically-identified pattern of increased skin conductance can be associated with a hot flash and/or help to predict a hot flash. In an example, a wearable sensor can be a sweat sensor. In an example, a wearable sensor can be a capacitance hygrometry sensor.

In an example, a wearable sensor can be an EEG sensor or other electromagnetic brain activity sensor. In an example, brainwaves can be measured and analyzed using a subset and/or combination of five clinical frequency bands: Delta, Theta, Alpha, Beta, and Gamma. In an example, a system can analyze changes in brainwaves in a single frequency band, changes in brainwaves in multiple frequency bands, or changes in brainwaves in a first frequency band relative to those in a second frequency band. In an example, a system can analyze repeating electromagnetic patterns by analyzing their frequency of repetition, their frequency band or range of repetition, their recurring amplitude, their wave phase, and/or their waveform. In an example, one or more of these changes in brainwaves can be associated with a hot flash and/or help to predict a hot flash.

In an example, a wearable sensor can be a heart rate sensor. In an example, a wearable sensor can be an electrocardiogram (ECG) sensor. In an example, an increase in heart rate can be associated with a hot flash and/or help to predict a hot flash. In an example, a change in pulse can be associated with a hot flash and/or help to predict a hot flash. In an example, a wearable sensor can be a blood pressure sensor. In an example, a wearable sensor can measure changes in one or more pressures selected from the group consisting of: diastolic blood pressure, systolic blood pressure, and mean arterial blood pressure. In an example, a reduction in blood pressure can be associated with a hot flash and/or help to predict a hot flash. In an example, a specifically-identified pattern of decreased blood pressure can be associated with a hot flash and/or help to predict a hot flash.

In an example, a wearable sensor can be a blood flow sensor. In an example, a wearable sensor can measure changes in blood flow in a person's finger or forearm. In an example, a wearable sensor can be a plethysmographic sensor. In an example, a wearable sensor can measure changes in blood flow through the brain. In an example, a wearable sensor can measure middle cerebral artery blood velocity. In an example, a reduction in blood flow through the brain can be associated with a hot flash and/or help to predict a hot flash. In an example, a specifically-identified pattern of decreased blood flow through the brain can be associated with a hot flash and/or help to predict a hot flash.

In an example, a wearable sensor can be a respiratory function sensor. In an example, a wearable sensor can measure respiratory effort, respiration rate, and/or nasal airflow. In an example, a change in respiration can be associated with a hot flash and/or help to predict a hot flash. In an example, a specifically-identified pattern of change in respiratory function can be associated with a hot flash and/or help to predict a hot flash. In an example, patterns of body motion can be associated with a hot flash and/or help to predict a hot flash. In an example, a wearable sensor can measure skin sympathetic nerve activity. In an example, an increase in skin sympathetic nerve activity can be associated with a hot flash and/or help to predict a hot flash.

In an example, a wearable sensor can be a body motion sensor. In an example, a wearable sensor can be selected from the group consisting of: accelerometer, electromagnetic bend sensor, electromyographic (EMG) sensor, gyroscope, inclinometer, inertial motion sensor, optical bend sensor, piezoelectric bend sensor, and strain gauge. In an example, data from one or more wearable body motion sensors can be used to identify one or more hand gestures which control the activation and/or operation of a cooling and/or heating member. In an example, data from one or more wearable body motion sensors can be used to identify one or more body configurations and/or postures which control the activation and/and operation of a cooling and/or heating member.

In an example, a first hand gesture or body configuration can be voluntarily and consciously initiated by a person (when the person has been aroused from sleep by a hot flash) in order to activate a cooling and/or heating member to cool air near the person. In an example, this first hand gesture or body configuration can comprise a "pushing away from the body" motion. In an example, a second hand gesture or body configuration can be voluntarily and consciously initiated by a person (when the person has been aroused from sleep by a hot flash) in order to stop the cooling and/or hearing member from cooling air near the person. In an example, this second hand gesture or body configuration can comprise a "drawing toward the body" motion.

In an example, a hand gesture or body configuration (such as tossing and turning in bed) can be caused by a hot flash, even when a person is asleep and/or only partially conscious. In an example, such an unconscious or partially-conscious hand gesture or body configuration can trigger activation of a cooling and/or heating member. In an example, this unconscious or partially-conscious body configuration can comprise a change (or sequence of changes) in sleeping orientation, such as rolling from side to back, from side to front, from front to back, or vice versa.

In an example, patterns of body motion can also help to differentiate changes in skin conductance from causes other than a hot flash. In an example, a wearable sensor can be an eye movement sensor and/or an electrooculography (EOG) sensor. In an example, hot flashes may be less common during rapid eye movement (REM) due to a decrease in thermoregulatory effector response. In an example, data from an eye movement sensor can increase the accuracy of hot flash prediction. In an example, a wearable sensor can be a biochemical sensor. In an example, a wearable sensor can measure changes in one or more of the following biochemicals: catecholamine, epinephrine, estradiol, estrone, follicle-stimulating hormone, luteinizing hormone, norepinephrine, and immunoreactive neurotensin. In an example, a change in one or more of these biochemicals can be associated with a hot flash and/or help to predict a hot flash.

In an example, a wearable sensor can be a thermal energy sensor. In an example, a wearable sensor can be selected from the group consisting of: core body temperature sensor, skin temperature sensor, thermistor, and thermometer. In an example, a sensor can be an electromagnetic energy sensor. In an example, a wearable sensor can be selected from the group consisting of: action potential sensor, capacitance hygrometry sensor, conductivity sensor, electrocardiogram (ECG) sensor, electroencephalography (EEG) sensor, electrogastrographic monitor, electromagnetic brain activity sensor, electromyography (EMG) sensor, electrooculography (EOG) sensor, galvanic skin response (GSR) sensor, Hall-effect sensor, humidity sensor, impedance sensor, magnetic field sensor, magnetometer, muscle function monitor, neural impulse monitor, neurosensor, piezocapacitive sensor, piezoelectric sensor, piezoresistive sensor, REM sensor, resistance sensor, RF sensor, skin conductance sensor, sternal skin conductance (SSC) sensor, sweat sensor, sympathetic nerve activity sensor, tissue impedance sensor, variable impedance sensor, variable resistance sensor, and voltmeter.

In an example, a wearable sensor can be a light energy sensor. In an example, a wearable sensor can be selected from the group consisting of: analytical chromatography sensor, backscattering spectrometry sensor, camera, chemiluminescence sensor, chromatography sensor, infrared light sensor, infrared spectroscopy sensor, laser sensor, light intensity sensor, light-spectrum-analyzing sensor, mass spectrometry sensor, near-infrared spectroscopy sensor, optical sensor, optical sensor, optoelectronic sensor, photoelectric sensor, photoplethysmographic sensor, spectral analysis sensor, spectrometry sensor, spectrophotometer sensor, spectroscopic sensor, ultraviolet light sensor, ultraviolet spectroscopy sensor, variable-translucence sensor.

In an example, a wearable sensor can be a circulatory system sensor. In an example, a wearable sensor can be selected from the group consisting of: blood flow sensor, blood pressure sensor, brain blood flow sensor, heart rate sensor, mean arterial blood pressure sensor, middle cerebral artery blood velocity sensor, pulse sensor, and systolic blood pressure sensor. In an example, a wearable sensor can be a motion sensor. In an example, a wearable sensor can be selected from the group consisting of: body motion sensor, eye movement sensor, inertial motion sensor, plethysmographic sensor, and pressure sensor. In an example, a wearable sensor can be a biochemical sensor. In an example, a wearable sensor can be selected from the group consisting of: biochemical sensor, epinephrine sensor, estradiol sensor, follicle-stimulating hormone (FSH) sensor, immunoreactive neurotensin sensor, luteinizing hormone (LH) sensor, and norepinephrine sensor. In an example, a wearable sensor can be selected from the group consisting of: airflow sensor, respiration rate sensor, and respiratory function sensor.

In an example, a wearable sensor can be in electromagnetic communication with a person's skin. In an example, a wearable sensor can measure skin conductivity or impedance. In an example, a wearable sensor can measure electromagnetic energy which is emitted from a person's nerves and/or muscles. In an example, a wearable sensor can measure the spectrum of light which is reflected from, or passed through, a person's tissue. In an example, a wearable sensor can be a vasoconstriction sensor. In an example, a wearable sensor can be in gaseous communication with a person's skin. In an example, a sensor can collect data concerning the chemical content of gaseous emissions from a person's skin. In an example, a wearable sensor can be in fluid communication with a person's skin. In an example, a sensor can collect data concerning the chemical content of fluid emissions from a person's skin. In an example, a wearable sensor can be sound energy sensor.

In an example, this system can comprise two or more different types of wearable sensors. In an example, multivariate analysis of data from two or more different types of sensors can detect and/or predict hot flashes with a higher level of accuracy than data from only one type of wearable sensor. In an example, the statistical interaction of two or more physiological variables, measured by two or more different types of sensors, can detect and/or predict hot flashes more accurately than either of the physiological variables alone. In an example, multivariate analysis of skin conductance level and core body temperature can predict a hot flash more accurately than analysis of either of these metrics alone.

In an example, this system can comprise one of the following pairs of wearable sensors: body temperature sensor and skin conductance sensor, body temperature sensor and EEG sensor, body temperature sensor and heart rate sensor, body temperature sensor and blood pressure sensor, body temperature sensor and blood flow sensor, body temperature sensor and body motion sensor, body temperature sensor and respiratory function sensor, skin conductance sensor and eye movement sensor, skin conductance sensor and biochemical sensor, skin conductance sensor and neurosensor, skin conductance sensor and EEG sensor, skin conductance sensor and heart rate sensor, and skin conductance sensor and blood pressure sensor.

In an example, this system can comprise one of the following pairs of wearable sensors: EEG sensor and blood flow sensor, EEG sensor and body motion sensor, EEG sensor and respiratory function sensor, EEG sensor and eye movement sensor, EEG sensor and biochemical sensor, EEG sensor and neurosensor, heart rate sensor and EEG sensor, heart rate sensor and blood pressure sensor, heart rate sensor and blood flow sensor, heart rate sensor and body motion sensor, heart rate sensor and respiratory function sensor, heart rate sensor and eye movement sensor, and heart rate sensor and biochemical sensor.

In an example, this system can comprise one of the following pairs of wearable sensors: blood pressure sensor and neurosensor, blood pressure sensor and EEG sensor, blood pressure sensor and blood flow sensor, blood pressure sensor and body motion sensor, blood flow sensor and respiratory function sensor, blood flow sensor and eye movement sensor, blood flow sensor and biochemical sensor, blood flow sensor and neurosensor, and blood flow sensor and skin conductance sensor. In an example, this system can comprise one of the following pairs of wearable sensors: body motion sensor and blood pressure sensor, body motion sensor and blood flow sensor, body motion sensor and respiratory function sensor, body motion sensor and eye movement sensor, body motion sensor and biochemical sensor, body motion sensor and neurosensor, respiratory function sensor and skin conductance sensor, respiratory function sensor and heart rate sensor, respiratory function sensor and blood pressure sensor, respiratory function sensor and blood flow sensor, respiratory function sensor and body motion sensor, and respiratory function sensor and eye movement sensor.

In an example, this system can comprise one of the following pairs of wearable sensors: eye movement sensor and biochemical sensor, eye movement sensor and neurosensor, eye movement sensor and body temperature sensor, eye movement sensor and EEG sensor, eye movement sensor and heart rate sensor, eye movement sensor and blood pressure sensor, and eye movement sensor and blood flow sensor. In an example, this system can comprise one of the following pairs of wearable sensors: biochemical sensor and body motion sensor, biochemical sensor and respiratory function sensor, biochemical sensor and eye movement sensor, biochemical sensor and neurosensor, biochemical sensor and body temperature sensor, neurosensor and heart rate sensor, neurosensor and blood pressure sensor, neurosensor and blood flow sensor, neurosensor and body motion sensor, neurosensor and respiratory function sensor, neurosensor and eye movement sensor, and neurosensor and biochemical sensor.

In an example, demographic and health-related characteristics of the person wearing the device can be incorporated into a multivariate statistical model to detect and/or predict the occurrence of a hot flash. In an example, these demographic and health-related characteristics can be selected from the group consisting of: age, alcohol use, anxiety level, body mass index (BMI), caffeine use, education level, gender, height, hours of sleep, menopausal status, nicotine use, nutritional profile, physical activity level, race/ethnicity, stress level, tobacco use, and weight. In an example, characteristics of the person's local environment can be incorporated into a multivariate statistical model to detect and/or predict the occurrence of a hot flash. In an example, these environmental characteristics can be selected from the group consisting of: ambient humidity level, ambient light level, ambient sound level, ambient temperature, location, and time of day.

In the example shown in FIG. 83, power source 8303 is a rechargeable battery. In an example, a power source can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy.

In the example shown in FIG. 83, cooling and/or heating member 8307 is an intra-room cooling and/or heating member. An intra-room cooling and/or heating member is located entirely within the room in which the person wearing the device is sleeping. In an example, an intra-room cooling and/or heating member can be a heat pump, heat exchanger, air conditioner, electric blanket, electric pad, electric mattress, electric room heater, or combustion-based room heater within the room in which a person is sleeping. In an example, an intra-room cooling and/or heating member can comprise one or more components selected from the group consisting of: compressor; heat exchanger or heat pump; air fan, blower, turbine, or impellor; air circulation pathway; liquid fan, blower, turbine, or impellor; liquid circulation pathway; electric heating coils; combustible substance reservoir; ice reservoir and/or compartment to contain ice; wireless data receiver; wireless data transmitter; and data processor.

In an example, an intra-room cooling and/or heating member can cool air that is in close proximity to a person's body when an increase in body temperature is detected and/or predicted based on analysis of data from a wearable sensor worn by the person. In an example, an intra-room cooling and/or heating member can cool air in proximity to a sleeping person by transferring thermal energy between locations within the room in which the person is sleeping.

In an example, an intra-room cooling and/or heating member can cool air in proximity to a sleeping person by: (a) extracting thermal energy from a portion of air in the room using a compressor, heat pump, and/or heat exchanger, thereby cooling that portion of air (b) transferring the extracted thermal energy to a location in the room that is distal to the person, and (c) sending (and/or circulating) the cooled air in proximity to the person. In an example, an intra-room cooling and/or heating member can cool air in proximity to a sleeping person by: (a) extracting thermal energy from a liquid using a compressor, heat pump, and/or heat exchanger, thereby cooling that liquid (b) transferring the extracted thermal energy to a location in the room that is distal to the person, and (c) sending (or circulating) the cooled liquid in proximity to the person. In an example, "distal to the person" can be defined as being more than six foot away from the person. In an example, "distal to the person" can be defined as being more than one foot away from the person.

In an example, an intra-room cooling and/or heating member can cool air in proximity to a sleeping person using an intra-room ice reservoir. In an example, the system can send (or circulate) air or liquid through channels which are in thermal communication with ice within an ice reservoir. This cools the air or liquid, which is then sent (or circulated) in proximity to the sleeping person. In an example, the system can include a closable ice reservoir which a person fills with ice before going to sleep. Since the ice reservoir can be closed, moisture from the melting ice does not increase the humidity of air in the room. One advantage of using an ice reservoir in an intra-room cooling and/or heating member for cooling is that there is net decrease in the total thermal energy in the room when ice is brought into the room at the beginning of the night.

In an example, an intra-room cooling and/or heating member can send (or circulate) cooled air between a bed covering (such as an upper sheet or blanket) which is over the sleeping person and a sleeping surface (such as a lower sheet, mattress pad, or mattress) which is below the sleeping person. In a two-person bed, the system can be configured to selectively send (or circulate) cooled air only on the side of the bed where the person wearing the device is sleeping. In an example, the system can automatically detect which on side of the bed this person is sleeping and selectively cool that side of the bed. In an example, selective cooling of only one side a bed can be accomplished by selecting sending air through a subset of air pathways, channels, or vents.

In an example, an intra-room cooling and/or heating member can send (or circulate) cooled liquid through channels in a bed covering (such as an upper sheet or blanket) which is over the sleeping person or through channels in a sleeping surface (such as a lower sheet, mattress pad, or mattress) which is below the sleeping person. In a two-person bed, the system can be configured to selectively send (or circulate) cooled liquid only on the side of the bed where the person wearing the device is sleeping. In an example, the system can automatically detect which on side of the bed this person is sleeping and selectively cool that side of the bed. In an example, selective cooling of only one side a bed can be accomplished by selecting sending liquid through a subset of liquid channels.

In an example, an intra-room cooling and/or heating member can heat air that is in close proximity to a person's body when a decrease in body temperature is detected and/or predicted based on analysis of data from a wearable sensor worn by the person. In an example, an intra-room cooling and/or heating member can heat air in proximity to a sleeping person by transferring thermal energy between locations within the room in which the person is sleeping.

In an example, an intra-room cooling and/or heating member can heat air in proximity to a sleeping person by: (a) extracting thermal energy from a location in the room that is distal to the person using a compressor, heat pump, and/or heat exchanger; (b) transferring the extracted thermal energy to a portion of air in the room; (c) and sending (and/or circulating) the heated air in proximity to the person. In an example, an intra-room cooling and/or heating member can heat air in proximity to a sleeping person by: (a) extracting thermal energy from a location in the room that is distal to the person using a compressor, heat pump, and/or heat exchanger; (b) transferring the extracted thermal energy to a liquid; (c) and sending (and/or circulating) the heated liquid in proximity to the person.

In an example, an intra-room cooling and/or heating member can send (or circulate) heated air between a bed covering (such as an upper sheet or blanket) which is over the sleeping person and a sleeping surface (such as a lower sheet, mattress pad, or mattress) which is below the sleeping person. In a two-person bed, the system can be configured to selectively send (or circulate) heated air only on the side of the bed where the person wearing the device is sleeping. In an example, the system can automatically detect which on side of the bed this person is sleeping and selectively heat that side of the bed. In an example, selective cooling of only one side a bed can be accomplished by selecting sending air through a subset of air pathways, channels, or vents.

In an example, an intra-room cooling and/or heating member can send (or circulate) heated liquid through channels in a bed covering (such as an upper sheet or blanket) which is over the sleeping person or through channels in a sleeping surface (such as a lower sheet, mattress pad, or mattress) which is below the sleeping person. In a two-person bed, the system can be configured to selectively send (or circulate) heated liquid only on the side of the bed where the person wearing the device is sleeping. In an example, the system can automatically detect which on side of the bed this person is sleeping and selectively heat that side of the bed. In an example, selective cooling of only one side a bed can be accomplished by selecting sending liquid through a subset of liquid channels.

In an example, an intra-room cooling and/or heating member can heat air in proximity to a sleeping person by generating heat by electrical resistance and/or combustion, instead of (or in addition to) transferring thermal energy between locations within the room in which a person is sleeping. In an example, an intra-room cooling and/or heating member can be selected from the group consisting of: an electric blanket, an electric heating pad, an electric mattress, an electrically-heated water bed, an electric room heater, an electric space heater, an electric baseboard heater, and a combustion-based room heater. In an example, in a two-person bed, a system can be configured to selectively and/or primarily heat the side of the bed wherein the person with the wearable sensor is sleeping.

In various general examples which can also include exo-room (e.g. window mounted) systems and building-wide (e.g. central HVAC) systems, a cooling and/or heating member can be selected from the group consisting of: air-cooled garment, central air conditioning unit, central boiler, central furnace, central heating unit, central HVAC system, combustion-based room heater, electric baseboard heater, electric blanket, electric mattress, electric room heater, gas fireplace, heat exchanger, heat pump, heated and/or cooled blanket, heated and/or cooled mattress, heated and/or cooled water bed, heated garment, heating pad, intra-room air conditioner, intra-room heat pump and/or exchanger, liquid-cooled garment, room radiator, smart home environmental control system, space heater, thermally-controlled water bed, and window-mounted air conditioner.

In an example, a cooling and/or heating member can cool air in close proximity to a person's body when data from a wearable sensor indicates that that the person's body temperature is above a selected temperature level. In an example, a cooling and/or heating member can cool air in close proximity to the person's body when data from the wearable sensor indicates that that the person is having a hot flash. In an example, a cooling and/or heating member can circulate cool air between a bed cover (such as a blanket or upper sheet) and a sleeping surface (such as a lower sheet, mattress pad, or mattress) when data from a wearable sensor indicates that that the person's body temperature is above the selected temperature level.

In an example, a cooling and/or heating member can proactively cool air in close proximity to the person's body when statistical analysis of data from the wearable sensor predicts that the person's body temperature is likely to increase soon. In an example, a cooling and/or heating member can proactively cool air in close proximity to the person's body when statistical analysis of data from the wearable sensor predicts that the person is likely to have a hot flash soon. In an example, a cooling and/or heating member can circulate cool air between a bed cover (such as a blanket or upper sheet) and a sleeping surface (such as a lower sheet, mattress pad, or mattress) when statistical analysis of data from a wearable sensor predicts that that the person's body temperature is likely to increase soon.

In an example, a cooling and/or heating member can heat air in close proximity to the person's body when data from the wearable sensor indicates that that the person's body temperature is below a selected temperature level. In an example, a cooling and/or heating member can circulate warm air between a bed cover (such as a blanket or upper sheet) and a sleeping surface (such as a lower sheet, mattress pad, or mattress) when data from a wearable sensor indicates that that the person's body temperature is below the selected temperature level.

In an example, a cooling and/or heating member can proactively heat air in close proximity to a person's body when statistical analysis of data from a wearable sensor predicts that the person's body temperature is likely to decrease soon. In an example, a cooling and/or heating member can proactively heat air in close proximity to the person's body when statistical analysis of data from the wearable sensor predicts that the person is likely to have a chill soon. In an example, a cooling and/or heating member can circulate warm air between a bed cover (such as a blanket or upper sheet) and a sleeping surface (such as a lower sheet, mattress pad, or mattress) when statistical analysis of data from a wearable sensor predicts that that the person's body temperature is likely to decrease soon.

In an example, data from one or more wearable sensors can be analyzed using multivariate statistical methods in order to detect and/or predict a change in a person's body temperature. In an example, data from one or more wearable sensors can be analyzed using multivariate statistical methods in order to detect and/or predict a hot flash. In an example, a first set of parameters concerning the cooling and/or heating of air in close proximity to a sleeping person can be controlled based on a second set of parameters concerning statistical analysis of data from one or more wearable sensors. In an example, the first set of parameters can be selected from the group consisting of: duration of cooling and/or heating; thermal transfer rate in cooling and/or heating; flow rate for the flow of air or liquid; target temperature for air or liquid; and target temperature for skin and/or body temperature. In an example, the second set of parameters can be selected from the group consisting of: value of a metric measured by a wearable sensor at a given point in time; change in value in a metric measured by a wearable sensor during a span of time; rate of increase in a metric measured by a wearable sensor during a span of time; pattern of increase in a metric measured by a wearable sensor during a span of time; interaction between two metrics measured by two different types of wearable sensors; interaction between a metric measured by a wearable sensor and other characteristics of the sleeping person; and interaction between a metric measured by a wearable sensor and local environmental characteristics.

In an example, this invention can be embodied in a system and/or method for controlling the temperature of air near a sleeping person based on a metric measured by a sensor worn by that person. In an example, this metric can be selected from the group consisting of: skin temperature, core body temperature, skin conductance, skin impedance, and strength of brainwaves in a selected frequency range.

In an example, a cooling and/or heating member can be triggered to start cooling and/or heating air near a sleeping person when a metric measured by a sensor worn by that person has a value which is less than a selected minimum value or is greater than a selected maximum value. In an example, a cooling and/or heating member can be triggered to start cooling and/or heating air near a sleeping person when a multivariate function of metrics measured by two or more wearable sensors has a value which is less than a selected minimum value or is greater than a selected maximum value.

In an example, a cooling and/or heating member can be triggered to start cooling and/or heating air near a sleeping person when a metric measured by a sensor worn by that person changes by more than a minimum change value during a selected amount of time. In an example, a cooling and/or heating member can be triggered to start cooling and/or heating air near a sleeping person when a multivariate function of metrics measured by two or more wearable sensors changes by more than a minimum change value during a selected amount of time.

In an example, a cooling and/or heating member can be triggered to start cooling and/or heating air near a sleeping person when the rate of change of a metric measured by a sensor worn by that person has a value which is greater than a selected maximum rate. In an example, a cooling and/or heating member can be triggered to start cooling and/or heating air near a sleeping person when the rate of change of a multivariate function of metrics measured by two or more wearable sensors has a value which is greater than a selected maximum rate.

In an example, a cooling and/or heating member can be triggered to start cooling and/or heating air near a sleeping person when a metric measured by a sensor worn by that person varies in a pre-identified pattern during a selected amount of time. In an example, a cooling and/or heating member can be triggered to start cooling and/or heating air near a sleeping person when a multivariate function of metrics measured by two or more wearable sensors varies in a pre-identified pattern during a selected amount of time.

In an example, a cooling and/or heating member can be triggered to start cooling and/or heating air near a sleeping person when a metric measured by a sensor worn by that person varies in a pre-identified wave pattern during a selected amount of time. In an example, a cooling and/or heating member can be triggered to start cooling and/or heating air near a sleeping person when a multivariate function of metrics measured by two or more wearable sensors varies in a pre-identified wave pattern during a selected amount of time.

In an example, a cooling and/or heating member can be triggered to stop cooling and/or heating air near a sleeping person when a metric measured by a sensor worn by that person has a value which is greater than a selected minimum value or is less than a selected maximum value. In an example, a cooling and/or heating member can be triggered to stop cooling and/or heating air near a sleeping person when a multivariate function of metrics measured by two or more wearable sensors has a value which is greater than a selected minimum value or is less than a selected maximum value.

In an example, a cooling and/or heating member can be triggered to stop cooling and/or heating air near a sleeping person when the rate of change of a metric measured by a sensor worn by that person has a value which is less than a selected maximum rate. In an example, a cooling and/or heating member can be Ztriggered to stop cooling and/or heating air near a sleeping person when the rate of change of a multivariate function of metrics measured by two or more wearable sensors has a value which is less than a selected maximum rate.

In an example, a cooling and/or heating member can be triggered to stop cooling and/or heating air near a sleeping person when a metric measured by a sensor worn by that person varies in a pre-identified pattern during a selected amount of time. In an example, a cooling and/or heating member can be triggered to stop cooling and/or heating air near a sleeping person when a multivariate function of metrics measured by two or more wearable sensors varies in a pre-identified pattern during a selected amount of time.

In an example, a cooling and/or heating member can be triggered to stop cooling and/or heating air near a sleeping person after a selected amount of time. In an example, this amount of time can depend on the values of one or more metrics measured by sensors worn by the person. In an example, this amount of time can depend on the amounts by which one or more metrics were lower than a selected minimum value or greater than a selected maximum value when a cooling and/or heating member was triggered to start cooling and/or heating.

In an example, data from one or more wearable sensors can be analyzed using one or more statistical methods selected from the group consisting of: multivariate linear regression; least squares estimation; factor analysis; Fourier Transformation; mean; median; multivariate logit; principal components analysis; spline function; auto-regression; centroid analysis; correlation; covariance; decision tree analysis; Kalman filter; linear discriminant analysis; linear transform; logarithmic function; logit analysis; Markov model; multivariate parametric classifiers; non-linear programming; orthogonal transformation; pattern recognition; random forest analysis; spectroscopic analysis; variance; artificial neural network; Bayesian filter or other Bayesian statistical method; chi-squared; eigenvalue decomposition; logit model; machine learning; power spectral density; power spectrum analysis; probit model; support vector machine; and time-series analysis. Relevant example and component variations discussed elsewhere in this disclosure or in priority-linked disclosures can also be applied to this example, but are not repeated here to avoid narrative redundancy.

Figure 84:
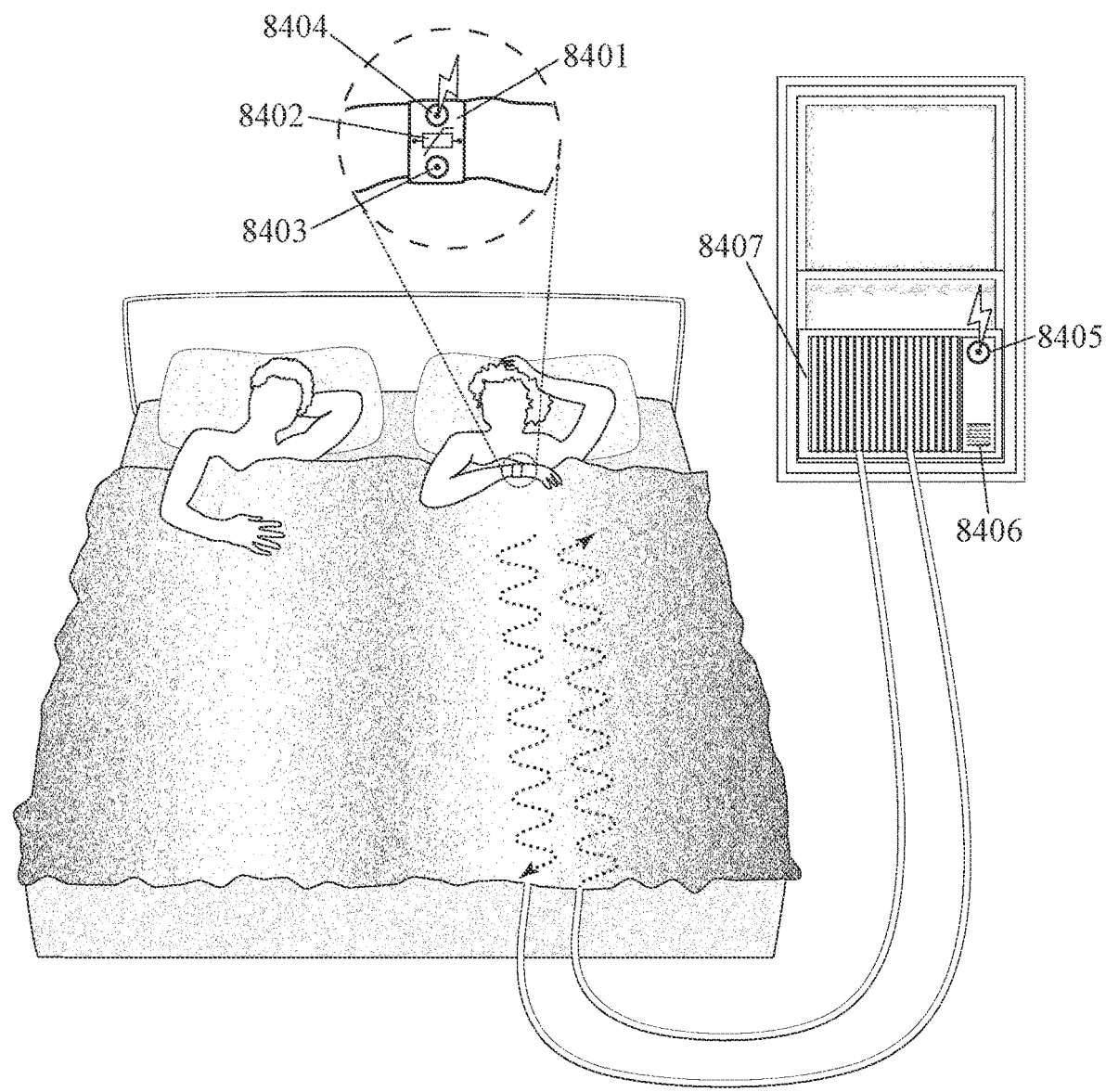
FIG. 84 shows a system which changes the temperature of air in proximity to a sleeping person based on data from a wearable thermal energy sensor, using a window-mounted air conditioner.

FIG. 84 shows another example of how this invention can be embodied in a system for changing the temperature of air in close proximity to the body of a sleeping person. This example is similar to the one shown in FIG. 83, except that the cooling and/or heating member is an exo-room cooling and/or heating member instead of an intra-room cooling and/or heating member. For example, instead of an intra-room cooling and/or heating member which transfers thermal energy between air proximal to the person and another location in the room, an exo-room cooling and/or heating member transfers thermal energy between air proximal to the person and a location outside the room. In this example, an exo-room cooling and/or heating member comprises a window-mounted air conditioner. As was the case in FIG. 83, a dashed-line circle in the upper central portion of FIG. 84 shows an enlarged view of a wearable attachment member which is worn on a person's wrist.

Specifically, FIG. 84 shows an example of how this invention can be embodied in a system for changing the temperature of air in close proximity to the body of a sleeping person comprising: (a) a wearable attachment member 8401 that is configured to be worn by a person while they sleep; (b) a wearable sensor 8402 which is part of, or attached to, the wearable attachment member, wherein this wearable sensor collects data concerning the person's current body temperature and/or data used to predict the person's future body temperature; (c) a power source 8403 which is part of, or attached to, the wearable attachment member; (d) a wireless data transmitter 8404 which is part of, or attached to, the attachment member; (e) a wireless data receiver 8405, wherein data from the wearable sensor is transmitted from the wireless data transmitter to the wireless data receiver; (f) a data processing unit 8406 which processes data from the wearable sensor; and (g) a cooling and/or heating member 8407 whose operation changes the temperature of air in close proximity to the sleeping person in response to data concerning the person's current body temperature and/or data used to predict the person's future body temperature. The various examples of a wearable attachment member, a wearable sensor, a power source, and multivariate statistical analysis of sensor data which were discussed concerning the example shown in FIG. 83 can also apply to the example shown here in FIG. 84.

In the example shown in FIG. 84, cooling and/or heating member 8407 is an exo-room cooling and/or heating member. An exo-room cooling and/or heating member includes a component which is in thermal communication with a location outside the room in which a person is sleeping. This can be particularly advantageous for cooling air near the sleeping person because thermal energy from air near the person can be transferred outside the room instead of within the room. This makes it easier to keep the air around the person cool because it does not heat the surrounding air in the room. In the example shown here in FIG. 84, an exo-room cooling and/or heating member comprises a window-mounted air conditioner. Alternatively, as will be shown in a subsequent figure, an exo-room cooling and/or heating member can be a building-wide cooling and/or heating member. In an example, a building-wide cooling and/or heating member can be a central HVAC (heating, ventilation, and air conditioning) system.

In an example, an exo-room cooling and/or heating member can be a heat pump, heat exchanger, and/or air conditioner which is in thermal communication with a location outside a room in which a person is sleeping. In an example, an exo-room cooling and/or heating member can comprise one or more components selected from the group consisting of: compressor; heat exchanger or heat pump; air fan, blower, turbine, or impellor; air circulation pathway; liquid fan, blower, turbine, or impellor; liquid circulation pathway; wireless data receiver; wireless data transmitter; and data processor.

In an example, an exo-room cooling and/or heating member can cool air that is in close proximity to a person's body when an increase in body temperature is detected and/or predicted based on analysis of data from a wearable sensor worn by the person. In an example, an exo-room cooling and/or heating member can cool air close to a sleeping person by transferring thermal energy between that air and a location outside the room in which the person is sleeping. In an example, an exo-room cooling and/or heating member can cool air in proximity to a sleeping person by: (a) extracting thermal energy from air within (or outside) a room using a compressor, heat pump, and/or heat exchanger, thereby cooling that air; (b) transferring the extracted thermal energy to a location outside the room; and then (c) sending (and/or circulating) the cooled air in proximity to the person. In an example, an exo-room cooling and/or heating member can cool air in proximity to a sleeping person by: (a) extracting thermal energy from a liquid using a compressor, heat pump, and/or heat exchanger, thereby cooling that liquid; (b) transferring the extracted thermal energy to a location outside the room; and then (c) sending (and/or circulating) the cooled liquid in proximity to the person.

In an example, an exo-room cooling and/or heating member can send (or circulate) cooled air between a bed covering (such as an upper sheet or blanket) which is over a sleeping person and a sleeping surface (such as a lower sheet, mattress pad, or mattress) which is below the sleeping person. In a two-person bed, the system can be configured to selectively send (or circulate) cooled air only on the side of the bed where the person wearing the device is sleeping. In an example, the system can automatically detect which on side of the bed this person is sleeping and selectively cool that side of the bed. In an example, selective cooling of only one side a bed can be accomplished by selecting sending air through a subset of air pathways, channels, or vents.

In an example, an exo-room cooling and/or heating member can send (or circulate) cooled liquid through channels in a bed covering (such as an upper sheet or blanket) which is over a sleeping person or through channels in a sleeping surface (such as a lower sheet, mattress pad, or mattress) which is below the sleeping person. In a two-person bed, the system can be configured to selectively send (or circulate) cooled liquid only on the side of the bed where the person wearing the device is sleeping. In an example, the system can automatically detect which on side of the bed this person is sleeping and selectively cool that side of the bed. In an example, selective cooling of only one side a bed can be accomplished by selecting sending liquid through a subset of liquid channels.

In an example, an exo-room cooling and/or heating member can heat air that is in close proximity to a person's body when a decrease in body temperature is detected and/or predicted based on analysis of data from a wearable sensor worn by the person. In an example, an exo-room cooling and/or heating member can heat air close to a sleeping person by transferring thermal energy between that air and a location outside the room in which the person is sleeping. In an example, an exo-room cooling and/or heating member can heat air in proximity to a sleeping person by: (a) extracting thermal energy from a location outside the room using a compressor, heat pump, and/or heat exchanger; (b) transferring the extracted thermal energy to air; and then (c) sending (and/or circulating) the heated air in proximity to the person. In an example, an exo-room cooling and/or heating member can heat air in proximity to a sleeping person by: (a) extracting thermal energy from a location outside the room using a compressor, heat pump, and/or heat exchanger; (b) transferring the extracted thermal energy to a liquid; and then (c) sending (and/or circulating) the heated liquid in proximity to the person.

In an example, an exo-room cooling and/or heating member can send (or circulate) heated air between a bed covering (such as an upper sheet or blanket) which is over a sleeping person and a sleeping surface (such as a lower sheet, mattress pad, or mattress) which is below the sleeping person. In a two-person bed, the system can be configured to selectively send (or circulate) heated air only on the side of the bed where the person wearing the device is sleeping. In an example, the system can automatically detect which on side of the bed this person is sleeping and selectively heat that side of the bed. In an example, selective heating of only one side a bed can be accomplished by selecting sending air through a subset of air pathways, channels, or vents.

In an example, an exo-room cooling and/or heating member can send (or circulate) heated liquid through channels in a bed covering (such as an upper sheet or blanket) which is over a sleeping person or through channels in a sleeping surface (such as a lower sheet, mattress pad, or mattress) which is below the sleeping person. In a two-person bed, the system can be configured to selectively send (or circulate) heated liquid only on the side of the bed where the person wearing the device is sleeping. In an example, the system can automatically detect which on side of the bed this person is sleeping and selectively heat that side of the bed. In an example, selective heating of only one side a bed can be accomplished by selecting sending liquid through a subset of liquid channels.

In various general examples which can also include a building-wide (e.g. central HVAC) system, a cooling and/or heating member can be selected from the group consisting of: air-cooled garment, central air conditioning unit, central boiler, central furnace, central heating unit, central HVAC system, combustion-based room heater, electric baseboard heater, electric blanket, electric mattress, electric room heater, gas fireplace, heat exchanger, heat pump, heated and/or cooled blanket, heated and/or cooled mattress, heated and/or cooled water bed, heated garment, heating pad, exo-room air conditioner, exo-room heat pump and/or exchanger, liquid-cooled garment, room radiator, smart home environmental control system, space heater, thermally-controlled water bed, and window-mounted air conditioner. Relevant example variations from other figures discussed herein can also be applied to the example which is shown in FIG. 84. Relevant example and component variations discussed elsewhere in this disclosure or in priority-linked disclosures can also be applied to this example, but are not repeated here to avoid narrative redundancy.

Figure 85:
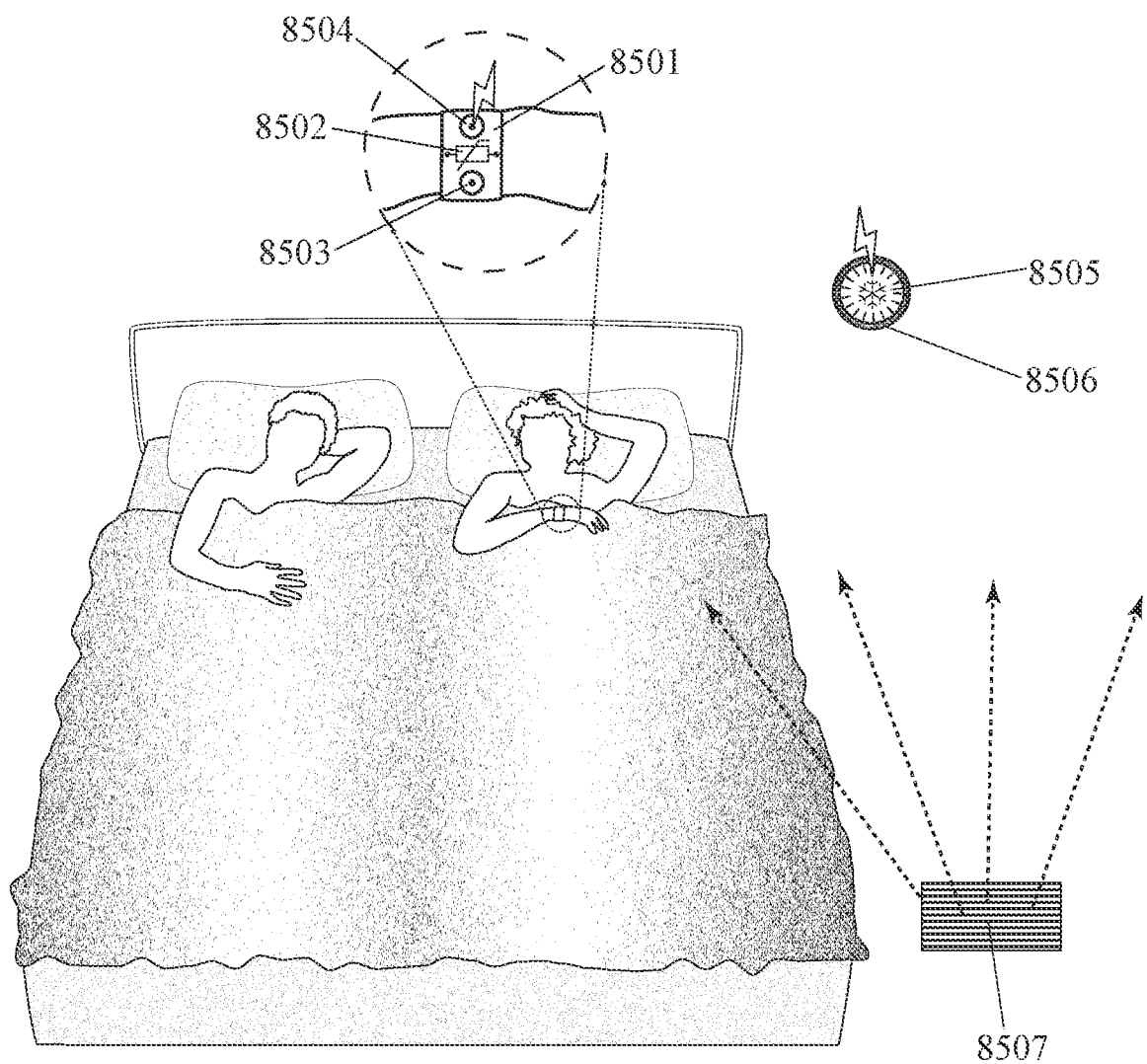
FIG. 85 shows a system which changes the temperature of air in proximity to a sleeping person based on data from a wearable thermal energy sensor, using a central HVAC system.

FIG. 85 shows another example of how this invention can be embodied in a system for changing the temperature of air in close proximity to the body of a sleeping person. This example is similar to the one shown in FIG. 84, except that the cooling and/or heating member is a building-wide system. In this example, the cooling and/or heating member comprises a central heating, ventilation, and air conditioning (HVAC) system. In this example, there is a room-specific environmental control unit which is part of the central HVAC system. The wearable device worn by the sleeping person is in electronic communication with this control unit. As was the case in FIG. 84, a dashed-line circle in the upper central portion of FIG. 85 shows an enlarged view of a wearable attachment member which is worn on a person's wrist.

Specifically, FIG. 85 shows an example of how this invention can be embodied in a system for changing the temperature of air in close proximity to the body of a sleeping person comprising: (a) a wearable attachment member 8501 that is configured to be worn by a person while they sleep; (b) a wearable sensor 8502 which is part of, or attached to, the wearable attachment member, wherein this wearable sensor collects data concerning the person's current body temperature and/or data used to predict the person's future body temperature; (c) a power source 8503 which is part of, or attached to, the wearable attachment member; (d) a wireless data transmitter 8504 which is part of, or attached to, the attachment member; (e) a wireless data receiver 8505, wherein data from the wearable sensor is transmitted from the wireless data transmitter to the wireless data receiver; (f) a data processing unit 8506 which processes data from the wearable sensor; and (g) a cooling and/or heating member 8507 whose operation changes the temperature of air in close proximity to the sleeping person in response to data concerning the person's current body temperature and/or data used to predict the person's future body temperature.

The various examples of a wearable attachment member, a wearable sensor, a power source, multivariate statistical analysis of sensor data, cooling and/or heating member components, and air and/or liquid circulation methods which were discussed concerning the examples shown in FIGS. 83 and 84 can also apply to the example shown here in FIG. 85. In an example, data from wearable sensor 8502 can be sent from wireless data transmitter 8504 to wireless data receiver 8505 which is part of a room-specific environmental control unit. In an example, when analysis of this data indicates that body temperature of the sleeping person is changing or predicts that the body temperature of the sleeping person will change soon, then the room-specific environmental control unit changes the operation of a central HVAC system to change the temperature of air circulated through the room. In an alternative example, a room-specific environmental control unit can trigger a central HVAC system to change the temperature of air or liquid circulated through an upper bed covering (such as a blanket or upper sheet), lower sleeping surface (such as a lower sheet, mattress pad, or mattress), or between an upper bed covering and lower sleeping surface. Relevant example variations from other figures discussed herein can also be applied to the example which is shown in FIG. 85. Relevant example and component variations discussed elsewhere in this disclosure or in priority-linked disclosures can also be applied to this example, but are not repeated here to avoid narrative redundancy.

Figure 86:
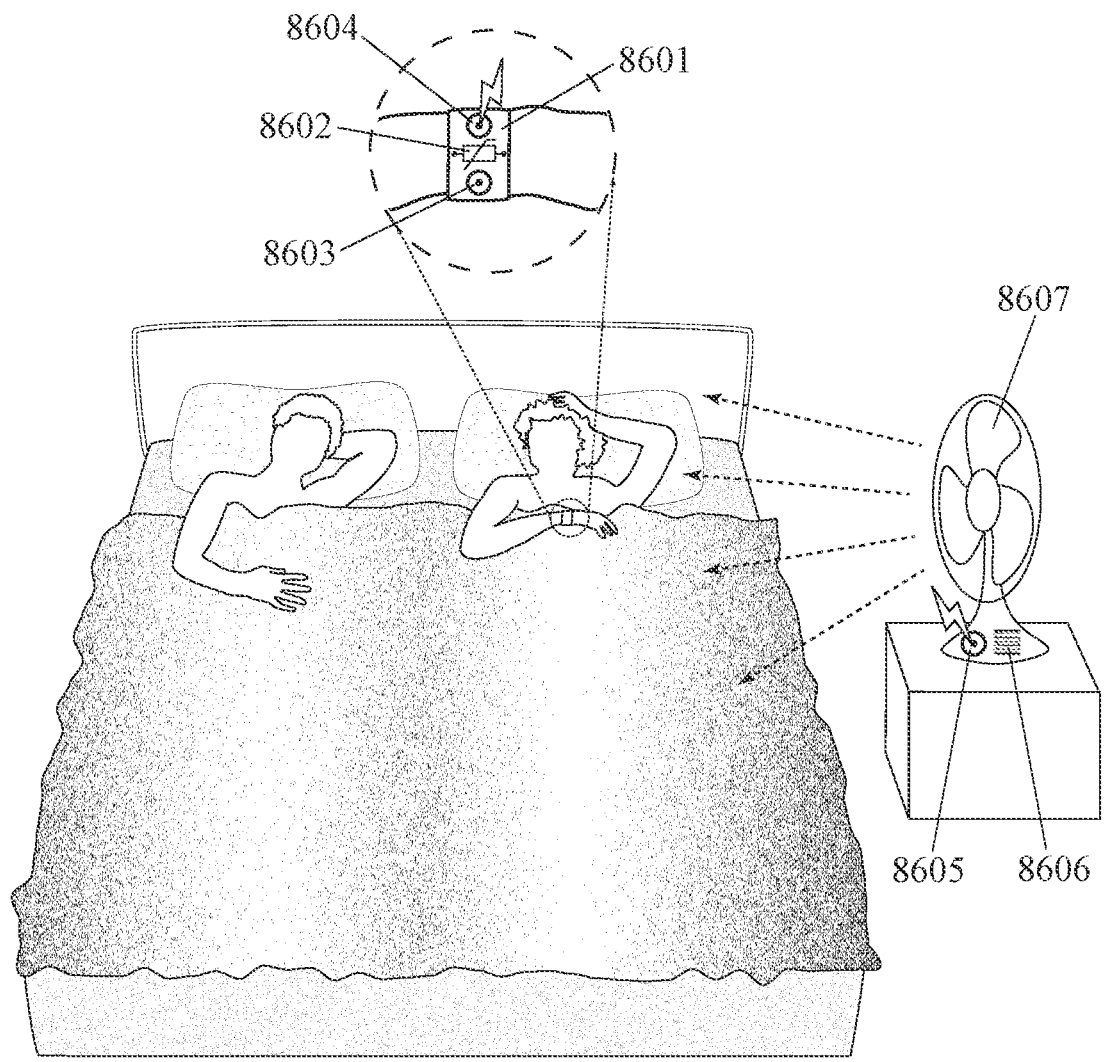
FIG. 86 shows a system which changes airflow in proximity to a sleeping person based on data from a wearable thermal energy sensor, using a fan.

FIG. 86 shows an example of how this invention can be embodied in a system for changing the flow of air in close proximity to the body of a sleeping person. This example is similar to the one shown in FIG. 83, except that it includes an airflow-accelerating member which changes the flow of air near a person instead of a cooling and/or heating member which changes the temperature of air near a person. In this example, an airflow-accelerating member is a portable fan. In an example, an airflow-accelerating member can be selected from the group consisting of: portable fan, window fan, floor fan, room fan, bed fan, ceiling fan, and central HVAC fan. In an example, an airflow-accelerating member can change one or more aspects of airflow selected from the group consisting of: airflow speed, airflow volume; airflow pathway; airflow direction; airflow pressure; airflow composition; and airflow source. As was the case in FIG. 83, a dashed-line circle in the upper central portion of FIG. 86 shows an enlarged view of a wearable attachment member which is worn on a person's wrist.

Specifically, FIG. 86 shows an example of how this invention can be embodied in a system for changing airflow near a sleeping person comprising: (a) a wearable attachment member 8601 that is configured to be worn by a person while they sleep; (b) a wearable sensor 8602 which is part of, or attached to, the wearable attachment member, wherein this wearable sensor collects data concerning the person's current body temperature and/or data used to predict the person's future body temperature; (c) a power source 8603 which is part of, or attached to, the wearable attachment member; (d) a wireless data transmitter 8604 which is part of, or attached to, the attachment member; (e) a wireless data receiver 8605, wherein data from the wearable sensor is transmitted from the wireless data transmitter to the wireless data receiver; (f) a data processing unit 8606 which processes data from the wearable sensor; and (g) an airflow-accelerating member 8607 whose operation changes airflow near the sleeping person in response to data concerning the person's current body temperature and/or data used to predict the person's future body temperature. The various examples of a wearable attachment member, a wearable sensor, a power source, and multivariate statistical analysis of sensor data which were discussed concerning the example shown in FIG. 83 can also apply to the example shown here in FIG. 86.

In this example, airflow-accelerating member 8607 is a portable fan which whose outbound airflow is directed toward the sleeping person. In an example, an airflow-accelerating member can be selected from the group consisting of: portable fan, window fan, floor fan, room fan, bed fan, packers fan, ceiling fan, and central HVAC fan. In an example, an airflow-accelerating member can change one or more aspects of airflow near sleeping person which are selected from the group consisting of: airflow speed, airflow volume; airflow pathway; airflow direction; airflow pressure; airflow composition; and airflow source. In an example, airflow near the sleeping person can be changed in response to data from a wearable sensor by simply turning the airflow-accelerating member on or off. In an example, airflow near the sleeping person can be changed in response to data from the wearable sensor by changing the rotational speed of an airflow-accelerating member. In an example, airflow near the sleeping person can be changed in response to data from the wearable sensor by changing the direction of outbound airflow from an airflow-accelerating member.

In another example, an airflow-accelerating member can direct (or circulate) air through a bed. In an example, an airflow-accelerating member can direct air through an upper bed covering (such as a blanket or upper sheet), through a lower sleeping surface (such as a lower sheet, mattress pad, or mattress), between an upper bed covering and a lower sleeping surface. In an example, the speed, volume, pathway, direction, pressure, and/or composition of airflow between an upper bed covering and a lower sleeping surface can be changed in response to data from the wearable sensor. In an example, the speed, volume, pathway, direction, pressure, composition, and/or source of airflow between an upper bed covering and a lower sleeping surface on a first side of a bed can be selectively changed relative to the speed, volume, pathway, direction, pressure, composition, and/or source of airflow between an upper bed covering and a lower sleeping surface on a second side of the bed. Relevant example variations from other figures discussed herein can also be applied to the example which is shown in FIG. 86. Relevant example and component variations discussed elsewhere in this disclosure or in priority-linked disclosures can also be applied to this example, but are not repeated here to avoid narrative redundancy.

Figure 87:
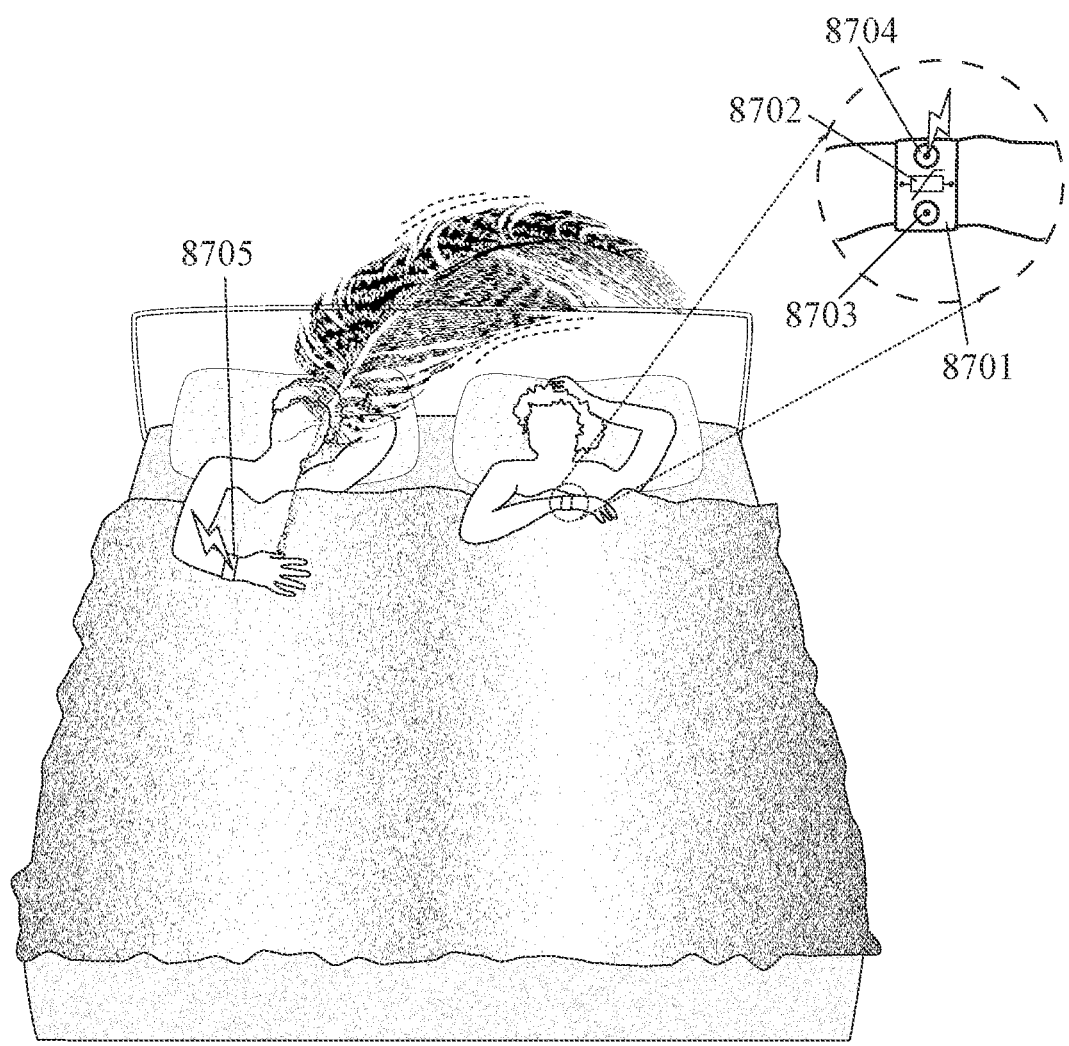
FIG. 87 shows a system which changes airflow in proximity to a sleeping person based on data from a wearable thermal energy sensor via an interactive spousal engagement mechanism.

FIG. 87 shows another example of how this invention can be embodied in a system for changing airflow near a sleeping person. This example is similar to the one shown in FIG. 86 except that it provides an opportunity to earn valuable husband points. Specifically, FIG. 87 shows an example of how this invention can be embodied in a system for changing airflow near a sleeping wife comprising: (a) a wearable attachment member 8701 that is configured to be worn by a sleeping wife; (b) a wearable sensor 8702 which is part of, or attached to, the wearable attachment member, wherein this wearable sensor collects data concerning the wife's body temperature; (c) a power source 8703 which is part of, or attached to, the wearable attachment member; (d) a wireless data transmitter 8704 which is part of, or attached to, the attachment member; (e) a wireless device 8705 that is worn by a husband; and (f) an airflow-accelerating member 8707, wherein this airflow-accelerating member is moved gently back and forth by the husband to create airflow when wireless device 8705 notifies the husband that his wife is having a hot flash. In an example, airflow-accelerating member 8707 can be an ostrich feather.

In an example, this invention can be embodied in a system for changing the temperature of air in close proximity to the body of a sleeping person comprising: a wearable attachment member that is configured to be worn by a person while they sleep; a wearable sensor which is part of, or attached to, the wearable attachment member, wherein this wearable sensor collects data concerning the person's current body temperature and/or data used to predict the person's future body temperature; a power source which is part of, or attached to, the wearable attachment member; a wireless data transmitter which is part of, or attached to, the attachment member; a wireless data receiver, wherein data from the wearable sensor is transmitted from the wireless data transmitter to the wireless data receiver; a data processing unit which processes data from the wearable sensor; and a cooling and/or heating member whose operation changes the temperature of air in close proximity to the sleeping person in response to data concerning the person's current body temperature and/or data used to predict the person's future body temperature.

In an example, the wearable attachment member can be selected from the group consisting of: adhesive patch, amulet, ankle band, ankle bracelet, ankle strap, arm band, artificial finger nail, bandage, belt, bra, bracelet, cap, cardiac monitor, CPAP or other respiratory mask, ear bud, ear muffs, ear plug, ear ring, ECG monitor, EEG monitor, EMG monitor, electronically-functional tattoo, EOG monitor, eye mask, eye patch, eyewear, finger ring, finger sleeve, fitness band, forearm band, forearm sleeve, glove, hair band, hat, headband, headphones, heart monitor, lower body garment, necklace, pajamas, pants, shirt, sleep band, smart belt, smart watch, sock, sternal conductance monitor, sternal patch, torso band, underpants, undershirt, wrist band, and wrist sleeve. In an example, the wearable sensor can be a temperature sensor and/or a thermal energy sensor. In an example, the wearable sensor can be a tissue conductance sensor and/or a tissue conductivity sensor. In an example, the wearable sensor can be an EEG sensor and/or an electromagnetic brain activity sensor.

In an example, the wearable sensor can be selected from the group consisting of: action potential sensor, biochemical sensor, blood flow sensor, blood pressure sensor, motion sensor, brain blood flow sensor, camera, capacitance hygrometry sensor, chemiluminescence sensor, chromatography sensor, conductivity sensor, electrocardiographic (ECG) sensor, electroencephalographic (EEG) sensor, electrogastrographic (EOG) monitor, electromagnetic brain activity sensor, electromagnetic resistance sensor, electromyographic (EMG) sensor, electrooculographic (EOG) sensor, epinephrine sensor, estradiol sensor, eye movement sensor, fluorescence sensor, follicle-stimulating hormone (FSH) sensor, galvanic skin response (GSR) sensor, gas chromatography sensor, Hall-effect sensor, heart rate sensor, humidity sensor, immunoreactive neurotensin sensor, impedance sensor, inertial motion sensor, infrared light sensor, infrared spectroscopy sensor, ion mobility spectroscopic sensor, laser sensor, light intensity sensor, light-spectrum-analyzing sensor, luteinizing hormone (LH) sensor, magnetic field sensor, magnetometer, mass spectrometry sensor, mean arterial blood pressure sensor, middle cerebral artery blood velocity sensor, muscle function monitor, near-infrared spectroscopy sensor, neural impulse monitor, neurosensor, norepinephrine sensor, optical sensor, optoelectronic sensor, photoelectric sensor, photoplethysmographic sensor, piezocapacitive sensor, piezoelectric sensor, piezoresistive sensor, plethysmographic sensor, pressure sensor, pulse sensor, Raman spectroscopy sensor, REM sensor, respiratory function sensor, RF sensor, skin conductance or conductivity sensor, spectral analysis sensor, spectrometry sensor, spectrophotometer sensor, spectroscopic sensor, sternal skin conductance (SSC) sensor, sweat sensor, sympathetic nerve activity sensor, systolic blood pressure sensor, thermal energy sensor, tissue impedance sensor, ultraviolet light sensor, ultraviolet spectroscopy sensor, variable impedance sensor, variable resistance sensor, variable-translucence sensor, and voltmeter.

In an example, the values of a first set of parameters concerning cooling and/or heating air in close proximity to a sleeping person can be changed in response to the values of a second set of parameters concerning data from one or more wearable sensors. In an example, the values of a first set of parameters concerning cooling and/or heating air in close proximity to a sleeping person can be controlled by the values of a second set of parameters concerning data from one or more wearable sensors. In an example, the first set of parameters can be selected from the group consisting of: duration of cooling and/or heating; thermal transfer rate in cooling and/or heating; flow rate for the flow of air or liquid; target temperature for air or liquid; and target temperature for skin and/or body temperature. In an example, the second set of parameters can be selected from the group consisting of: value of a metric measured by a wearable sensor at a given point in time; change in value in a metric measured by a wearable sensor during a span of time; rate of increase in a metric measured by a wearable sensor during a span of time; pattern of increase in a metric measured by a wearable sensor during a span of time; interaction between two metrics measured by two different types of wearable sensors; interaction between a metric measured by a wearable sensor and other characteristics of the sleeping person; and interaction between a metric measured by a wearable sensor and local environmental characteristics.

In an example, the cooling and/or heating member can cool air in proximity to a sleeping person by: (a) extracting thermal energy from a portion of air in a room where the person is sleeping, using a compressor, heat pump, and/or heat exchanger, thereby cooling that portion of air (b) transferring the extracted thermal energy to a distal location in the room in which the person is sleeping, and (c) sending and/or circulating the cooled air in proximity to the person. In an example, the cooling and/or heating member can cool air in proximity to a sleeping person by: (a) extracting thermal energy from a liquid using a compressor, heat pump, and/or heat exchanger, thereby cooling that liquid (b) transferring the extracted thermal energy to a location in a room that is distal to the person, and (c) sending and/or circulating the cooled liquid in proximity to the person. In an example, the cooling and/or heating member can send and/or circulate air or liquid through channels which are in thermal communication with ice within an ice reservoir.

In an example, the cooling and/or heating member can cool air in proximity to a sleeping person by: (a) extracting thermal energy from air using a compressor, heat pump, and/or heat exchanger, thereby cooling that air; (b) transferring the extracted thermal energy to a location outside the room in which the person is sleeping; and then (c) sending and/or circulating the cooled air in proximity to the person.

In an example, the cooling and/or heating member can cool air in proximity to a sleeping person by: (a) extracting thermal energy from a liquid using a compressor, heat pump, and/or heat exchanger, thereby cooling that liquid; (b) transferring the extracted thermal energy to a location outside the room in which the person is sleeping; and then (c) sending and/or circulating the cooled liquid in proximity to the person.

In an example, the cooling and/or heating member can send and/or circulate cooled air between a bed covering which is over the sleeping person and a sleeping surface which is below the sleeping person. In an example, the cooling and/or heating member can send and/or circulate cooled liquid through channels in a bed covering which is over the sleeping person and/or through channels in a sleeping surface which is below the sleeping person. In an example, the cooling and/or heating member can selectively send and/or circulate cooled air on either a first side of a two-person bed or a second side of the two-person bed. In an example, the cooling and/or heating member can selectively send and/or circulate cooled liquid on a either a first side of a two-person bed or a second side of the two-person bed.

In an example, this invention can be embodied in a system for changing airflow near a sleeping person comprising: a wearable attachment member that is configured to be worn by a person while they sleep; a wearable sensor which is part of, or attached to, the wearable attachment member, wherein this wearable sensor collects data concerning the person's current body temperature and/or data used to predict the person's future body temperature; a power source which is part of, or attached to, the wearable attachment member; a wireless data transmitter which is part of, or attached to, the attachment member; a wireless data receiver, wherein data from the wearable sensor is transmitted from the wireless data transmitter to the wireless data receiver; a data processing unit which processes data from the wearable sensor; and an airflow-accelerating member whose operation changes airflow near the sleeping person in response to data concerning the person's current body temperature and/or data used to predict the person's future body temperature. In an example, the airflow-accelerating member can change one or more aspects of airflow near the sleeping person which are selected from the group consisting of: airflow speed, airflow volume; airflow pathway; airflow direction; airflow pressure; airflow composition; and airflow source. Relevant example and component variations discussed elsewhere in this disclosure or in priority-linked disclosures can also be applied to this example, but are not repeated here to avoid narrative redundancy.

This invention is a system which automatically changes the firmness and/or configuration of a portion of a mattress on which a person sleeps based on changes in the person's body motion, body configuration, and/or snoring. The person's body motion or body configuration can be measured by a wearable motion sensor. The firmness and/or configuration of the portion of the mattress can be changed by inflation or deflation of the mattress or by electromagnetic adjustment of the compressive resistance of mattress springs.

In an example, a system can automatically change the firmness and/or configuration of (a portion of) a mattress on which a person sleeps in order to improve the person's sleep and/or the sleep of the person's bed partner. In an example, a system can automatically change the firmness and/or configuration of a mattress based on changes in the person's body motion or body configuration. In an example, the person's body motion or body configuration can be measured by a motion sensor which the person wears. In an example, the firmness and/or configuration of (a portion of) a mattress on which a person sleeps can be changed when a motion sensor detects that the person is restless.

In an example, the firmness and/or configuration of (a portion of) a mattress on which a person sleeps can be automatically changed by inflation or deflation of (portions of) the mattress by an air pump. In an example, the firmness and/or configuration of (a portion of) a mattress on which a person sleeps can be changed by automatic adjustment of the compressive resistance of springs in (portions of) the mattress by an electromagnetic actuator. In an example, the longitudinal slope or the lateral slope of a mattress can be automatically changed in response to changes in a person's body motion or body configuration. In an example, this system can automatically change the firmness and/or configuration of (a portion of) a mattress on which a person sleeps when the person snores in order to reduce their snoring and improve the sleep of the person's bed partner.

In an example, a system for modifying a person's sleep environment can comprise: a wearable motion sensor that is configured to be worn by a sleeping person in order to measure the person's body motion or body configuration; and a mattress on which the person sleeps, wherein the firmness of the mattress is automatically changed based on the person's body motion or body configuration. In an example, the firmness of the mattress is automatically increased when the person is restless based on data from the wearable motion sensor. In an example, the firmness of the mattress is automatically increased by inflation of the mattress when the person is restless based on data from the wearable motion sensor. In an example, the firmness of the mattress is automatically increased by an increase in the compressive resistance of springs in the mattress when the person is restless based on data from the wearable motion sensor.

In an example, the firmness of a mattress is automatically decreased when the person is restless based on data from the wearable motion sensor. In an example, the firmness of a mattress is automatically decreased by deflation of the mattress when the person is restless based on data from the wearable motion sensor. In an example, the firmness of a mattress is automatically decreased by a decrease in the compressive resistance of springs in the mattress when the person is restless based on data from the wearable motion sensor.

In an example, a system for modifying a person's sleep environment can comprise: a wearable motion sensor that is configured to be worn by a sleeping person in order to measure the person's body motion or body configuration; and a mattress on which the person sleeps, wherein the shape, motion, slope, tilt, or configuration of the mattress is automatically changed based on the person's body motion or body configuration. In an example, the longitudinal slope or other longitudinal configuration of the mattress is automatically changed based on the person's body motion or body configuration. In an example, the lateral slope or other lateral configuration of the mattress is automatically changed based on the person's body motion or body configuration.

In an example, a system for modifying a person's sleep environment can comprise: a snoring sensor which is configured to be in proximity to a sleeping person; and a mattress on which the person sleeps, wherein the configuration of the mattress is automatically changed when data from the snoring sensor indicates that the person is snoring.

In an example, the firmness of the mattress is automatically increased when data from the snoring sensor indicates that the person is snoring. In an example, the firmness of the mattress is automatically increased by inflation of the mattress when data from the snoring sensor indicates that the person is snoring. In an example, the firmness of the mattress is automatically increased by an increase in the compressive resistance of springs in the mattress when data from the snoring sensor indicates that the person is snoring.

In an example, the firmness of a mattress is automatically decreased when data from the snoring sensor indicates that the person is snoring. In an example, the firmness of a mattress is automatically decreased by deflation of a mattress when data from the snoring sensor indicates that the person is snoring. In an example, the firmness of a mattress is automatically decreased by a decrease in the compressive resistance of springs in a mattress when data from the snoring sensor indicates that the person is snoring. In an example, the longitudinal slope or other longitudinal configuration of a mattress is automatically changed when data from the snoring sensor indicates that the person is snoring. In an example, the lateral slope or other lateral configuration of a mattress is automatically changed when data from the snoring sensor indicates that the person is snoring. In an example, a mattress is automatically vibrated or oscillated when data from the snoring sensor indicates that the person is snoring.

In an example, a system to improve the sleep of a person who has hot flashes can comprise: a biometric sensor to detect when a sleeping person is having a hot flash; and a cooling mechanism to temporarily cool the sleeping person during the hot flash. In an example, a system to improve the sleep of a person who has hot flashes can comprise: a biometric sensor to predict a sleeping person's hot flash; and a cooling mechanism to temporarily cool the sleeping person before and/or during the hot flash. In an example, a biometric sensor can be worn by the person in a wearable device or integrated into an article of clothing. In an example, the biometric sensor can be incorporated into a bed mattress, pad, frame, blanket, or pillow.

In an example, a biometric sensor can be part of a wrist band or arm band which is worn by a sleeping person. In an example, a biometric sensor can be part of a finger ring. In an example, a biometric sensor can be part of a necklace or collar. In an example, a biometric sensor can be incorporated into an adhesive skin patch. In an example, a biometric sensor can be part of a headband, a sleep mask, or a cap. In an example, a biometric sensor can be incorporated into a waist band or bra. In an example, a biometric sensor can be incorporated into a sock, nightgown, or other article of clothing.

In an example, a biometric sensor can be an electromagnetic energy sensor. In an example, a biometric sensor can measure the electromagnetic activity of an organ (such as a person's brain) or other body tissue. In another example, a biometric sensor can be an electromyographic (EMG) sensor. In an example, a biometric sensor can be an electroencephalographic (EEG) sensor which measures a person's brain activity. In an example, a biometric sensor can be a dry EEG sensor. In an example, a biometric sensor can be an EEG sensor which is part of a sleep mask, headband, cap, collar, ear buds, headphones, skin patch, eye mask, or article of clothing.

In an example, the ratio of the power of electromagnetic activity in (two) different EEG frequency bands or changes in this ratio can be analyzed in order to detect and/or predict hot flashes. In an example, the mean intra-band frequency within a selected EEG band or changes in this mean can be analyzed in order to detect and/or predict hot flashes. In an example, the locations of selected patterns of electromagnetic activity in different areas of a sleeping person's brain or changes in these locations can be analyzed in order to detect and/or predict hot flashes.

In an example, a biometric sensor can comprise electroconductive fibers which are sewn or woven into fabric. In an example, a biometric sensor can comprise electroconductive fibers which are sewn or woven into an article of clothing. In an example, a biometric sensor can comprise multiple electroconductive layers which are incorporated into an article of clothing. In an example, a biometric sensor can comprise two elastic electroconductive layers which are separated by an elastic nonconductive layer in order to form a capacitive sensor. In an example, a biometric sensor can be made with elastomeric material (such as polydimethylsiloxane) which is impregnated or doped with electroconductive particles (such as carbon, copper, silver, or gold particles). In an example, a biometric sensor can comprise electroconductive ink which is printed onto fabric and/or clothing.

In an example, a biometric sensor can be a wearable impedance sensor which is worn by a sleeping person to detect and/or predict when they will have a hot flash. In an example, a biometric sensor can be a wearable capacitance sensor to detect and/or predict a hot flash. In an example, a biometric sensor can comprise a wearable conductivity sensor to detect and/or predict hot a flash. In an example, a biometric sensor can comprise a wearable resistance sensor to detect and/or predict a hot flash. In an example, a biometric sensor can comprise a wearable permittivity sensor to detect and/or predict a hot flash. In an example, a biometric sensor can measure changes in skin or other body tissue permittivity to detect and/or predict hot flashes. In an example, a biometric sensor can measure electromagnetic energy emitted from nerves or muscles.

In an example, a biometric sensor can collect data concerning changes in skin or other body tissue impedance or capacitance in order to detect and/or predict hot flashes. In an example, a biometric sensor can measure changes in skin or other body tissue conductivity or resistance to detect and/or predict hot flashes. In an example, a biometric sensor can be a sternal skin conductance sensor which is used to detect and/or predict hot flashes. In an example, a biometric sensor can be an ECG sensor. In an example, a hot flash can be predicted by a combination of a rapid increase in sternal skin conductance and an increase in heart rate.

In an example, an electromagnetic energy sensor can be part of a device which is worn by a sleeping person and collects data which is analyzed to predict when the person will have a hot flash. In an example, an electromagnetic energy sensor can be part of a finger ring. In an example, an electromagnetic energy sensor can be part of a collar or necklace. In an example, an electromagnetic energy sensor can be incorporated into an adhesive skin patch or smart tattoo. In an example, an electromagnetic energy sensor can be part of a headband, sleep mask, or cap. In an example, an electromagnetic energy sensor can be incorporated into a waistband. In an example, an electromagnetic energy sensor can be part of a sock, nightgown, bra, or other article of clothing. In an example, an electromagnetic energy sensor can be part of a cap, a collar, a finger ring, a headband, a sleep mask, a sock, a wristband, an armband, an article of clothing, an eye mask, or pajamas. In an example, an electromagnetic energy sensor can be part of a wrist band or arm band.

In an example, a biometric sensor can be a spectroscopic sensor which is worn by a sleeping person. In an example, a spectroscopic sensor can direct beams of infrared light or near-infrared light toward a person's body, wherein these beams of light are reflected from a person's body tissue and changes in the spectra of these beams caused by interaction with the person's body are analyzed in order to detect and/or predict a hot flash. In an example, beams of infrared or near infrared light can be transmitted through a person's body tissue in order to detect and/or predict a hot flash.

In an example, one or more spectroscopic sensors can be part of a wrist band or arm band. In an example, a circumferential array of spectroscopic sensors can be distributed around the circumference of a wrist band or arm band in order to collect data which is used to detect and/or predict a hot flash. In an example, a spectroscopic sensor can be part of a finger ring. In an example, a spectroscopic sensor can be incorporated into a collar or necklace. In an example, a spectroscopic sensor can be incorporated into an adhesive skin patch or smart tattoo. In an example, a spectroscopic sensor can be part of a headband, sleep mask, or cap. In an example, a spectroscopic sensor can be incorporated into a waistband. In an example, a spectroscopic sensor can be incorporated into a sock, nightgown, bra, or other article of clothing.

In an example, a biometric sensor can be a blood oxygenation sensor. In an example, changes in a person's oxygenation levels can be used to detect and/or predict a hot flash. In an example, an oxygenation sensor can be worn on a sleeping person's finger, wrist, or ear. In an example, a biometric sensor can comprise a hydration sensor. In an example, changes in a person's hydration levels can be used to detect and/or predict a hot flash. In an example, a hydration sensor can be worn on a sleeping person's finger, wrist, or ear. In an example, changes in a person's follicle stimulating hormone and/or serotonin levels can be used to detect and/or predict a hot flash.

In an example, a biometric sensor can be a thermometer, thermistor, or other thermal energy sensor. In an example, a thermal energy sensor can be worn by a sleeping person. In an example, a thermal energy sensor can be part of a wrist band or arm band. In an example, a thermal energy sensor can be incorporated into a finger ring. In an example, a thermal energy sensor can be part of a collar or necklace. In an example, a thermal energy sensor can be incorporated into an adhesive skin patch or smart tattoo. In an example, a thermal energy sensor can be part of a headband, sleep mask, or cap. In an example, a thermal energy sensor can be incorporated into a waistband. In an example, a thermal energy sensor can be incorporated into a sock, nightgown, bra, or other article of clothing.

In an example, multiple thermal energy sensors can be worn at different locations on a sleeping person in order to measure patterns of thermal energy and changes in those patterns. In an example, static or dynamic changes in temperature at different locations on a person's body can predict a hot flash. In an example, a central-to-peripheral radiating pattern of increases in body temperature can predict a hot flash. In an example, a head-to-foot wave of increases in body temperature can predict a hot flash. In an example, one or more thermal energy sensors worn on a person's torso, combined with one or more thermal energy sensors worn on a person's wrists, hands, legs, or feet, can better measure changing patterns of body temperature which can predict a hot flash better than a thermal energy sensor on a single body location.

In an example, a biometric sensor can comprise an infrared camera (or sensor) which records the thermal patterns a sleeping person's body. In an example, data from an infrared camera (or sensor) can collect data concerning the overall temperature of a sleeping person's body, changes in that temperature over time, the relative temperatures of different areas of the sleeping person's body, and/or changes in those relative temperatures over time. In an example, temperature variation among different body members or changes in that variation can predict the onset of a hot flash. In an example, thermal energy patterns in a person's body which are measured by an infrared camera (or sensor) can be analyzed to predict when the person will have a hot flash. In an example, an infrared camera (or sensor) can be incorporated into, or attached to, the headboard or frame of a bed. In an example, an infrared camera (or sensor) can be incorporated into a bed mattress or mattress pad to record patterns of body thermal energy which are used to predict hot flashes.

In an example, a system to improve the sleep of a person who has hot flashes can comprise: a biometric sensor array to predict and/or detect a sleeping person's hot flash; and a cooling mechanism to temporarily cool the sleeping person during the hot flash. In an example, a biometric sensor array for detecting and/or predicting a hot flash can comprise a grid or matrix of individual biometric sensors. In an example, a biometric sensor array can comprise a grid or matrix of perpendicular rows and columns of individual sensors. In an example, a biometric sensor array can comprise a nested and/or concentric array of individual sensors. In an example, a biometric sensor array can be incorporated into a mattress pad or article of sleepwear.

In an example, a biometric sensor array can comprise a grid or matrix of electromagnetic energy sensors. In an example, a biometric sensor array can comprise a grid, or matrix of perpendicular rows and columns of electromagnetic energy sensors. In an example, a biometric sensor array can comprise a nested and/or concentric array of electromagnetic energy sensors. In an example, a biometric sensor array can comprise a grid or matrix of spectroscopic sensors. In an example, a biometric sensor array can comprise a grid or matrix of perpendicular rows and columns of spectroscopic sensors. In an example, a biometric sensor array can comprise a nested and/or concentric array of spectroscopic sensors.

In an example, a cooling mechanism can comprise a pair of pajamas, a nightgown, or another article of sleepwear which temporarily cools a sleeping person's body. In an example, a pair of pajamas, a nightgown, or another article of sleepwear can temporarily cool selected portions of a sleeping person's body. In an example, fluid-filled channels (e.g. microfluidic channels) can be incorporated into an article of sleepwear. In an example, flows of cool fluid through these channels can cool a sleeping person. In an example, cool fluid can be pumped through fluidic channels in sleepwear in response to a detected and/or predicted hot flash. In an example, air-filled channels can be incorporated into an article of sleepwear. In an example, flows of cool air through these channels can cool a sleeping person. In an example, cool air can be pumped through these channels in sleepwear in response to a detected and/or predicted hot flash.

In an example, a cooling mechanism can be a bed mattress which temporarily cools a sleeping person's body. In an example, a cooling mechanism can be a bed mattress through which cool fluid is pumped to temporarily cool a sleeping person's body. In an example, a cooling mechanism can comprise a bed mattress with tubes or channels through which cool fluid flows in order to cool a sleeping person's body. In an example, a cooling mechanism can be a bed mattress through which cool air is pumped to temporarily cool a sleeping person's body. In an example, a cooling mechanism can comprise a bed mattress with tubes or channels through which cool air flows in order to cool a sleeping person's body.

In an example, a cooling mechanism can comprise a bed mattress with a perpendicular grid or matrix of air channels through which cool air flows in order to cool a sleeping person's body. In an example, a cooling mechanism can comprise a bed mattress with a perpendicular grid or matrix of fluid channels through which cool fluid flows in order to cool a sleeping person's body. In an example, a cooling mechanism can comprise a bed mattress with a nested grid or matrix of air channels through which cool air flows in order to cool a sleeping person's body. In an example, a cooling mechanism can comprise a bed mattress with a nested grid or matrix of fluid channels through which cool fluid flows in order to cool a sleeping person's body.

In an example, a cooling mechanism can be a mattress pad or blanket which temporarily cools (a selected portion of) a sleeping person's body. In an example, a cooling mechanism can be a mattress pad or blanket through which cool air or liquid is pumped to temporarily cool a sleeping person's body. In an example, a cooling mechanism can comprise a mattress pad or blanket with tubes or channels through which cool air or liquid flows in order to cool a sleeping person's body. In an example, a cooling mechanism can comprise a mattress pad or blanket with a perpendicular grid or matrix of air channels through which cool air flows in order to cool a sleeping person's body. In an example, a cooling mechanism can comprise a mattress pad or blanket with a perpendicular grid or matrix of fluid channels through which cool fluid flows in order to cool a sleeping person's body. In an example, a cooling mechanism can comprise a mattress pad or blanket with a nested grid or matrix of air channels through which cool air flows in order to cool a sleeping person's body. In an example, a cooling mechanism can comprise a mattress pad or blanket with a nested grid or matrix of fluid channels through which cool fluid flows in order to cool a sleeping person's body.

In an example, a cooling mechanism can comprise an impellor, turbine, or fan which directs a flow cool air toward a sleeping person. In an example, a cooling mechanism for addressing hot flashes can be a bed mattress from which cool air flows toward a sleeping person's body. In an example, a cooling mechanism can be a mattress pad from which cool air flows toward a sleeping person's body. In an example, a cooling mechanism can be an article of sleepwear from which cool air flows toward a sleeping person's body. In an example, a cooling mechanism can comprise an impellor, turbine, or fan which directs a pulse of cool air toward a sleeping person.

In an example, a cooling mechanism can comprise an impellor, turbine, or fan which sends a laminar flow cool air over a sleeping person. In an example, a cooling mechanism can comprise an impellor, turbine, or fan which sends a laminar flow cool air over a sleeping person. In an example, a cooling mechanism can comprise an impellor, turbine, or fan which directs a flow cool air through the space between bed sheets. In an example, a cooling mechanism can comprise an impellor, turbine, or fan which directs a pulse of cool air through the space between bed sheets.

In an example, a cooling mechanism can further comprise a window unit air conditioner. In an example, cool liquid or air can be directed from a window unit air conditioner to a person's bed through a flexible insulated lumen or duct. In an example, such a flexible lumen or duct can be connected to a bed mattress, mattress pad, or blanket at the foot of a person's bed. In an example, such a flexible lumen or duct can be connected to a bed mattress underneath a person's bed. In an example, a cooling mechanism can further comprise an ice container. In an example, cool liquid or air can be directed from an ice container to a person's bed through a flexible insulated lumen or duct. In an example, such a flexible lumen or duct can be connected to a bed mattress, mattress pad, or blanket at the foot of a person's bed. In an example, such a flexible lumen or duct can be connected to a bed mattress underneath a person's bed. In an example, cool liquid or air can be directed from a window unit air conditioner to a person's sleepwear through a flexible insulated lumen or duct. In an example, cool liquid or air can be directed from an ice container to a person's sleepwear through a flexible insulated lumen or duct.

In an example, a system to reduce a person's snoring can comprise: a microphone (or other sonic energy sensor) to detect when a person is snoring; and a snore-reduction mechanism to reduce the snoring. In an example, a microphone to detect snoring can be attached to a bed headboard or frame. In an example, a microphone (or other sonic energy sensor) to detect snoring can be embedded in a pillow. In an example, a system can reduce the impact of snoring on the bed partner of the snoring person even if it does not reduce the snoring itself. In an example, a system to reduce the impact of a person's snoring on their bed partner can comprise: a microphone (or other sonic energy sensor) to detect when a person is snoring; and a noise-reduction or noise-masking mechanism to reduce the impact of the person's snoring on their bed partner.

In an example, a microphone to detect snoring can be part of bedside device. In an example, a microphone to detect snoring can be part of a cell phone. In an example, a microphone to detect snoring can be embedded into a bed mattress or blanket. In an example, a microphone to detect snoring can be worn by a sleeping person. In an example, a microphone to detect snoring can be part of a smart watch or wrist band. In an example, a microphone to detect snoring can be in a headband, sleep mask, eye mask, ear buds, or cap. In an example, a microphone to detect snoring can be in a necklace or collar. In an example, a microphone to detect snoring can be part of a mouth guard, dental appliance, or other intra-oral device.

In an example, a system to reduce a person's snoring can comprise: a vibration sensor to detect when a person is snoring; and a snore-reduction mechanism to reduce the person's snoring. In an example, a system to reduce the impact of a person's snoring on their bed partner can comprise: a vibration sensor to detect when a person is snoring; and a noise-reduction or noise-masking mechanism to reduce the degree to which the person's snoring is heard by their bed partner. In an example, a vibration sensor to detect snoring can be attached to a bed headboard or frame. In an example, a vibration sensor can be embedded in a pillow. In an example, a vibration sensor can be embedded in a bed mattress, pad, or blanket. In an example, a vibration sensor to detect snoring can be worn by a sleeping person. In an example, a vibration sensor can be a in a smart watch or wrist band. In an example, a vibration sensor to detect snoring can be in a headband, sleep mask, eye mask, ear buds, or cap. In an example, a vibration sensor to detect snoring can be in a necklace or collar. In an example, a vibration sensor to detect snoring can be in a mouth guard, dental appliance, or other intra-oral device.

In an example, a snore-reducing mechanism can comprise a bed mattress, mattress pad, or pillow whose firmness or softness is automatically changed when a person who is sleeping on it snores, wherein this change causes the person to stop snoring. In an example, a snore-reducing mechanism can comprise a bed mattress, mattress pad, or pillow whose firmness or softness is automatically changed when a person who is sleeping on it snores, wherein this change causes the person to shift their body configuration which stops their snoring. In an example, the firmness or softness of a bed mattress, mattress pad, or pillow can be changed by inflation or deflation. In an example, the firmness or softness of a bed mattress, mattress pad, or pillow can be changed by changing the pressure in an array of flexible air-filled tubes, channels, or columns in the mattress, pad, or pillow.

In an example, the firmness or softness of a bed mattress, mattress pad, or pillow can be changed by one or more electromagnetic actuators. In an example, the firmness or softness of a bed mattress, mattress pad, or pillow can be changed by changing the electrical current passing through solenoids in the mattress, pad, or pillow. In an example, the firmness or softness of a bed mattress, mattress pad, or pillow can be changed by changing the pressures in hydraulic actuators. In an example, the firmness or softness of a selected portion of a bed mattress, pad, or pillow can be changed by changing the pressures in a selected subset of an array of flexible fluid-filled tubes, channels, or columns in the mattress, pad, or pillow. In an example, the firmness or softness of a selected portion of a bed mattress, pad, or pillow can be changed by changing the pressures in a selected subset of an array of flexible air-filled tubes, channels, or columns in the mattress, pad, or pillow.

In an example, a snore-reducing mechanism can comprise one or more actuators which change the configuration and/or articulation of a bed, wherein this change causes the person to stop snoring. In an example, a change in bed configuration can cause a person to shift from sleeping on their back to sleeping on their side or front. In an example, a snore-reducing mechanism can comprise one or more actuators which change the configuration and/or articulation of a bed, wherein this change causes the person to change their body configuration which stops their snoring.

In an example, a snore-reducing mechanism can comprise one or more actuators which change the slope of a bed. In an example, a snore-reducing mechanism can comprise one or more actuators which change the lateral (e.g. side to side) slope of a bed or a portion (e.g. half) of a bed. In an example, a snore-reducing mechanism can comprise one or more actuators which change the longitudinal (e.g. head to foot) slope of a bed or a portion of a bed. In an example, a snore-reducing mechanism can comprise one or more actuators which change the lateral (e.g. side to side) slope of a bed or a portion (half) of a bed mattress. In an example, a snore-reducing mechanism can comprise one or more actuators which change the longitudinal (e.g. head to foot) slope of a bed or a portion of a bed mattress.

In an example, a snore-reducing mechanism can comprise one or more actuators which change the contour of a selected area of a bed. In an example, a snore-reducing mechanism can comprise one or more actuators which selectively change the height, slope, or angle of the head portion of a bed. In an example, a snore-reducing mechanism can comprise one or more actuators which selectively change the height, slope, or angle of a central portion of a bed. In an example, a snore-reducing mechanism can comprise one or more actuators which change a bed from a flat configuration to a Fowler configuration or a Trendelenburg configuration, or vice versa. In an example, a snore-reducing mechanism can comprise one or more actuators which selectively change the height of selected sections of a bed. In an example, a snore-reducing mechanism can comprise one or more actuators which selectively change the height of a pillow.

In an example, a snore-reduction mechanism can comprise a first component which tracks the location of a sleeping person's head and a second component which directs a flow or pulse of air toward the person's head when they snore. In an example, a snore-reduction mechanism can comprise a device which directs a flow or pulse of cool air toward a sleeping person's neck or mouth, wherein the flow or pulse of cool air causes the person to stop snoring. In an example, this device can be mounted on, or integrated into, the headboard of a bed. In an example, a snore-reduction mechanism can comprise a pillow which directs a flow or pulse of cool air toward a sleeping person's neck or mouth. In an example, a snore-reduction mechanism can comprise a bed mattress or pad which directs a flow or pulse of cool air toward a sleeping person's neck or mouth. In an example, a snore-reduction mechanism can comprise a collar which directs a flow or pulse of cool air toward a sleeping person's neck or mouth.

In an example, a snore-reduction mechanism can comprise a device which directs a flow or pulse of warm air toward a sleeping person's neck or mouth, wherein the flow or pulse of warm air causes the person to stop snoring. In an example, this device can be mounted on, or integrated into, the headboard of a bed. In an example, a snore-reduction mechanism can comprise a pillow which directs a flow or pulse of warm air toward a sleeping person's neck or mouth. In an example, a snore-reduction mechanism can comprise a bed mattress or pad which directs a flow or pulse of warm air toward a sleeping person's neck or mouth. In an example, a snore-reduction mechanism can comprise a collar which directs a flow or pulse of warm air toward a sleeping person's neck or mouth.

In an example, a snore-reduction mechanism can comprise an impellor, turbine, or fan on a bed headboard which directs a flow or pulse of cool air toward a sleeping person's neck or mouth. In an example, a snore-reduction mechanism can comprise an impellor, turbine, or fan in a bed mattress or mattress pad which directs a flow or pulse of cool air toward a sleeping person's neck or mouth. In an example, a snore-reduction mechanism can comprise an impellor, turbine, or fan in a collar which directs a flow or pulse of cool air toward a sleeping person's neck or mouth. In an example, a snore-reduction mechanism can comprise an impellor, turbine, or fan in a pillow which directs a flow or pulse of cool air toward a sleeping person's neck or mouth.

In an example, a snore-reduction mechanism can comprise an impellor, turbine, or fan on a bed headboard which directs a flow or pulse of warm air toward a sleeping person's neck or mouth. In an example, a snore-reduction mechanism can comprise an impellor, turbine, or fan in a bed mattress or mattress pad which directs a flow or pulse of warm air toward a sleeping person's neck or mouth. In an example, a snore-reduction mechanism can comprise an impellor, turbine, or fan in a collar which directs a flow or pulse of warm air toward a sleeping person's neck or mouth. In an example, a snore-reduction mechanism can comprise an impellor, turbine, or fan in a pillow which directs a flow or pulse of warm air toward a sleeping person's neck or mouth.

In an example, a snore-reduction mechanism can direct a series of air pulses toward a person's head, mouth, or neck to reduce the person's snoring. In an example, the frequency of pulses in a series of air pulses can be selected based on characteristics of the person's snoring so as to optimally reduce snoring. In an example, a snore-reduction mechanism can direct a series of cool air pulses toward a person's head, mouth, or neck to reduce the person's snoring. In an example, a snore-reduction mechanism can direct a series of warm air pulses toward a person's head, mouth, or neck to reduce the person's snoring.

In an example, a snore-reduction mechanism can comprise a vibrating device which whose vibrations cause a person to stop snoring. In an example, a vibrating device can be worn by the person. In an example, a wearable device which vibrates can be a wrist band or arm band. In an example, a wearable device which vibrates can be a necklace or collar. In an example, a wearable device which vibrates can be a headband or sleep mask. In an example, a vibrating device can be part of a bed or bedding. In an example, a snore-reducing mechanism can comprise a bed mattress or mattress pad which vibrates when a person snores. In an example, a snore-reducing mechanism can comprise a pillow which vibrates when a person snores.

In an example, a snore-reduction mechanism can comprise a mouth guard or dental appliance which emits a flow or pulse of cool air into a person's mouth. In an example, a snore-reduction mechanism can comprise a mouth guard or dental appliance which emits a flow or pulse of warm air within a person's mouth. In an example, a snore-reduction mechanism can comprise an impellor, turbine, or fan in a mouth guard or dental appliance which emits a flow or pulse of cool air within a person's mouth. In an example, a snore-reduction mechanism can comprise an impellor, turbine, or fan in a mouth guard or dental appliance which emits a flow or pulse of warm air within a person's mouth. In an example, a snore-reduction mechanism can comprise a mouth guard or dental appliance which vibrates when a person snores, wherein the vibration causes the person to stop snoring.

In an example, a snore-reduction mechanism can be a mouth and/or nose mask which directs of flow or pulse of air into a person's mouth when they snore. In an example, a snore-reduction mechanism can be a mouth and/or nose mask with an impellor, fan, or propeller which directs of flow or pulse of air into a person's mouth when they snore. In an example, a system for reducing a person's snoring can comprise: a mouth, nose, and/or face mask; a microphone; and an impellor or fan within the mask; wherein the impellor or fan is activated to direct a flow or pulse of air into the person's mouth when the person snores. In an example, the mask can further comprise a heating element which warms the flow or pulse of air. In an example, the mask can further comprise a cooling element which cools the flow or pulse of air.

In an example, a snore-reduction mechanism can comprise a mouth guard or dental appliance which automatically emits electromagnetic energy within a person's mouth when the person snores. In an example, this electromagnetic energy may be at level which is insufficient to wake the person up or cause pain, but which is sufficient to stimulate muscles in the person's tongue and/or other soft tissue to cause retraction of that tissue. In an example, this electromagnetic energy may serve a neurostimulation function. In an example, a snore-reduction mechanism can comprise a mouth guard or dental appliance with an array of air-filled channels or chambers which enables a sequential waving motion along its surface. In an example, a snore-reduction mechanism can comprise a mouth guard or dental implant worn in the mouth of a sleeping which is remotely-activated to emit a selected taste or smell when the person snores, wherein the taste or smell causes the person to stop snoring.

In an example, a system can reduce the impact of snoring on the bed partner of a snoring person even if it does not reduce the snoring itself. In an example, a snore-reducing mechanism of such a system can comprise a speaker which generates sounds when a person snores. In an example, these sounds can comprise sound waves with an inverse pattern relative to the sound waves of snoring so as to at least partially cancel the snoring sounds at selected locations. In an example, these sounds can comprise sound waves with an inverse pattern relative to the sound waves of snoring so as to at least partially cancel the snoring sounds in the area where a bed partner sleeps. In another example, these sounds can comprise sound waves with an inverse pattern relative to the sound waves of a snoring person on one half of a bed so as to at least partially cancel the snoring sounds on the other half of the bed. In an example, these sounds can be selected to at least partially mask snoring.

In an example, a speaker to cancel or mask snoring sounds can be mounted on, or integrated into, a bed headboard or frame. In an example, a speaker to cancel or mask snoring sounds can be embedded within a pillow. In an example, a speaker to cancel or mask snoring sounds can be incorporated into a headband, a pair of soft headphones, or ear buds which are worn by the snoring person's bed partner.

In an example, a snore-reducing mechanism can comprise a movable sound barrier with: a first configuration in which the barrier extends into a space between a first person and a second person in a bed; and a second configuration in which the barrier does not extend into this space. In an example, a sound barrier can be automatically moved from its second configuration to its first configuration when one of the two people snores. In an example, a sound barrier can be flexible. In an example, a sound barrier can be made from fabric. In an example, a sound barrier can be inflated. In an example, a sound barrier can contain a vacuum-filled space.

In an example, a sound barrier can be a curtain which (automatically) slides across a longitudinal rod above and between the two sides of a bed. In an example, a sound barrier can be a curtain which (automatically) unrolls down (or rolls back up) from a longitudinal spool above and between the two sides of a bed. In an example, a sound barrier can extend (e.g. slide) into the space between the sides of a bed. In an example, a sound barrier can automatically extend out from a bed headboard. In an example, a sound barrier can be inflatable. In an example, a sound barrier can extend into the space between the two people by being automatically inflated and retract from this space by being automatically deflated.

In an example, a selective sound-transmission system for a sleeping person can selectively transmit certain types of environmental sounds which are desired to be heard by the sleeping person and block (e.g. filter out) the rest of environmental sounds. In an example, a selective sound-transmission system for a sleeping person can selectively block (filter out) different types of environmental sounds which the sleeping person does not want to hear and transmit the rest of environmental sounds. In an example, a selective sound-transmission system for a sleeping person can enable a person to select certain types of environmental sounds which are to be transmitted to the person and block other environmental sounds. In an example, a selective sound-transmission system for a sleeping person can enable a person to select certain types of environmental sounds which are to be blocked from hearing by the person and transmit other environmental sounds. In an example, a selective sound-transmission system for a sleeping person can selectively transmit human voices and block other sounds. In an example, a selective sound-transmission system for a sleeping person can block snoring and transmit other sounds. In an example, a selective sound-transmission system for a sleeping person can block music and transmit other sounds.

In an example, a selective sound-transmission system for a sleeping person can comprise: a microphone; a speaker, and an adjustable sound filtering mechanism. In an example, a microphone can be worn by the person as part of a headband, ear buds, necklace, sleep mask, or wrist band. In an example, a microphone can be part of a bed headboard, pillow, mattress, or pad. In an example, a microphone can be part of a cell phone or beside device. In an example, a speaker can be part of a headband, soft headphones, ear buds, cap, or hat which is worn by a sleeping person. In an example, a wearable device can block direct transmission of environmental sounds to a sleeping person so that the only environmental sounds which are heard by the person are those which are recorded by a microphone and reproduced by a speaker, after selective filtering of certain sounds.

In an example, a system to help prevent pressure ulcers on a person in bed can comprise: one or more sensors which collect information on the shape and force of contact between a person and a bed; and a contact-adjusting mechanism which automatically changes the shape and force of contact between the person and the bed based on information from the one or more sensors in order to prevent pressure ulcers. In an example, a sensor to collect information on the shape and force of contact between a person and a bed can be a capacitive pressure sensor in a bed mattress, mattress pad, or article of clothing. In an example, a capacitive pressure sensor can have three layers—a first conductive layer, a second conductive layer, and a non-conductive layer between the first and second layers. In an example, a contact-adjusting mechanism can comprise one or more actuators which move a mattress or mattress pad.

In an example, a sensor to collect information on the shape and force of contact between a person and bed can be selected from the group consisting of: electroconductive fibers sewn or woven into an article of clothing; electromagnetic field sensors in a bed mattress or pad; electromagnetic stretch sensors or light-energy-transmitting stretch sensors sewn or woven into an article of clothing; an infrared camera whose images are used to track the configuration of a sleeping person; and microfluidic pathways woven into a mattress pad or article of clothing.

In an example, a sensor to collect information on the shape and force of contact between a person and bed can be a perpendicular grid or matrix of: electromagnetic energy sensors in a bed mattress, pad, or article of clothing; pressure sensors in a bed mattress, pad, or article of clothing; or motion sensors in a bed mattress, pad, or article or clothing. In an example, a sensor to collect information on the shape and force of contact between a person and bed can be a nested arcuate array of: electromagnetic energy sensors in a bed mattress, pad, or article of clothing; pressure sensors in a bed mattress, pad, or article of clothing; or motion sensors in a bed mattress, pad, or article or clothing.

In an example, selective activation of one or more electromagnetic, pneumatic, or hydraulic actuators in a selected portion of a mattress can change the contour of a bed mattress or pad in a selected area. In an example, one or more actuators can change the firmness or softness of a bed in selected areas in response to a person's body configuration. In an example, one or more actuators can change the firmness or softness of a bed in selected areas in response to the shape and force of contact between a person's body and a bed. In an example, a contact-adjusting mechanism can comprise a bed mattress or pad with an array of air-filled channels, chambers, or columns. In an example, selective inflation or deflation of air-filled channels, chambers, or columns in selected portions of a mattress can change the contour of a bed mattress or pad in selected areas.

In an example, a system to help prevent pressure ulcers on a person in bed can comprise a bed mattress or pad with an upper surface which moves in an undulating manner. In an example, a system to help prevent pressure ulcers on a person in bed can comprise a bed mattress or pad with an upper surface which moves in a sinusoidally-undulating manner. In an example, a bed mattress or pad can comprise an array of fluid-filled or air-filled channels, chambers, or columns which whose pressures or volumes are varied in a sequential manner to cause moving undulation of the top the bed mattress or pad to help avoid pressure ulcers.

In an example, an moving undulating bed mattress or pad can have undulating waves which move in a lateral (e.g. left to right, or vice versa) manner over the top the mattress or pad. In an example, a moving undulating bed mattress or pad can have undulating waves which move in a longitudinal (e.g. head to foot, or vice versa) manner over the top of the mattress or pad. In an example, a moving undulating bed mattress or pad can have undulating waves which radiate outwards from the center of the mattress or pad. In an example, a moving undulating bed mattress or pad can have undulating waves which move in a random manner across the top of the mattress or pad. In an example, a bed mattress or pad with a sequentially waving and/or undulating upper contour can avoid continuous pressure points of contact between a person and a bed and thus avoid pressure ulcers. In an example, moving undulations can be sinusoidal undulations.

In an example, the timing, speed, size, and/or direction of moving undulations in an undulating bed mattress or pad can be adjusted based on information from one or more biometric sensors worn by a sleeping person. In an example, the timing, speed, size, and/or direction of moving undulations in an undulating bed mattress or pad can be adjusted based on the shape and force of contact between a sleeping person and the mattress or pad. In an example, a bed mattress or pad may move less when a person is asleep than when the person is awake. In an example, a bed mattress or pad may more less when contact between the person and the mattress is distributed over larger area and move more when contact is more concentrated in smaller areas. In an example, the timing, speed, size, and/or direction of moving undulations in an undulating bed mattress or pad can be adjusted based on an array of pressure sensors in the bed mattress or pad. In an example, the timing, speed, size, and/or direction of moving undulations in an undulating bed mattress or pad can be adjusted based on an array of pressure sensors in pajamas or other sleepwear worn by a person on the mattress or pad. In an example, the timing, speed, size, and/or direction of moving undulations in an undulating bed mattress or pad can be adjusted based on oxygenation sensors in pajamas worn by a person on the mattress or pad.

Figure 88:
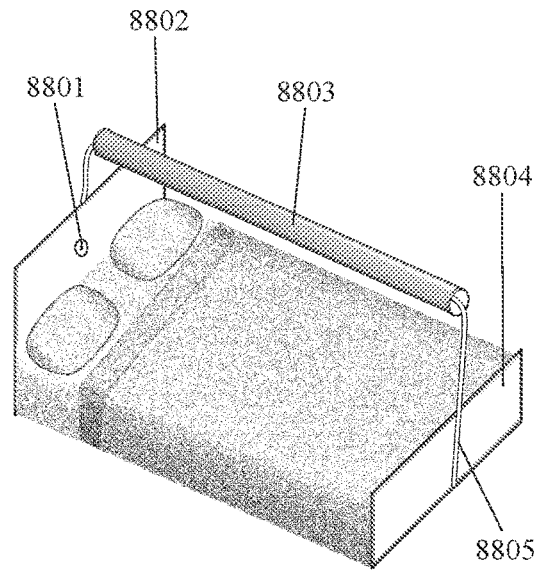
FIGS. 88 and 89 show a roll-down partition that creates acoustic zones in a bed.
Figure 89:
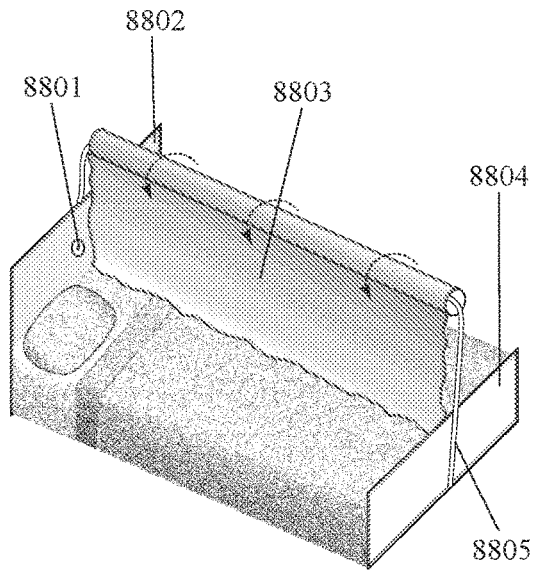

FIGS. 88 and 89 show two views, at two different times, of an example of a device which creates a plurality of adjustable acoustic and/or thermal zones in a bed comprising: a longitudinal beam 8805 which spans a space above a bed in a longitudinal manner, from the head 8802 of the bed to the foot 8804 of the bed; a movable acoustically-insulating and/or thermally-insulating partition 8803 with a retracted configuration (shown in FIG. 88) in which the partition is wrapped around, recessed within, folded onto, or held up against the longitudinal beam and an extended configuration (shown in FIG. 89) in which the partition extends downward from the longitudinal beam toward the surface of the bed, dividing the bed into a plurality of (e.g. two) longitudinal acoustic and/or thermal zones; and a sensor 8801, wherein the partition is automatically moved from its retracted configuration to its extended configuration in response to analysis of data from the sensor.

In an example, a longitudinal beam can have a soccer-goal-frame shape, an inverted "U" shape, and/or arch shape. In an example, side portions of a longitudinal beam can extend downward from the ends of an upper portion of the longitudinal beam which spans a space above the bed. In an example, a longitudinal beam (and/or the side pieces thereof) can be attached to the head of a bed frame and to the foot of the bed frame. In an example, side pieces of a longitudinal beam can be held in place by insertion between a mattress and a box spring. In an example, a longitudinal beam (and/or the side pieces thereof) can be attached to the headboard of a bed and to the footboard of the bed. In an example, a longitudinal beam (and/or the side pieces thereof) can be attached to the lateral center of the head of a bed frame (and/or headboard) and to the lateral center of the foot of the bed frame (and/or footboard). In an example, an upper portion of a longitudinal beam can be between 2 and 6 feet above the upper surface of a bed and/or the uppermost layer of bedding (e.g. a blanket, bed spread, quilt, or comforter on the bed).

In an example, this device can include a cylindrical roller, which rotates around the longitudinal beam, wherein the movable partition is rolled (e.g. rolled, wrapped, wound, or coiled) around the roller in its retracted configuration and is unrolled (e.g. unrolled, unwrapped, unwound, or uncoiled) from the roller in its extended configuration. In an example, there can be a cylindrical roller inside a hollow longitudinal beam, wherein the movable partition is rolled around the roller in its retracted configuration and is unrolled from the roller in its extended configuration. In an example, a device can further comprise an electromagnetic motor which rotates a cylinder around which a movable partition is rolled (e.g. rolled, wrapped, wound, or coiled). In an example, an electromagnetic motor can be activated in response to analysis of data from a sensor. In an example, an electromagnetic motor can be directly activated (e.g. via remote control unit or cell phone application) by a person in the bed. In an example, a device can further comprise a spring and/or coil which is attached to a cylinder around which a movable partition is rolled (e.g. rolled, wrapped, wound, or coiled).

In an example, a partition can be flexible. In an example, a partition can be at least partially made from fabric. In an example, a flexible partition can be rolled up into its retracted configuration and unrolled down into its extended configuration. In an example, a flexible partition can comprise a plurality of flexibly-connected sections (e.g. slats or louvers) which are connected by flexible joints. In an example, a flexible partition can comprise a plurality of flexibly-connected horizontal sections (e.g. slats or louvers) which connected by flexible joints. This is not the first time that louvers have been found in bed. In an example, a partition can comprise a plurality of sections connected by flexible joints so that the partition can be folded into its retracted configuration and unfolded into its extended configuration. In another example, a partition can be pleated (e.g. like an accordion or bellows) so that it can be folded into its retracted configuration and unfolded into its extended configuration.

In an example, a partition can extend downward into contact with the uppermost layer of bedding (e.g. a blanket, bead spread, quilt, or comforter on a bed) in its extended configuration. In an example, a partition can have a weighted lower section (e.g. having a greater weight per volume than the rest of the partition) so that it rests snuggly on the uppermost layer of bedding (e.g. a blanket, bead spread, quilt, or comforter on a bed) in its extended configuration. In an example, a partition can further comprise a conformable and/or compressible lower section which conforms to the shape of the uppermost layer of bedding (e.g. a blanket, bead spread, quilt, or comforter on a bed) in its extended configuration.

In an example, a partition can have acoustically-insulating material and/or a sound-dampening structure which decreases the transmission of sound between zones in a bed. In an example, a partition can be made with thermal-insulating material and/or a thermal-insulating structure (e.g. air pockets) which decreases the transmission of thermal energy between zones in a bed. In an example, a partition can comprise an outer fabric layer and an interior portion which is filled with particles, clumps, beads, blocks, panels, or strands of insulating material. In an example, at least the lower portion of a partition can be made with breathable material for safety in case it comes into contact with a sleeping person when it is extended.

In an example, this device can include one or more sensors. In an example, a movable partition can be automatically moved from its retracted configuration to its extended configuration in response to analysis of data from a sensor. In an example, a movable partition can be automatically moved from its retracted configuration to its extended configuration when a sensor detects snoring. In an example, a movable partition can be automatically moved from its retracted configuration to its extended configuration when a sensor detects or predicts a hot flash or night sweat for one of the people in the bed. In an example, a movable partition can be automatically moved from its retracted configuration to its extended configuration when one or more sensors (e.g. EEG sensors or motion sensors) detect that both people in bed have fallen asleep. In an example a device can be set to automatically move a partition from its retracted configuration to its extended configuration at a preset time. In an alternative example, retraction or extension of a moveable partition can be activated directly by a person in the bed (e.g. via a remote control unit or cell phone application). In yet another example, a device may not have a sensor and a partition can be moved (e.g. pulled down or pushed up) manually by a person in the bed.

In an example, a sensor can be part of (or attached to) a device. In an example, a sensor can be part of (or attached to) a beam or a movable partition of a device. In an example, a sensor can be part of a system which includes the beam and movable partition. In an example, a system can have a sensor which is in wireless communication with an electromagnetic motor which moves the movable partition. In an example, a sensor can be a wearable sensor which is worn by a sleeping person. In an example, a sensor can be part of a wearable device (e.g. a smart watch, EEG monitoring headband, or smart garment which is worn by a sleeping person) which is in wireless communication with a data processor which controls an electromagnetic motor which moves the movable partition. In an example, a sensor can be an environmental sensor which monitors one or more environmental variables selected from the group consisting of: ambient temperature, ambient humidity level, ambient sound level or type, ambient light level or type, pressure and/or body contact, motion, and vibration. In an example, a sensor can be a biometric sensor which monitors one or more biometric variables selected from the group consisting of: body temperature, skin moisture level, body tissue conductance, body tissue impedance, body motion, body contact pressure, heart rate, and brain wave patterns (e.g. EEG signals).

In an example, a sensor can be a microphone or other sound sensor. In an example, analysis of data from a sensor can detect snoring. In an example, a movable partition can be automatically extended downward into its extended configuration when snoring is detected. This can reduce the amount of snoring noise which is transmitted between zones in the bed. This can help couples who would like to sleep together, but for whom loud snoring by one partner interferes with the sleep of the other partner. A device with an acoustic-insulating partition that deploys when snoring is detected can enable a couple to smooch and fall asleep in the same bed with less chance of subsequent sleep disturbance by snoring. This is why this device can be branded as the "Smooch n' Snore™" with the corresponding tagline—"Smooch n' Snore. Couch no more."

In an example, a sensor can be a thermal energy sensor. When two people in the same bed have different sleep temperature preferences, then a thermally-insulating partition between them can help to create two different thermal zones in the bed. In an example, a sensor can be a worn on a person. In an example, a sensor can be a body temperature sensor, a body tissue conductance sensor, a body tissue impedance sensor, a spectroscopic sensor, and/or an EEG sensor. In an example, if analysis of data from the sensor indicates a change in a person's body temperature (e.g. a hot flash or night sweat) and/or predicts an upcoming change in the person's temperature (e.g. a hot flash or night sweat), then a system comprising the partition and the wearable sensor can automatically extend the partition to thermally isolate different zones in the bed. In an example, thermal isolation of different zones by extension of a partition can be done before (or during) selective and/or temporary cooling and/or heating of one of the bed zones.

In an example, a device which creates a plurality of adjustable longitudinal acoustic and/or thermal zones in a bed can further include an electromagnetic motor which moves a partition from its retracted configuration to its extended configuration, or vice versa. In an example, an electromagnetic motor can roll (e.g. roll, wrap, wind, or coil) a flexible partition into its retracted configuration and unroll (e.g. unroll, unwrap, unwind, or uncoil) the partition into its extended configuration. In an example, an electromagnetic motor can fold (e.g. fold or collapse) a flexible partition into its retracted configuration and unfold (e.g. unfold or expand) the partition into its extended configuration. In an example, an electromagnetic motor can be triggered by analysis of data from a sensor. In an example, an electromagnetic motor can be triggered by detection of snoring or a hot flash. In an example, an electromagnetic motor can be activated remotely by a person in the bed (e.g. via a remote control unit or cell phone application). In an example, a device which creates a plurality of adjustable longitudinal acoustic and/or thermal zones in a bed can include a data processing unit (e.g. which analyzes data from the sensor and controls the operation of an electromagnetic motor) and a wireless data transmitter/receiver. Design variations discussed elsewhere in this disclosure or in priority-linked disclosures can also be applied to this example where relevant.

Figure 90:
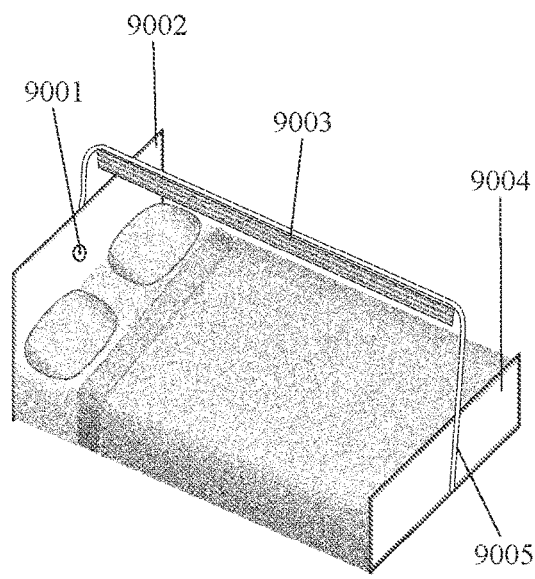
FIGS. 90 and 91 show a fold-down partition that creates acoustic zones in a bed.
Figure 91:
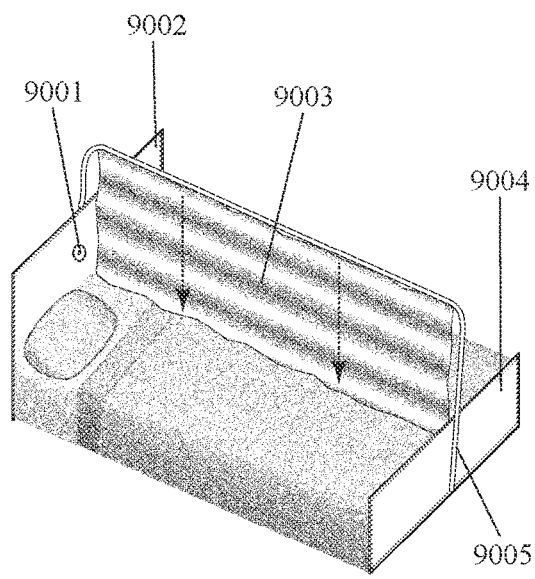

FIGS. 90 and 91 show two views, at two different times, of an example of a device which creates a plurality of adjustable acoustic and/or thermal zones in a bed comprising: a longitudinal beam 9005 which spans a space above a bed in a longitudinal manner, from the head 9002 of the bed to the foot 9004 of the bed; a movable acoustically-insulating and/or thermally-insulating partition 9003 with a retracted configuration (shown in FIG. 90) in which the partition is folded up against the longitudinal beam and an extended configuration (shown in FIG. 91) in which the partition is unfolded downward from the longitudinal beam toward the surface of the bed, dividing the bed into a plurality of (e.g. two) longitudinal acoustic and/or thermal zones; and a sensor 9001, wherein the partition is automatically moved from its retracted configuration to its extended configuration in response to analysis of data from the sensor.

In an example, a movable partition can be pleated and/or folded like an accordion, fire bellows, or window blinds. In an example, a pleated and/or folded partition can comprise a plurality of flexibly-connected (horizontal) sections (e.g. slats or louvers) which are connected by flexible joints. In an example, a pleated and/or folded partition can be folded upwards into its retracted configuration and unfolded downwards into its extended configuration, in a manner similar to the operation of retractable horizontal window blinds. In an example, a pleated and/or folding partition can be further comprise two or more cords, wherein pulling the cords upwards causes the partition to fold upwards into its retracted configuration and loosening the cords causes the partition to unfold downwards into its extended configuration.

In an example, this device can include one or more sensors. In an example, a movable partition can be automatically moved from its retracted configuration to its extended configuration in response to analysis of data from a sensor. In an example, a movable partition can be automatically moved from its retracted configuration to its extended configuration when a sensor detects snoring. In an example, a movable partition can be automatically moved from its retracted configuration to its extended configuration when a sensor detects or predicts a hot flash or night sweat for one of the people in the bed. In an example, a movable partition can be automatically moved from its retracted configuration to its extended configuration when one or more sensors (e.g. EEG sensors or motion sensors) detect that both people in bed have fallen asleep. In an example a device can be set to automatically move a partition from its retracted configuration to its extended configuration at a preset time. In an alternative example, retraction or extension of a moveable partition can be activated directly by a person in the bed (e.g. via a remote control unit or cell phone application). In yet another example, a device may not have a sensor and a partition can be moved (e.g. pulled down or pushed up) manually by a person in the bed.

In an example, a sensor can be part of (or attached to) a device. In an example, a sensor can be part of (or attached to) a beam or a movable partition of a device. In an example, a sensor can be part of a system which includes the beam and movable partition. In an example, a system can have a sensor which is in wireless communication with an electromagnetic motor which moves the movable partition. In an example, a sensor can be a wearable sensor which is worn by a sleeping person. In an example, a sensor can be part of a wearable device (e.g. a smart watch, EEG monitoring headband, or smart garment which is worn by a sleeping person) which is in wireless communication with a data processor which controls an electromagnetic motor which moves the movable partition. In an example, a sensor can be an environmental sensor which monitors one or more environmental variables selected from the group consisting of: ambient temperature, ambient humidity level, ambient sound level or type, ambient light level or type, pressure and/or body contact, motion, and vibration. In an example, a sensor can be a biometric sensor which monitors one or more biometric variables selected from the group consisting of: body temperature, skin moisture level, body tissue conductance, body tissue impedance, body motion, body contact pressure, heart rate, and brain wave patterns (e.g. EEG signals).

In an example, a sensor can be a microphone or other sound sensor. In an example, analysis of data from a sensor can detect snoring. In an example, a movable partition can be automatically extended downward into its extended configuration when snoring is detected. This can reduce the amount of snoring noise which is transmitted between zones in the bed. This can help couples who would like to sleep together, but for whom loud snoring by one partner interferes with the sleep of the other partner. A device with an acoustic-insulating partition that deploys when snoring is detected can enable a couple to smooch and fall asleep in the same bed with less chance of subsequent sleep disturbance by snoring.

In an example, a sensor can be a thermal energy sensor. When two people in the same bed have different sleep temperature preferences, then a thermally-insulating partition between them can help to create two different thermal zones in the bed. In an example, a sensor can be a worn on a person. In an example, a sensor can be a body temperature sensor, a body tissue conductance sensor, a body tissue impedance sensor, a spectroscopic sensor, and/or an EEG sensor. In an example, if analysis of data from the sensor indicates a change in a person's body temperature (e.g. a hot flash or night sweat) and/or predicts an upcoming change in the person's temperature (e.g. a hot flash or night sweat), then a system comprising the partition and the wearable sensor can automatically extend the partition to thermally isolate different zones in the bed. In an example, thermal isolation of different zones by extension of a partition can be done before (or during) selective and/or temporary cooling and/or heating of one of the bed zones.

In an example, a device which creates a plurality of adjustable longitudinal acoustic and/or thermal zones in a bed can further include an electromagnetic motor which moves a partition from its retracted configuration to its extended configuration, or vice versa. In an example, an electromagnetic motor can fold (e.g. fold or collapse) a flexible partition into its retracted configuration and unfold (e.g. unfold or expand) the partition into its extended configuration. In an example, an electromagnetic motor can be triggered by analysis of data from a sensor. In an example, an electromagnetic motor can be triggered by detection of snoring or a hot flash. In an example, an electromagnetic motor can be activated remotely by a person in the bed (e.g. via a remote control unit or cell phone application). In an example, a device which creates a plurality of adjustable longitudinal acoustic and/or thermal zones in a bed can include a data processing unit (e.g. which analyzes data from the sensor and controls the operation of an electromagnetic motor) and a wireless data transmitter/receiver. Design variations discussed elsewhere in this disclosure or in priority-linked disclosures can also be applied to this example where relevant.

Figure 92:
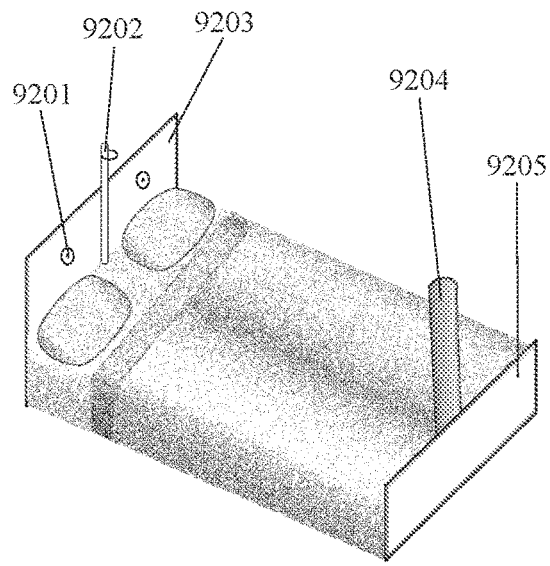
FIGS. 92 and 93 show a longitudinally-moving partition, spanning from the foot to the head of a bed, that creates acoustic zones in a bed.
Figure 93:
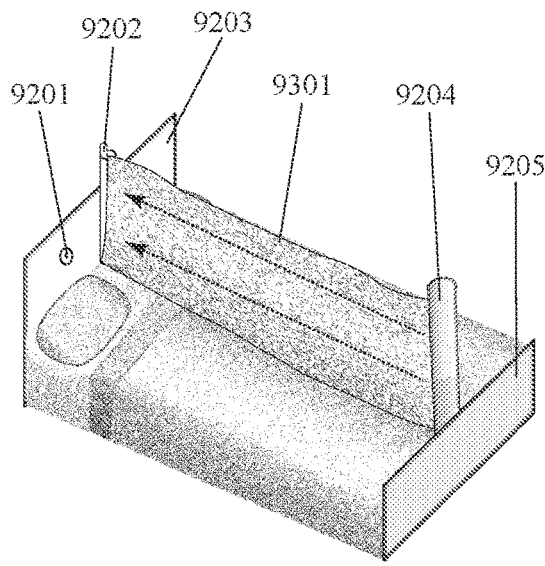

FIGS. 92 and 93 show two views, at two different times, of an example of a device which creates a plurality of adjustable acoustic and/or thermal zones in a bed comprising: a first post (e.g. a vertical post, rod, or arm) 9202 at the head 9203 of the bed; a second post (e.g. a vertical post, rod, arm, or rotating cylinder) 9204 at the foot 9205 of the bed; a movable acoustically-insulating and/or thermally-insulating partition 9301 with a retracted configuration (shown in FIG. 92) in which the partition is wrapped around, recessed within, folded onto, or held up against the second post and an extended configuration (shown in FIG. 93) in which the partition extends out from the second post toward the head of the bed and is attached to the first post, dividing the bed into a plurality of (e.g. two) longitudinal acoustic and/or thermal zones; and one or more sensors (including sensor 9201), wherein the partition is automatically moved from its retracted configuration to its extended configuration in response to analysis of data from the one or more sensors.

In a variation on this example, a movable partition can be attached directly to a headboard instead of a first post (e.g. vertical post, rod, or arm) at the head of a bed. In an example, a movable partition can be attached to a first post or to a headboard by a hook, loop, snap, clip, button, ring, buckle, or hook-and-eye fabric. In a variation on this example, a movable partition can be extended from the head of a bed to the foot of the bed, instead of being extended from the foot of the bed to the head of the bed. In an example, a movable acoustically-insulating and/or thermally-insulating partition can have a retracted configuration in which the partition is wrapped around, recessed within, folded onto, or held up against a first post at the head of the bed and an extended configuration in which the partition extends out from the first post toward a second post at the foot of the bed. In an example, a movable acoustically-insulating and/or thermally-insulating partition can have a retracted configuration in which the partition is wrapped around, recessed within, folded onto, or held up against a headboard and an extended configuration in which the partition extends out toward the foot of the bed and is attached to a footboard.

In an example, a device can automatically move a partition from its retracted configuration to its extended configuration when one or more sensors detect snoring. In an example, a movable partition can be automatically moved from its retracted configuration to its extended configuration when one or more sensors detect or predict a hot flash or night sweat for one or both of people in a bed. In an example, a movable partition can be automatically moved from its retracted configuration to its extended configuration when one or more sensors (e.g. EEG sensors or motion sensors) detect that both people in a bed have fallen asleep. In an example, a device can be set to automatically move a partition from its retracted configuration to its extended configuration at a preset time. In an example, retraction or extension of a moveable partition can be activated directly by a person in the bed (e.g. via a remote control unit or cell phone application). In an example, a device may not have a sensor and a partition can be moved (e.g. pulled over the bed) manually by a person in the bed.

In an example, a device which creates a plurality of adjustable longitudinal acoustic and/or thermal zones in a bed can further include an electromagnetic motor which moves a partition from its retracted configuration to its extended configuration, or vice versa. In an example, an electromagnetic motor can be triggered by analysis of data from a sensor. In an example, an electromagnetic motor can be triggered by detection of snoring or a hot flash. In an example, an electromagnetic motor can be activated remotely by a person in the bed (e.g. via a remote control unit or cell phone application). In an example, a device which creates a plurality of adjustable longitudinal acoustic and/or thermal zones in a bed can include a data processing unit (e.g. which analyzes data from the sensor and controls the operation of an electromagnetic motor) and a wireless data transmitter/receiver. Design variations discussed elsewhere in this disclosure or in priority-linked disclosures can also be applied to this example where relevant.

Figure 94:
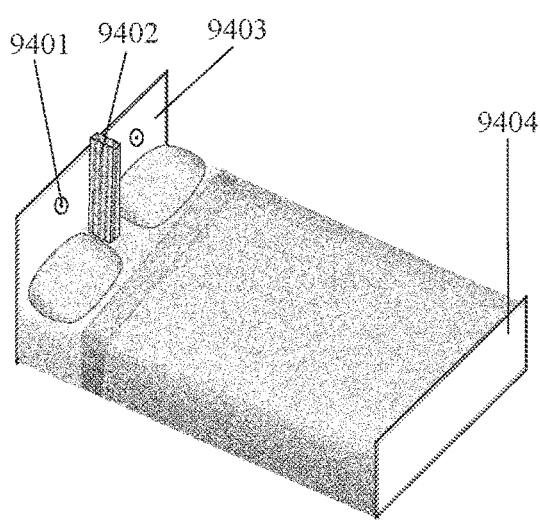
FIGS. 94 and 95 show a longitudinally-inflating partition that creates acoustic zones in a bed.
Figure 95:
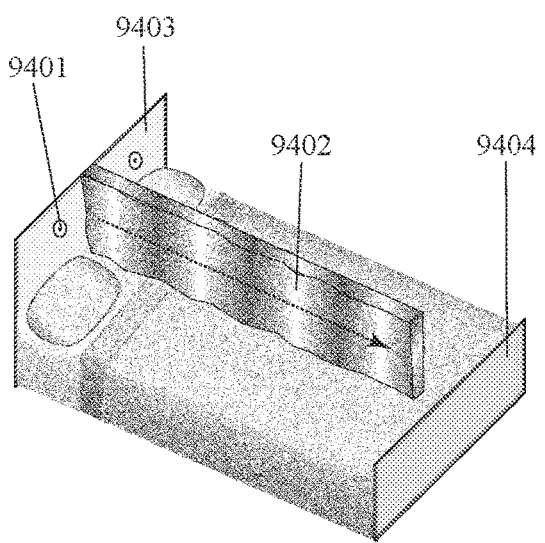

FIGS. 94 and 95 show two views, at two different times, of an example of a device which creates a plurality of adjustable acoustic and/or thermal zones in a bed comprising: an inflatable acoustically-insulating and/or thermally-insulating partition 9402 with a retracted configuration (shown in FIG. 94) at the head 9403 of a bed and an extended configuration (shown in FIG. 95) which extends out from the head of the bed toward the foot 9404 of the bed, dividing the bed into a plurality of (e.g. two) longitudinal acoustic and/or thermal zones; and one or more sensors (including sensor 9401), wherein the partition is automatically inflated from its retracted configuration to its extended configuration in response to analysis of data from the one or more sensors.

In an example, an inflatable partition can be made with elastic components so that it contracts and/or shrinks into its retracted configuration when it is deflated and/or when it is no longer filled with pressurized air. In an example, an inflatable partition can be attached to a headboard of a bed. In an example, an inflatable partition can be housed in a recess in a headboard in its retracted (e.g. deflated) configuration. In an example, a device can include a headboard with a recess in which an inflatable partition is housed in its retracted (e.g. deflated) configuration. In an example, an inflatable partition can be made with elastic components so that it contracts and/or shrinks into a recess in the headboard when it is deflated.

In an example, an inflatable partition can span the entire length of a bed when it is in its extended (e.g. inflated) configuration. In an example, an inflatable partition can span between 50% and 75% of the length of a bed when it is in its extended (e.g. inflated) configuration. In an example, an inflatable partition can span a central longitudinal axis of a bed when it is in its extended (e.g. inflated) configuration. In an example, this device can include an air pump which automatically inflates the inflatable partition. In an example, this device can include an air pump which automatically changes the air pressure inside the inflatable partition. In an example, the inflatable partition can extend outward into its extended configuration when its internal air pressure is high (e.g. high relative to ambient atmospheric pressure) and shrink back into its retracted configuration when its internal air pressure is low (e.g. low relative to ambient atmospheric pressure). In an example, an air pump can be automatically activated based on analysis of data from one or more sensors. In an alternative example, an air pump can be directly activated by a person in the bed (e.g. via a remote control unit or cell phone application).

In an example, an inflatable partition can be automatically inflated from its retracted (e.g. deflated) configuration to its extended (e.g. inflated) configuration when one or more sensors detect snoring. In an example, an inflatable partition can be automatically inflated from its retracted (e.g. deflated) configuration to its extended (e.g. inflated) configuration when one or more sensors detect or predict a hot flash or night sweat for one or both of the people in a bed. In an example, an inflatable partition can be automatically inflated from its retracted (e.g. deflated) configuration to its extended (e.g. inflated) configuration when one or more sensors (e.g. EEG sensors or motion sensors) detect that both people in a bed have fallen asleep. In an example a device can be set to automatically inflate a partition from its retracted (e.g. deflated) configuration to its extended (e.g. inflated) configuration at a preset time. In an alternative example, inflation or deflation of an inflatable partition can be activated directly by a person in the bed (e.g. via a remote control unit or cell phone application). In an example, a device can further comprise speech recognition functionality and can extend the partition when one of two people in a bed states that they have a headache.

In an example, a device which creates a plurality of adjustable longitudinal acoustic and/or thermal zones in a bed can further include an air pump which inflates a partition from its retracted (e.g. deflated) configuration to its extended (e.g. inflated) configuration, or vice versa. In an example, an air pump can be triggered by analysis of data from a sensor. In an example, an air pump can be triggered by detection of snoring or a hot flash. In an example, an air pump can be activated remotely by a person in the bed (e.g. via a remote control unit or cell phone application). In an example, a device which creates a plurality of adjustable longitudinal acoustic and/or thermal zones in a bed can include a data processing unit (e.g. which analyzes data from the sensor and controls the operation of an air pump) and a wireless data transmitter/receiver. Design variations discussed elsewhere in this disclosure or in priority-linked disclosures can also be applied to this example where relevant.

Figure 96:
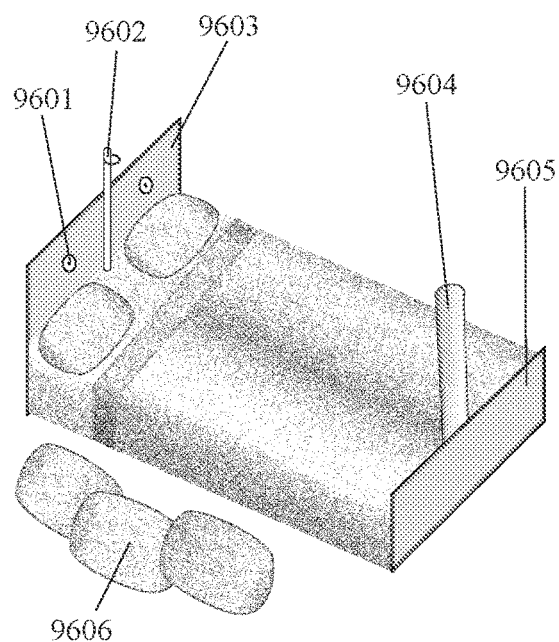
FIGS. 96 through 98 show a longitudinally-moving partition, into which pillows are inserted, that creates acoustic zones in a bed.
Figure 97:
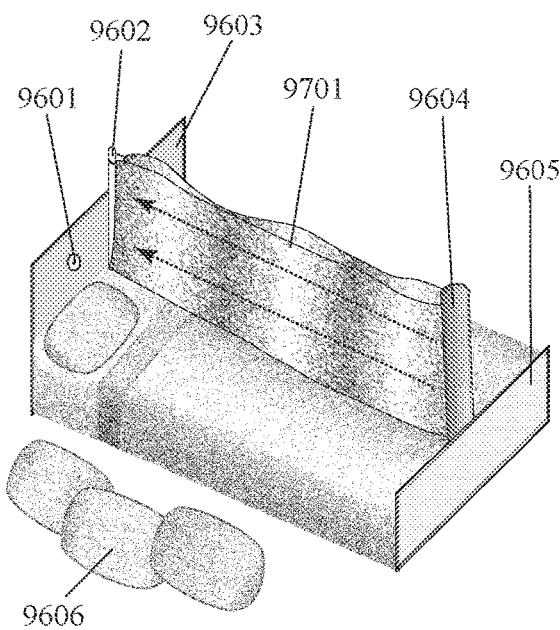
Figure 98:
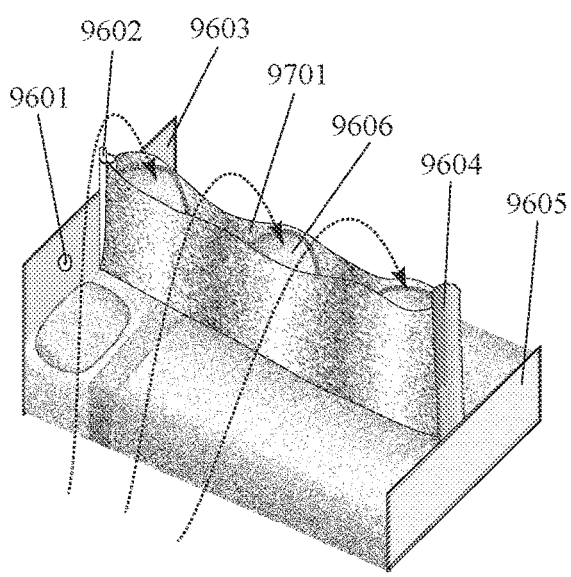

FIGS. 96 through 98 show three views, at three different times, of an example of a system which creates a plurality of adjustable acoustic and/or thermal zones in a bed comprising: a first post (e.g. a vertical post, rod, or arm) 9602 at the head 9603 of the bed; a second post (e.g. a vertical post, rod, arm, or rotating cylinder) 9604 at the foot 9605 of the bed; a movable acoustically-insulating and/or thermally-insulating partition 9701 with a retracted configuration (as shown in FIG. 96) in which the partition is wrapped around, recessed within, folded onto, or held up against the second post and an extended configuration (as shown in FIGS. 97 and 98) in which the partition extends out from the second post toward the head of the bed and is attached to the first post, dividing the bed into a plurality of (e.g. two) longitudinal acoustic and/or thermal zones; one or more sensors (including 9601), wherein the partition is automatically moved from its retracted configuration to its extended configuration in response to analysis of data from the one or more sensors; and a plurality of pillows or cushions (including 9606) which are inserted into the partition (as shown in FIG. 98) when the partition is in its extended configuration.

In an example, a movable partition can have pockets or compartments into which pillows (or cushions) are inserted. In an example, insertion of pillows (or cushions) into a partition increases the acoustic insulation and/or thermal insulation value of the partition. In an example, a partition can be made from fabric which would not be great for acoustic and/or thermal insulation by itself, but which forms pockets or compartments which hold pillows (or cushions) which do provide a high level of acoustic and/or thermal insulation between bed zones. In an example, a partition can have between 2 and 5 pockets or compartments into which pillows (or cushions) are inserted. In an example, a partition can have pockets or compartments which are configured to receive standard (e.g. conventional size, non-customized) pillows. Alternatively, a partition can have pockets or compartments which are configured to receive pillows (or cushions) which are specifically designed for this system and/or device.

In a variation on this example, a movable partition can be attached directly to a headboard instead of a first post (e.g. vertical post, rod, or arm) at the head of a bed. In an example, a movable partition can be attached to a first post or to a headboard by a hook, loop, snap, clip, button, ring, buckle, or hook-and-eye fabric. In a variation on this example, a movable partition can be extended from the head of a bed to the foot of the bed, instead of being extended from the foot of the bed to the head of the bed. In an example, a movable acoustically-insulating and/or thermally-insulating partition can have a retracted configuration in which the partition is wrapped around, recessed within, folded onto, or held up against a first post at the head of the bed and an extended configuration in which the partition extends out from the first post toward a second post at the foot of the bed. In an example, a movable acoustically-insulating and/or thermally-insulating partition can have a retracted configuration in which the partition is wrapped around, recessed within, folded onto, or held up against a headboard and an extended configuration in which the partition extends out toward the foot of the bed and is attached to a footboard.

In an example, a system can automatically move a partition from its retracted configuration to its extended configuration when one or more sensors detect snoring. In an example, a movable partition can be automatically moved from its retracted configuration to its extended configuration when one or more sensors detect or predict a hot flash or night sweat for one or both of people in a bed. In an example, a movable partition can be automatically moved from its retracted configuration to its extended configuration when one or more sensors (e.g. EEG sensors or motion sensors) detect that both people in a bed have fallen asleep. In an example, a system can be set to automatically move a partition from its retracted configuration to its extended configuration at a preset time. In an example, retraction or extension of a moveable partition can be activated directly by a person in the bed (e.g. via a remote control unit or cell phone application). In an example, a system may not have a sensor and a partition can be moved (e.g. pulled over the bed) manually by a person in the bed.

In an example, a system which creates a plurality of adjustable longitudinal acoustic and/or thermal zones in a bed can further include an electromagnetic motor which moves a partition from its retracted configuration to its extended configuration, or vice versa. In an example, an electromagnetic motor can be triggered by analysis of data from a sensor. In an example, an electromagnetic motor can be triggered by detection of snoring or a hot flash. In an example, an electromagnetic motor can be activated remotely by a person in the bed (e.g. via a remote control unit or cell phone application). In an example, a system which creates a plurality of adjustable longitudinal acoustic and/or thermal zones in a bed can include a data processing unit (e.g. which analyzes data from the sensor and controls the operation of an electromagnetic motor) and a wireless data transmitter/receiver. Design variations discussed elsewhere in this disclosure or in priority-linked disclosures can also be applied to this example where relevant.

FIGS. 99 through 102 show four views, at four different times, of an example of a device which creates a plurality of adjustable acoustic and/or thermal zones in a bed comprising: a headboard 9904; a movable acoustically-insulating and/or thermally-insulating partition with a retracted configuration (shown in FIG. 99) inside the headboard and an extended configuration (shown in FIG. 102) extending out from the headboard toward the foot 9905 of the bed, dividing the bed into a plurality of (e.g. two) longitudinal acoustic and/or thermal zones; wherein the partition further comprises a movable rod 9903 (e.g. rod, post, or arm) which is inside the headboard in the retracted configuration; wherein the partition further comprises folding sections 9902 which are folded within the headboard in the retracted configuration and unfold out from the headboard toward foot of the bed in the extended configuration; and one or more sensors (including sensor 9901), wherein the partition is automatically moved from its retracted configuration to its extended configuration in response to analysis of data from the one or more sensors.

Figure 99:
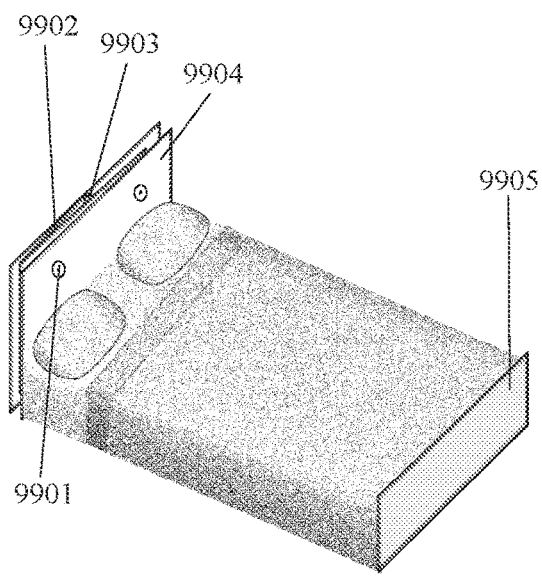
FIGS. 99 through 102 show a folding partition which rises up and swings out from a headboard to create acoustic zones in a bed.
Figure 100:
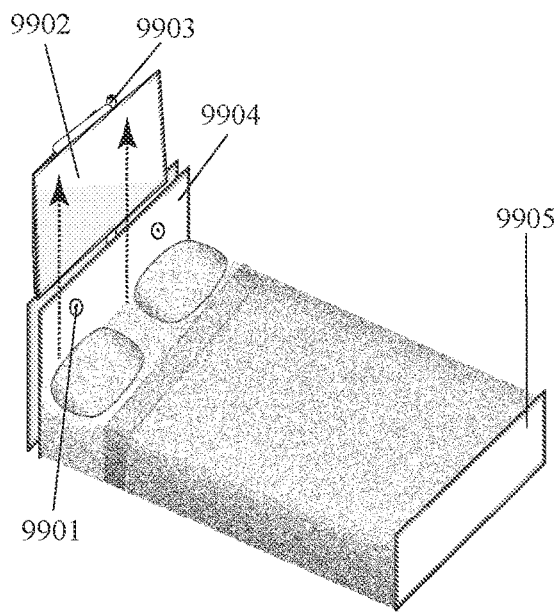
Figure 101:
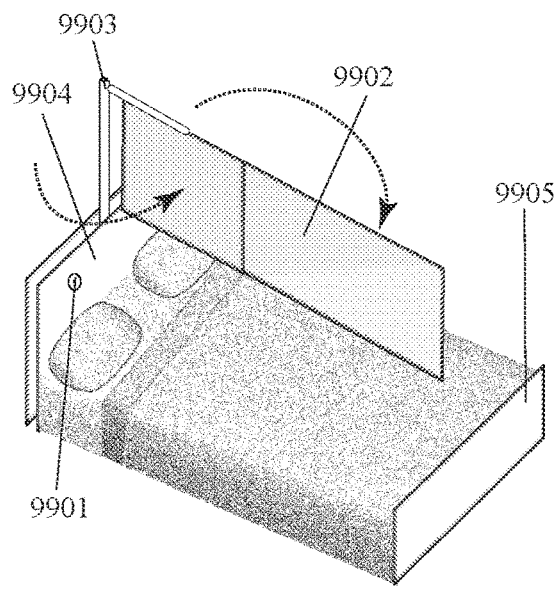
Figure 102:
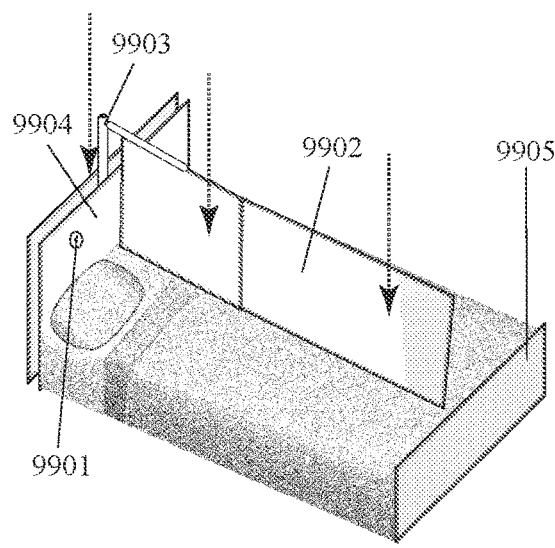

FIG. 99 shows the partition is in its retracted configuration, substantially hidden within a recess in the headboard. FIG. 100 shows the partition having been moved upward out of the headboard. FIG. 101 shows the rod having been rotated and the folding sections of the partition having been unfolded away from the headboard toward the foot of the bed. FIG. 102 shows the unfolded partition having been lowered onto the uppermost layer of bedding (e.g. a blanket, bed spread, quilt, or comforter on the bed). In an example, one or more of the folding sections of a partition can be attached to the rod. In an example, the rod can move up from a recess in a headboard as the partition moves from its retracted configuration to its extended configuration. In an example, a rod can move upward, rotate, and then move downward as a partition is moved from its retracted configuration to its extended configuration.

In an example, a partition can have two or more folding sections (e.g. panels). In an example, these two or more folding sections can be connected by one or more joints or hinges. In an example, folding sections (e.g. panels) of a movable partition can be substantially parallel to each other when the partition is in its retracted configuration and can be substantially co-planar when the partition is in its extended configuration. In an example, folding sections in a partition can be different sizes. In an example, one or more sections which are closer to the headboard when the partition is in its extended configuration can be smaller than one or more sections which are farther from the headboard.

In an example, a device can automatically move a partition from its retracted configuration to its extended configuration when one or more sensors detect or predict snoring, a hot flash, or a night sweat. In an example, a movable partition can be automatically moved when one or more sensors (e.g. EEG sensors or motion sensors) detect that people in a bed have fallen asleep. In an example, a device can automatically move a partition at a preset time. In an example, retraction or extension of a partition can be activated directly by a person in the bed (e.g. via a remote control unit or cell phone application). In an example, a device may not have a sensor and a partition can be moved manually by a person in the bed.

In an example, a device which creates a plurality of adjustable longitudinal acoustic and/or thermal zones in a bed can further include an electromagnetic motor which moves a partition from its retracted configuration to its extended configuration, or vice versa. In an example, an electromagnetic motor can be triggered by analysis of data from a sensor. In an example, an electromagnetic motor can be triggered by detection of snoring or a hot flash. In an example, an electromagnetic motor can be activated remotely by a person in the bed (e.g. via a remote control unit or cell phone application). In an example, a device or system can further comprise a data processing unit (e.g. which analyzes data from the sensor and controls the operation of an electromagnetic motor) and a wireless data transmitter/receiver. Design variations discussed elsewhere in this disclosure or in priority-linked disclosures can also be applied to this example where relevant.

FIGS. 103 through 106 show four views, at four different times, of an example of a device which creates a plurality of adjustable acoustic and/or thermal zones in a bed comprising: a headboard 10303; a movable acoustically-insulating and/or thermally-insulating partition with a retracted configuration (shown in FIG. 103) inside the headboard and an extended configuration (shown in FIG. 106) extending out from the headboard toward the foot 10304 of the bed, dividing the bed into a plurality of (e.g. two) longitudinal acoustic and/or thermal zones; wherein the partition further comprises a plurality of sections, including 10302 and 10601, which are telescoped, folded, and/or deflated within the headboard in the retracted configuration and extended, unfolded, and/or inflated outward from the headboard toward foot of the bed in the extended configuration; and one or more sensors (including sensor 10301), wherein the partition is automatically moved from its retracted configuration to its extended configuration in response to analysis of data from the one or more sensors.

Figure 103:
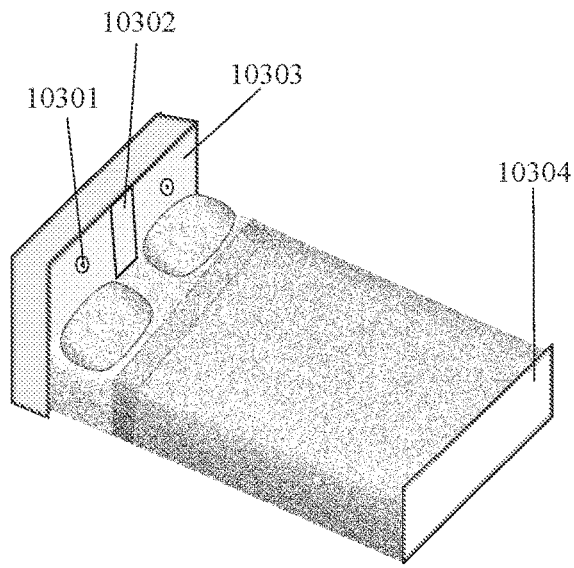
FIGS. 103 through 106 show a longitudinally-extending partition which folds out from a headboard to create acoustic zones in a bed.
Figure 104:
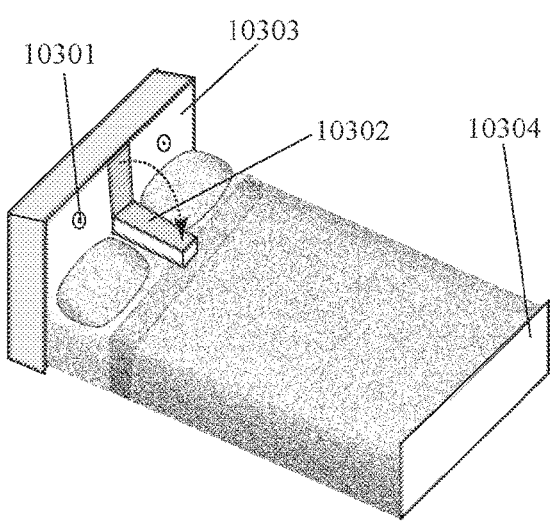
Figure 105:
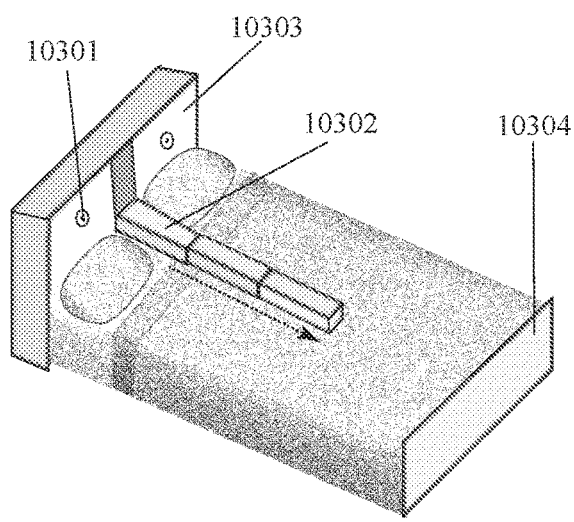
Figure 106:
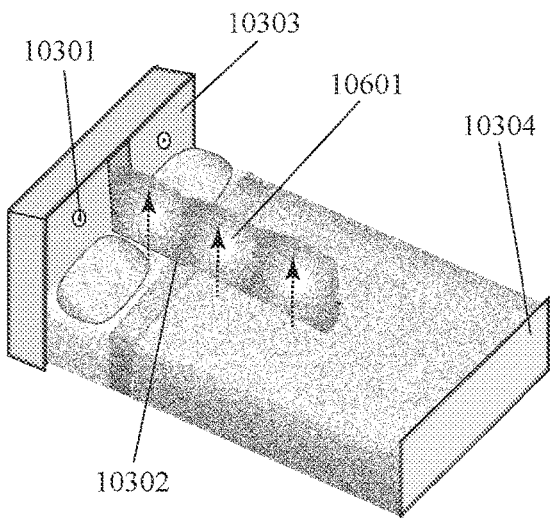

FIG. 103 shows a partition in its retracted configuration, hidden within a recess in a headboard. FIG. 104 shows the partition having been pivoted out from the recess in the headboard. FIG. 105 shows multiple sections of the partition having been extended (e.g. telescoped) away from the headboard toward the foot of the bed. FIG. 106 shows multiple sections of the partition having been inflated upwards, thereby separating the bed into two longitudinal acoustic and/or thermal zones.

In an example, a device can further include an electromagnetic motor and/or air pump which move a partition from its retracted configuration to its extended configuration, or vice versa. In an example, an electromagnetic motor and/or air pump can be triggered by analysis of data from a sensor. In an example, an electromagnetic motor and/or air pump can be triggered by detection of snoring or a hot flash. In an example, an electromagnetic motor and/or air pump can be activated remotely by a person in the bed (e.g. via a remote control unit or cell phone application). In an example, a device or system can further comprise a data processing unit (e.g. which analyzes data from the sensor and controls the operation of an electromagnetic motor and/or air pump) and a wireless data transmitter/receiver. Design variations discussed elsewhere in this disclosure or in priority-linked disclosures can also be applied to this example where relevant.

Figure 107:
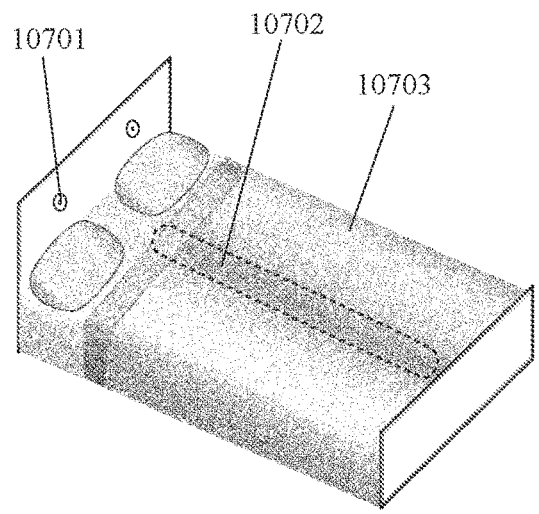
FIGS. 107 and 108 show a bed covering with a vertically-inflatable central portion that creates acoustic zones in a bed.
Figure 108:
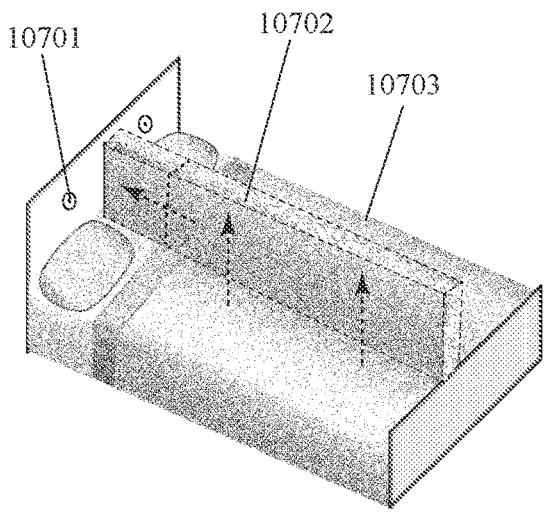

FIGS. 107 and 108 show two views, at two different times, of an example of a device which creates a plurality of adjustable acoustic and/or thermal zones in a bed comprising: a bed covering 10703 (e.g. blanket, bed spread, quilt, or comforter) with a central longitudinal inflatable section 10702; wherein the inflatable section has a lowered configuration (shown in FIG. 107) which is substantially flat with the surface of the bed and a raised configuration (shown in FIG. 108) which extends upward from the surface of the bed thereby dividing the bed into a plurality of (e.g. two) longitudinal acoustic and/or thermal zones; and one or more sensors (including sensor 10701), wherein the inflatable section is automatically inflated from its lowered configuration to its raised configuration in response to analysis of data from the one or more sensors.

In an example, an inflatable section can further comprise an inflatable chamber within a fabric pocket or compartment. In an example, an inflatable section can have an extension which spans the gap from a bed covering to a headboard when the inflatable section is inflated. In an example, an inflatable section can have an extension which unfolds to span the gap from a bed covering to a headboard when the inflatable section is inflated. In an example, a device can further include an air pump. In an example, an air pump can be triggered by analysis of data from a sensor. In an example, an air pump can be triggered by detection of snoring or a hot flash. In an example, an air pump can be activated directly by a person in the bed via a remote control unit or a cell phone application. In an example, a device or system can further comprise a data processing unit and a wireless data transmitter/receiver. Design variations discussed elsewhere in this disclosure or in priority-linked disclosures can also be applied to this example where relevant.

Figure 109:
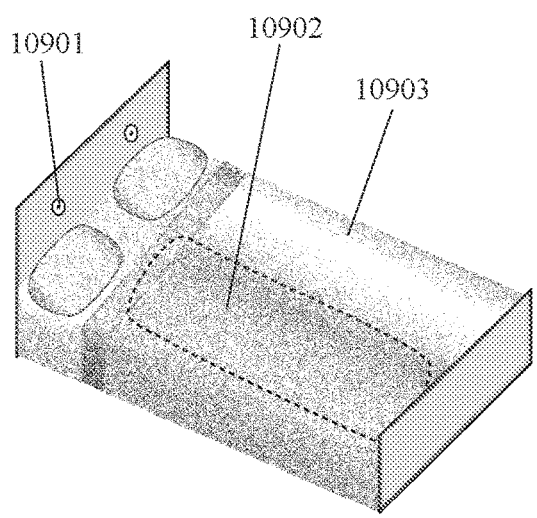
FIGS. 109 and 110 show a bed covering with a flip-up-inflatable central portion that creates acoustic zones in a bed.
Figure 110:
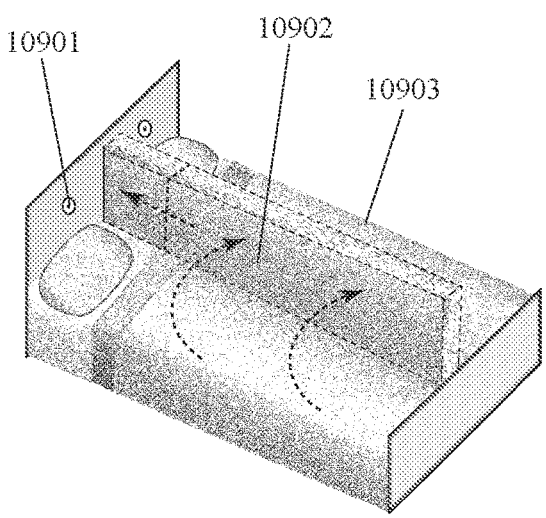

FIGS. 109 and 110 show two views, at two different times, of an example of a device which creates a plurality of adjustable acoustic and/or thermal zones in a bed comprising: a bed covering 10903 (e.g. blanket, bed spread, quilt, or comforter) with a longitudinal inflatable section 10902; wherein the inflatable section has a lowered configuration (shown in FIG. 109) which is substantially flat on one side of the bed and a raised configuration (shown in FIG. 110) which extends upward from the longitudinal axis of the bed thereby dividing the bed into a plurality of (e.g. two) longitudinal acoustic and/or thermal zones; and one or more sensors (including sensor 10901), wherein the inflatable section is automatically inflated from its lowered configuration to its raised configuration in response to analysis of data from the one or more sensors.

In an example, an inflatable section can further comprise an inflatable chamber within a fabric pocket or compartment. In an example, an inflatable section can have an extension which spans the gap from a bed covering to a headboard when the inflatable section is inflated. In an example, an inflatable section can have an extension which unfolds to span the gap from a bed covering to a headboard when the inflatable section is inflated. In an example, a device can further include an air pump. In an example, an air pump can be triggered by analysis of data from a sensor. In an example, an air pump can be triggered by detection of snoring or a hot flash. In an example, an air pump can be activated directly by a person in the bed via a remote control unit or a cell phone application. In an example, a device or system can further comprise a data processing unit and a wireless data transmitter/receiver. Design variations discussed elsewhere in this disclosure or in priority-linked disclosures can also be applied to this example where relevant.

Figure 111:
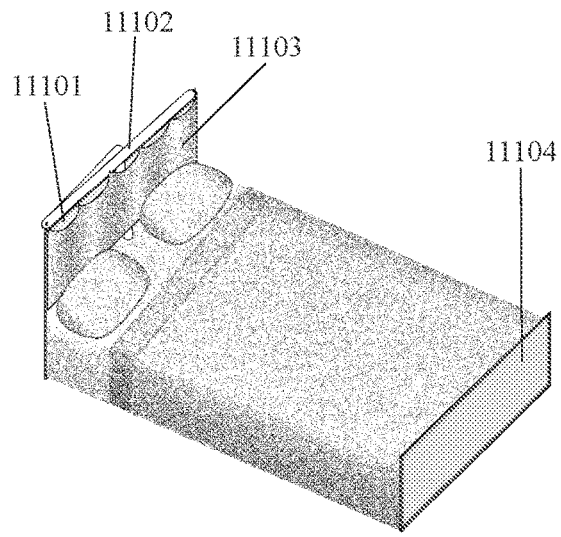
FIGS. 111 and 112 show a folding partition which swings out from a headboard to create acoustic zones in a bed.
Figure 112:
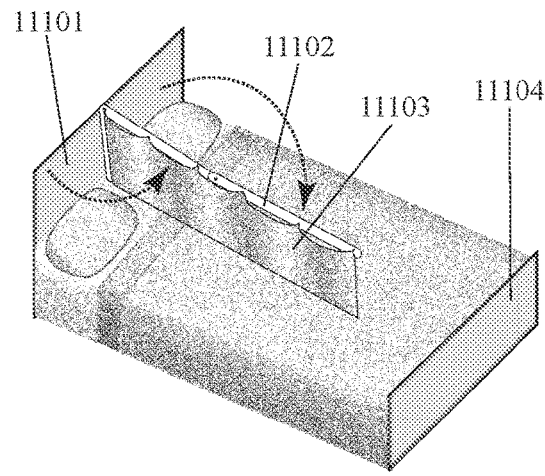

FIGS. 111 and 112 show two views, at two different times, of an example of a device which creates a plurality of adjustable acoustic and/or thermal zones in a bed comprising: a headboard 11101; and a movable partition, wherein the movable partition further comprises a folding arm 11102 and a curtain 11103 attached to the folding arm, wherein the movable partition has a retracted configuration which is substantially aligned with the headboard and an extended configuration which extends out from the headboard toward the foot of the bed, thereby dividing the bed into a plurality of (e.g. two) longitudinal acoustic and/or thermal zones. In an example, the partition can span the central longitudinal axis of the bed. In an example, a partition can comprise a plurality of folding panels which are attached to the folding arm, instead of a curtain. Design variations discussed elsewhere in this disclosure or in priority-linked disclosures can also be applied to this example where relevant.

Figure 113:
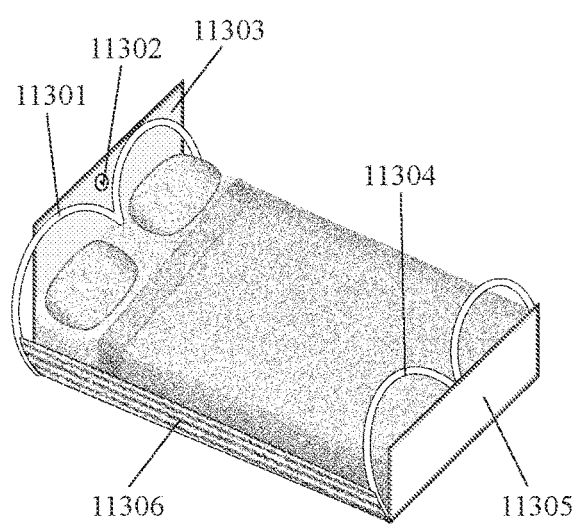
FIGS. 113 and 114 show movable partitions, attached to arches at the head and foot of a bed, that create acoustic zones in the bed.
Figure 114:
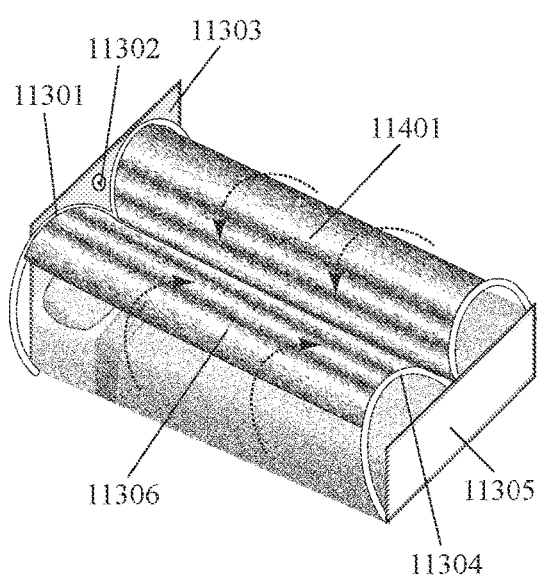

FIGS. 113 and 114 show two views, at two different times, of an example of a device which creates a plurality of adjustable acoustic and/or thermal zones in a bed comprising: a first set of one or more lateral arches (or ribs) (including 11301) at the head 11303 of a bed; a second set of one or more lateral arches (or ribs) (including 11304) at the foot 11305 of the bed; one or more flexible movable partitions (11306 and 11401), each of which longitudinally spans the bed from an arch (or rib) in the first set to an arch (or rib) in the second set; wherein a movable partition has a first configuration (shown in FIG. 113) which is down along the side of the bed and a second configuration (shown in FIG. 114) which is above the upper surface of the bed (e.g. above a blanket, bed spread, quilt, or comforter) thereby dividing the bed into a plurality of (e.g. two) longitudinal acoustic and/or thermal zones; and one or more sensors 11302, wherein a movable partition is automatically moved from its first configuration to its second configuration in response to analysis of data from the one or more sensors.

In an example, one end of a movable partition can be connected to an arch (or rib) in the first set of arches (or ribs) and the other end of the movable partition can be connected to an arch (or rib) in the second set of arches (or ribs). In an example, the ends of a movable partition can slide along (a track in) an arch (or rib) as the partition is moved from its first configuration to its second configuration, or vice versa. In an example, a partition in its second configuration can span from the central longitudinal axis of a bed to a space above one side of the bed. In an example, a partition in its second configuration can have a shape which is a section of a cylinder. In an example, a partition in its second configuration can have a shape which is a quarter of a cylinder. In an example, a partition in its second configuration can have a shape which between a quarter and a half of a cylinder.

In an example, a device can further include an electromagnetic motor which moves a partition from its first configuration to its second configuration, or vice versa. In an example, an electromagnetic motor can be triggered by analysis of data from a sensor. In an example, an electromagnetic motor can be triggered by detection of snoring or a hot flash. In an example, an electromagnetic motor can be activated directly by a person in the bed via a remote control unit or a cell phone application. In an example, a device or system can further comprise a data processing unit (e.g. which analyzes data from the sensor and controls the operation of an electromagnetic motor) and a wireless data transmitter/receiver. Design variations discussed elsewhere in this disclosure or in priority-linked disclosures can also be applied to this example where relevant.

Figure 115:
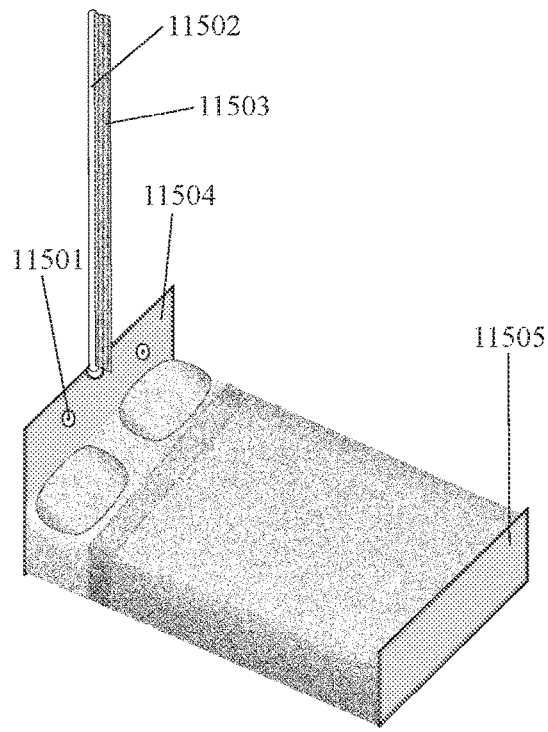
FIGS. 115 and 116 show a petition which pivots down from the head of a bed to create acoustic zones in the bed.
Figure 116:
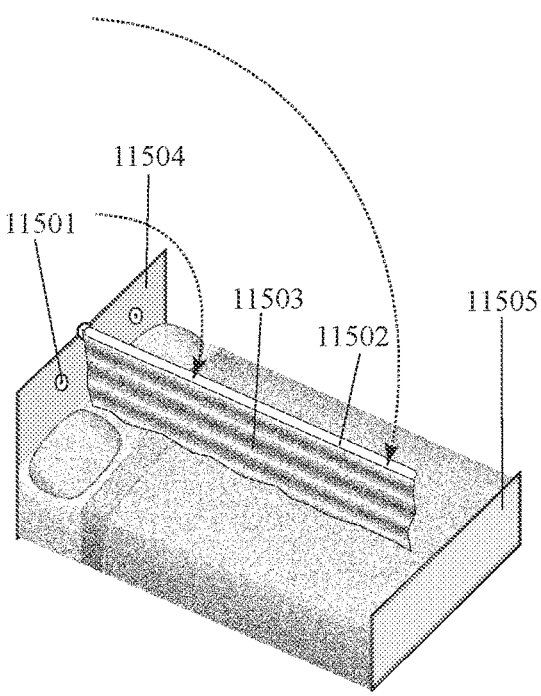

FIGS. 115 and 116 show two views, at two different times, of an example of a device which creates a plurality of adjustable acoustic and/or thermal zones in a bed comprising: a movable rod 11502 whose base is at the head 11504 of a bed; a flexible longitudinal partition 11503 which is attached to the rod; wherein the rod and partition have a first configuration (shown in FIG. 115) in which the rod and a longitudinal axis of the partition are substantially vertical and a second configuration (shown in FIG. 116) in which the rod and a longitudinal axis of the partition are substantially horizontal, extending away from the head of the bed toward the foot 11505 of the bed and the partition divides the bed into a plurality of (e.g. two) longitudinal acoustic and/or thermal zones; and one or more sensors (including 11501), wherein the rod and partition are automatically moved from their first configuration to their second configuration in response to analysis of data from the one or more sensors.

In an example, the top of a rod can pivot around the base of the rod (at the head of the bed), moving toward the foot of the bed as the rod and partition are moved from their first configuration to their second configuration. In an example, a rod can be moved from its first configuration to its second configuration, or vice versa, by an electromagnetic motor. In an example, in its first configuration, a rod can extend between 2 and 6 feet above the head and/or headboard of a bed. In an example, the base of a rod can be attached to a headboard. In an example, the base of a rod can be attached to a bed frame. In an example, the base of a rod can be inserted between a mattress and a box spring at the head of a bed. In an example, a partition attached to a rod can have pleats which fold or unfold (e.g. like an accordion or bellows) as the partition changes configuration. In an example, in its second configuration, a partition attached to a rod can hang down from a rod like a curtain.

In an example, an electromagnetic motor can be triggered to move a rod and partition by analysis of data from a sensor. In an example, an electromagnetic motor can be triggered to move a rod and partition by detection of snoring or a hot flash. In an example, an electromagnetic motor can be activated directly by a person in the bed via a remote control unit or a cell phone application. In an example, a device or system can further comprise a data processing unit (e.g. which analyzes data from the sensor and controls the operation of an electromagnetic motor) and a wireless data transmitter/receiver. Design variations discussed elsewhere in this disclosure or in priority-linked disclosures can also be applied to this example where relevant.

Figure 117:
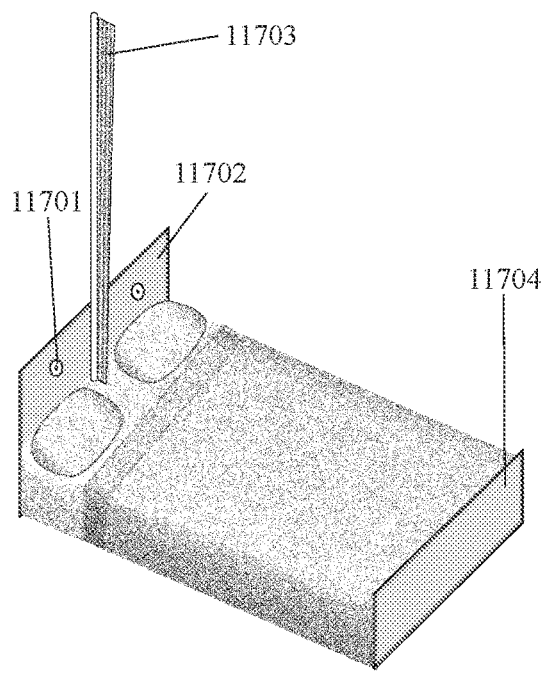
FIGS. 117 and 118 show a fan-shaped petition which extends downward from the head of a bed to create acoustic zones in the bed.
Figure 118:
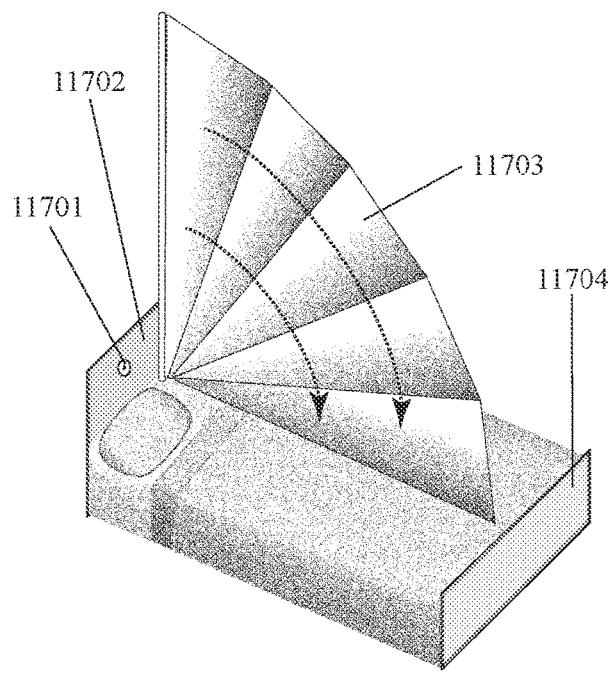

FIGS. 117 and 118 show two views, at two different times, of an example of a device which creates a plurality of adjustable acoustic and/or thermal zones in a bed comprising: a pleated partition 11703 whose base is attached to the head 11702 of a bed, wherein the partition has a first configuration (shown in FIG. 117) in which the partition is folded and substantially-vertical and a second configuration (shown in FIG. 118) in which the partition is unfolded like a handheld-fan, with a side of the partition extending downward and toward the foot 11704 of the bed, thereby dividing the bed into a plurality of (e.g. two) longitudinal acoustic and/or thermal zones; and one or more sensors (including 11701), wherein the partition is automatically moved from its first configuration to its second configuration in response to analysis of data from the one or more sensors.

In an example, a partition can be moved from its first configuration to its second configuration, or vice versa, by an electromagnetic motor. In an example, in its first configuration, a partition can extend between 2 and 6 feet above the head and/or headboard of a bed. In an example, the base of a partition can be attached to a headboard, attached to a bed frame, or inserted between a mattress and a box spring at the head of a bed. In an example, a partition can unfold like a handheld fan, an accordion, or a bellows as it changes into its second configuration. In an example, the perimeter of a partition can have a quarter-disk shape when the partition is in its second configuration. In an example, both sides of a partition can be substantially-vertical in the partition's first configuration. In an example, one side of a partition can remain substantially-vertical and the other side of the partition can become substantially-horizontal in the partition's second configuration.

In an example, an electromagnetic motor can be triggered to move a partition by analysis of data from a sensor. In an example, an electromagnetic motor can be triggered to move a partition by detection of snoring or a hot flash. In an example, an electromagnetic motor can be activated directly by a person in the bed via a remote control unit or a cell phone application. In an example, a device or system can further comprise a data processing unit (e.g. which analyzes data from the sensor and controls the operation of an electromagnetic motor) and a wireless data transmitter/receiver. Design variations discussed elsewhere in this disclosure or in priority-linked disclosures can also be applied to this example where relevant.

Figure 119:
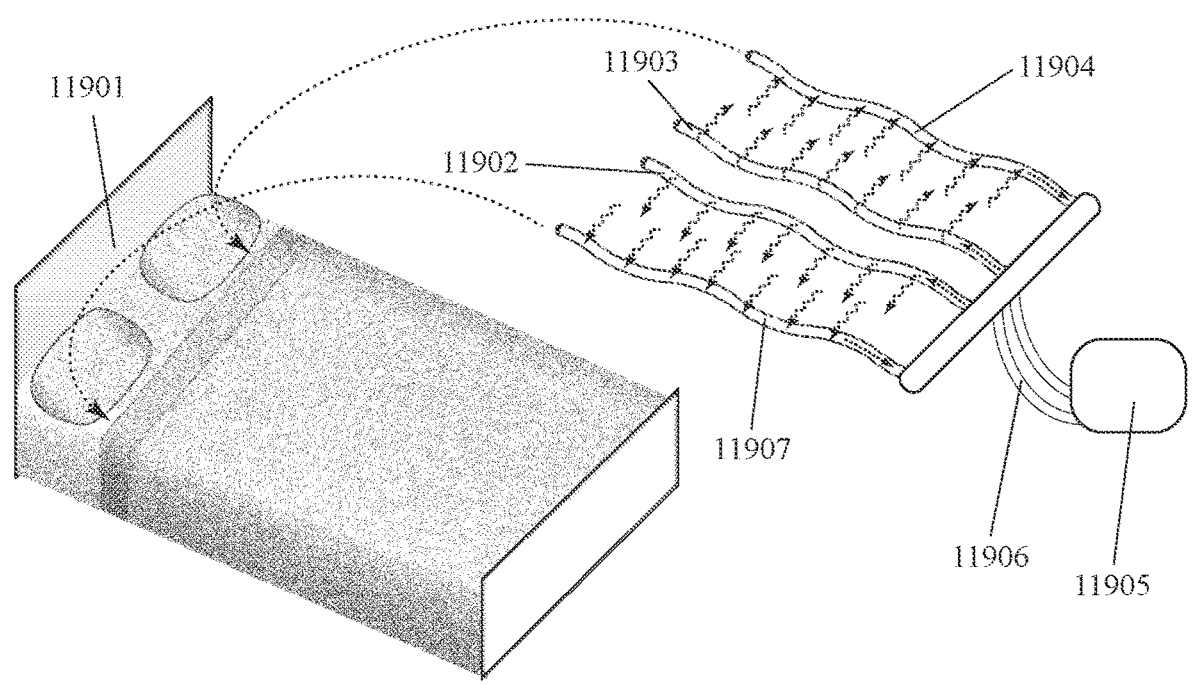
FIGS. 119 and 120 show a device with two sets of flexible longitudinal air tubes, for air outflow and inflow, that are inserted between bedding layers to create thermal zones in a bed.
Figure 120:
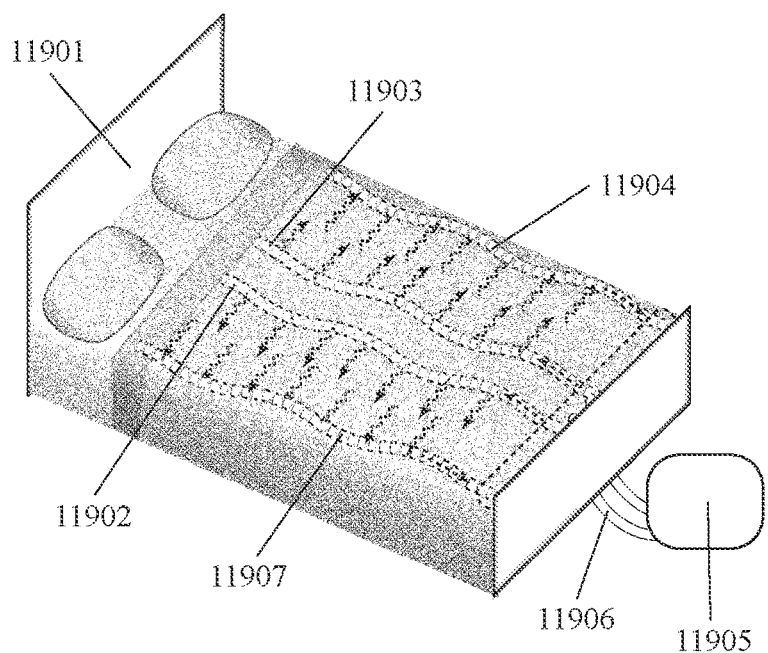

FIGS. 119 and 120 show two views of an example of a device which creates a plurality of adjustable thermal zones in a bed comprising: an air-conditioning unit 11905 which cools and/or heats air; a first set of flexible longitudinal air tubes (11902 and 11903) which are inserted into a space between two layers of bedding in a bed 11901 (e.g. into the space wherein a person sleeps between a lower sheet and an upper sheet), wherein air tubes in the first set have holes, wherein air tubes in the first set deliver air into the space through the holes, and wherein this delivered air comes from the air-conditioning unit; and a second set of flexible longitudinal air tubes (11904 and 11907) which are inserted into the space, wherein air tubes in the second set have holes, wherein air tubes in the second set draw air out from the space through the holes, and wherein this drawn air goes to the air-conditioning unit. In an example, there can also be one or more air channels, such as 11906, between the air tubes and the air-conditioning unit. The right side of FIG. 119 shows this device before it has been inserted into a bed (shown on the left side of FIG. 119). FIG. 120 shows this device after it has been inserted into the bed.

In an example, an air tube can be flexible, longitudinal, and compressible. In an example, an air tube can be similar in appearance and shape to a "pool noodle"—which is a longitudinal foam toy and/or flotation device used in swimming pools. Accordingly, this product may be branded as the "Cool Noodle™" system. In an example, an air tube can be made with a material which has a low durometer and/or Shore value. In an example, an air tube can be made with a material which has a durometer and/or Shore value between 10 and 40. In an example, an air tube can be made with a material which has a durometer and/or Shore value between 20 and 60. In an example, an air tube can have a hollow interior through which air flows and a soft, compressible outer layer. In an example, an air tube can have an air-impermeable central core (air impermeable apart from the holes through which air can flow) and a soft, air-permeable foam and/or fabric outer layer. Since the air tubes are flexible, a person can adjust which portions of their body are cooled or warmed by moving air tubes closer to, or farther from, different portions of their body. Since the air tubes are soft and compressible, they are not uncomfortable in close proximity to, or even contact with, a person's body.

In an example, an air tube can have a generally circular cross-sectional shape. In an example, an air tube can have an elliptical or oval cross-sectional shape. In an example, an air tube can have a circumference which is between 2 and 8 inches. In an example, an air tube can have a circumference which is between 4 and 10 inches. In an example, an air tube can have a length which is between 3 and 7 feet. In an example, air tubes can extend from the foot of a bed to the "top" portion of an upper sheet or blanket (wherein "top" means closest to the head of the bed). In an example, an air tube can have an undulating and/or sinusoidal longitudinal shape. As shown in FIG. 120, an air tube can be in fluid communication with an air-conditioning unit through connections at the foot of a bed.

In an example, there can be four flexible longitudinal air tubes in a bed. In an example, on each side (e.g. right side and left side) of a bed, there can be one air inflow tube (which delivers air into a space between bedding layers) and one air outflow tube (which draws air out from that space). This can create two different, adjustable, thermal zones in a bed. In an example, there can be a pair of air tubes (one for air inflow and one for air outflow) on each side (e.g. right side and left side) of a bed. In an example, inflow and outflow tubes in a pair of air tubes can be between 2 and 5 feet apart from each other. In an example, inflow and outflow tubes in a pair of air tubes can be between 2 and 5 feet apart from each other at the foot of the bed. In an example, inflow and outflow air tubes on one side of a bed can be substantially parallel to each other.

In an example, the circumference of an air channel inside an air tube can vary along the length of the air tube. In an example, the circumference of an air channel inside an air tube can be larger in a portion of the air tube which is closer to the foot of a bed than in a portion of the air tube which is farther from the foot of the bed. In an example, the size of holes and/or the spacing between holes in an air tube can vary along the length of the air tube. In an example, the size of holes in an air tube can be smaller and/or the spacing between holes can be greater in a portion of the air tube which is closer to the foot of a bed than in a portion of the air tube which is farther from the foot of the bed. In an example, the distribution of holes around the cross-sectional circumference of an air tube can be non-uniform for better thermal isolation of different zones in a bed. For example, holes in an air tube through which air is delivered into a space between bedding layers can be along just one side of the air tube.

In an example, air tubes can be inserted into a space where a person sleeps, such as between a lower sheet (e.g. "bottom sheet") and an upper sheet (e.g. "top sheet"). This location enables a person to easily move the air tubes closer to, or father way from, selected portions of their body to adjust the degree and location of body cooling or warming. For example, if a person's feet are cold, but their torso is warm, then the person can move air tubes delivering warm air close to their feet (or move their feet close to the air tubes) and move air tubes away from their torso (or move their torso away from the air tubes). Similarly, if a person's feet are cold, but their torso is warm, then the person can move air tubes delivering cool air close to their torso (or move their torso close to the air tubes) and move air tubes away from their feet (or move their feet away from the air tubes). This enables convenient and locationally-precise body warming or cooling. Alternatively, air tubes can be inserted into a bedding layer above the space where a person sleeps. For example, air tubes can be inserted between an upper sheet and a blanket above that sheet. Although this latter location may make it harder for a person to move the air tubes, it may give them greater freedom of movement between the sheets.

In an example, this device can change air qualities other than just air temperature. In an example, this device can also dehumidify (or humidify) air which circulates through the air tubes and the space between bedding layers. In an example, this device can purify air which circulates through the air tubes and the space between bedding layers, such as by filtering air which passes through the air conditioner. In an example, an air conditioning unit can further comprise an air impellor (e.g. a fan) and a heat exchanger.

In an example, this device can further comprise a sensor, wherein air is circulated through the air conditioner and the space between bedding layers in response to analysis of data from the sensor. In an example, a sensor can be a temperature sensor or humidity sensor. In an example, a sensor can be a wearable sensor. In an example, cooling air circulation can be triggered when a hot flash or night sweat is detected or predicted by a wearable sensor. In an example, a device or system can further comprise a data processing unit (e.g. which analyzes data from the sensor and controls the operation of the air conditioning unit) and a wireless data transmitter/receiver. Design variations discussed elsewhere in this disclosure or in priority-linked disclosures can also be applied to this example where relevant.

Figure 121:
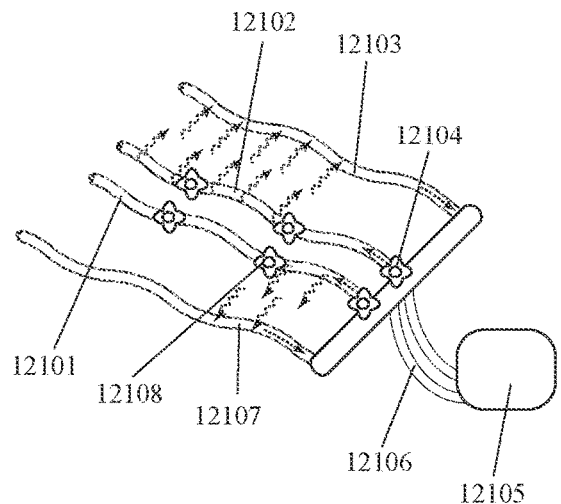
FIGS. 121 and 122 show a device with two sets of flexible longitudinal air tubes and manually-adjustable air valves that create thermal zones in a bed.
Figure 122:
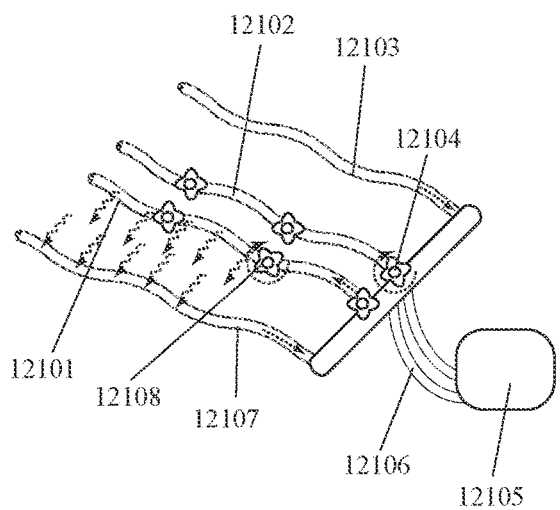

FIGS. 121 and 122 show two views of an example of a device which creates a plurality of adjustable thermal zones in a bed comprising: an air-conditioning unit 12105 which cools and/or heats air; a first set of flexible longitudinal air tubes (12101 and 12102) which are inserted into a space between two layers of bedding in a bed (e.g. into the space wherein a person sleeps between a lower sheet and an upper sheet), wherein air tubes in the first set have holes, wherein air tubes in the first set deliver air into the space through the holes, and wherein this delivered air comes from the air-conditioning unit; a second set of flexible longitudinal air tubes (12103 and 12107) which are inserted into the space, wherein air tubes in the second set have holes, wherein air tubes in the second set draw air out from the space through the holes, and wherein this drawn air goes to the air-conditioning unit; and a plurality of manually-adjustable air valves (including 12104 and 12108) which control the flow of air through air tubes in the first set of air tubes. In an example, there can also be one or more air channels, such as 12106, between the air tubes and the air-conditioning unit.

FIG. 121 shows this device when a plurality of manually-adjustable air valves are in a first configuration, causing air flow through a first array of locations within the bed. FIG. 122 shows this device when the plurality of manually-adjustable air valves have been manually adjusted into a second configuration, thereby causing air flow through a second array of locations within the bed. In an example, a person in bed change manually adjust one or more valves and thus change the pattern of air circulation near their body. In an example, air valves can be adjusted (e.g. opened or closed) by being manually turned and/or rotated. In an example, a person in a bed can change which portions of their body are cooled and/or warmed by manually adjusting different valves on air tubes near their body. This can enable relatively precise cooling and warming of selected portions of the person's body. In an example, a caregiver can selectively adjust valves on air tubes to selectively provide greater air circulation over (or near) portions of a bedridden person's body which are at risk for forming bed ulcers. In an example, there can also be a plurality of air valves which control the flow of air through air tubes in the second set of air tubes.

In an example, this device can further comprise a sensor, wherein air is circulated through the air conditioner and the space between bedding layers in response to analysis of data from the sensor. In an example, a sensor can be a temperature sensor or humidity sensor. In an example, a sensor can be a wearable sensor. In an example, cooling air circulation can be triggered when a hot flash or night sweat is detected or predicted by a wearable sensor. In an example, a device or system can further comprise a data processing unit (e.g. which analyzes data from the sensor and controls the operation of the air conditioning unit) and a wireless data transmitter/receiver. Design variations discussed elsewhere in this disclosure or in priority-linked disclosures can also be applied to this example where relevant.

Figure 123:
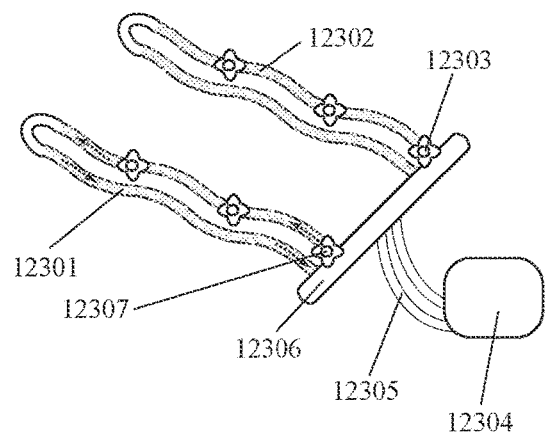
FIGS. 123 and 124 show a device with flexible longitudinal fluid flow loops and manually-adjustable fluid flow valves that create thermal zones in a bed.
Figure 124:
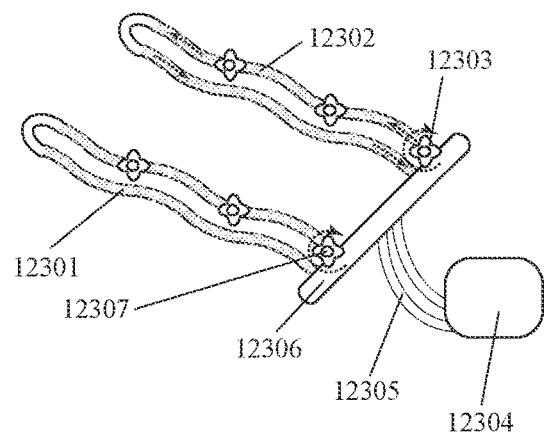

FIGS. 123 and 124 show two views of an example of a device which creates a plurality of adjustable thermal zones in a bed comprising: a fluid cooling and/or heating unit 12304 which cools and/or heats fluid (e.g. water); a first flexible longitudinal fluid tube loop 12301 which is inserted into a space between two layers of bedding in a bed (e.g. into the space wherein a person sleeps between a lower sheet and an upper sheet), wherein fluid which has been cooled and/or heating by the cooling and/or heating unit flows through the first flexible longitudinal fluid tube loop; a second flexible longitudinal fluid tube loop 12302 which is inserted into the space, wherein fluid which has been cooled and/or heating by the cooling and/or heating unit flows through the first flexible longitudinal fluid tube loop; and a plurality of manually-adjustable fluid valves (including 12303 and 12307) which control the flow of fluid through the fluid tube loops. In an example, there can also be one or more fluid channels, such as 12305 and 12306, between the fluid tube loops and the fluid cooling and/or heating unit.

FIG. 123 shows this device when a plurality of manually-adjustable fluid valves are in a first configuration, causing fluid flow through a first set (or subset) of loops (or portions of loops) within the bed. FIG. 124 shows this device when the plurality of manually-adjustable fluid valves have been manually adjusted into a second configuration, thereby causing fluid flow through a second set (or subset) of loops (or portions of loops) within the bed. In an example, a person in bed can manually adjust one or more valves and thus change the pattern of fluid circulation near their body. In an example, fluid valves can be adjusted by being manually turned and/or rotated. In an example, a person in a bed can change which portions of their body are cooled and/or warmed by manually adjusting different valves on fluid tubes near their body. This can enable relatively precise cooling and warming of selected portions of the person's body. In an example, the circulating fluid can be water.

In an example, a fluid tube loop can be flexible, longitudinal, and compressible. In an example, a fluid tube loop can be made with a material which has a low durometer and/or Shore value. In an example, a fluid tube loop can be made with a material which has a durometer and/or Shore value between 10 and 40. In an example, a fluid tube loop can be made with a material which has a durometer and/or Shore value between 20 and 60. In an example, a fluid tube loop can have a hollow interior through which fluid flows and a soft, compressible outer layer. In an example, a fluid tube loop can have a fluid-impermeable central core and a soft foam and/or fabric outer layer. Since the fluid tube loops are flexible, a person can adjust which portions of their body are cooled or warmed by moving fluid tube loops closer to, or farther from, different portions of their body. Since the fluid tube loops are soft and compressible, they are not uncomfortable in close proximity to, or even contact with, a person's body.

In an example, a tube in a fluid tube loop can have a generally circular cross-sectional shape. In an example, a tube in a fluid tube loop can have an elliptical or oval cross-sectional shape. In an example, a tube in a fluid tube loop can have a circumference which is between 3 and 7 inches. In an example, a tube in a fluid tube loop can have a circumference which is between 5 and 10 inches. In an example, a fluid tube loop can have a length which is between 3 and 7 feet. In an example, fluid tube loops can extend from the foot of a bed to the "top" portion of an upper sheet or blanket (wherein "top" means closest to the head of the bed). In an example, a fluid tube loop can have an undulating and/or sinusoidal longitudinal shape. In an example, there can be two or four flexible longitudinal fluid tube loops in a bed. In an example, on each side (e.g. right side and left side) of a bed, there can be one or two fluid inflow tube loops. This can create two different, adjustable, thermal zones in a bed. As show in FIG. 124, a fluid tube loop can be in fluid communication with a fluid cooling and/or heating unit through connections at the foot of a bed.

In an example, fluid tube loops can be inserted into a space where a person sleeps, such as between a lower sheet (e.g. "bottom sheet") and an upper sheet (e.g. "top sheet"). This location enables a person to easily move the fluid tube loops closer to, or father way from, selected portions of their body to adjust the degree and location of body cooling or warming. For example, if a person's feet are cold, but their torso is warm, then the person can move warm fluid tube loops close to their feet (or move their feet close to them) and move them away from their torso (or move their torso away from them). Similarly, if a person's feet are cold, but their torso is warm, then the person can move cooling tube loops close to their torso (or move their torso close to them) and move them away from their feet (or move their feet away from them). This enables convenient and locationally-precise body warming or cooling. Alternatively, fluid tube loops can be inserted into a bedding layer above the space where a person sleeps. For example, fluid tube loops can be inserted between an upper sheet and a blanket above that sheet. Although this latter location may make it harder for a person to move the fluid tube loops, it may give them greater freedom of movement between the sheets.

In an example, this device can further comprise a sensor, wherein fluid is circulated through the fluid cooling and/or heating unit and through the loops in response to analysis of data from the sensor. In an example, a sensor can be a temperature sensor or humidity sensor. In an example, a sensor can be a wearable sensor. In an example, cooling fluid circulation can be triggered when a hot flash or night sweat is detected or predicted by a wearable sensor. In an example, a device or system can further comprise a data processing unit (e.g. which analyzes data from the sensor and controls the operation of the fluid cooling and/or heating unit) and a wireless data transmitter/receiver. Design variations discussed elsewhere in this disclosure or in priority-linked disclosures can also be applied to this example where relevant.

In an variation on this example, a device can comprise air tube loops which circulate air instead of fluid tube loops which circulate fluid. In an example, a device which creates a plurality of adjustable thermal zones in a bed can comprise: an air-conditioning unit which cools and/or heats air; a first flexible longitudinal air tube loop which is inserted into a space between two layers of bedding in a bed (e.g. into the space wherein a person sleeps between a lower sheet and an upper sheet), wherein the first flexible longitudinal air tube loop has a first set of holes through which air from the air-conditioning unit is delivered into the space and a second set of holes through which air is drawn out from the space toward the air-conditioning unit; a second flexible longitudinal air tube loop which is inserted into the space, wherein the second flexible longitudinal air tube loop has a third set of holes through which air from the air-conditioning unit is delivered into the space and a fourth set of holes through which air is drawn out from the space toward the air-conditioning unit; and a plurality of manually-adjustable air valves which control the flow of air through the air tube loops. In an example, there can also be one or more air channels between the air tube loops and the air-conditioning unit. Design variations discussed elsewhere in this disclosure or in priority-linked disclosures can also be applied to this example where relevant.

Figure 125:
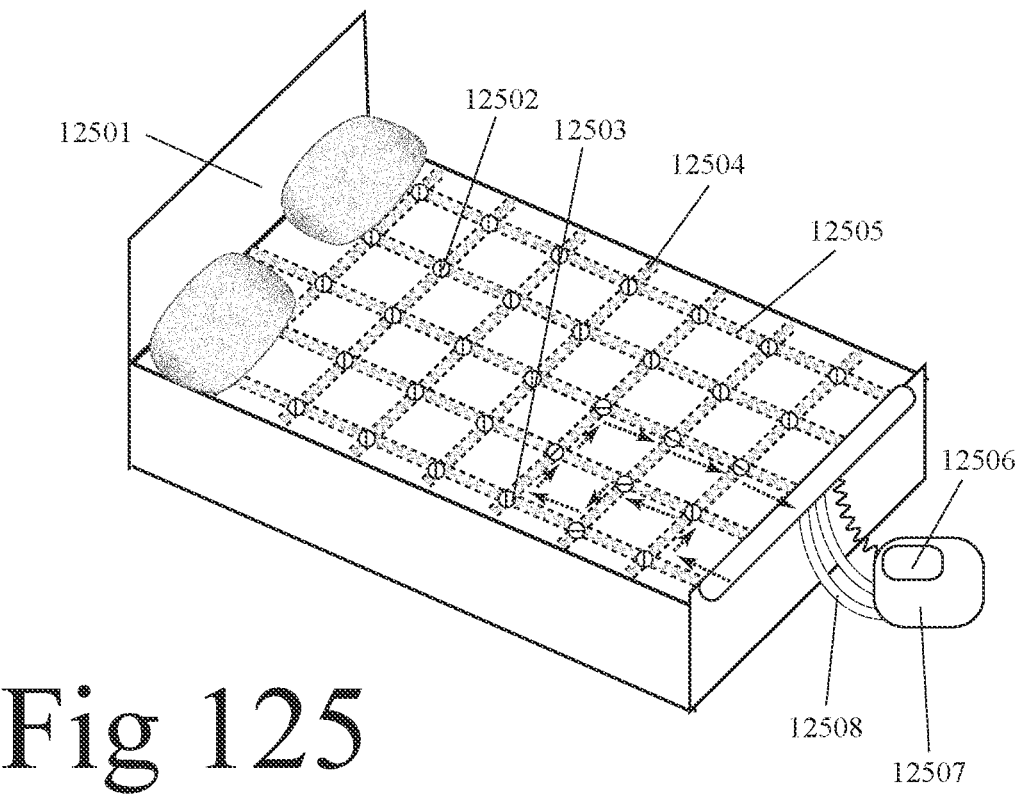
FIGS. 125 and 126 show a grid of fluid flow pathways and valves that create thermal zones in a bed.

FIGS. 125 and 126 show two views of an example of a device which creates a plurality of adjustable thermal zones in a bed comprising: a fluid cooling and/or heating unit 12507; a grid (or mesh) of fluid flow pathways (including fluid pathways 12504 and 12505) in a bedding component (e.g. mattress, mattress pad, or blanket) of a bed 12501; a plurality of fluid flow valves (including fluid flow valves 12502 and 12503) on the grid of fluid flow pathways; wherein fluid which has been cooled and/or heated by the fluid cooling and/or heating unit flows through a first set of the fluid flow pathways when a first set of the fluid flow valves have selected configurations (e.g. being closed, being open, and/or having a selected flow orientation) and flows through a second set of the fluid flow pathways when a second set of the fluid flow valves have selected configurations (e.g. being closed, being open, and/or having a selected flow orientation); and a data processing unit 12506 which controls which fluid flow valves are in which configuration at a given time. FIG. 125 shows this device at a first time when a first set of fluid flow valves in the grid have selected configurations, causing fluid to flow through a first set of fluid pathways in the grid. FIG. 126 shows this device at a second time when a second set of fluid flow valves in the grid have selected configurations, causing fluid to flow through a second set of fluid pathways in the grid. In an example, there can also be one or more fluid channels, such as 12508, between the grid and the fluid cooling and/or heating unit.

In an example, this device can further comprise a plurality of (electromagnetic, hydraulic, or pneumatic) actuators which change the configurations of fluid flow valves. In an example, actuators can be electromagnetic motors which rotate fluid flow valves. In an example, a data processing unit can control the configurations of fluid flow valves by controlling the operation of these actuators. In an example, a data processing unit can be in electromagnetic communication with actuators via wires or can be in wireless electromagnetic communication with actuators. In an example, a data processing unit can create one or more different-size and different-shape cooling and/or heating zones in the bed by controlling which fluid flow valves are in which configuration (e.g. being closed, being open, or having a selected flow orientation) at a given time.

In an example, a grid (or mesh) of fluid flow pathways can be incorporated into a bed mattress. In an example, a grid (or mesh) of fluid flow pathways can be incorporated into a mattress pad. In an example, a grid (or mesh) of fluid flow pathways can be incorporated into a blanket. In an example, an orthogonal grid of fluid flow pathways can comprise a row and column grid of fluid pathways, wherein rows in the grid span a bed laterally (from right to left, or vice versa) and columns in the grid span the bed longitudinally (from head to foot, or vice versa). In an example, an orthogonal grid of fluid flow pathways can comprise at least four fluid pathway rows and six fluid pathway columns. In an example, an orthogonal grid of fluid flow pathways can comprise at least eight fluid pathway rows and twelve fluid pathway columns.

In an example, fluid flow pathways in a grid of fluid flow pathways can be substantially straight. In an example, fluid flow pathways in a grid of fluid flow pathways can be arcuate. In an example, fluid flow pathways in a grid of fluid flow pathways can be undulating, serpentine, and/or sinusoidal. In an example, a grid (or mesh) of fluid flow pathways can be a two-way orthogonal grid (with rows and columns of fluid flow pathways) which form quadrilateral areas between intersecting (or overlapping) rows and columns of fluid flow pathways. In an example, a grid (or mesh)

or fluid flow pathways can be a three-way grid which forms triangular areas between intersecting (or overlapping) fluid flow pathways. In an example, a grid (or mesh) or fluid flow pathways can be a honeycomb grid which forms hexagonal areas between intersecting (or overlapping) fluid flow pathways.

In an example, fluid flow valves can be located where fluid flow pathways intersect (or overlap) in a grid. In an example, fluid flow pathways can be coplanar. In an example, fluid flow pathways can intersect at fluid flow valves in the grid. In an example, fluid flow valves can be located where fluid flow pathways intersect in a grid. In an example, fluid flow pathways can overlap where they cross each other. In an example, a grid of fluid flow pathways can be a woven grid of fluid flow pathways. In an example, there can be fluid flow valves wherever fluid flow pathways intersect (or overlap) in a grid. In an example, there can be fluid flow valves at only a subset of all intersections between fluid flow pathways in a grid. In an example, there can be fluid flow valves at a subset of intersections comprising between 10% and 50% of all intersections between fluid flow pathways in a grid. In an example, there can be fluid flow valves at a subset of intersections comprising less than 10% of all intersections between fluid flow pathways in a grid.

In an example, fluid flow valves can have different configurations which are changed by actuators which are, in turn, controlled by a data processing unit. In an example, a fluid flow valve can have a closed configuration in which no fluid flows through the valve. In an example, a fluid flow valve can have one possible open configuration in which fluid flows through the valve in a single direction. In an example, a fluid flow valve can have multiple possible directionally-open configurations, wherein each directionally-open configuration directs fluid in a different direction and/or through a different downstream fluid flow pathway. In an example, cooling and/or heating zones with different shapes and/or sizes can be created by moving different fluid flow valves in the grid into different closed, open, or directionally-open configurations. This can enable a person to selectively cool and/or heat different portions of their body (at different times).

In an example, a fluid flow valve at the intersection of two fluid pathways in an orthogonal grid (e.g. a grid with fluid flow rows and columns) can have different possible configurations selected from the group consisting of: a closed configuration, with no fluid flowing through the valve; a straight-open configuration, allowing fluid flow to continue in a straight direction along a fluid pathway row or column; directionally-open-right, directing fluid flow to the right from a fluid pathway column to a fluid pathway row, or vice versa; and directionally-open-left, directing fluid flow to the left from a fluid pathway column to a fluid pathway row, or vice versa. In an example, a fluid flow valve can enable a fluid inflow to be split into outflows in multiple directions (e.g. partially right and partially left) rather than all in one direction (e.g. entirely right). In an example, a quadrilateral fluid flow pattern can be configured a sequence of fluid flow valves in an orthogonal grid to redirect fluid flow in a right, left, left, left sequence. In an example, a serpentine fluid flow pattern can be configured a sequence of fluid flow valves in an orthogonal grid to redirect fluid flow in a right, left, left, right sequence.

In an example, the sizes and shapes of one or more cooling and/or heating zones can formed and changed by one or more people in the bed via one or more remote control units or cell phone applications. In an example, this device can further comprise a plurality of sensors. In an example, the sizes and shapes of one or more cooling and/or heating zones can be formed or changed based on analysis of data from a plurality of sensors. In an example, one or more sensors can be temperature sensors. In an example, one or more sensors can be pressure or motion sensors. In an example, these sensors can be part of the bedding component of this device. In an example, one or more sensors which serve as inputs for a data processing unit can be worn by one or more people in the bed. In an example, one or more sensors can be (skin) tissue conductance or impedance sensors. In an variation on this example, a device can comprise a grid of air flow pathways instead of a grid of fluid flow pathways with airflow valves instead of fluid flow valves, wherein the air flow pathways have holes through which cooled and/or heated air is delivered into (and withdrawn from) a space below the covers of a bed. Design variations discussed elsewhere in this disclosure or in priority-linked disclosures can also be applied to this example where relevant.

FIG. 127 shows an example of a device which creates a plurality of adjustable thermal zones in a bed comprising: a fluid cooling and/or heating unit 12705; a data processing unit 12704; an upper bedding layer 12702 (e.g. the upper layer of a mattress, mattress pad, and/or a sheet) on which a person 12701 sleeps; a middle bedding layer 12710 (e.g. a middle layer of a mattress or mattress pad) which has a plurality (e.g. a grid, matrix, and/or array) of pressure sensors, wherein data from the pressure sensors is sent to the data processing unit, and wherein analysis of data from the pressure sensors indicates an area 12709 directly under the person's body; and a lower bedding layer 12708 (e.g. a middle layer of a mattress or mattress pad) which has a plurality (e.g. a grid, matrix, and/or array) of fluid flow pathways and fluid flow valves, wherein the configurations of the fluid flow valves are controlled by the data processing unit, and wherein the configurations of the fluid flow valves are selectively configured to direct fluid from the fluid cooling and/or heating unit through flow pathways 12707 which are in the area directly under the person's body. The lower portion of FIG. 127 shows a top view of this device on a bed 12703. The upper portion of FIG. 127 shows an exploded, multi-level view of this device. In an example, there can also be one or more fluid channels, such as 12706, between the bedding layers and the fluid cooling and/or heating unit.

In an example, this device can further comprise a plurality of (electromagnetic, hydraulic, or pneumatic) actuators which change the configurations of fluid flow valves. In an example, actuators can be electromagnetic motors which rotate fluid flow valves. In an example, a data processing unit can control the configurations of fluid flow valves by controlling the operation of these actuators. In an example, a data processing unit can be in electromagnetic communication with actuators via wires or can be in wireless electromagnetic communication with actuators. In an example, a data processing unit can create one or more different-size and different-shape cooling and/or heating zones in the bed by controlling which fluid flow valves are in which configuration (e.g. being closed, being open, or having a selected flow orientation) at a given time.

In an example, a grid (or mesh) of fluid flow pathways can be incorporated into a bed mattress. In an example, a grid (or mesh) of fluid flow pathways can be incorporated into a mattress pad. In an example, a grid (or mesh) of fluid flow pathways can be incorporated into a blanket. In an example, an orthogonal grid of fluid flow pathways can comprise a row and column grid of fluid pathways, wherein rows in the grid span a bed laterally (from right to left, or vice versa) and columns in the grid span the bed longitudinally (from head to foot, or vice versa). In an example, an orthogonal grid of fluid flow pathways can comprise at least four fluid pathway rows and six fluid pathway columns. In an example, an orthogonal grid of fluid flow pathways can comprise at least eight fluid pathway rows and twelve fluid pathway columns.

In an example, fluid flow pathways in a grid of fluid flow pathways can be substantially straight. In an example, fluid flow pathways in a grid of fluid flow pathways can be arcuate. In an example, fluid flow pathways in a grid of fluid flow pathways can be undulating, serpentine, and/or sinusoidal. In an example, a grid (or mesh) of fluid flow pathways can be a two-way orthogonal grid (with rows and columns of fluid flow pathways) which form quadrilateral areas between intersecting (or overlapping) rows and columns of fluid flow pathways. In an example, a grid (or mesh) or fluid flow pathways can be a three-way grid which forms triangular areas between intersecting (or overlapping) fluid flow pathways. In an example, a grid (or mesh) or fluid flow pathways can be a honeycomb grid which forms hexagonal areas between intersecting (or overlapping) fluid flow pathways.

In an example, fluid flow valves can be located where fluid flow pathways intersect (or overlap) in a grid. In an example, fluid flow pathways can be coplanar. In an example, fluid flow pathways can intersect at fluid flow valves in the grid. In an example, fluid flow valves can be located where fluid flow pathways intersect in a grid. In an example, fluid flow pathways can overlap where they cross each other. In an example, a grid of fluid flow pathways can be a woven grid of fluid flow pathways. In an example, there can be fluid flow valves wherever fluid flow pathways intersect (or overlap) in a grid.

In an example, fluid flow valves can have different configurations which are changed by actuators which are, in turn, controlled by a data processing unit. In an example, a fluid flow valve can have a closed configuration in which no fluid flows through the valve. In an example, a fluid flow valve can have one possible open configuration in which fluid flows through the valve in a single direction. In an example, a fluid flow valve can have multiple possible directionally-open configurations, wherein each directionally-open configuration directs fluid in a different direction and/or through a different downstream fluid flow pathway. In an example, cooling and/or heating zones with different shapes and/or sizes can be created by moving different fluid flow valves in the grid into different closed, open, or directionally-open configurations. This can enable a person to selectively cool and/or heat different portions of their body (at different times).

In an example, a fluid flow valve at the intersection of two fluid pathways in an orthogonal grid (e.g. a grid with fluid flow rows and columns) can have different possible configurations selected from the group consisting of: a closed configuration, with no fluid flowing through the valve; a straight-open configuration, allowing fluid flow to continue in a straight direction along a fluid pathway row or column; directionally-open-right, directing fluid flow to the right from a fluid pathway column to a fluid pathway row, or vice versa; and directionally-open-left, directing fluid flow to the left from a fluid pathway column to a fluid pathway row, or vice versa. In an example, a fluid flow valve can enable a fluid inflow to be split into outflows in multiple directions (e.g. partially right and partially left) rather than all in one direction (e.g. entirely right).

In an variation on this example, a device can comprise a grid of air flow pathways instead of a grid of fluid flow pathways with airflow valves instead of fluid flow valves, wherein the air flow pathways have holes through which cooled and/or heated air is delivered into (and withdrawn from) a space below the covers of a bed. Design variations discussed elsewhere in this disclosure or in priority-linked disclosures can also be applied to this example where relevant.

I claim:

1. A device which creates a plurality of adjustable thermal zones in a bed comprising:
    a fluid cooling and/or heating unit;
    a grid of fluid flow pathways in a bedding component of a bed;
    a plurality of fluid flow valves on the grid of fluid flow pathways;
    wherein fluid which has been cooled and/or heated by the fluid cooling and/or heating unit flows through a first set of the fluid flow pathways when a first set of the fluid flow valves have selected configuration and flows through a second set of the fluid flow pathways when a second set of the fluid flow valves have selected configurations;
    wherein the cooled and/or heated fluid is retained within the grid of fluid flow pathways;
    wherein the fluid flow pathways create a closed loop of cooled and/or heated fluid between the bedding component and the fluid cooling and/or heating unit;
    a data processing unit which controls which fluid flow valves are in which configuration at a given time; and
    a plurality of pressure sensors, wherein data from the pressure sensors is sent to the data processing unit, wherein analysis of data from the pressure sensors indicates an area directly under a person's body, and wherein the configurations of the fluid flow valves are selectively configured to direct fluid from the fluid cooling and/or heating unit through fluid flow pathways which are in the area directly under the person's body.

2. The device of claim 1, further comprising one or more remote control units, wherein the one or more remote control units are operable to change a size and/or a shape of the plurality of adjustable thermal zones.

3. The device of claim 1, further comprising a sensor, wherein a size and/or a shape of the plurality of adjustable thermal zones are formed and/or changed in response to an analysis of data from the sensor.

4. The device of claim 1, wherein the data processing unit analyzes data from a sensor and controls the operation of the fluid cooling and/or heating unit based on the analyzed data.

5. The device of claim 1, wherein the grid of fluid flow pathways forms quadrilateral areas, triangular areas, and/or honeycomb areas between intersecting and/or overlapping fluid flow pathways.

6. The device of claim 1, wherein the grid of fluid flow pathways includes rows that span the lateral width of the bed and columns that span the longitudinal length of the bed.

7. The device of claim 1, wherein the plurality of fluid flow valves are located where the fluid flow pathways intersect in the grid of fluid flow pathways.

8. The device of claim 1, wherein the grid of fluid flow pathways is incorporated into a blanket.

9. The device of claim 1, further comprising electromagnetic actuators, hydraulic actuators, and/or pneumatic actuators, wherein the electromagnetic actuators, the hydraulic actuators, and/or the pneumatic actuators are operable to change the configuration of the fluid flow valves controlled by the data processing unit.

* * * * *